United States Patent
Huesca et al.

(10) Patent No.: US 8,969,372 B2
(45) Date of Patent: *Mar. 3, 2015

(54) ARYL IMIDAZOLES AND THEIR USE AS ANTI-CANCER AGENTS

(75) Inventors: Mario Huesca, Toronto (CA); Raed Al-Qawasmeh, Amman (JO); Aiping H. Young, Toronto (CA); Yoon Lee, Mississauga (CA)

(73) Assignee: Aptose Boisciences Inc., Ontario (CA)

( * ) Notice: Subject to any disclaimer, the term of this patent is extended or adjusted under 35 U.S.C. 154(b) by 969 days.

This patent is subject to a terminal disclaimer.

(21) Appl. No.: 10/579,149

(22) PCT Filed: Nov. 15, 2004

(86) PCT No.: PCT/IB2004/052433

§ 371 (c)(1),
(2), (4) Date: Jan. 19, 2007

(87) PCT Pub. No.: WO2005/047266

PCT Pub. Date: May 26, 2005

(65) Prior Publication Data

US 2007/0123553 A1    May 31, 2007
US 2008/0262015 A9    Oct. 23, 2008

Related U.S. Application Data

(60) Provisional application No. 60/520,279, filed on Nov. 14, 2003, provisional application No. 60/599,509, filed on Aug. 6, 2004.

(51) Int. Cl.
| | |
|---|---|
| *A61K 31/4745* | (2006.01) |
| *A61K 31/4188* | (2006.01) |
| *A61K 31/4178* | (2006.01) |
| *C07D 233/64* | (2006.01) |
| *C07D 235/02* | (2006.01) |
| *C07D 401/14* | (2006.01) |
| *C07D 403/04* | (2006.01) |
| *C07D 403/14* | (2006.01) |
| *C07D 409/14* | (2006.01) |
| *C07D 495/04* | (2006.01) |

(52) U.S. Cl.
CPC .......... *C07D 233/64* (2013.01); *A61K 31/4178* (2013.01); *A61K 31/4188* (2013.01); *A61K31/4745* (2013.01); *C07D 235/02* (2013.01); *C07D 401/14* (2013.01); *C07D 403/04* (2013.01); *C07D 403/14* (2013.01); *C07D 409/14* (2013.01); *C07D 495/04* (2013.01)
USPC ............ 514/285; 514/396; 514/393; 514/397

(58) Field of Classification Search
CPC .......... A61K 31/4178; A61K 31/4188; A61K 31/4745; C07D 233/64; C07D 235/02; C07D 401/14; C07D 403/04; C07D 403/14; C07D 409/14; C07D 495/04
See application file for complete search history.

(56) References Cited

U.S. PATENT DOCUMENTS

| | | | |
|---|---|---|---|
| 3,279,918 A | 10/1966 | Cassiers et al. ..................... 90/1 |
| 3,297,710 A | 1/1967 | Silversmith ................... 260/309 |
| 3,714,181 A | 1/1973 | Lantos | |
| 4,089,747 A | 5/1978 | Bruschi ........................... 435/10 |
| 4,423,046 A | 12/1983 | Carlson ....................... 514/228.8 |
| 4,466,976 A | 8/1984 | Klose et al. ................... 514/397 |
| 4,585,771 A | 4/1986 | Klose et al. ................... 514/220 |
| 4,705,855 A | 11/1987 | Desideri et al. ............... 544/370 |
| 4,721,670 A | 1/1988 | Osada et al. ................... 435/28 |
| 4,902,705 A | 2/1990 | Hirota et al. .................. 514/397 |
| 4,970,226 A | 11/1990 | Sun et al. ...................... 514/397 |
| 5,011,472 A | 4/1991 | Aebischer | |
| 5,023,252 A | 6/1991 | Hseih | |
| 5,024,935 A | 6/1991 | McClune et al. .............. 435/7.1 |
| 5,047,318 A | 9/1991 | Snyder et al. ..................... 435/5 |
| 5,496,702 A | 3/1996 | Bishop et al. .................. 435/7.9 |
| 5,514,550 A | 5/1996 | Findlay et al. .................... 435/6 |
| 5,656,644 A | 8/1997 | Adams et al. ................. 514/341 |
| 5,686,455 A | 11/1997 | Adams et al. ................. 514/256 |
| 5,693,589 A | 12/1997 | Goswami et al. ............. 503/227 |
| 5,700,826 A | 12/1997 | Mjalli et al. .................. 514/397 |
| 5,753,687 A | 5/1998 | Mjalli et al. .................. 514/396 |
| 5,916,891 A | 6/1999 | Adams et al. ................. 514/256 |

| | | | | |
|---|---|---|---|---|
| 5,945,418 | A | 8/1999 | Bemis et al. | 514/248 |
| 6,060,216 | A | 5/2000 | Ichikawa et al. | 430/284.1 |
| 6,117,609 | A | 9/2000 | Maeda | 430/138 |
| 6,194,441 | B1 | 2/2001 | Roberts et al. | 514/340 |
| 6,268,370 | B1 | 7/2001 | Adams et al. | 514/256 |
| 6,521,655 | B1 | 2/2003 | Beers et al. | 514/397 |
| 7,115,645 | B2 | 10/2006 | Halfbrodt et al. | |
| 7,291,404 | B2 | 11/2007 | Aziz et al. | |
| 7,718,685 | B2 | 5/2010 | Shin et al. | |
| 7,884,120 | B2 | 2/2011 | Al-Qawasmeh | |
| 7,888,118 | B2 | 2/2011 | Shin et al. | |
| 7,989,089 | B2 | 8/2011 | Wang et al. | |
| 8,148,392 | B2 | 4/2012 | Huesca et al. | |
| 8,394,815 | B2 | 3/2013 | Al-Qawasmeh | |
| 2004/0127527 | A1 | 7/2004 | Hongu et al. | 514/365 |
| 2004/0176601 | A1 | 9/2004 | Goulet et al. | 546/46 |
| 2004/0265628 | A1 | 12/2004 | Wang et al. | |
| 2007/0105929 | A1 | 5/2007 | Al-Qawasmeh | 514/393 |
| 2007/0123553 | A1 | 5/2007 | Huesca et al. | 514/285 |
| 2011/0152337 | A1 | 6/2011 | Al-Qawasmeh | |
| 2013/0177632 | A1 | 7/2013 | Al-Qawasmeh | |

FOREIGN PATENT DOCUMENTS

| | | | |
|---|---|---|---|
| CA | 1195325 | 10/1985 | |
| CA | 2351694 | 7/1993 | |
| CN | 1289774 | 9/1999 | |
| CN | 1289775 | 9/1999 | |
| DE | 3141063 | 10/1985 | |
| EP | 0077024 | 4/1983 | |
| EP | 165588 | 12/1985 | |
| EP | 0 812 829 | 12/1997 | |
| EP | 1428831 | 6/2004 | |
| JP | 11199582 | 7/1999 | |
| JP | 2000-273088 | 10/2000 | |
| JP | 2002-275458 | 9/2002 | |
| JP | 2002-364578 | 12/2002 | |
| WO | WO 93/14081 | 7/1993 | |
| WO | WO 95/03297 | 2/1995 | |
| WO | WO 96/18626 | 6/1996 | |
| WO | WO 97/36587 | 10/1997 | |
| WO | WO 98/27065 | 6/1998 | |
| WO | WO 98/27108 | 6/1998 | |
| WO | WO 99/01128 | 1/1999 | |
| WO | WO 99/02155 | 1/1999 | |
| WO | WO 99/07701 | 2/1999 | |
| WO | WO 00/33836 | 6/2000 | |
| WO | WO 00/59541 | 10/2000 | |
| WO | WO 00-68206 | 11/2000 | |
| WO | WO 00-68266 | 11/2000 | |
| WO | WO 00/78761 | * 12/2000 | C07D 487/04 |
| WO | WO 01/26467 | 4/2001 | |
| WO | WO 02/24680 | 3/2002 | |
| WO | WO 02/46168 | 6/2002 | |
| WO | WO 02/072576 | 9/2002 | |
| WO | WO 02083111 | 10/2002 | |
| WO | WO 03/004023 | 1/2003 | |
| WO | WO 03/032984 | 4/2003 | |
| WO | WO 03/066579 | 8/2003 | |
| WO | WO 03/087026 | 10/2003 | |
| WO | WO 2004-005264 | 1/2004 | |
| WO | WO 2004/016086 | 2/2004 | |
| WO | WO 2004016086 | 2/2004 | |
| WO | WO 2005/047266 | 5/2005 | |

OTHER PUBLICATIONS

Dora et al. ("Synthesis of Some Fused 2-Arylimidazoles and their Derivatives" J. Indian Chem. Soc. LVI, 1979, 620-624).*
International Search Report (ISR) of the International Searching Authority, date of mailing Apr. 4, 2005; International Application No. PCT/IB2004/052433.
Abdel-Meguid et al., "An orally bioavailable HIV-1 protease inhibitor containing an imidazole-derived peptide bond replacement: Crystallographic and pharmacokinetic analysis," *Chemistry*, 1994, 33:11671-11677.
Adams et al., "Pyrimidinylimidazole inhibitors of p38: Cyclic N-1 imidazole substituents enhance p38 kinase inhibition and oral activity," *Bioorg. Med. Chem. Lett.*, 2001, 11:2867-2870.
Antolini et al., "Analogues of 4,5-bis(3,5-dichlorophenyl)-2-trifluoromethyl-1H-imidazole as potential antibacterial agents," *Bioorg. Med. Chem. Lett.*, 1999, 9:1023-1028.
Armesto et al., "A new site selective synthesis of benzoin esters, synthesis of symmetrically and unsymmetrically substituted benzils," *Synthesis*, 1988, 799-801.
Bhaduri et al., "Potential Antifertility Agents. Synthesis of 2,4,5-Substituted Imidazoles", Central Drug Res. Inst. Lucknow, India, *Indian J. Chem.*, 1966, 4(9):419-420.
Botana et al.,"*p-(1H-Phenanthro[9,10-d]imidazol-2-yl)- Substituted Calix[4]arene, a Deep Cavity for Guest Inclusion*", Departmento de Quimica Organica, Universidad Autonoma de Madrid, Spain, *Organic Letters*, 2004, 6(7):1091-1094.
Bu et al., "A novel approach to synthesis of tricyanovinylthiophene for heterocyclic imidazole nonliner optical chromophores," *Tetrahedron Lett.*, 1996, 37:7331-7334.
Chao et al., Palladium catalyst in DMSO for the oxidation of tolans to benzils, *Polyhedron*, 2000, 1975-1983.
Chi et al., "Palladium catalyst in DMSO for the oxidation of tolans to benzils," *Synth. Comm.*, 1994, 24(15), 2119-2122.
Cuenda, et al., "Activation of stress-activated protein kinase-3 (SAPK3) by cytokines and cellular stresses is mediated via SAPKK3 (MKK6); comparison of the specificities of SAPK3 and SAPK2 (RK/p38),"*EMBO J.*, 1997, 16:295-305.
Cuenda, et al., "SB 203580 is a specific inhibitor of a MAP kinase homologue which is stimulated by cellular stresses and interleukin-1," *Febs Lett*, 1995, 364:229-33.
Database WPI, Section Ch. Week 199940, Derwent Publications Ltd, London, GB, Class B02, AN 1999-474062 (XP002268773) & JP 11 199582 (english abstract) A (Sagami Chem Res Cent), Jul. 27, 1999.
Demirayak et al., "Synthesis of Certain Derivatives of Ethyl α-[(phenanthro[9,10-d]imidazol-2-yl)phenoxy]alkanoate", *Acta Pharmaceutica Turcica*, 1989, 31(1):19-25.
Downey et al., "Degradation of DNA by 1,-10-phenanthroline," *Biochem Biophys Res Commun*, 1980, 93(1):264-70.
Fischer et al., "Dissociation constants of the conjugate acids of substituted benzyl phenyl ketones and of alkyl-substituted benzophenomes," *J. Am. Chem. Soc*. 1961, 83:4208-4210.
Gales et al., "Characterization of *Pseudomonas aeruginosa* isolates: Occurense rates, antimicrobial susceptibility patterns, and molecular typing in the global SENTRY antimicrobial surveillance program, 1997-1999," *Clin. Infect. Dis.*, 2001, 32:S146-155.
Guijarro et al., "The reaction of active zinc with organic bromides," *J. Am. Chem. Soc.*, 1999, 121:4155-4157.
Heerding et al., "1,4-disubstituted imidazoles are potential antibacterial agents functioning as inhibitors of enoyl acyl carrier protein reductase (FabI)," *Bioorg. Med. Chem. Lett*., 2001, 11:2061-2065.
Isikdag et al., "QSAR of inhibitory activities by 2,4,5-trisubstituted imidazole derivatives on tubifex worms," *Acta Pharmaceutica Urica* 1995, 37(1):19-24.
Krieg et al., *Naturforsch*. 1967, 22b:132-141 (English translation).
Kimura et al., "*Preparation of 4-(4,5-diphenyl-1H-imidazol-2-yl)benzaldehyde and its Practical Synthetic Use in the Synthesis of Unsymmetrically Substituted Imidazoles*", Department of Chemistry, Okayama University, Okayama Japan, ITE Letters on Batteries, New Technologies & Medicine, 2002, 3(1), pp. 30-34.
Lee et al., "A protein kinase involved in the regulation of inflammatory cytokine biosynthesis," *Nature*, 1994, 327:739-745.
Lewis J.R., "Muscarine, imidazole, oxazole, thiazole and peptide alkaloids, and other miscellaneous alkaloids," *Nat. Prod. Rep.*, 1998, 15:371-395.
Lewis J.R., "Muscarine, imidazole, oxazole, thiazole and peptide alkaloids, and other miscellaneous alkaloids," *Nat. Prod. Rep.*, 1998, 15:417-437.
Lewis J.R., "Miscellaneous alkaloids: Amaryllidaceae, sceletium, muscarine, imidazole, oxazole, peptide miscellaneous alkaloids," *Nat. Prod. Rep.*, 1999, 16:389-416.
Liu et al., "Enantiomeric ruthenium(II) complexes binding to DNS: binding modes and enantioselectivity,"*JBIC*, 2000, 5:119-128.
LoGrasso et al., "Kinetic mechanism fro p38 MAP kinase," *Biochemistry*, 1997, 36:10422-10427.
Mann et al., "1,10-phenanthroline inhibits glycosylphosphatidylinositol anchoring by preventing phosphoethanolamine addition to glycosylphosphatidylinositol anchor precursurors," Biochemistry, 2001, 40(5);1205-13.

McLay et al., "The discovery of RPR 200765A, a p38 MAP kinase inhibitor displaying a good oral anti-arthritic efficacy," Bioorg. Med. Chem., 2001, 9:537-554.

Moylan et al., "Synthesis and Nonlinear Optical Properties of Donor-Acceptor Substituted Triaryl Azole Derivatives", Almaden Res. Cent. IBM, San Jose, CA, USA, Chemistry of Materials, 1993, 5(10):1499-1508.

Pan et al., "DNA-binding proteins as site-specific nucleases," Mol Microbiol, 1994, 12(3):335-42.

Sarshar et al. "2,4,5-trisubstituted imidazoles: Novel nontoxic modulators of P-glycoprotein mediated multidrug resistance Part 1," Bioorg. Med. Chem. Lett., 2000, 10:2599-2601.

Sarshar et al., "Imidazole libraries on solid support," Tetrahedron Lett. 1996, 37:835-838.

Shulman et al., "Action of 1,10-phenanthroline transition metal chelates on P388 mouse lymphocytic leukaemic cells," Chem Biol Interact, 1977, 16(1): 89-99.

Sigman et al., "Oxygen-dependent cleavage of DNA by the 1,10-phenanthroline cuprous complex," J Biol Chem, 1979, 254(24):12269-72.

Springman et al., "Zinc content and function in human fibroblast collegenase," Biochemistry, 1995, 34(48):15713-20.

Tanaseichuk et al., Uch. Zap., Mord. Univ. (1971), No. 81, 95-7 (From: Ref. Zh., Khim. 1972, Abstr. No. 12zh318 (English translation).

Xu et al. "Effects of the ancillary ligands of polypyridyl ruthenium(II) complexes on the DNA-binding behaviors," 2003, 27:1255-1263.

Zeytinoglu et al., "Mutagenicity Assay in Salmonella for Thirteen 2-Substituted-1H-phenanthro (9,10-d) Imidazoles", Department of Biology, Faculty of Science, Anadolu University, Eskisehir, Turkey, Drug and Chemical Toxicology, 26(4):245-257.

Zhang et al., "Mutagenicity assay in salmonella for thirteen 2-substituted-1H-phenanthro (9,10-d) imidazoles," Bioorg. Med. Chem. Lett., 2000, 10:2603-2605.

Chemical Abstracts Registry No. 309285-51-6.
Chemical Abstracts Registry No. 330449-52-0.
Chemical Abstracts Registry No. 332148-67-1.
Chemical Abstracts Registry No. 404904-57-0.

Lock et al., Molecular mechanisms of growth inhibition induced by novel aryl-imidazole compounds in human cancer cells Presented at IBC's 9th Annual World Congress Drug Discovery Technology Meeting (Boston Aug. 8-13, 2004) Abstract.

Press Release Lorus Therapeutics Inc., "Lorus Announces Discovery of Novel Low Molecular Weight Compounds with Anticancer and Antibacterial Activity," May 12, 2004.

Press Release Lorus Therapeutics Inc. "Lorus Therapeutics Inc to Present Results of Novel Anticancer Small Molecule Studies," Aug. 9, 2004.

Office Action issued in U.S. Appl. No. 10/525,690, filed Jul. 20, 2009, Al-qawasmeh et al.

Decision to Grant Chinese Patent Application 201010168726.8, dated Nov. 6, 2013.

Decision to Grant European for Patent Application EP03787546, dated May 22, 2014.

Gao, D., et al., "Synthesis and electroluminescence properties of an organic europium complex," Journal of Alloys and Compounds 358(1-2):188-192, 2003.

Guan, M., et al., Bright Red Light-Emitting Electroluminescence Devices based on a functionalize Europium Comples, New Journal of Chemistry 27(12): 1731.

International Preliminary Examinatin Report for PCTCA0301229, dated Dec. 3, 2004.

Nippon Kagaku Zasshi 1971, 92, 365-370.

Xiong, Ya, et al, "Interaction of polypyridyl ruthenium(II) complexes containing non-planar ligands with DNA," J. Chem. Soc, 1:19-24, 1999.

Xu, et al., Synthesis and spectroscopic RNA binding studies of [Ru(phen)2MHPIP]<2+>, Inorganic Chemistry Communications,Amsterdam, 6(6):766-768, 2003.

Arroyo et al.; Therapy of Murine Aspergillosis with Amphotericin B in Combination with Rifampin or 5-Fluorocytosine; Antimicrobial Agents and Chemotheraphy; 1977; pp. 21-25; American Society for Microbiology; Washington, DC, USA.

C.G. Wermuth, Hiroshi Nagase (translation supervisor), Saishin Spyaku Kagaku, Jo kan, Technomics Corporation, 1 1998. p. 243-248 (Japanese Version)—(Corresponding to C.G. Wermuth, The Practice of Medicinal Chemistry, Molecular Variations Based on Isosteric Replacements, 1996, 203-237, Academic Press (English version).

Diekema et al; Survey of Infections due to Staphylococcus Species: Frequency of Occurence and Antimicrobial Susceptibility of Isolates Collected in the United States, Canada, Latin America, Europe, and the Western PacificRegion for the Sentry Antimicrobial Surveillance Program, 1997-1999; Clinical Infectious Diseases; 2001; 32:S114-132; University of Chicago Press; Chicago, IL, USA.

Ekwall, Bjorn; Screening of Toxic Compounds in Mammalian Cell Cultures; Annals New York Academy of D Sciences; 1983; 407: 64-77; Blackwell Publishing.

Ghannoum et al; Susceptibility Testing of Fungi: Current Status of Correlation of In Vitro Data with Clinical Outcome; D Journal of Clinical Microbiology; 1996; 34: 489-495; American Society for Microbiology; Washington, DC, USA.

Goto et al; Improved efficacy with nonsimultaneous administration of netilmicin and minocycline against methicillin—resistant Staphylococcus aureus in in vitro and in vivo models; International Journal of Antimicrobial Agents; 1999; 11 :39-46; International Society of Chemotherapy; Elsevier Science B,V.; United Kingdom.

Hamish R. Michie; The value of animal models in the development of new drugs for the treatment of the sepsis syndrome; Journal for Antimicrobial Chemotherapy; 1998; 41: 47-49; British Society for Antimicrobial Chemotherapy; Birmingham, UK.

Hoban et al; Worldwide Prevalence of Antimicrobial Resistance in Streptococcus pneumoniae, Haemophilus influenzas, and Moraxella catarrhalis in the SENTRY Antimicrobial Surveillance Program, 1997-1999; ClinicalInfectious Diseases; 2001: 32:S81-93; Infectious Disease Society of America; The University of Chicago Press; Chicago, IL, USA.

Horig et al., Journal ofTranslational Medicine 2004, 2(44).

Huesca et al; Adhesion and Virulence Properties of Epidemic Canadian Methicillin-Resistant Staphylococcus aureus Strain 1: Identification of Novel Adhesion Functions Associated with Plasmin-Sensitive Surface Protein; The Journal oflnfectious Disease; 2002; Infectious Diseases Society of America; The University of Chicago Press; Chicago, IL, USA.

Iwahi et al; Virulence of Escherichia Coli in Ascending Urinary-Tract Infection in Mice; Journal of MedicalMicrobiology; 1982; 15:303-316; The Society for General Microbiology; High Wire Press.

Klose et al; The Suckling Mouse Model of Cholera; Trends in Microbiology; 2000; 8:189-91; Elsevier Science Ltd.

International Search Report (ISR) of the International Searching Authority, date of mailing Apr. 4, 2005; International Application No. PCT/182004/052433.

Isikdag et al; QSAR of Inhibitory Activities by 2,4,5-Trisubstituted Imidazole Derivatives on Tubifex Worms; ActaPharmaceutica Turcica; 1995; 37(1 ):19-24.

Kimura et al., New Technologies & Medicine, 2002, 3(1 ):30-34.

Lantos, "Reaction of Phenanthrenequinone with Ammonium Acetate," J. Org. Chern., 40(11)1641-1642 (1975).

LoGrasso et al; Kinetic Mechanism for p38 MAP Kinase; Biochemistry; 1997; 36: 10422-10427; American Chemical Society; Rahway, New Jersey, USA.

McLay et al; The Discovery of RPR 200765A, a p38 MAP Kinase Inhibitor Displaying a Good Oral Anti-Arthritic Efficacy; Bioorganic & Medicinal Chemistry; 2001; 9: 537-554; Elsevier Science Ltd; Amsterdam, The Netherlands.

Moylan et al., "Synthesis and Nonlinear Optical Properties of Donor-Acceptor 875 Substituted Triaryl Azole Derivatives", Almaden Res. Cent. IBM, San Jose, CA, USA,Chemistry of Materials, 1993, 5(10):1499-1508.

Pan et al., "DNA-binding proteins as site-specific nucleases," Mol Microbial, 1994, 12(3):335-42.

Pechkin, A.A. el, al., Synthesis and Properties of 2-(2-Furyl)-and 2-(2-Thienyl)-1-methylphenanthro[9, 1 0-d]imidazoles, Russian Journal of Organic Chemistry (Translation of Zhurnal Organicheskoi Khimii), 2002, 38(5):726-730.

Registry No. 309285-51-6, entered Registry file on STN on Dec. 18, 2000.

Registry No. 332148-67-1, entered Registry file on STN on Apr. 21, 2001.

Registry No. 404904-57-0, entered Registry file on STN on Apr. 10, 2002.

Registry No. 416872-13-4, entered into Registry file in STN on May 16, 2002.

Sarshar et al; 2,4,5-Trisubstituted Imidazoles: Novel Nontoxic Modulators of P-glycoprotein Mediated Multidrug Resistance. Part 1; Biorganic and Medicinal Chemistry Letters; 2000; 10:2599-2601; Elsevier Science Ltd;Philadelphia, PA, USA.

Schafer et al., Drug Discovery Today, 2008, 13 (21/22), 913-916.

Sigman et al.., "Oxygen-dependent cleavage of DNA by the 1,1 0-phenanthroline cuprous complex," J Biol Chem, 1979, 254(24): 12269-72.

Simor et al.; 1999 Canada Communicable Disease Report; 25: 105-108.

Springman et al., "Zinc content and function in human fibroblast collegenase," Biochemistry, 1995, 34(48): 15713-20.

Steck et al., "Reactions of Phenanthraquinone and Retenequinone with Aldehydes and Ammonium Acetate in Acetic Acid Solution," J. Am. Chem. Soc., 65:452-456 (1943).

Steve Sternberg; The Emerging Fungal Threat; Science; 1994; 266: 1632-1634; American Association for the Advancement of Science; Washington, DC, USA.

Tanaseichuk et al.; Uch. Zap., Mord. Univ. (1971), No. 81, 95-7 (From: Ref. Zh., Khim, 1972, Abstr. No. 12zh318 D (English abstract).

Thaler et al.; Evaluation of Single-Drug and Combination Antifungal Therapy in an Experimental Model of Candidiasis in Rabbits with Prolonged Neutropenia; The Journal of Infectious Diseases; 1988; 158: 80-88; University oChicago Press; Chicago, IL, USA.

Totsuka et al.; Combined effects of vancomycin and imipenem against methicillin-resistant *Staphylococcus aureus* (MRSA) in vitro and in vivo; Journal of Antimicrobial Chemotherapy; 1999; 44: 455-460; The British Society for Antimicrobial Chemotherapy; Birmingham, UK.

Walsh et al.; Effects of Preventive, Early, and Late Antifungal Chemotherapy with Fluconazole in Different Granulocytopenic Models of Experimental Disseminated Candidiasis; The Journal of Infectious Diseases; 1990; 161:755-760; University of Chicago Press; Chicago, IL, USA.

Written Opinion mailed on May 24, 2004 for International Application No. PCT/CA03/01229.

Xu et al., "Effects of the ancillary ligands of polypyridyl ruthenium (ii) complex(es) on the DNA-binding behaviors," New J. Chem., 2003, 27:1255-1263.

Zhang et al; 2,4,5-Trisumstituted Imidazoles: Novel Nontoxic Modulators of P-glycoprotein Mediated Multidrug Resistance, Part 2; Bioorganic & Medicinal Chemistry Letters; 2000; 1 0: 2603-2605; Elsevier Science Ltd; Philadelphia, PA, USA.

\* cited by examiner

*Primary Examiner* — Kortney L Klinkel
(74) *Attorney, Agent, or Firm* — Cooley LLP

(57) ABSTRACT

Therapeutically effective 2,4,5-trisubstituted imidazole compounds are provided. Also provided are methods of preparing the compounds and pharmaceutical compositions comprising the compounds alone or in combination with other agents. The present invention further provides for the use of the compounds as anti-cancer agents; wherein: R1 is aryl, substituted aryl, heterocycle, substituted heterocycle, heteroaryl, substituted heteroaryl or amino; R2 and R3 are independently aryl, substituted aryl, heterocycle, heteroaryl, substituted heterocycle, or substituted heteroaryl or R2 and R3 when taken together along with the carbon atoms they are attached to, form aryl or substituted aryl, and R4 is hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, aryl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl.

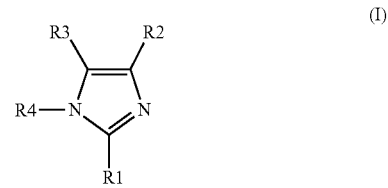

14 Claims, 24 Drawing Sheets

FIGURE 5
A.
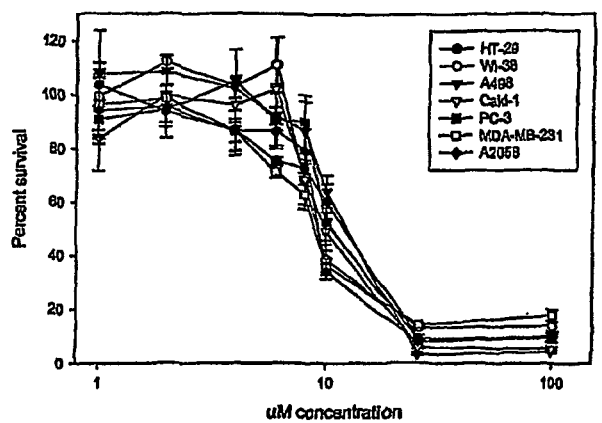
B.
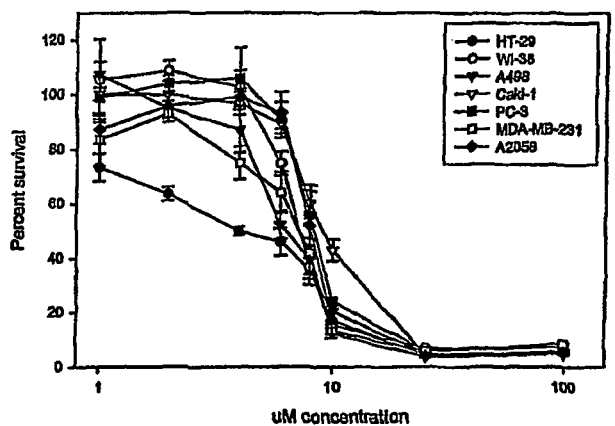
C.
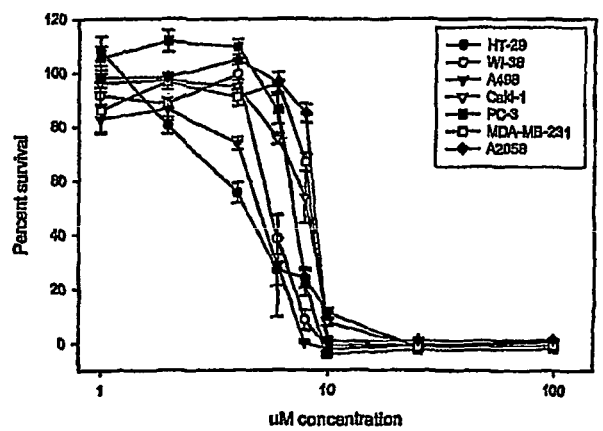

FIGURE 6
A.
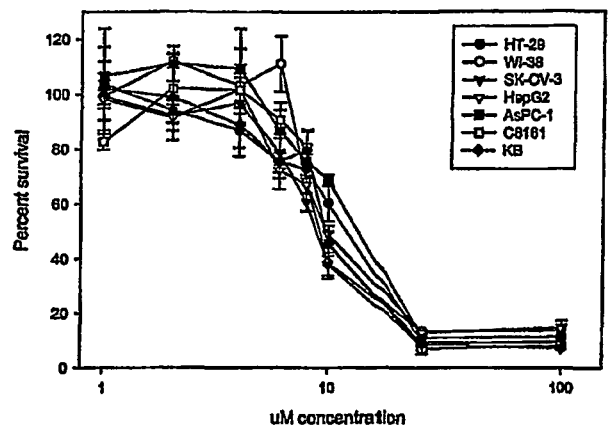
B.
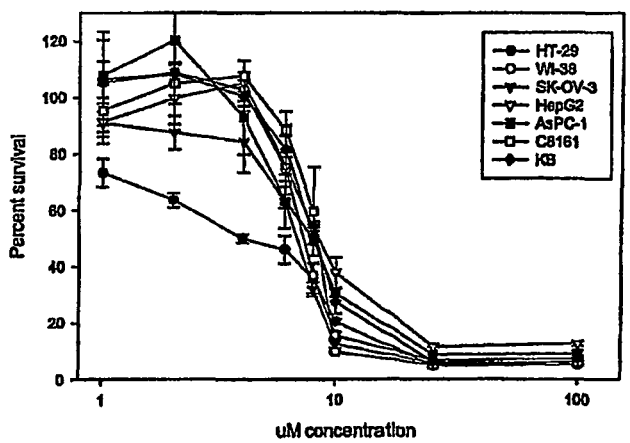
C.
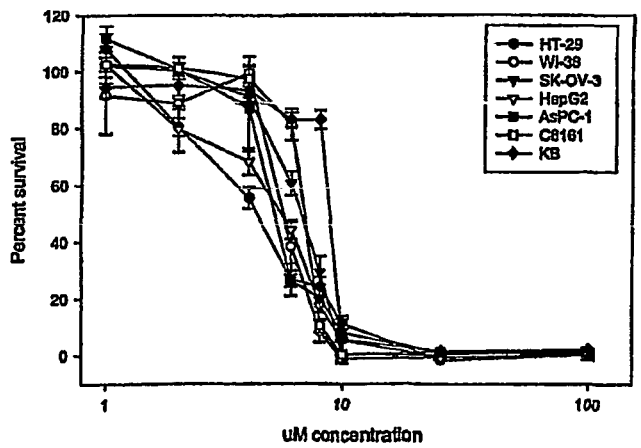

FIGURE 9A

| NCI ANTI-CANCER CELL LINE PANEL ||||||||
| Cell Line | Sex | Age | Histology | Comment | Treatment | Source |
|---|---|---|---|---|---|---|
| COLON |||||||
| COLO 205 | M | 70 | Adenocarcinoma | Can Res 38: 1345-1355, 1978 | Y | Ascites |
| HCC-2998 | | | Carcinoma | | N | |
| HCT-15 | | | Adenocarcinoma | Can Res 39: 1020-1025, 1979 | | |
| HCT-116 | | | Carcinoma | Can Res 41: 1761-1756, 1981 | | |
| HT29 | F | 44 | Adenocarcinoma, GR III | Human Tumor Cells In Vitro: 115-159, 1975 | | Primary |
| KM12 | | | Adenocarcinoma | Can Res 48: 1943-1948, 1988 | N | |
| SW-60 | M | 51 | Adenocarcinoma | Can Res 36: 4562-4569, 1976 | | Metastasis |
| CNS |||||||
| SF-268 | F | 24 | Anaplastic Astrocytoma | Acta Neuropathol 75: 92-103, 1987 | | |
| SF-295 | F | 67 | Glioblastoma-Multiforme | Acta Neuropathol 75: 92-103, 1987 | | |
| SF-539 | | | | J Neuropathol Exp Neurol 40: 201-229, 1981 | | |
| SNB-19 | M | 47 | Glioma | Cancer 47: 255, 1981 | N | |
| SNB-75 | F | | Astrocytoma | | N | |
| U251 | M | 75 | Glioblastoma | J Neuropathol Exp Neurol 40: 410-427, 1981 | | |
| LEUKEMIA |||||||
| CCRF-CEM | M | 4 | Acute Lymphoblastic Leukemia | Can Res 18: 522-529, 1965 | | |
| HL-60(TB) | F | 36 | Promyelocytic Leukemia | Nature 270: 347-349, 1977 | | PBL |
| K-562 | F | 53 | Chronic Myelogenous Leukemia | Blood 45: 321-334, 1975 | | Pleural Effusion |
| MOLT-4 | M | 19 | Acute Lymphoblastic Leukemia | JNCI 49: 891-895, 1972 | | PB |
| RPMI-8226 | M | 61 | Myeloma | Proc Soc Exp Biol Med 125: 1246-1250, 1967 | | PB |
| SR | M | 11 | Large Cell, Immunoblastic | | Y | |
| Lung |||||||
| A549/ATCC | M | 58 | Adenocarcinoma | JNCI 51: 1417-1423, 1973 | | Primary |
| EKVX | M | | Adenocarcinoma | | | |
| HOP-62 | F | 60 | Adenocarcinoma | | N | |
| HOP-92 | M | 62 | Large Cell, Undifferentiated | | N | |
| NCI-H23 | | | Adenocarcinoma | Can Res 45: 2913-2923, 1985 | N | |
| NCI-H226 | | | Squamous | Can Res 45: 2913-2923, 1985 | | |

FIGURE 9B

| NCI ANTI-CANCER CELL LINE PANEL ||||||| 
| Cell Line | Sex | Age | Histology | Comment | Treatment | Source |
| --- | --- | --- | --- | --- | --- | --- |
| LUNG (continued) |||||||
| NCI-H322M | | | Small Cell Bronchioalveolar Carcinoma | | N | |
| NCI-H460 | M | | Large Cell Carcinoma | Science 246: 491-494, 1989 | N | Pleural Effusion |
| NCI-H522 | | | Adenocarcinoma | Can Res 45: 2913-2923, 1985 | | |
| MAMMARY |||||||
| MCF7 | F | 69 | Adenocarcinoma | JNCI 51: 1409-1417, 1973 | Y | |
| NCI/ADR-RES | F | | Adenocarcinoma | JNCI 90(11): 6/3/1998 | | |
| HS 578T | F | 74 | Carcinosarcoma | JNCI 58: 1795-1806, 1977 | | Primary |
| MDA-MB-231 | F | 51 | Adenocarcinoma | JNCI 53: 661-674, 1974 | Y | |
| MDA-MB-435 | F | 31 | Adenocarcinoma | Can Res 40: 3118-3129, 1980 | N | |
| BT-549 | F | 72 | Papillary Infiltrating Ductal Carcinoma | No Publication | | Metastasis |
| T-47D* | F | 54 | Infiltrating Ductal Carcinoma | Eur J Cancer 15: 659-670, 1979 | | *not for commercial use |
| MELANOMA |||||||
| LOX IMVI | | | Malignant Amelanotic Melanoma | Int J Cancer 41: 442-449, 1988 | | |
| M14 | | | | | | |
| MALME-3M | M | 43 | Malignant Melanoma | Human Tumor Cells In Vitro, pp. 115-159, 1975 | | Metastasis |
| SK-MEL-2 | M | 60 | Malignant Melanoma | Human Tumor Cells In Vitro, pp. 115-159, 1975 | | Metastasis |
| SK-MEL-5 | | | Malignant Melanoma | PNAS 73: 3278-3282, 1976 | | Metastasis |
| SK-MEL-28 | | | Malignant Melanoma | PNAS 73: 3278-3282, 1976 | | |
| UACC-62 | | | | | | |
| UACC-257 | | | | | | |
| OVARIAN |||||||
| IGR-OV1 | F | 47 | Cystoadenocarcinoma | Can Res 45: 4970-4979, 1985 | N | |
| OVCAR-3 | F | 60 | Adenocarcinoma | Can Res 43: 5379-5389, 1983 | Y | Ascites |
| OVCAR-4 | F | 42 | Adenocarcinoma | Sem Oncol 11: 285-298, 1984 | Y | |
| OVCAR-5 | F | 67 | Adenocarcinoma | Sem Oncol 11: 285-298, 1984 | N | |
| SK-OV-3 | F | 64 | Adenocarcinoma | Human Tumor Cells In Vitro, pp. 115-159, 1975 | Y | Ascites |

| NCI ANTI-CANCER CELL LINE PANEL ||||||||
| Cell Line | Sex | Age | Histology | Comment | Treatment | Source |
| --- | --- | --- | --- | --- | --- | --- |
| PROSTATE |||||||
| DU-145 | M | 69 | Carcinoma | Int J Cancer 21: 274-281, 1978 | Y | |
| PC-3 | M | 62 | Adenocarcinoma | Invest Urol 17: 16-23, 1979 | Y | Metastasis |
| RENAL |||||||
| 786-O | M | 58 | Adenocarcinoma | In Vitro 12: 623-627, 1976 | N | |
| A498 | F | 52 | Adenocarcinoma | JNCI 51: 1417-1423, 1973 | | |
| ACHN | M | 22 | Renal Cell Carcinoma | Can Res 42: 4948-4953, 1982 | Y | Pleural Effusion |
| CAK-1 | M | 49 | Clear Cell Carcinoma | Human Tumor Cells In Vitro, pp. 115-159, 1975 | Y | Metastasis |
| RXF 393* | M | 54 | Poorly Differentiated Hypernephroma | Contrib Oncol 42, 1992 | N | *available only to DTP |
| SN12C | M | 43 | Carcinoma | Can Res 46: 4109-4115, 1986 | | |
| TK-10 | M | 43 | Spindle Cell Carcinoma | Can Res 47: 3856-3862, 1987 | N | |
| UO-31 | | | Carcinoma | | N | |

FIGURE 10
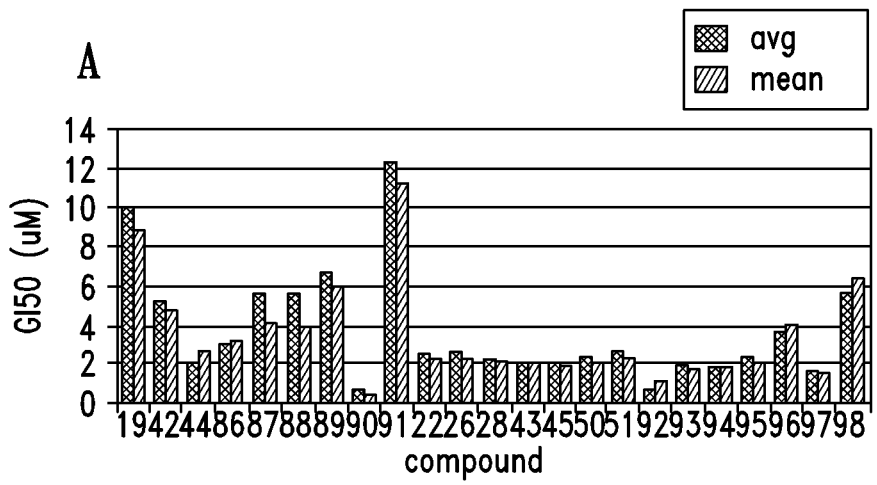
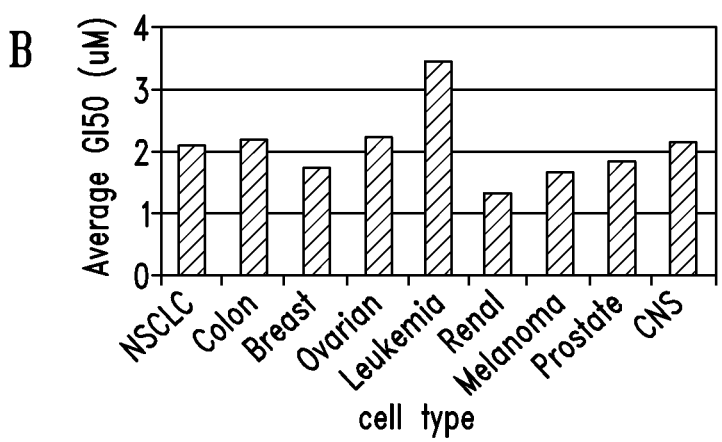
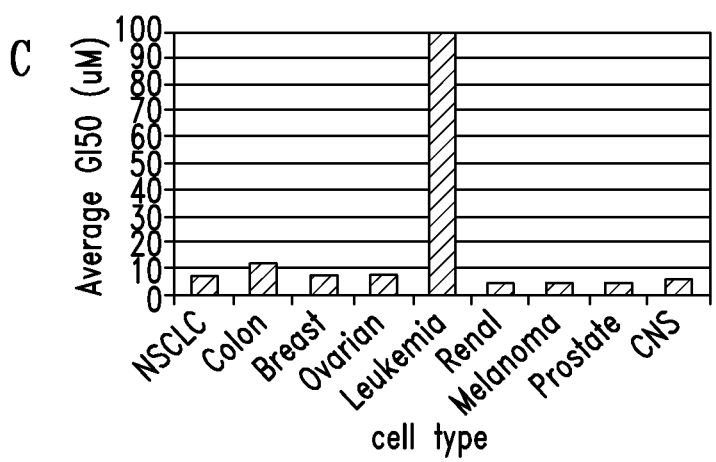

FIGURE 11
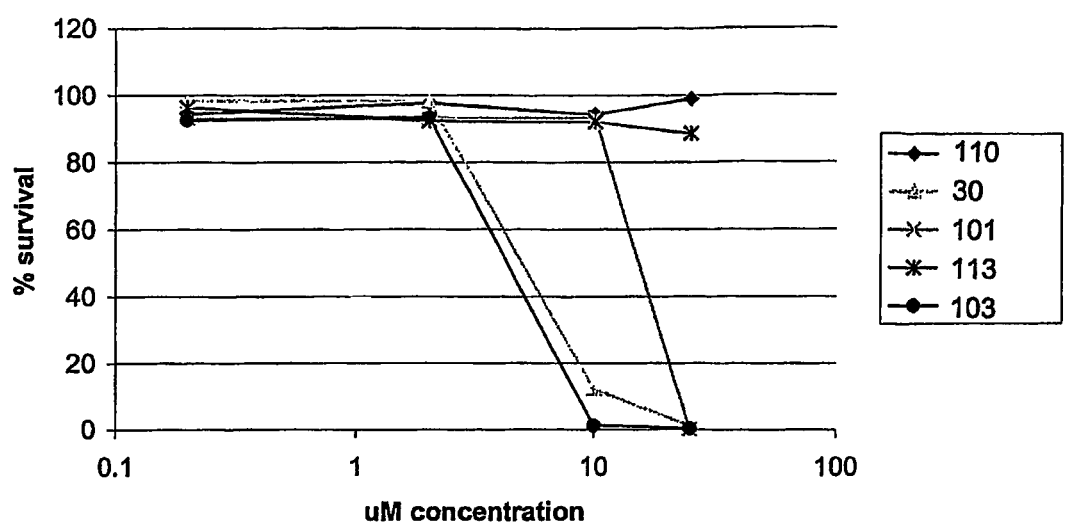
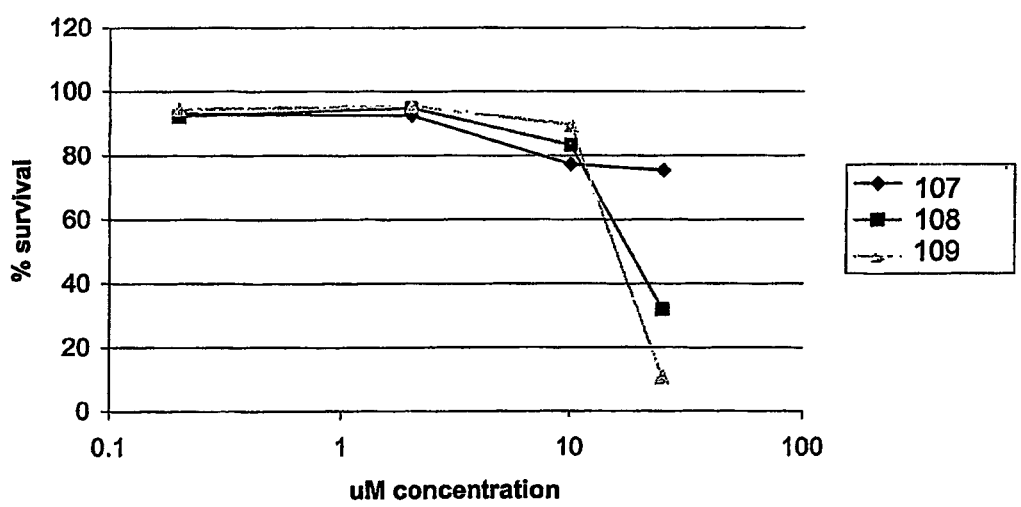

FIGURE 12
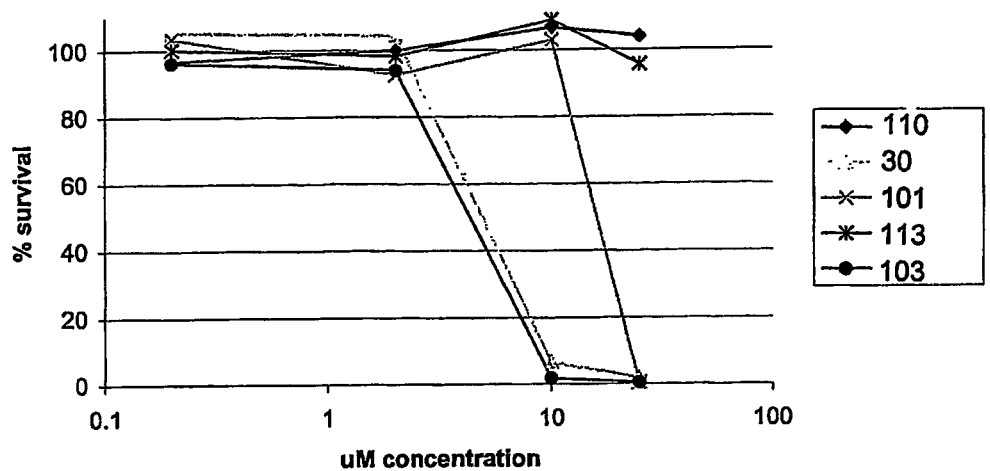
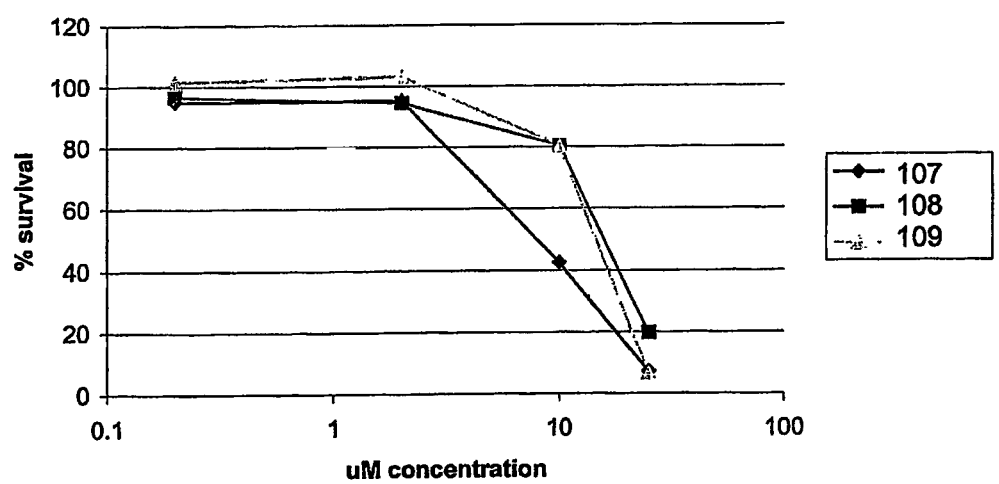

FIGURE 13
A.
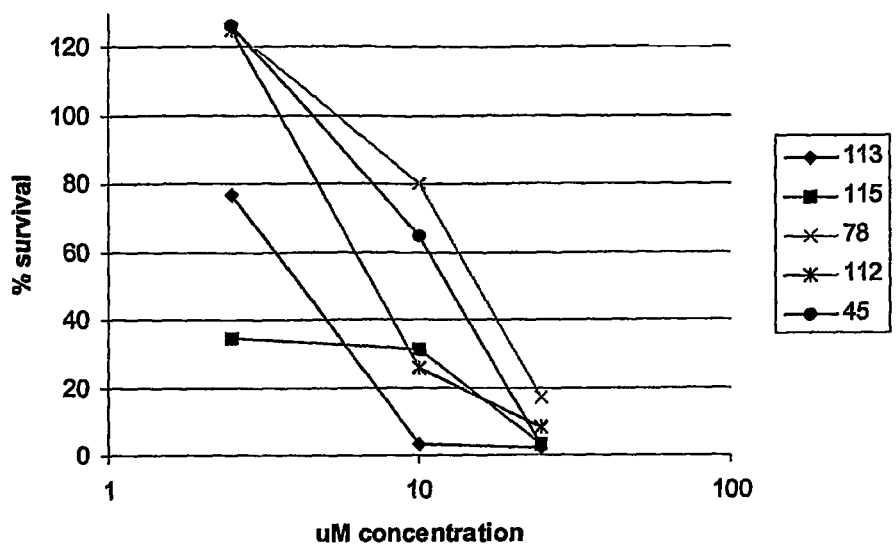
B.
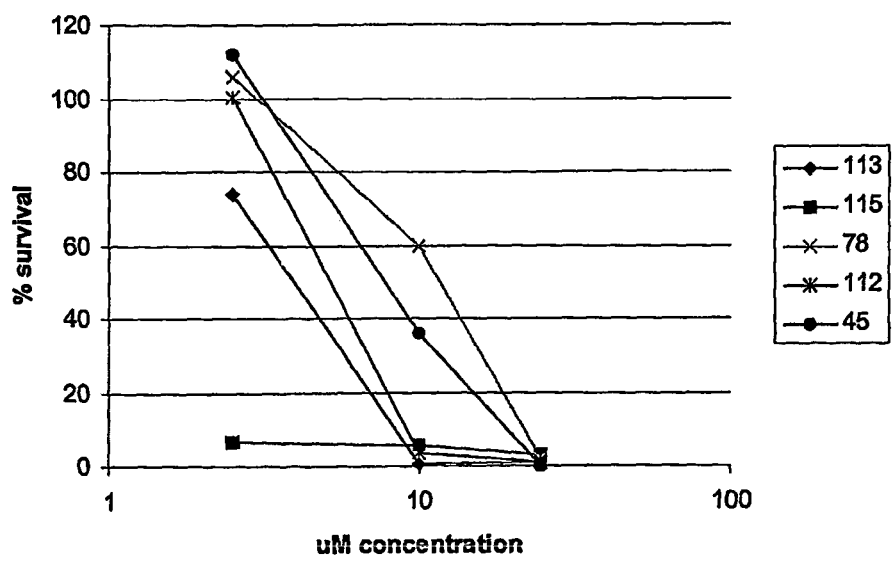

FIGURE 18
A.
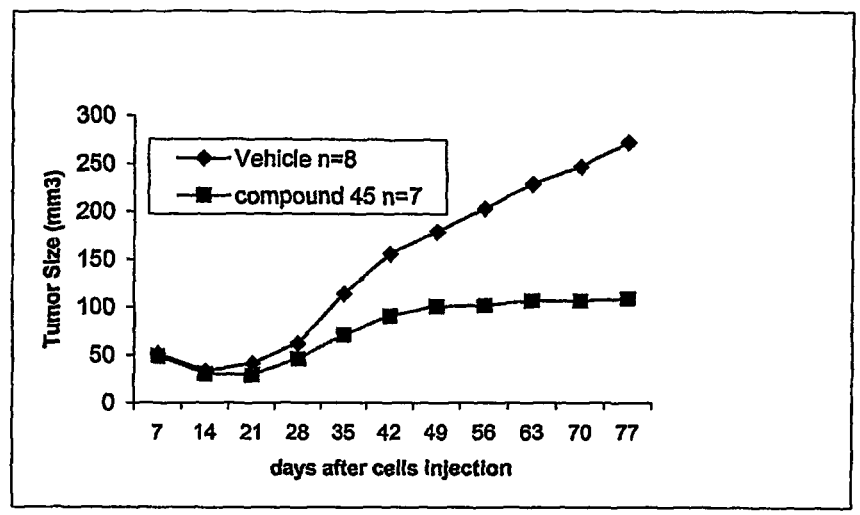
B.
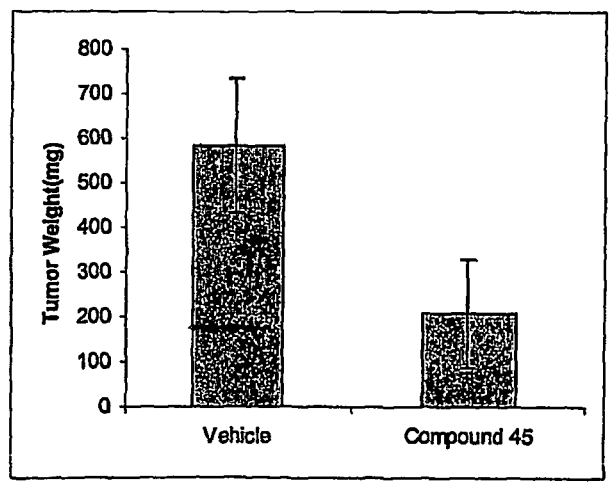

FIGURE 22
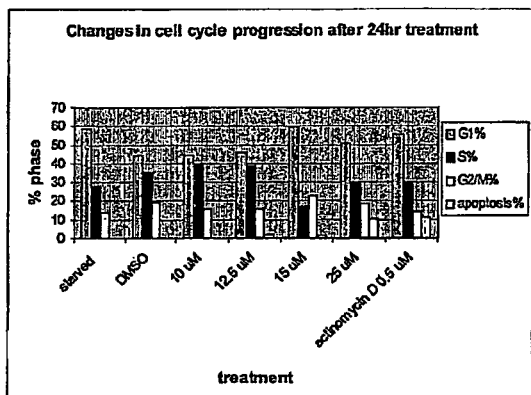
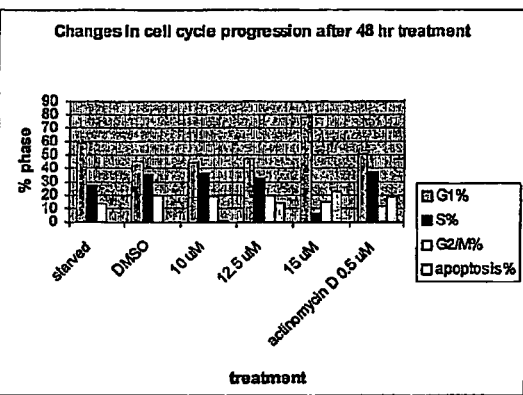

ARYL IMIDAZOLES AND THEIR USE AS ANTI-CANCER AGENTS

CROSS REFERENCE TO RELATED APPLICATIONS

The present application claims priority to U.S. Provisional Patent Applications No. 60/520,279, filed Nov. 14, 2003 and No. 60/599,509 filed Aug. 6, 2004, which applications are incorporated herein fully by this reference.

FIELD OF INVENTION

This invention pertains to the field of anti-cancer compounds and, in particular, to the use of therapeutically active 2,4,5-trisubstituted imidazole compounds in the treatment of cancer.

BACKGROUND OF THE INVENTION

A cancer is a malignant tumour of potentially unlimited growth. It is primarily the pathogenic replication (a loss of normal regulatory control) of various given types of cells found in the human body. By select mutation resulting from a primary lesion, the DNA of a cancer cell evolves and converts the cell into an autonomous system. Conventional cancer treatments have focused mainly on killing cancerous cells. Chemotherapeutic agents currently used for anti-cancer/anti-tumour therapy are selected for their toxicity towards rapidly proliferating cells. Most of them cause undesirable systemic effects such as cardiac or renal toxicity, marrow aplasia, alopecia, nausea and vomiting. During the last few years, many researchers have tried to eliminate these side effects by developing drugs having suitable physico-chemical properties allowing an increase of the availability of the drug to the tumour site. New molecules extracted from natural sources, synthetically or semi-synthetically produced, enzymes, radioisotopes, DNA toxins, various macromolecules, and antibodies against fibrin or against tumour-specific surface antigens are bound to drugs in an attempt to increase selectivity of the chemotherapeutic agents.

The effectiveness of most anticancer agents is greatly reduced because of their high toxicity and the nature of the illness. It is believed that the problem of high toxicity of the anticancer agents can be circumvented by chemical modifications of those structures in such a way that they act more specifically on tumour cells without increasing systemic toxicity. The research in this field is therefore mainly directed to the synthesis of anticancer agents which would possess high antineoplastic activity, low systemic toxicity and low mutagenicity on normal cells.

Heterocyclic compounds, especially heterocyclic azole derivatives, have been shown to have a wide spectrum of biological activities. One class of compounds with interesting biological activities is the imidazoles (derivatives containing a five-membered heterocyclic azole). A variety of biological activities have been reported for imidazole derivatives with different substitution patterns (Lee et al. *Nature* 1994 327: 739-745; Abdel-Meguid et al. *Biochemistry,* 1994, 33:11671; Heerding et al. *Bioorg. Med. Chem. Lett.* 2001, 11:2061-2065; Bu et al. *Tetrahedron Lett.* 1996, 37:7331-7334; Lewis J R. *Nat. Prod. Rep.* 1999, 16:389-418; Lewis J R. *Nat. Prod. Rep.* 1998, 15:417-437 and 371-395).

Biological activities have also been reported for aryl-imidazole derivatives, for example, these compounds can act as modulators of multi-drug resistance in cancer cells (Zhang et al. *Bioorg. Med. Chem. Lett.* 2000, 10:2603-2605), inhibitors of p38 MAP kinase (Adams et al. *Bioorg. Med. Chem. Lett.* 2001, 11:867-2870, McLay et. al. *Bioorg. Med. Chem.* 2001, 9:537-554) and of cytokines (U.S. Pat. Nos. 5,656,644; 5,686, 455; 5,916,891; 5,945,418; and 6,268,370), and inhibitors of bacterial growth (Antolini et al. *Bioorg. Med. Chem. Lett.* 1999, 9:1023-1028).

A few reports have indicated that triaryl-imidazole compounds can act as inhibitors of p38 MAP kinase (for example, see LoGrasso et al. *Biochemistry.* 1997, 36:10422-10427) and as modulators of multi-drug resistance in cancer cells (Sarshar et al. *Bioorg. Med. Chem. Lett.* 2000, 10:2599-2601), however, the majority of the literature indicates that these compounds have found use mainly as colour producing reagents (U.S. Pat. Nos. 4,089,747; 5,024,935; 5,047,318; 5,496,702; 5,514,550; and 5,693,589) and as photopolymerization initiators (U.S. Pat. Nos. 6,117,609 and 6,060,216), generally in dimeric form.

The potential anticancer activity of a number of compounds has been investigated by the National Cancer Institute (NC), which has undertaken a large scale screening of several thousand compounds to try to identify those that have potential therapeutic application in the treatment of cancer (NCI Yeast Anticancer Drug Screen). The screen is based on the ability of candidate compounds to inhibit the growth of *Saccharomyces cerevisiae* strains that have mutations in genes related to cell cycle control and DNA repair damage. Compounds are initially screened against a panel of six yeast strains at a single concentration (Stage0). Compounds with activity in Stage0 are re-screened against the same panel at two concentrations (Stage1). Selected compounds with activity in Stage1 that also show selectivity are re-screened against a panel of 13 yeast strains at five concentrations (Stage2). Many of the results from the screening have been made available on the NCI/DTP website. The approach adopted in this screen is dependent on a candidate compound exerting its activity on certain cellular pathways (i.e. cell cycle control or DNA repair damage). The results generated by this type of screen, therefore, represent a very preliminary stage of screening for potential anti-cancer drugs and do not necessarily correlate with the ability of a compound to inhibit the growth of cancer cells in vitro or in vivo.

The NCI also provides an in vivo screening program to try to identify potential anti-cancer drugs (NCI In Vivo Anticancer Drug Screen). Many of the results from this screening program are also available from the NCI/DTP website.

Amongst those compounds tested in one or both of the NCI screens are some aryl imidazole compounds (NCI #322334, 338970, 144033). None of these three compounds showed any activity in the In Vivo Anticancer Drug Screen, even though one of these compounds (NCI #338970) had been reported as active in Stage0 testing in the Yeast Anticancer Drug Screen. The fact that this compound was active in the yeast screen yet showed no activity in the in vivo assay confirms that a positive result in the yeast screen is not necessarily predictive of the utility of a compound as in anti-cancer therapeutic.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

It is an object of the present invention to provide a class of compounds which are 2,4,5-trisubstituted imidazole derivatives that have anti-cancer activity. In accordance with an aspect of the present invention there is provided a use of a compound having structural formula (I), or a salt thereof, as an anti-cancer agent:

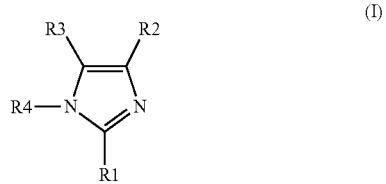

(I)

wherein:

R1 is aryl, substituted aryl, heterocycle, substituted heterocycle, heteroaryl, substituted heteroaryl or amino;

R2 and R3 are independently aryl, substituted aryl, heterocycle, heteroaryl, substituted heterocycle, or substituted heteroaryl or R2 and R3 when taken together along with the carbon atoms they are attached to, form aryl or substituted aryl, heterocycle, substituted heterocycle, heteroaryl, or substituted heteroaryl and R4 is hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, substituted alkylthiol, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano, —S(O)$_{0-2}$R wherein R is alkyl, substituted alkyl, aryl, substituted aryl, heterocycle, heteroaryl, substituted heterocycle, or substituted heteroaryl.

In accordance with another aspect of the present invention, there is provided a use of a compound having structural formula (I), or a salt thereof in the preparation of an anti-cancer composition.

In accordance with another aspect of the present invention, there is provided a compound having the structural formula:

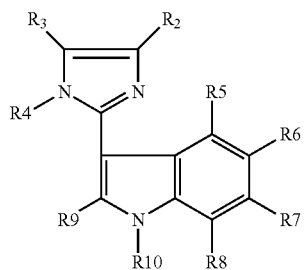

II or a salt thereof, wherein:

R2 and R3 are independently aryl, substituted aryl, heterocycle, heteroaryl, substituted heterocycle, or substituted heteroaryl or R2 and R3 when taken together along with the carbon atoms they are attached form aryl or substituted aryl, heterocycle, heteroaryl, substituted heterocycle, or substituted heteroaryl;

R4, R5, R6, R7, R8 and R9 are independently selected from hydrogen, halogen, hydroxyl, thiol, lower alkyl, substituted lower alkyl, lower alkenyl, substituted lower alkenyl lower alkynyl, substituted lower alkynyl, alkylalkenyl, alkyl alkynyl alkoxy, alkylthio, acyl, aryloxy, amino, amido, carboxyl, aryl, substituted aryl, heterocycle, heteroaryl, substituted heterocycle, heteroalkyl cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl;

R10 is H, alkyl, substituted alkyl, alkenyl, substituted alkenyl, alkynyl, substituted alkynyl, aryl, substituted aryl heteroaryl, substituted heteroaryl, acyl, —CH$_2$-aryl, —CH$_2$-heteroaryl.

In accordance with another aspect of the present invention, there is provided a compound having the structural formula:

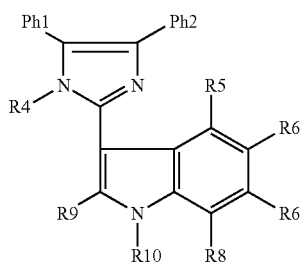

III or a salt thereon wherein:

Ph1 and Ph2 are independently selected from phenyl and substituted phenyl;

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl substituted aryl, heterocycle, heteroaryl, substituted heterocycle, or substituted heteroaryl; R10 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, —CH$_2$-heteroaryl.

In accordance with another aspect of the present invention; there is provided a compound having the structural formula.

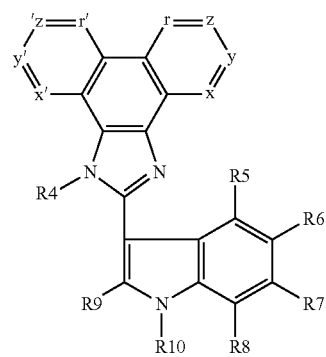

VI or a salt thereof wherein:

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano or —S(O)$_{0-2}$R wherein R is alkyl, substituted alkyl, aryl, substituted aryl, heterocycle, heteroaryl, substituted heterocycle, or substituted heteroaryl; R10 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, —CH$_2$-heteroaryl;
x is CR11 or N;
y is CR12 or N;
z is CR13 or N;
r is CR14 or N;
x' is CR15 or N;
y' is CR16 or N;
z' is CR17 or N;
r' is CR18 or N;
R11, R12, R13, R14, R15, R16, R17 and R18 are independently selected from hydrogen, halogen, hydroxyl, thiol, lower alkyl, substituted lower alkyl, alkenyl, alkenyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In accordance with another aspect of the present invention, there is provided a compound having the structural formula:

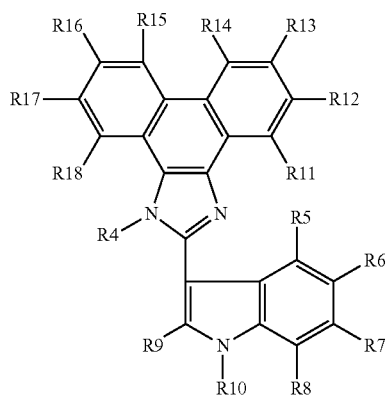

VII or a salt thereof, wherein:
R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl alkoxy, alkylthio, acyl, aryloxy, amino, amido, carboxyl, aryl, substituted aryl, heterocycle, heteroaryl, substituted heterocycle, heteroalkyl cycloalkyl substituted cycloalkyl, alkylcycloalkyl, alkylcycloheteroalkyl, nitro, cyano or —S(O)$_{0-2}$R wherein R is alkyl, substituted alkyl aryl, substituted aryl heterocycle, heteroaryl, substituted heterocycle, or substituted heteroaryl;
R10 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, —CH$_2$-heteroaryl;
R11, R12, R13, R14, R15, R16, R17 and R18 are independently selected from hydrogen, halogen, hydroxyl, thiol, lower alkyl, substituted lower alkyl, alkenyl, alkenyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl cycloalkyl, substituted cycloalkyl, alkylcycloalkyl, alkylcycloheteroalkyl, nitro, or cyano.

In accordance with another embodiment of the present invention, there is provided a use of a therapeutically effective amount of a compound of formula I:

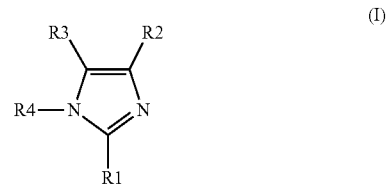

(I)

wherein:
R1 is aryl, substituted aryl, heterocycle, substituted heterocycle, heteroaryl, substituted heteroaryl or amino;
R2 and R3 are independently aryl, substituted aryl, heterocycle, heteroaryl, substituted heterocycle, or substituted heteroaryl or R2 and R3 when taken together along with the carbon atoms they are attached to, form aryl or substituted aryl, and
R4 is hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl,
to inhibit neoplastic cell growth or proliferation in a mammal.

In accordance with another embodiment of the present invention, there is provided a use of a therapeutically effective amount of a compound of formula I:

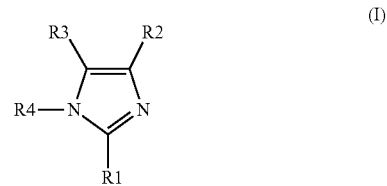

(I)

wherein:
R1 is aryl, substituted aryl, heterocycle, substituted heterocycle, heteroaryl, substituted heteroaryl or amino;
R2 and R3 are independently aryl, substituted aryl, heterocycle, heteroaryl, substituted heterocycle, or substituted heteroaryl or R2 and R3 when taken together along with the carbon atoms they are attached to, form aryl or substituted aryl, and
R4 is hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, ammo, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl,
in the treatment of cancer in a mammal in need thereof.

In accordance with another embodiment of the present invention, there is provided a compound selected from the compounds of structural formulae:

VIII

IX

X wherein:

R2 and R3 are independently aryl, substituted aryl, heterocycle, heteroaryl, substituted heterocycle, or substituted heteroaryl or R2 and R3 when taken together along with the carbon atoms they are attached to, form a aryl, substituted aryl, heterocycle, heteroaryl, substituted heterocycle, or substituted heteroaryl;

R4, R5, R6, R7, R8 and R9 are independently selected from hydrogen, halogen, hydroxyl thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, ammo, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl substituted aryl, heterocycle, heteroaryl, substituted heterocycle, or substituted heteroaryl.

In accordance with another embodiment of the present invention, there is provided a compound selected from the compounds of structural formulae:

XI

XII

XIII or a salt thereof, wherein:

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl;

x is CR11 or N;
y is CR12 or N;
z is CR13 or N;
r is CR14 or N;
x' is CR15 or N;
y' is CR16 or N;
z' is CR17 or N;
r' is CR18 or N;
R11, R12, R13, R14, R15, R16, R17 and R18' are independently selected from hydrogen, halogen, hydroxyl, thiol, lower alkyl, substituted lower alkyl, lower alkenyl substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl alkylcycloalkyl, alkylcycloheteroalkyl, nitro, or cyano.

In accordance with another embodiment of the present invention, there is provided a use of a compound of formula (I) in the manufacture of a medicament for the inhibition of neoplastic cell growth or proliferation.

In accordance with another embodiment of the present invention, there is provided a use of a compound of formula (I) in the manufacture of a medicament for the treatment of cancer.

In accordance with another aspect of the present invention, there is provided an anti-cancer composition comprising an effective amount of a compound having structural formula (I), or a salt thereof, and a carrier, diluent or excipient.

In accordance with another aspect of the present invention there is provided a method of inhibiting neoplastic cell growth or proliferation in a mammal comprising administering to said mammal a therapeutically effective amount of a compound selected from the compounds of general formula (I), (II), (III), (IV), (V), (VI), (VII), (VII), (IX), (X), (XI), (XII), and (XIII), or a salt thereof.

In accordance with another aspect of the present invention there is provided a method of treating cancer in a mammal comprising administering to said mammal a therapeutically effective amount of a compound selected from the compounds of general formula (I), (II), (III), (IV), (V), (VI), (VII), (VIII), (IX), (X), (XI), (XII) and (XIII), or a salt thereof.

BRIEF DESCRIPTION OF THE FIGURES

FIG. 5A-C depicts the effects of various concentrations of a compound 45 on the proliferation of cancer cell lines in vitro at different time intervals.

FIG. 6A-C depicts the effects of various concentrations of a compound 45 on the proliferation of cancer cell lines in vitro at different time intervals.

FIG. 9A-C present the cancer cell lines used to in the NCI screen used to determine the ability of compounds of Formula I to inhibit cancer cell proliferation in vitro.

FIG. 10A depicts the average and mean $GI_{50}$ values for various compounds of Formula I for a number of cancer cell lines; B depicts the average $GI_{50}$ values for compound 45 by cancer cell type and C depicts the average total growth inhibition (TGI) for compound 45 by cancer cell type.

FIG. 11 depicts the inhibition of H460 NSCLC cell proliferation in vitro by compounds of Formula I.

FIG. 12 depicts the inhibition of HT-29 colon carcinoma cell proliferation in vitro by compounds of Formula I.

FIG. 13 depicts the inhibition of HT-29 colon carcinoma cell proliferation in vitro by compounds of Formula I.

FIG. 18 depicts the effect of compound 45 on the growth of HepG2 hepatocarcinoma cells in vivo in CD-1 nude mice in terms of A tumour size, and B tumour weight.

FIG. 22 depicts the effects of compound 45 on the cell cycle in HT-29 colon adenocarcinoma cells.

DETAILED DESCRIPTION OF THE INVENTION

Figure 1:
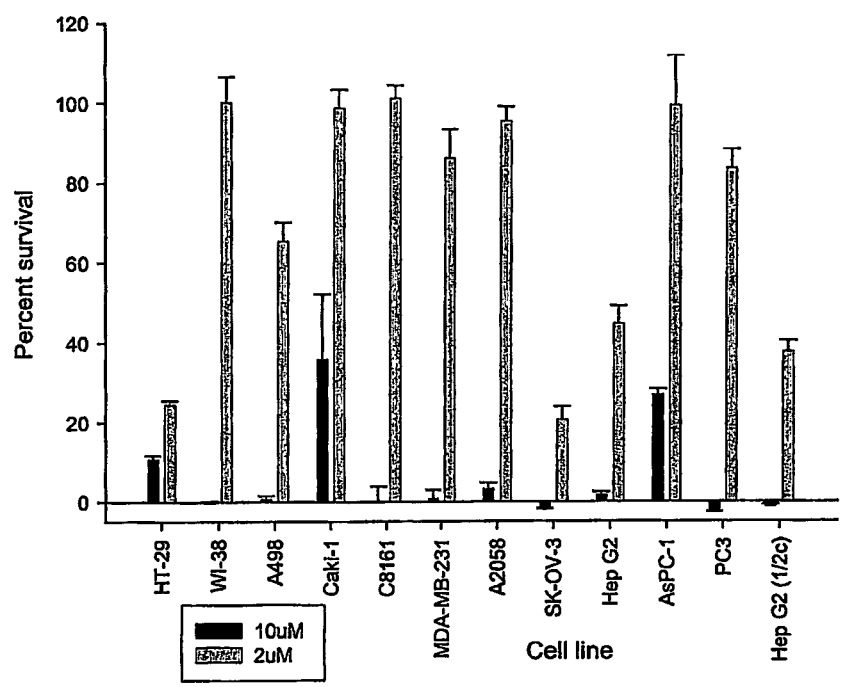
FIG. 1 depicts the effects of a compound 92 on the proliferation of various cancer cell lines in vitro.

The present invention provides a class of 2,4,5-trisubstituted imidazole compounds and for their use as anti-cancer agents. The present invention further provides for methods of inhibiting neoplastic cell growth and/or proliferation in an animal by administering to the animal an effective amount of a compound of Formula I, either alone or in combination with one or more standard chemotherapeutics.

DEFINITIONS

Unless defined otherwise, all technical and scientific terms used herein have the same meaning as commonly understood by one of ordinary skill in the art to which this invention pertains.

The terms are defined as follows:

The term "halogen" refers to fluorine, bromine, chlorine, and iodine atoms.

The term "hydroxyl" refers to the group —OH.

The term "thiol" or "mercapto" refers to the group —SH, and —$S(O)_{0-2}$.

The term "lower alkyl" refers to a straight chain or branched alkyl group of one to ten carbon atoms or a cyclic alkyl group of three to ten carbon atoms. This term is further exemplified by such groups as methyl, ethyl, n-propyl, i-propyl, n-butyl, t-butyl, 1-butyl (or 2-methylpropyl), cyclopropylmethyl, i-amyl, n-amyl, hexyl and the like.

The term "substituted lower alkyl" refers to lower alkyl as just described including one or more groups such as hydroxyl, thiol, alkylthiol, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, nitro, cyano. These groups may be attached to any carbon atom of the lower alkyl moiety.

The term "lower alkenyl" refers to a straight chain or branched hydrocarbon of two to ten carbon atoms or a cyclic hydrocarbon of three to ten carbon atoms, having at least one carbon to carbon double bond.

The term "substituted lower alkenyl" refers to lower alkenyl as just described including one or more groups such as hydroxyl, thiol, alkylthiol, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl aralkyl, heteroaralkyl, alkyl, alkenyl, alkynyl, alkyl alkenyl, alkyl alkynyl, alkyl cycloalkyl, alkyl cycloheteroalkyl nitro, cyano. These groups may be attached to any carbon atom to produce a stable compound.

The term "lower alkynyl" refers to a straight chain or branched hydrocarbon of two to ten carbon atoms having at least one carbon to carbon triple bond.

The term "substituted lower alkynyl" refers to lower alkynyl as just described including one or more groups such as hydroxyl, thiol, alkylthiol, halogen, alkoxy, amino, amido, carboxyl, cycloalkyl, substituted cycloalkyl, heterocycle, cycloheteroalkyl, substituted cycloheteroalkyl acyl, carboxyl aryl substituted aryl, aryloxy, hetaryl, substituted hetaryl, aralkyl, heteroaralkyl; alkyl, alkenyl, alkynyl, alkyl alkenyl, alkyl alkynyl, alkyl cycloalkyl, alkyl cycloheteroalkyl, nitro, cyano. These groups may be attached to any carbon atom to produce a stable compound.

The term "alkoxy" refers to the group —OR, where R is lower alkyl, substituted lower alkyl acyl, aryl, substituted aryl aralkyl substituted aralkyl, heteroalkyl heteroarylalkyl, cycloalkyl, substituted cycloalkyl, cycloheteroalkyl, or substituted cycloheteroalkyl as defined below.

The term "alkylthio" denotes the group —SR, —S(O)$_{n=1-2}$—R, where R is lower alkyl, substituted lower alkyl, aryl, substituted aryl aralkyl or substituted aralkyl as defined below.

The term "acyl" refers to groups —C(O)R, where R is hydrogen, lower alkyl substituted lower alkyl, aryl, substituted aryl, cycloalkyl or substituted cycloalkyl.

The term "aryloxy" refers to groups —OAr, where Ar is an aryl, substituted aryl, heteroaryl, or substituted heteroaryl group as defined below.

The term "amino" refers to the group NRR', where R and R' may independently be hydrogen, lower alkyl, substituted lower alkyl, aryl, substituted aryl, heteroaryl, cycloalkyl, or substituted heteroaryl as defined below, acyl, D or L amino acid or a protected form thereof.

The term "amido" refers to the group —C(O)NRR', where R and R' may independently be hydrogen, lower alkyl, substituted lower alkyl, aryl, substituted aryl, hetaryl, substituted hetaryl as defined below.

The term "carboxy" refers to the group —C(O)OR, where R may independently be hydrogen, lower alkyl, substituted lower alkyl aryl, substituted aryl, hetaryl, substituted hetaryl and the like as defined.

The terms "aryl" or "Ar" refer to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, phenanthryl, 9-fluorenyl, dibenzocycloheptatrienyl etc.).

The term "substituted aryl" refers to aryl optionally substituted with one or more functional groups, e.g., halogen, hydroxyl, thiol, lower, alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl aryloxy, amino, amido, carboxyl, aryl, substituted aryl, heterocycle, substituted heterocycle, heteroaryl, substituted heteroaryl heteroalkyl, substituted heteroalkyl, cycloalkyl, substituted cycloalkyl, alkylcycloalkyl, alkylcycloheteroalkyl, nitro, sulfamido, cyano or —N=CRR', wherein R and R' are independently selected from H, alkyl substituted alkyl, aryl, substituted aryl, heterocycle, substituted heterocycle, heteroaryl or substituted heteroaryl.

The term "heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl, indanyl or benzo[b]thienyl) and having at least one hetero atom, such as N, O or S, within the ring.

The term "substituted heterocycle" refers to heterocycle optionally substituted with, halogen, hydroxyl, thiol, lower alkyl, substituted lower alkyl, trifluoromethyl lower alkenyl, substituted lower alkenyl, lower alkyl, substituted lower alkynyl, alkylalkenyl, alkyl alkynyl, alkoxy, alkylthio, acyl, aryloxy, amino, amido, carboxyl, aryl, substituted aryl, heterocycle, substituted heterocycle, heteroaryl, substituted heteroaryl, heteroalkyl, substituted heteroalkyl, cycloalkyl, substituted cycloalkyl, alkylcycloalkyl, alkylcycloheteroalkyl, nitro, sulfamido or cyano and the like.

The terms "heteroaryl" or "hetaryl" refer to a heterocycle in which at least one heterocyclic ring is aromatic.

The term "substituted heteroaryl" refers to a heterocycle optionally mono or poly substituted with one or more functional groups, e.g., halogen, hydroxyl, thiol, lower alkyl, substituted lower alkyl, trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, substituted heterocycle, heteroaryl, substituted heteroaryl, heteroalkyl, substituted heteroalkyl, cycloalkyl, substituted cycloalkyl, alkylcycloalkyl, alkylcycloheteroalkyl, nitro, sulfamido, cyano or —N=CRR', wherein R and R' are independently selected from H, alkyl, substituted alkyl, aryl, substituted aryl, heterocycle, substituted heterocycle, heteroaryl or substituted heteroaryl and the like.

The term "aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkyl thio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "heteroalkyl" refers to the group —R-Het where Het is a heterocycle group and R is a lower alkyl group. Heteroalkyl groups can optionally be unsubstituted or substituted with e.g., halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "heteroarylalkyl" refers to the group —R-HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, aryl, aryloxy, heterocycle, hetaryl, substituted hetaryl, nitro, cyano, alkylthio, thiol, sulfamido and the like.

The term "cycloalkyl" refers to a cyclic or polycyclic alkyl group containing 3 to 15 carbon. For polycyclic groups, these may be multiple condensed rings in which one of the distal rings may be aromatic (e.g. tetrahydronaphthalene, etc.).

The term "substituted cycloalkyl" refers to a cycloalkyl group comprising one or more substituents with, e.g. halogen, hydroxyl, thiol, lower alkyl, substituted lower alkyl trifluoromethyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl cycloalkyl, substituted cycloalkyl, alkylcycloalkyl, alkylcycloheteroalkyl nitro, sulfamido or cyano and the like.

The term "cycloheteroalkyl" refers to a cycloalkyl group wherein one or more of the ring carbon atoms is replaced with a heteroatom (e.g., N, O, S or P).

The term "substituted cycloheteroalkyl" refers to a cycloheteroalkyl group as herein defined which contains one or more substituents, such as halogen, lower alkyl, lower alkoxy, lower alkylthio, trifluoromethyl, amino, amido, carboxyl, hydroxyl, aryl, aryloxy, heterocycle, hetaryl, substituted hetaryl, nitro, cyano, alkylthio, thiol, sulfamido and the like.

The term "alkyl cycloalkyl" refers to the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, lower alkylthio, trifluoromethyl, amino, amido, carboxyl, hydroxyl, aryl, aryloxy, heterocycle, hetaryl substituted hetaryl, nitro, cyano, alkylthio, thiol, sulfamido and the like.

The terms "therapy" and "treatment," as used interchangeably herein, refer to an intervention performed with the intention of alleviating the symptoms associated with, preventing the development of, or altering the pathology of a disease, disorder or condition. Thus, the terms therapy and treatment are used in the broadest sense, and include the prevention (prophylaxis), moderation, reduction, and curing of a disease, disorder or condition at various stages. Those in need of therapy/treatment include those already having the disease, disorder or condition as well as those prone to, or at risk of developing, the disease, disorder or condition and those in whom the disease, disorder or condition is to be prevented.

The term "subject" or "patient," as used herein, refers to an animal in need of treatment.

The term "animal," as used herein, refers to both human and non-human animals, including, but not limited to, mammals, birds and fish.

Administration of the compounds of the invention "in combination with" one or more further therapeutic agents, is intended to include simultaneous (concurrent) administration and consecutive administration. Consecutive administration is intended to encompass various orders of administration of the therapeutic agent(s) and the compound(s) of the invention to the subject.

As used herein, the term "about" refers to a +/−10% variation from the nominal value. It is to be understood that such a variation is always included in any given value provided herein, whether or not it is specifically referred to.

I. 2,4,5-Trisubstituted Imidazole Compounds

The present invention provides compounds of the general formula (I):

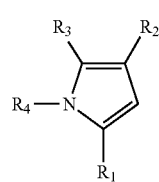

(I)

or a salt thereof wherein:

R1 is aryl, substituted aryl, heterocycle, substituted heterocycle, heteroaryl, substituted heteroaryl or amino;

R2 and R3 are independently aryl, substituted aryl, heterocycle, heteroaryl, substituted heterocycle, or substituted heteroaryl or R2 and R3 when taken together along with the carbon atoms they are attached to, form aryl or substituted aryl, heterocycle, substituted heterocycle, heteroaryl, or substituted heteroaryl;

R4 is hydrogen, halogen, hydroxyl, thiol, lower alkyl, substituted lower alkyl, lower alkenyl, substituted lower alkenyl, lower alkynyl, substituted lower alkynyl alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl.

In another embodiment of the present invention, the compound of formula (I) is other than Nortopsentin A, Nortopsentin B, Nortopsentin C and Nortopsentin D.

In another embodiment of the present invention, the compound of Formula I includes the compound of the structural formula:

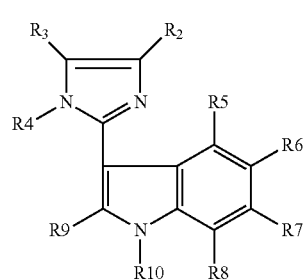

II or a salt thereof, wherein:

R2 and R3 are independently aryl, substituted aryl, heterocycle, heteroaryl, substituted heterocycle, or substituted heteroaryl or R2 and R3 when taken together along with the carbon atoms they are attached form aryl or substituted aryl, heterocycle, heteroaryl, substituted heterocycle, or substituted heteroaryl;

R4, R5, R6, R7, R8 and R9 are independently selected from hydrogen, halogen, hydroxyl, thiol, lower alkyl, substituted lower alkyl, lower alkenyl, substituted lower alkenyl lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl;

R10 is H, alkyl, substituted alkyl, alkenyl, substituted alkenyl, alkynyl, substituted alkynyl, aryl, substituted aryl, heteroaryl, substituted heteroaryl, acyl, —CH$_2$-aryl, —CH$_2$-heteroaryl.

In another embodiment of the invention, the compound of Formula II is other than Nortopsentin A, Nortopsentin B, Nortopsentin C and Nortopsentin D.

In another embodiment of the present invention, the compound of Formula II includes the compound of the structural formula III:

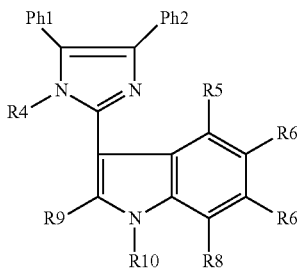

or a salt thereof, wherein:
Ph1 and Ph2 are independently selected from phenyl and substituted phenyl;
R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl substituted cycloalkyl, alkylcycloalkyl, alkylcycloheteroalkyl, nitro, cyano or —S(O)$_{0-2}$ wherein R is alkyl, substituted alkyl, aryl, substituted aryl, heterocycle, heteroaryl, substituted heterocycle, or substituted heteroaryl;
R10 is H, alkyl, substituted alkyl, alkenyl, substituted alkenyl, alkynyl, substituted alkynyl, aryl, substituted aryl, heteroaryl, substituted heteroaryl, acyl.

In another embodiment of the invention, the compound of Formula III is selected from:

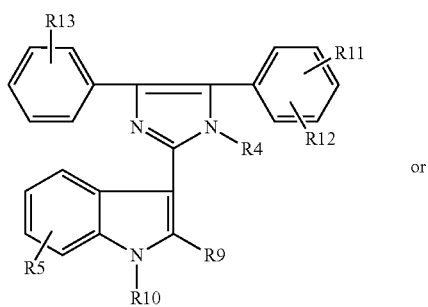

or

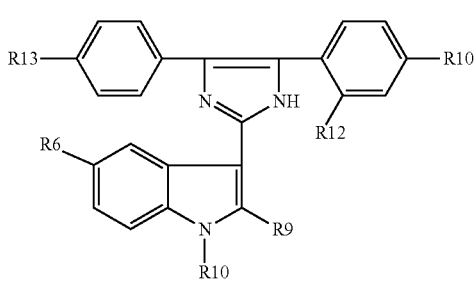

or a salt thereof, wherein:
R5, R6, R9, R11, R12 and R13 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, car-boxyl, aryl, substituted aryl, heterocycle, heteroaryl substituted heterocycle, heteroalkyl, cycloalkyl, substituted cycloalkyl, alkylcycloalkyl, alkylcycloheteroalkyl, nitro, or cyano;
R10 is H, alkyl, substituted alkyl, alkenyl, substituted alkenyl alkynyl, substituted alkynyl, aryl, substituted aryl, heteroaryl, substituted heteroaryl, acyl.

In another embodiment of the present invention, the compound of Formula I includes the compound of the structural formula:

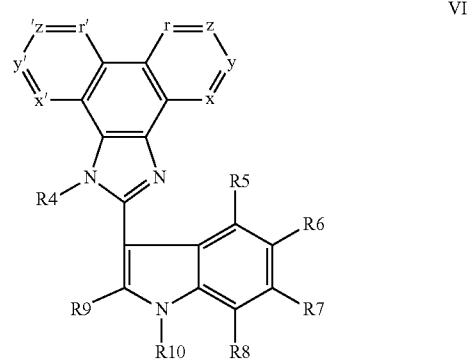

or a salt thereof, wherein:
R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl;
x is CR11 or N;
y is CR12 or N;
z is CR13 or N;
r is CR14 or N;
x' is CR15 or N;
y' is CR16 or N;
z' is CR17 or N;
r' is CR18 or N;
R10 is H, alkyl, substituted alkyl alkenyl, substituted alkenyl, alynyl, substituted alkynyl, aryl, substituted aryl, heteroaryl, substituted heteroaryl, acyl.
R11, R12, R13, R14, R15, R16, R17 and R18 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In another embodiment of the present invention, the compound of Formula I includes the compound of the structural formula:

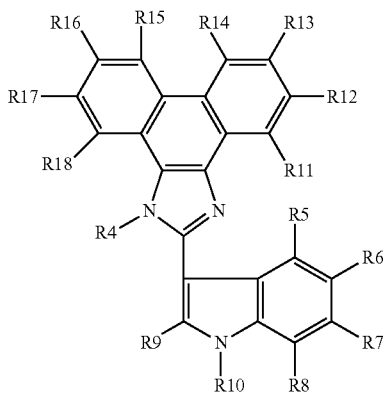

VII or a salt thereof, wherein:

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl alkylcycloheteroalkyl, nitro, or cyano or —S(O)$_{0-2}$R wherein R is alkyl substituted alkyl, aryl, substituted aryl, heterocycle, heteroaryl substituted heterocycle, or substituted heteroaryl;

R10 is H, alkyl, substituted alkyl alkenyl, substituted alkenyl, alkynyl, substituted alkynyl aryl, substituted aryl heteroaryl, substituted heteroaryl, acyl;

R11, R12, R13, R14, R15, R16, R17 and R18 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, or cyano.

In another embodiment of the present invention, the compound of Formula I includes the compound of the structural formula:

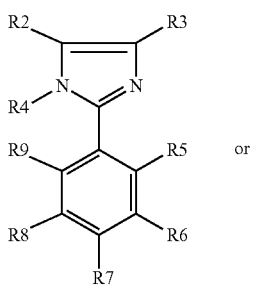

VIII or

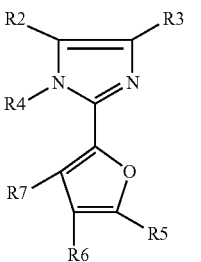

IX or

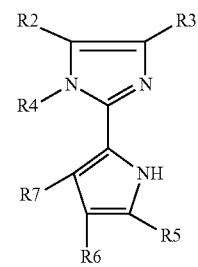

X wherein:

R2 and R3 are independently aryl, substituted aryl, heterocycle, heteroaryl, substituted heterocycle, or substituted heteroaryl or R2 and R3 when taken together along with the carbon atoms they are attached to, form a aryl, substituted aryl, heterocycle, heteroaryl, substituted heterocycle, or substituted heteroaryl;

R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl substituted heterocycle, or substituted heteroaryl.

In another embodiment of the present invention, the compound of Formula I includes the compound of the structural formula:

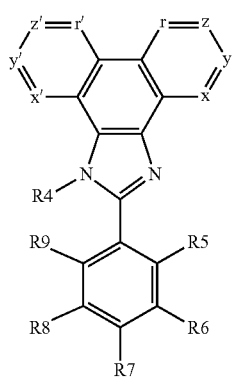

XI or

-continued

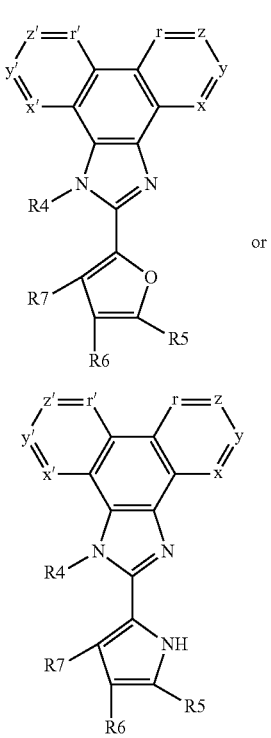

or a salt thereof, wherein:
R4, R5, R6, R7, R8 and R9 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl;
x is CR11 or N;
y is CR12 or N;
z is CR13 or N;
r is CR14 or N;
x' is CR15 or N;
y' is CR16 or N;
z' is CR17 or N;
r' is CR18 or N;
R11, R12, R13, R14, R15, R16, R17 and R18 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl alkoxy, alkylthio, acyl, aryloxy, amino, amido, carboxyl, aryl, substituted aryl heterocycle, heteroaryl, substituted heterocycle, heteroalkyl, cycloalkyl, substituted cycloalkyl, alkylcycloalkyl, alkylcycloheteroalkyl, nitro, or cyano.

In another embodiment, in the compounds of formula (XI) at least one of R11 to R18 is other than H.

In another embodiment, in the compounds of formula (XI) at least one of x, y, z, r, x', y', z' or r' is nitrogen.

In another embodiment the compound of formula (XI) is other than:

2-phenyl-1H-phenanthro[9,10-d]imidazole;
2-(2-methylphenyl)-1H-phenanthro[9,10-d]imidazole;
2-(3-iodophenyl)-1H-phenanthro[9,10-d]imidazole;
2-(4-dimethylaminophenyl)-1H-phenanthro[9,10-d]imidazole;
2-(4-nitrophenyl)-1H-phenanthro[9,10-d]imidazole;
1,2-diphenyl-1H-phenanthro[9,10-d]imidazole.

In another embodiment of the invention, the compound of Formula I is selected from:

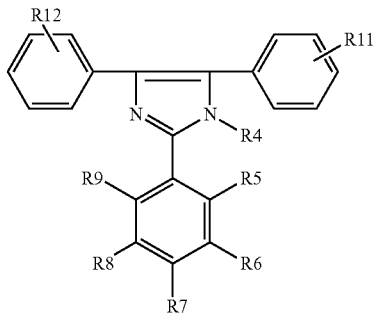

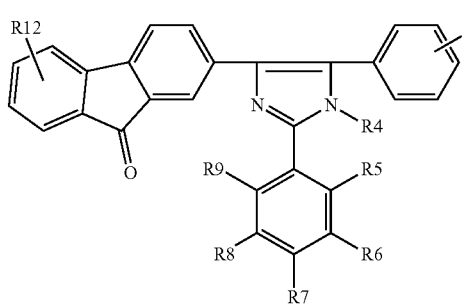

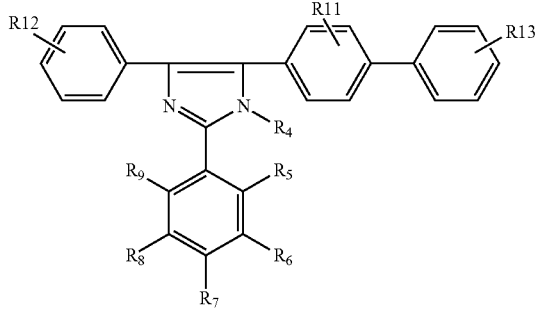

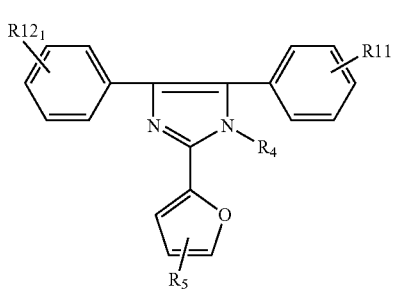

wherein:
R4, R5, R6, R7, R8, R9, R11, R12 and R13 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl, heterocycle, heteroaryl, substituted heterocycle, heteroalkyl, cycloalkyl, substituted cycloalkyl, alkylcycloalkyl, alkylcycloheteroalkyl, nitro, cyano or —S(O)$_{0-2}$R wherein R is alkyl, substituted alkyl, aryl, substituted aryl, heterocycle, heteroaryl, substituted heterocycle, or substituted heteroaryl.

In another embodiment of the invention the compound of Formula I is selected from:

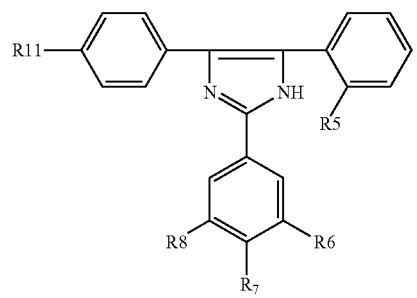

XVIII

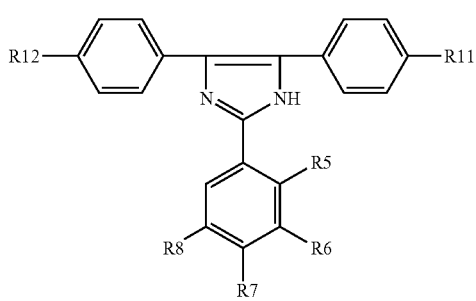

XIX

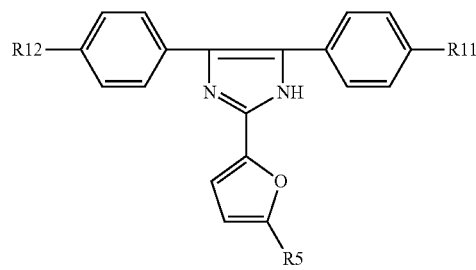

XX

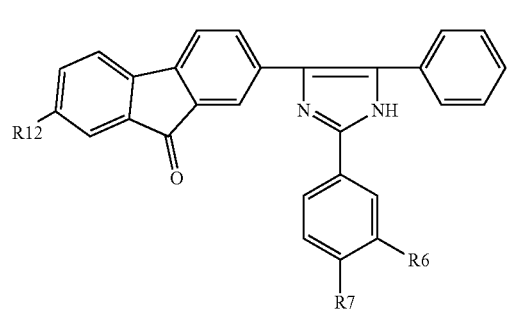

XXI

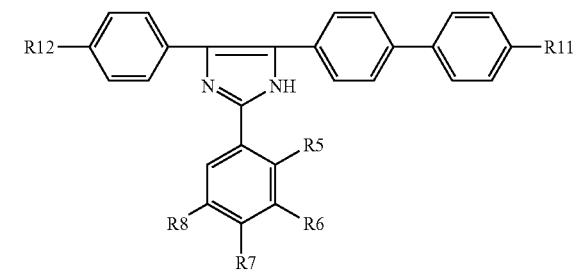

XXII

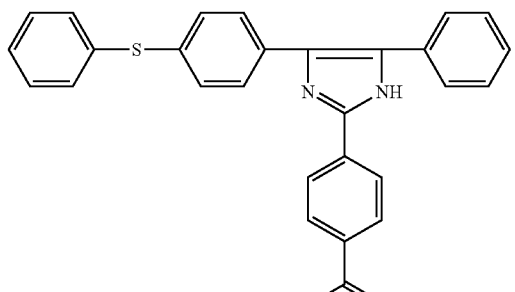

XXIII wherein:
R5, R6, R7, R8, R9, R11 and R12 are independently selected from hydrogen, halogen, hydroxyl, thiol, lower alkyl, substituted lower alkyl, lower alkenyl, substituted lower alkenyl, lower alkynyl, substituted lower alkynyl, alkylalkenyl, alkyl alkynyl, alkoxy, alkylthio, acyl, aryloxy, amino, amido, carboxyl, aryl, substituted aryl heterocycle, heteroaryl, substituted heterocycle, heteroalkyl, cycloalkyl, substituted cycloalkyl, alkylcycloalkyl, alkylcycloheteroalkyl, nitro, or cyano.

Compounds of the present invention include, but are not limited to the following exemplary compounds:

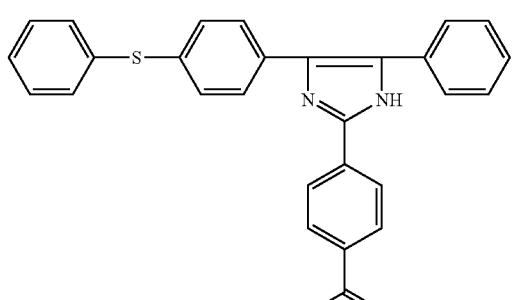

1

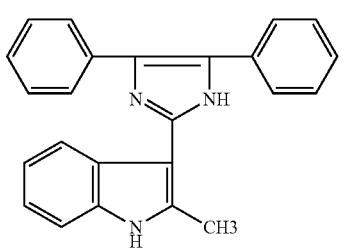

2

3
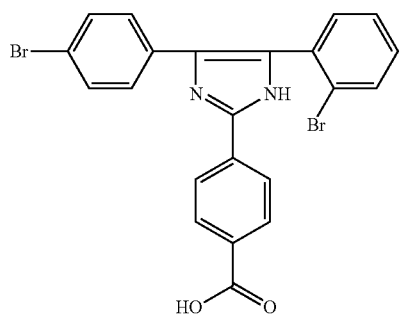
4
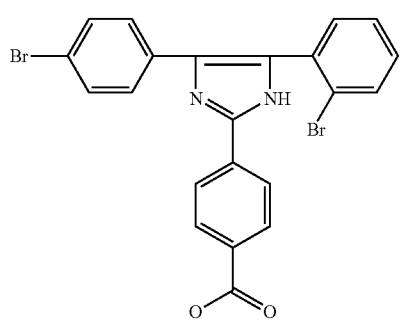
5
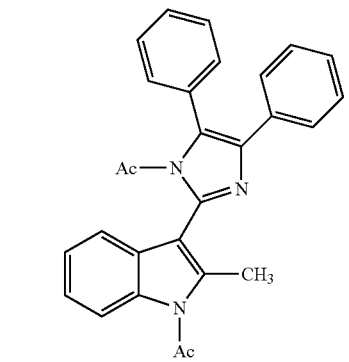
6
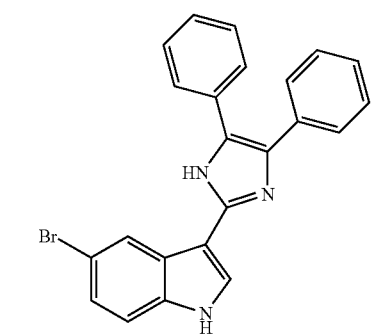
7
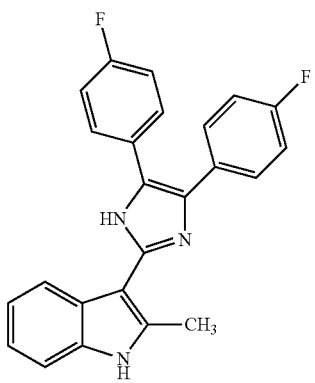
8
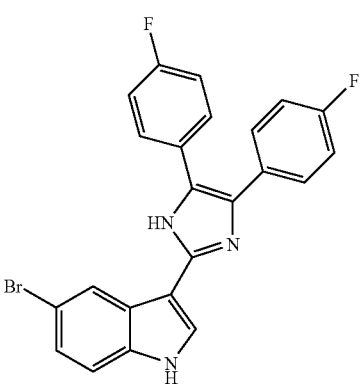
9
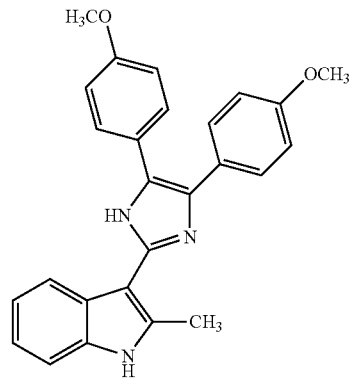
10
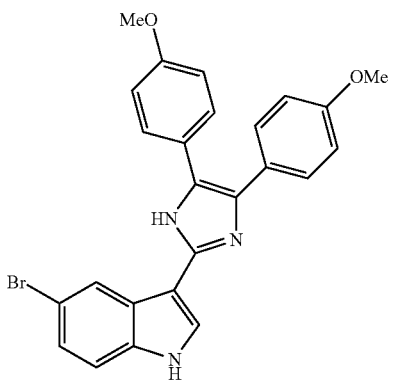

-continued
11
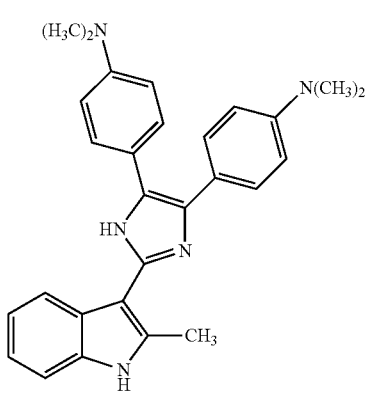
12
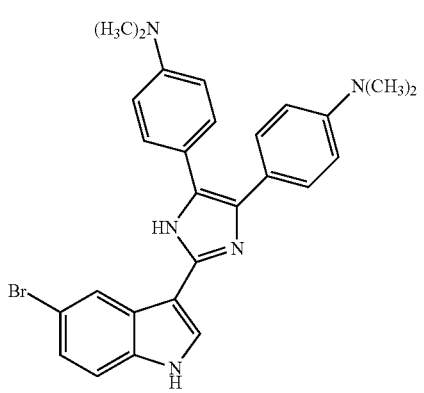
13
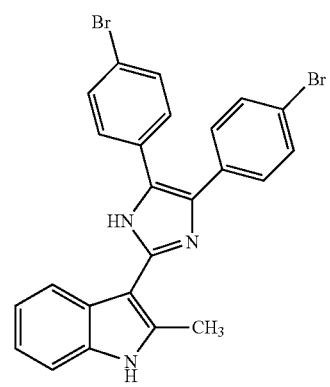
14
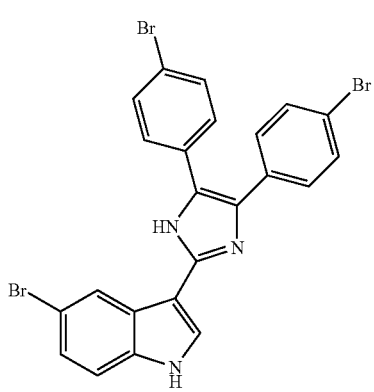
-continued
15
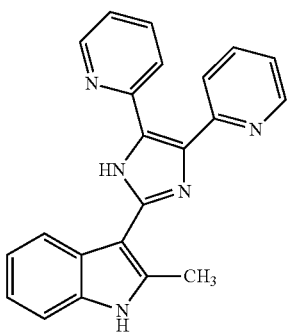
16
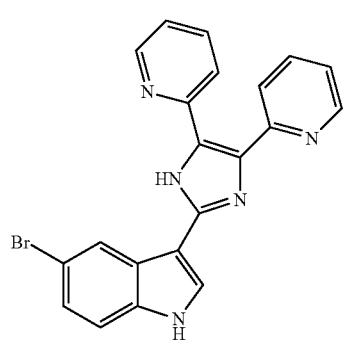
17
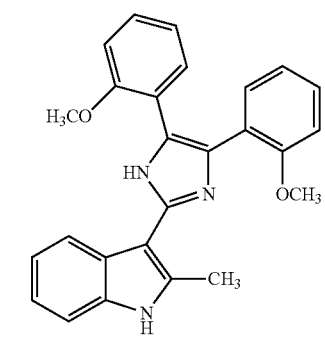
18
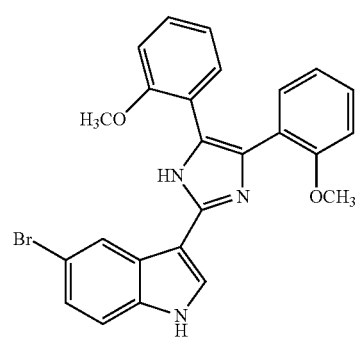

19
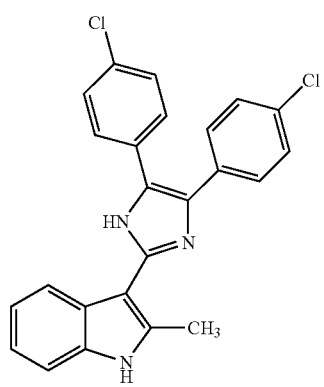
20
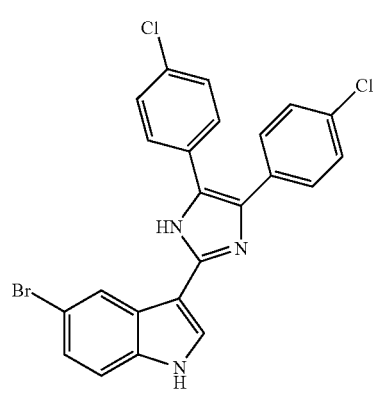
21
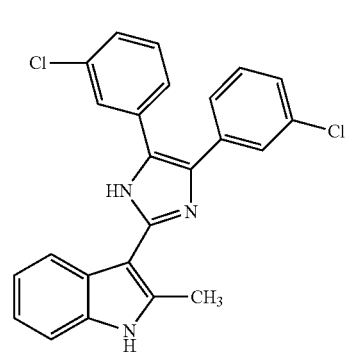
22
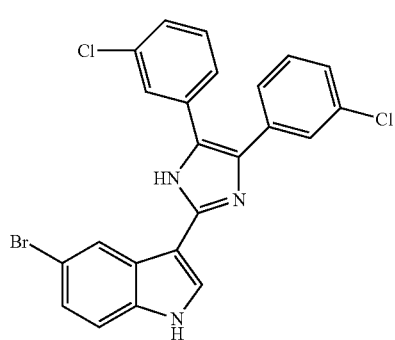
23
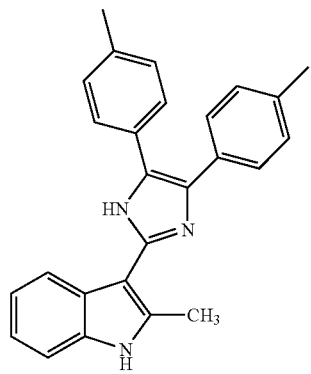
24
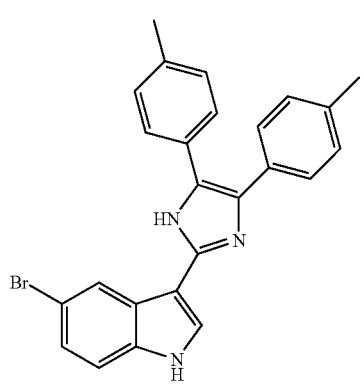
25
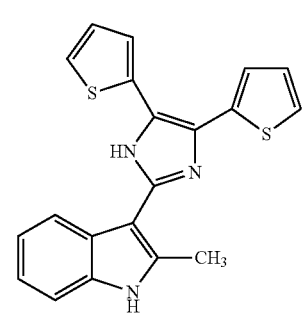
26
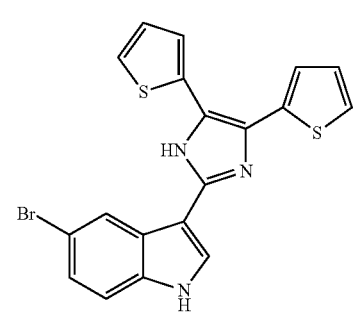

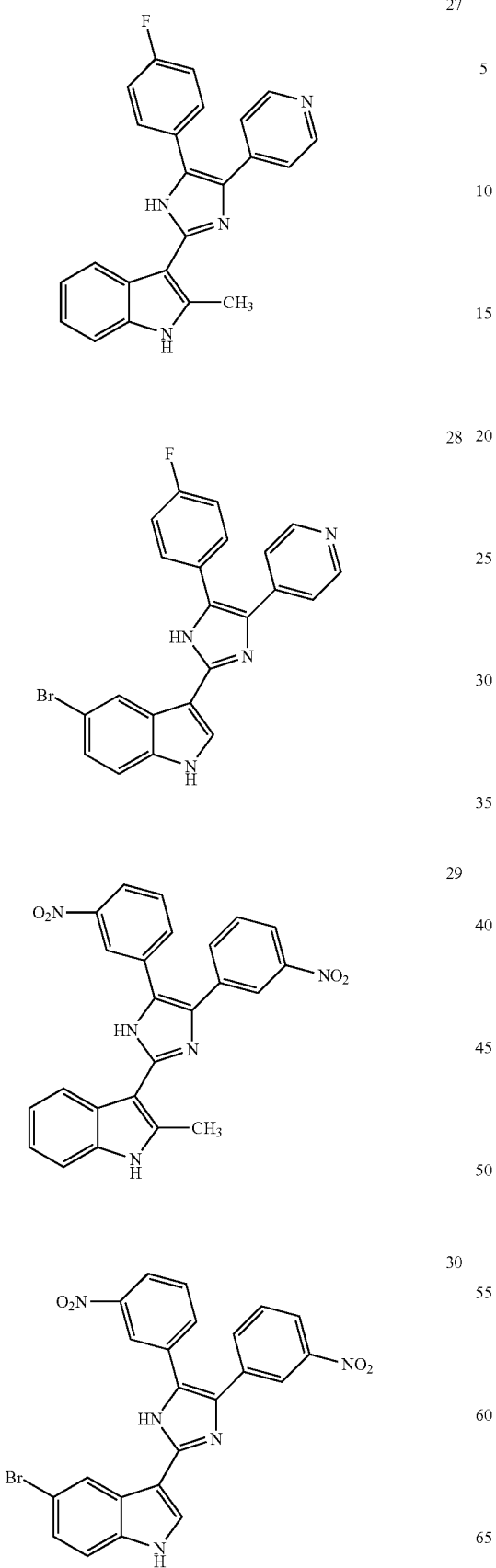
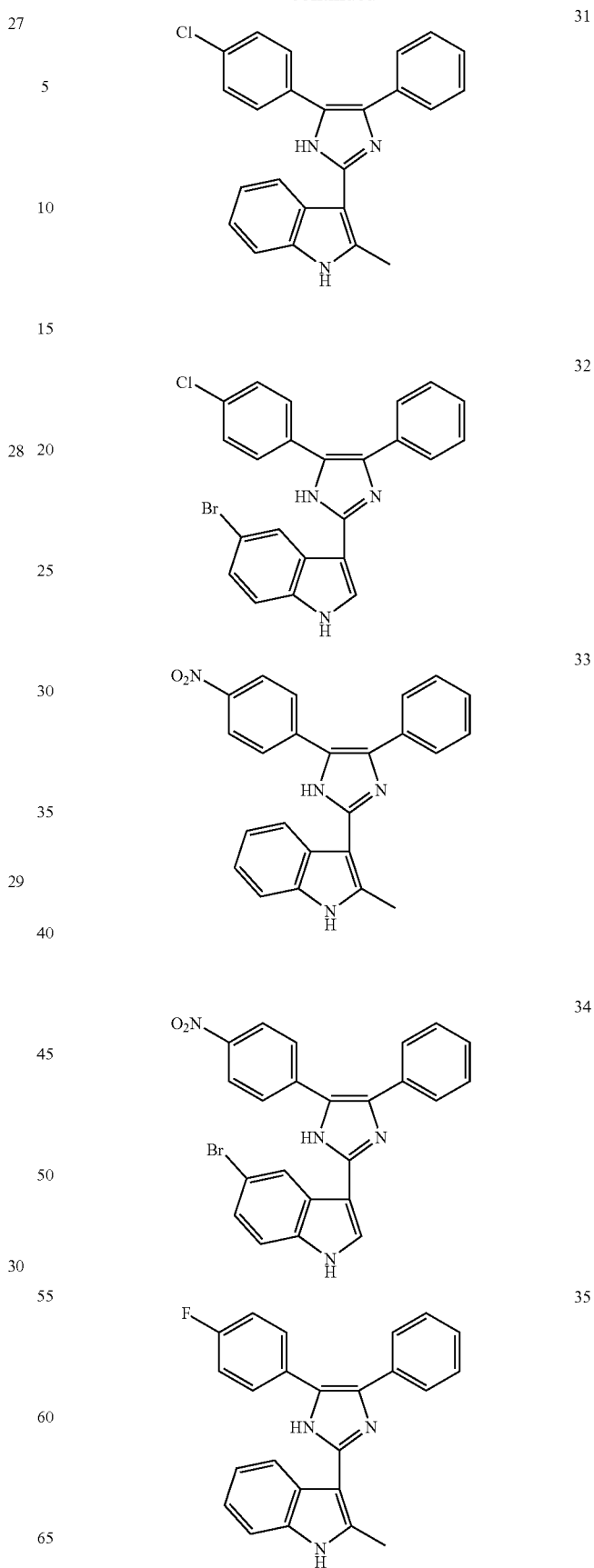

36
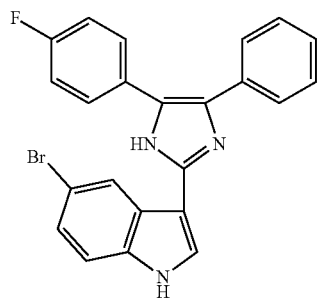
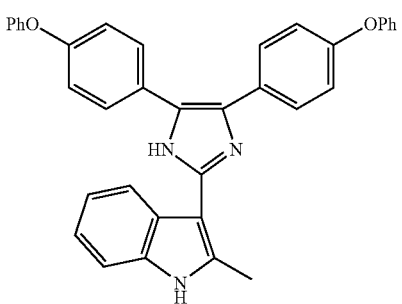
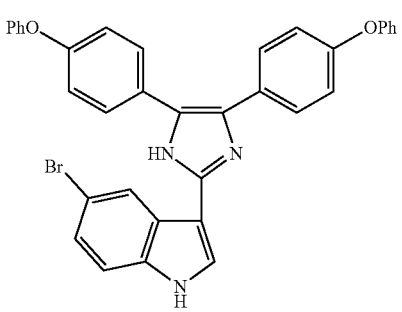
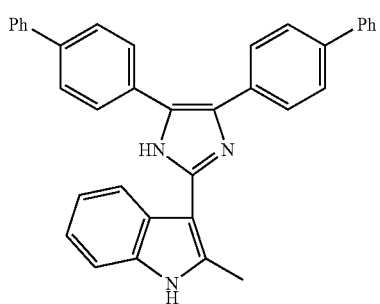
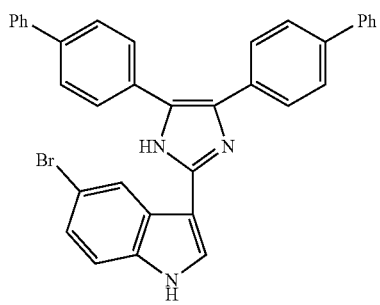
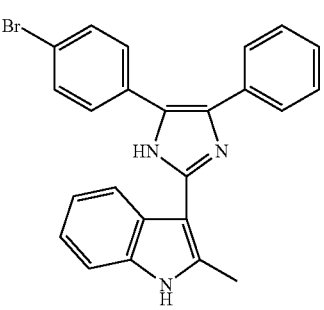
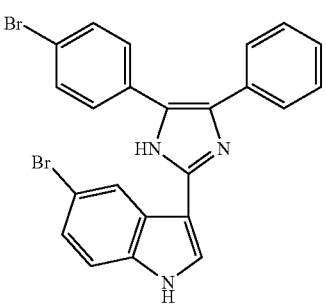
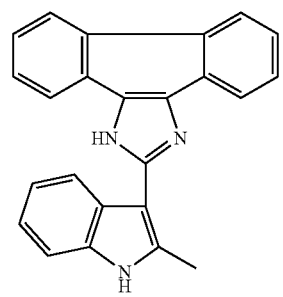
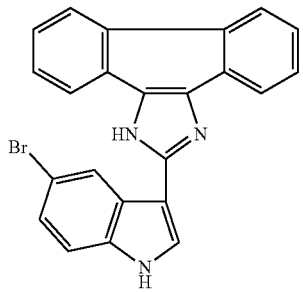

46 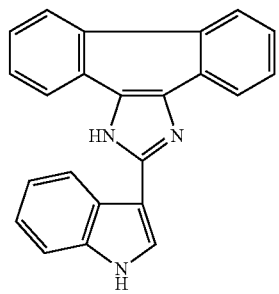
47 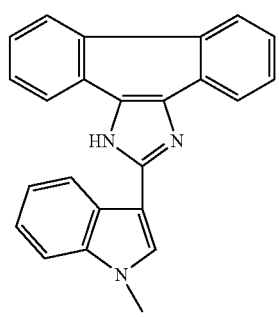
48 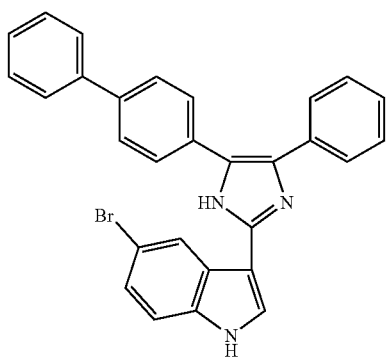
49 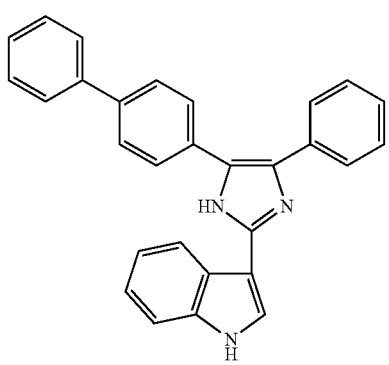
50 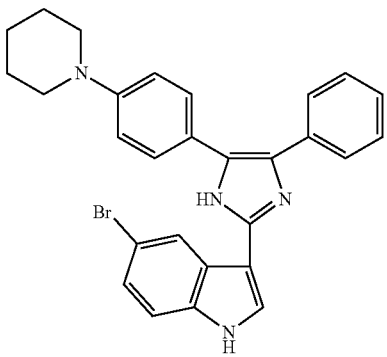
51 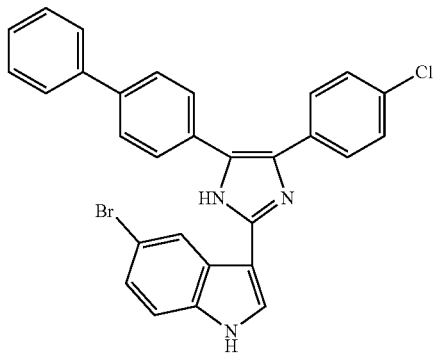
52 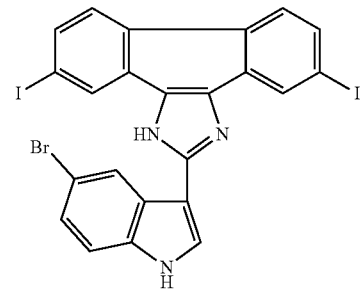
53 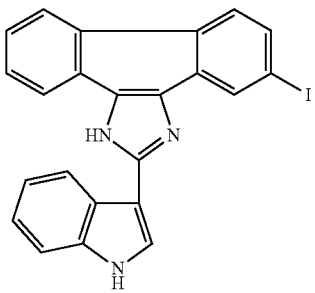
54 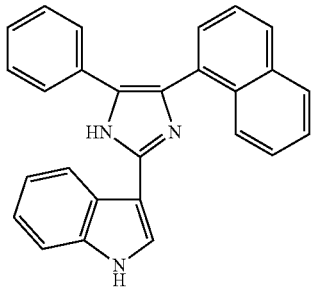

35
-continued
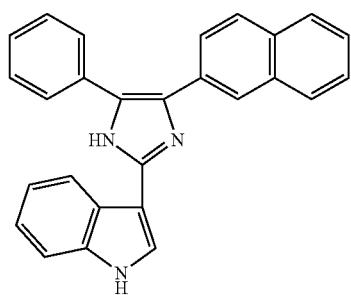
55
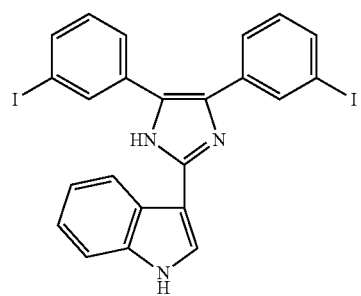
56
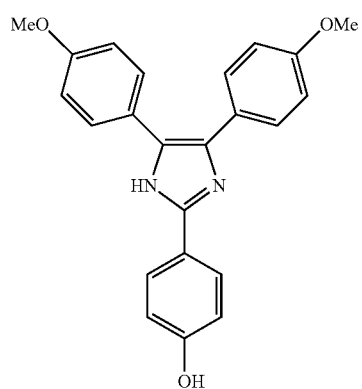
57
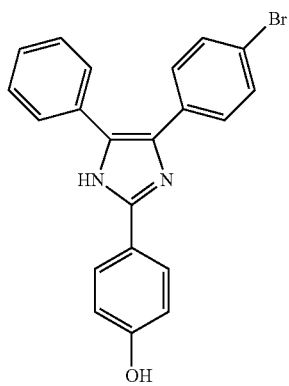
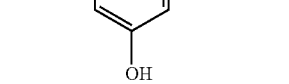
58
36
-continued
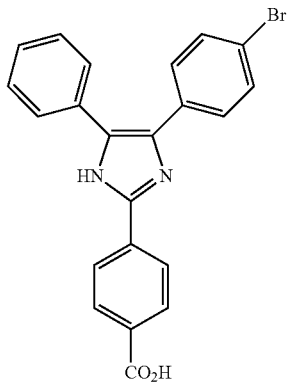
59
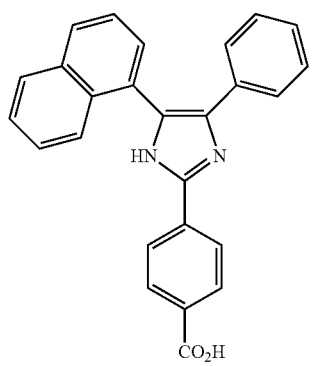
60
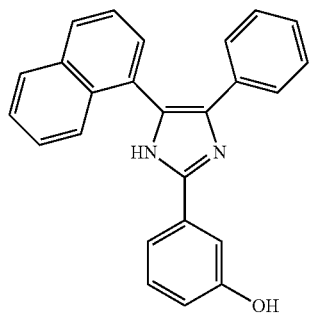
61
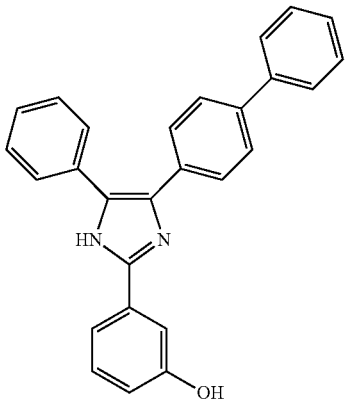
62

-continued
63
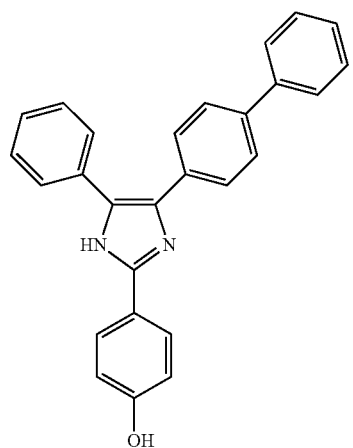
64
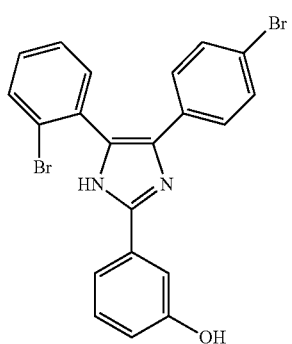
65
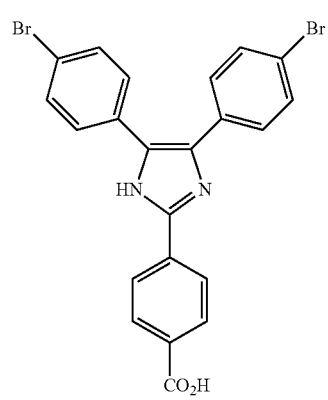
66
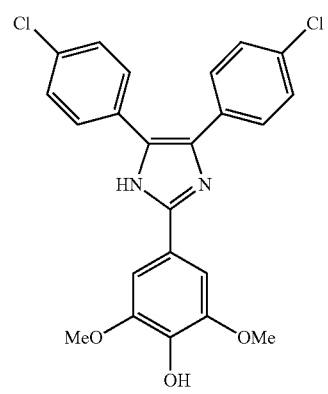
-continued
67
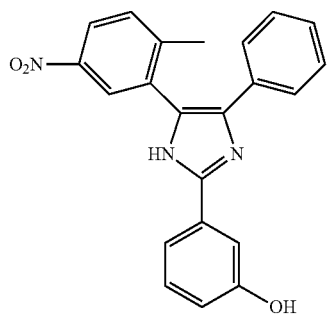
68
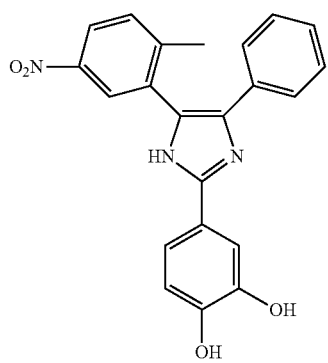
69
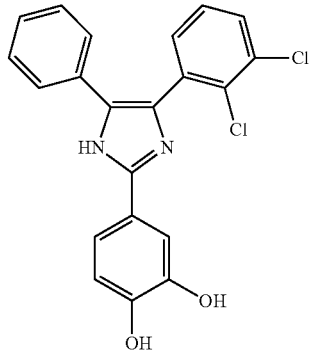
70
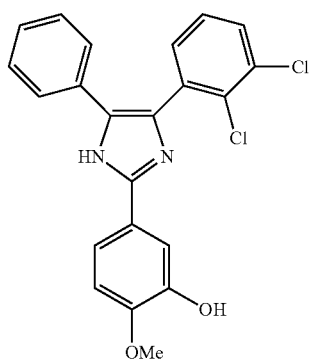

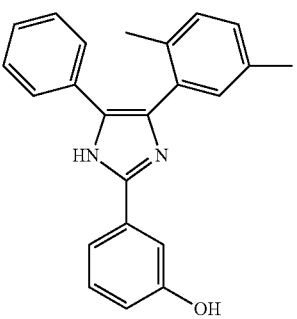
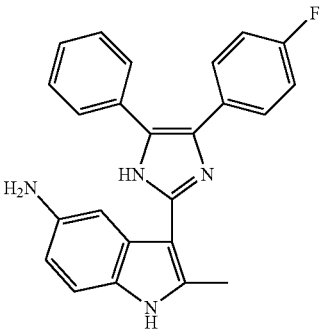
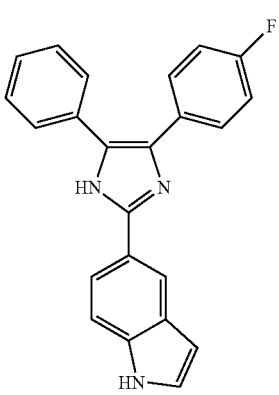
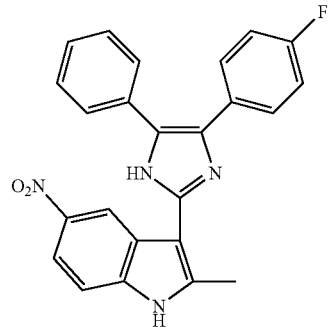
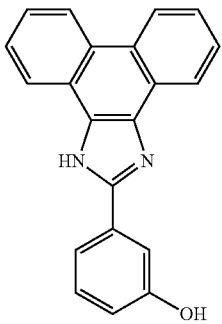

79
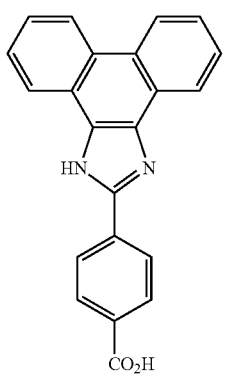
80
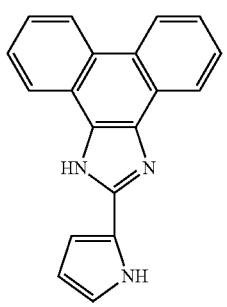
81
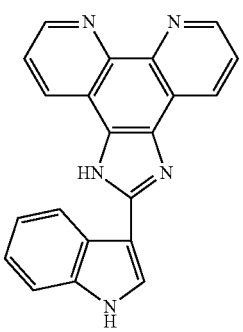
82
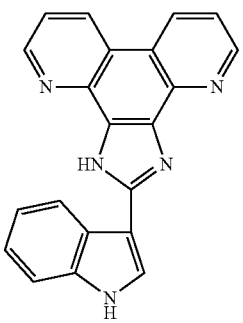
83
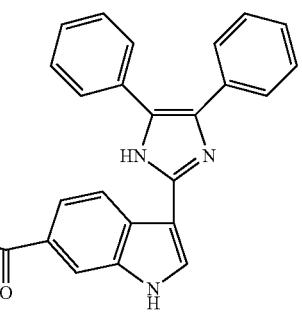
84
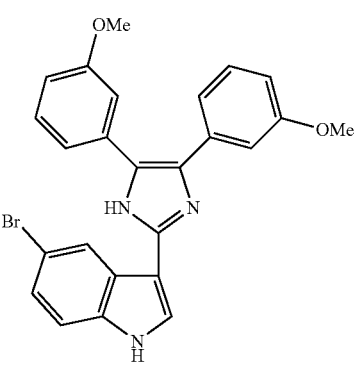
85
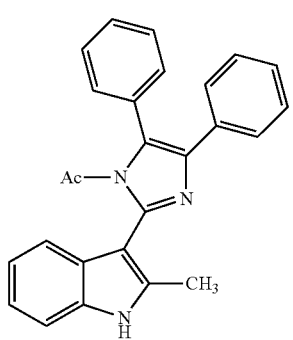
86
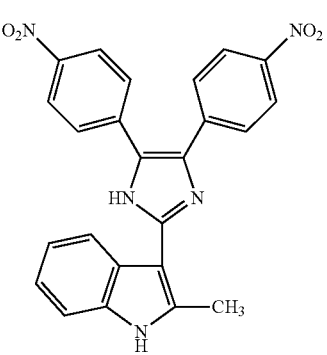
87
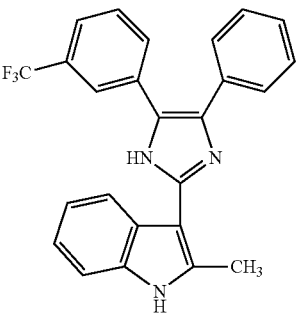

-continued
88
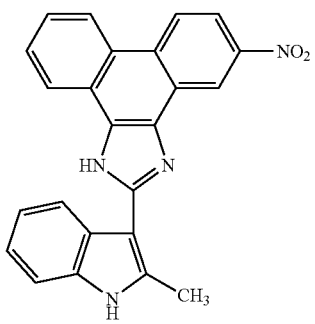
89
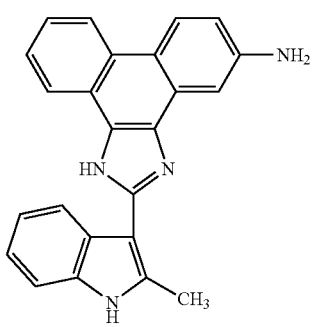
90
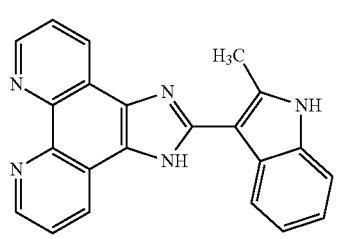
91
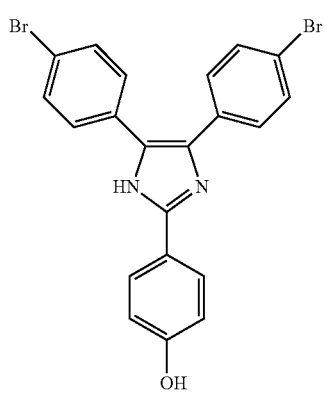
92
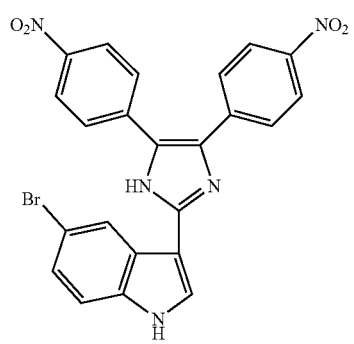
-continued
93
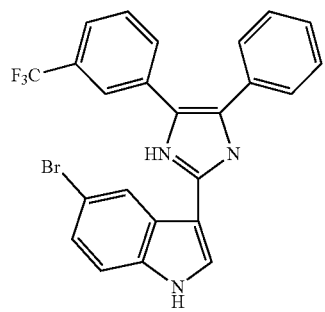
94
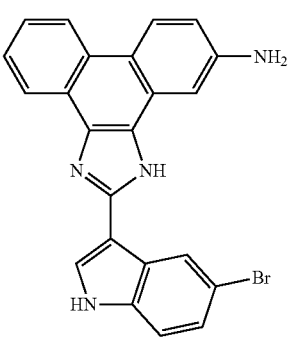
95
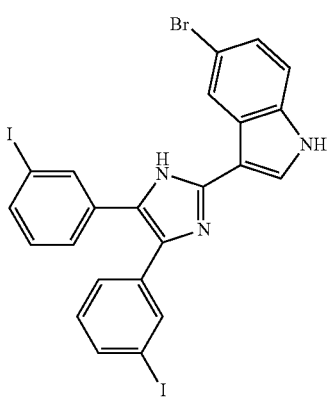
96
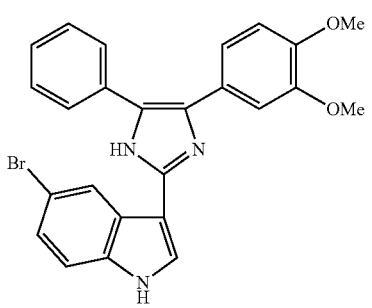
97
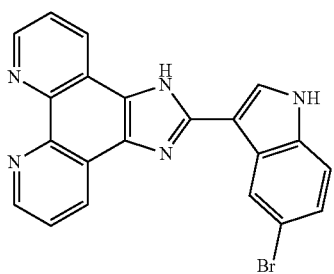

-continued
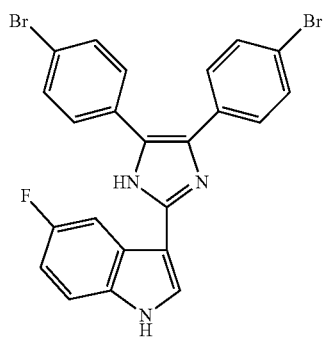
98
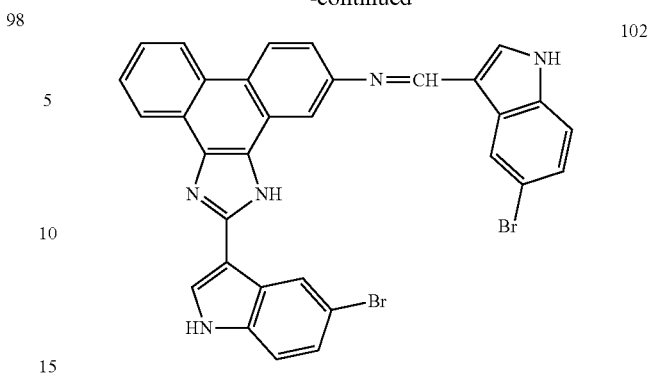
102
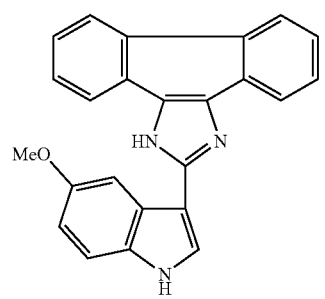
99
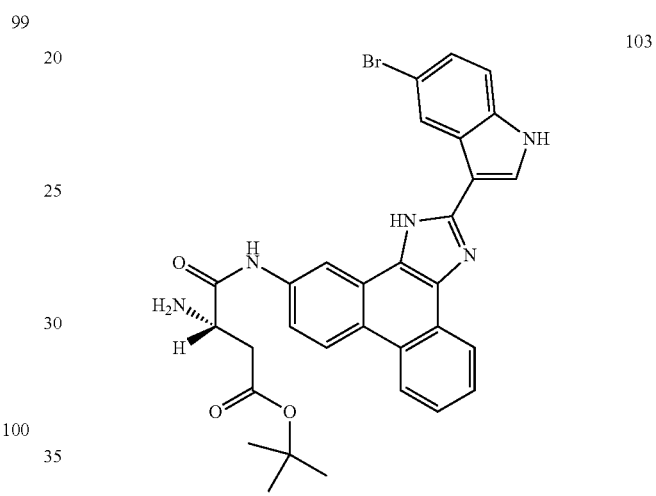
103
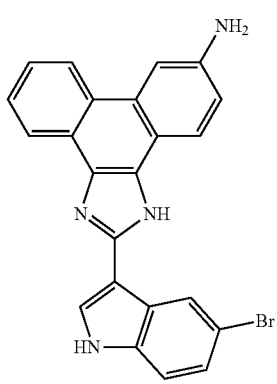
100
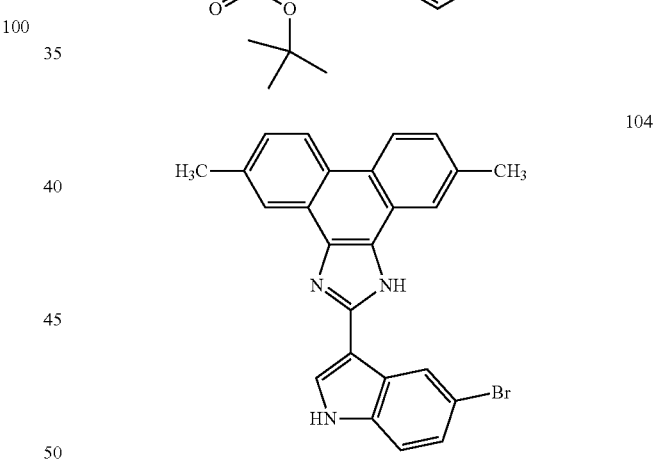
104
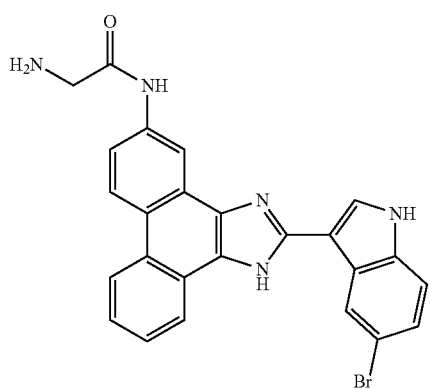
101
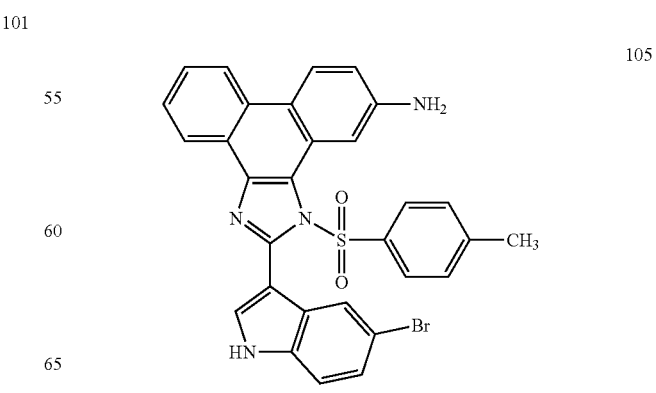
105

47
-continued
106
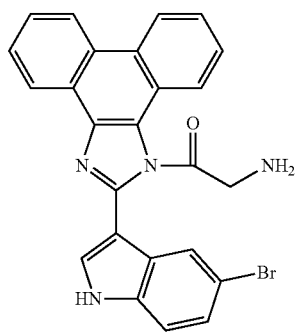
107
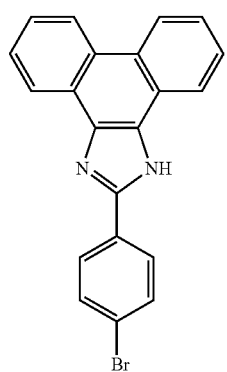
108
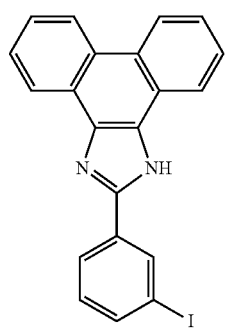
109
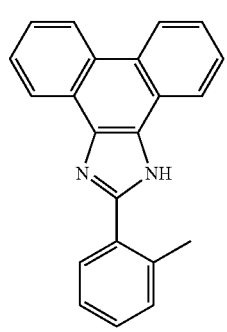
48
-continued
110
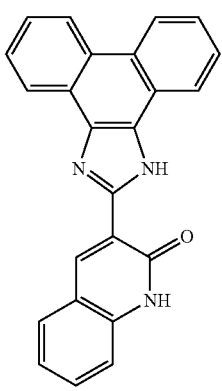
111
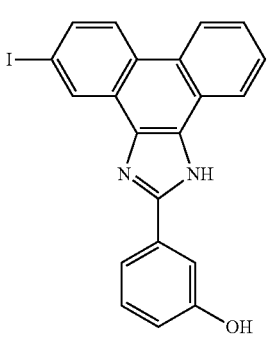
112
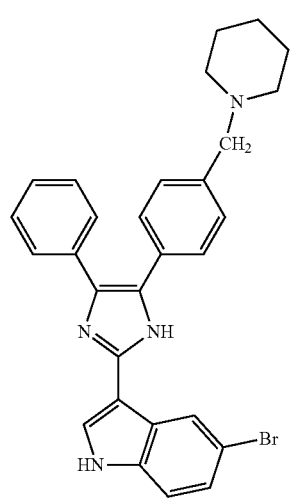

113
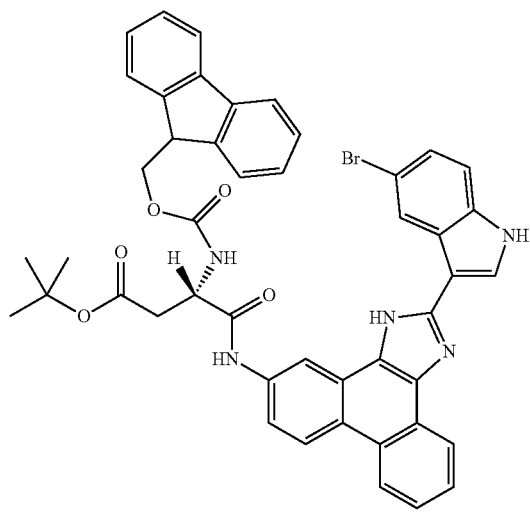
114
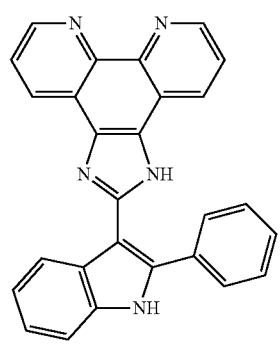
115
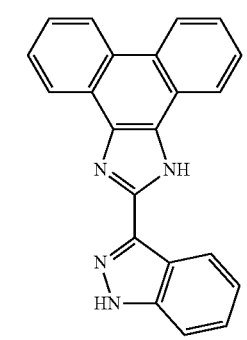
116
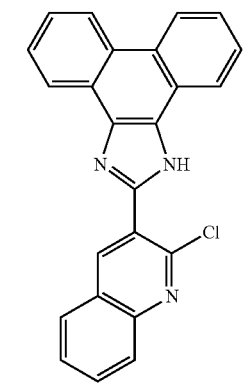
117
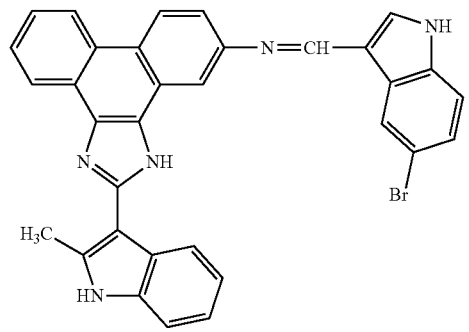
118
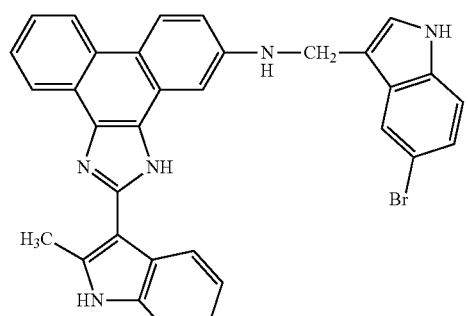
119
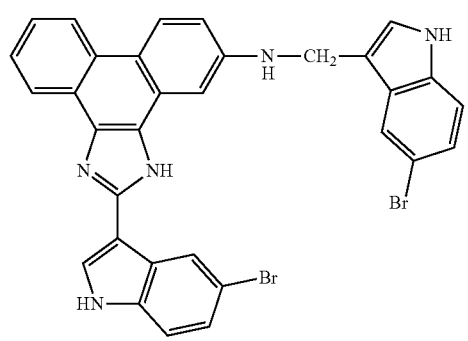
120
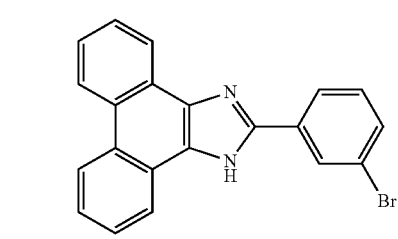
121
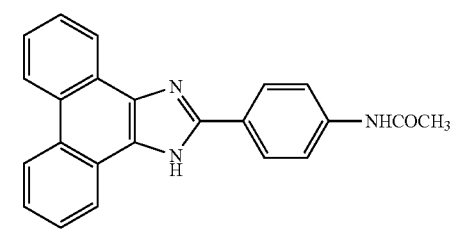

122
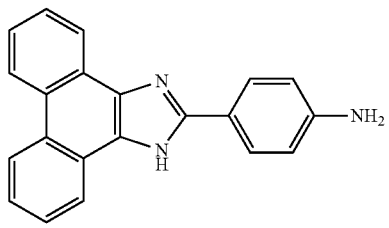
123
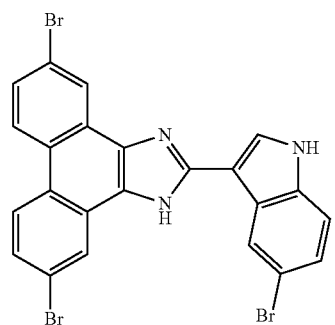
124
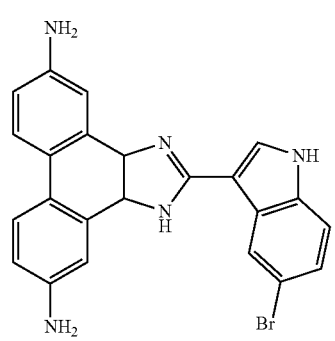
125
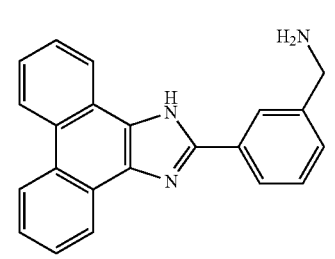
126
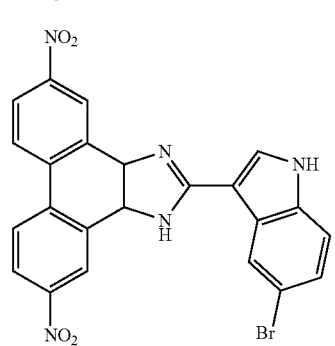
127
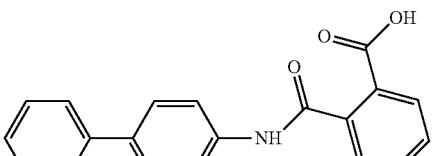
128
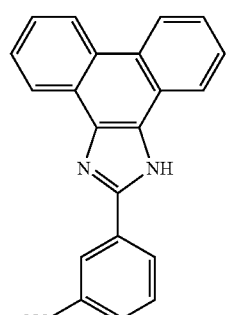
129
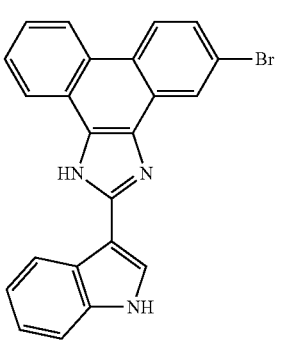
130
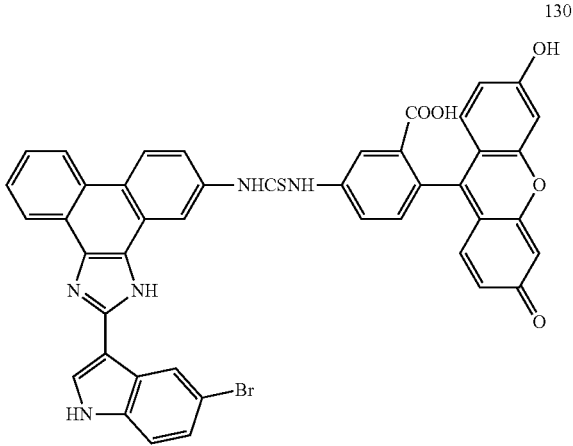

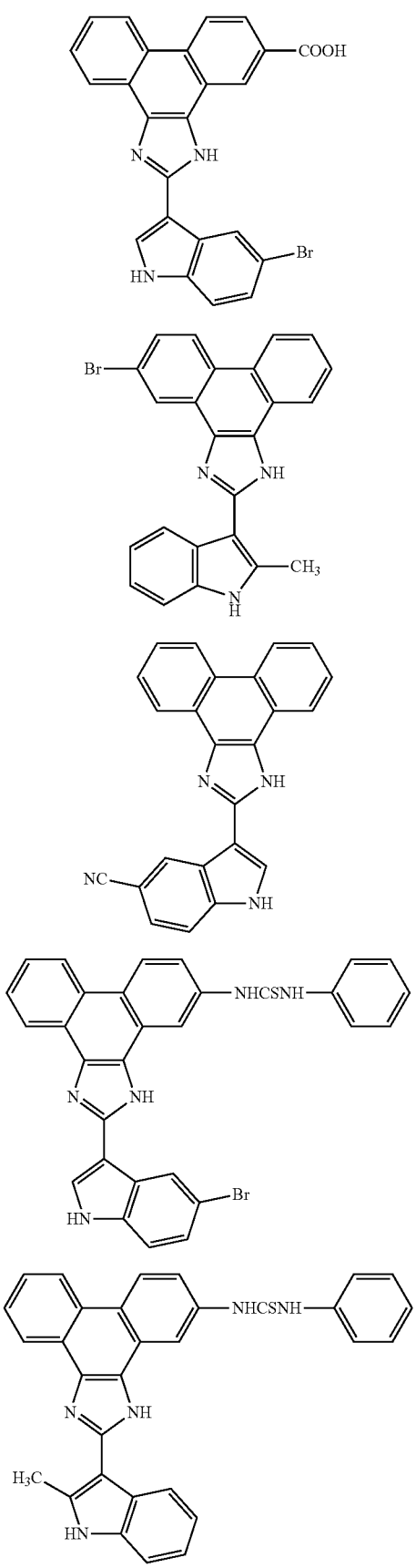
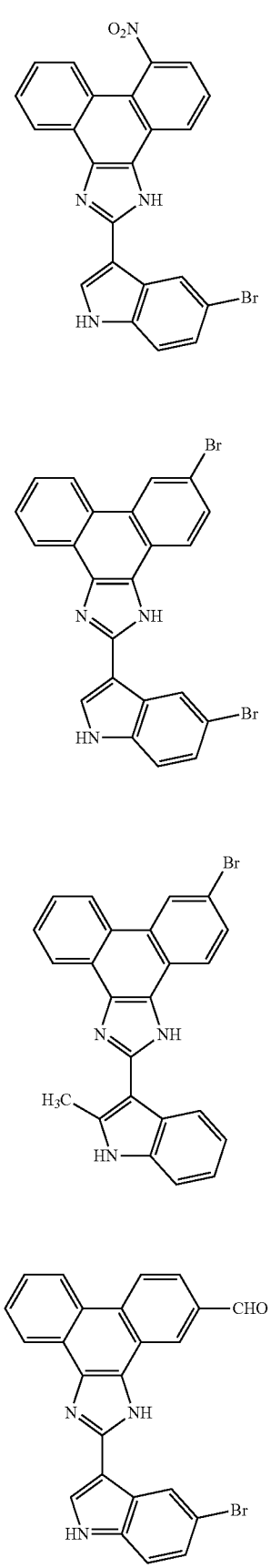

140
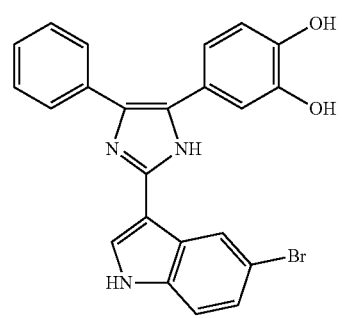
141
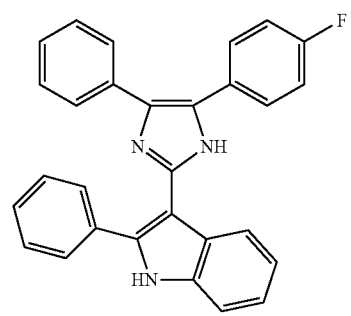
142
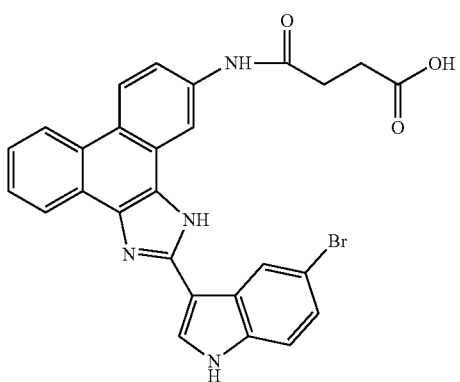
143
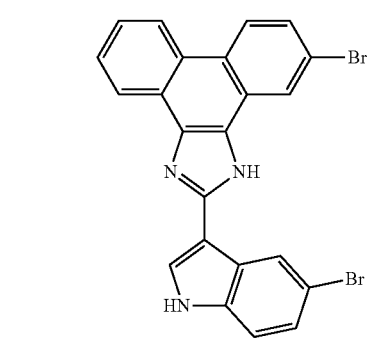
144
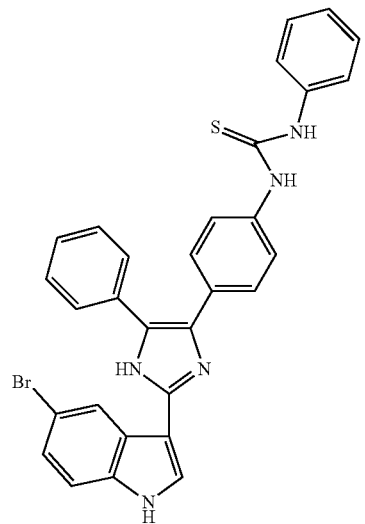
145
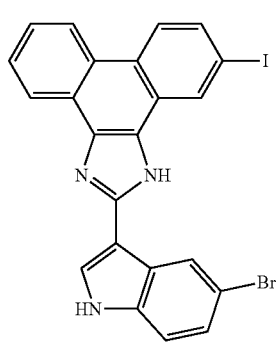
146
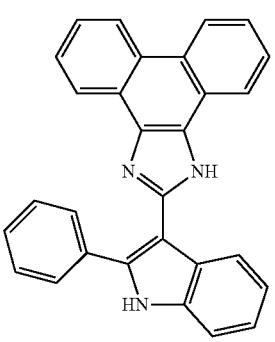
147
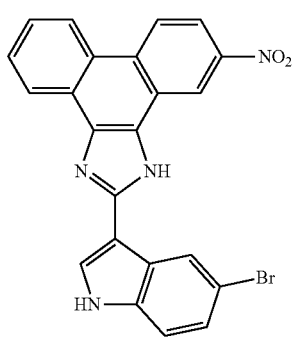

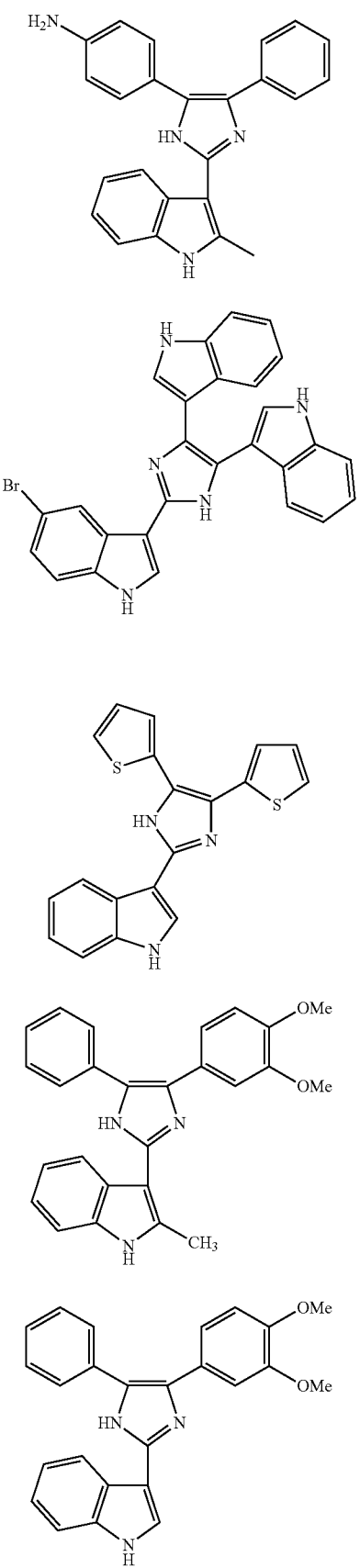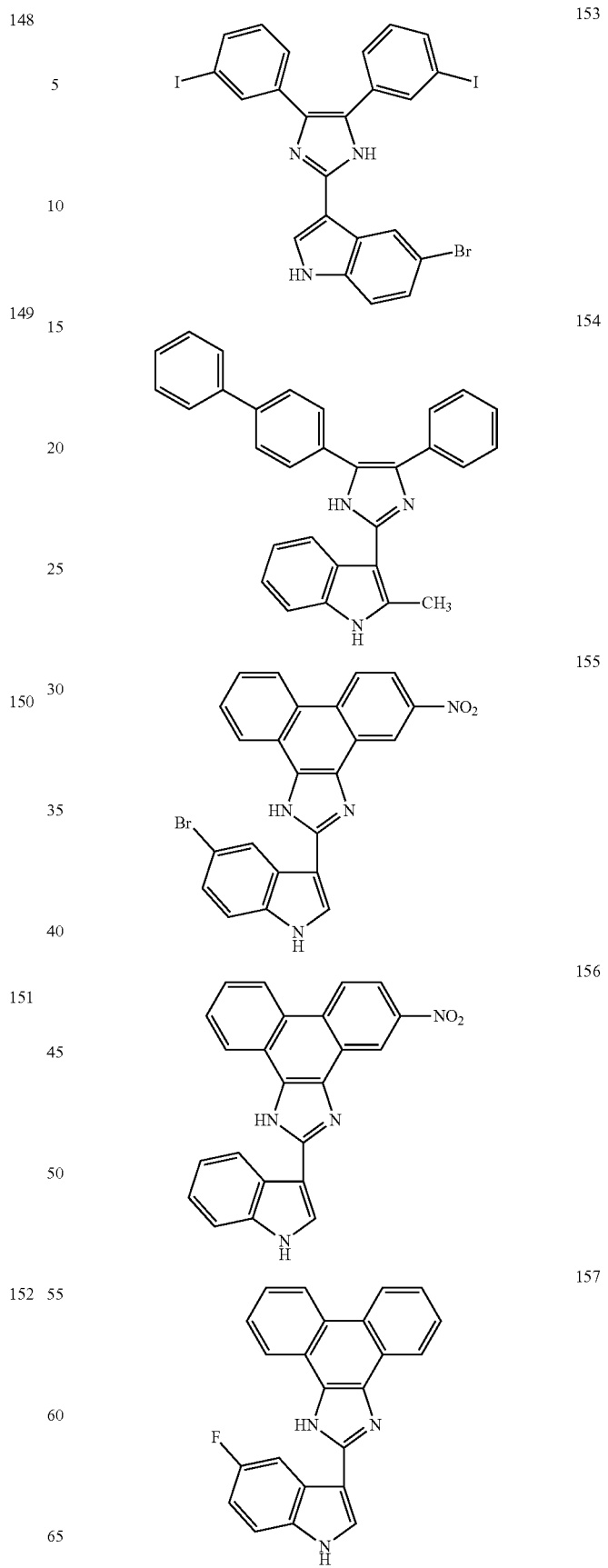

158
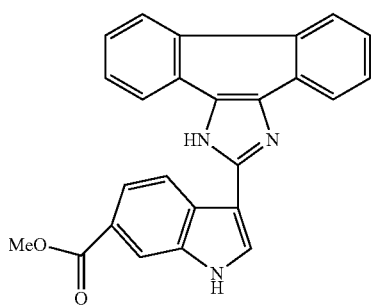
159
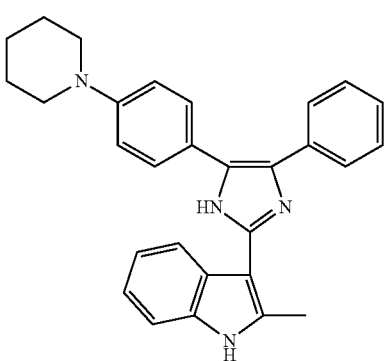
160
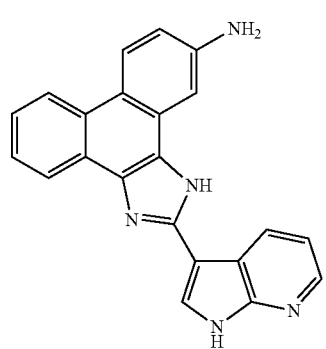
161
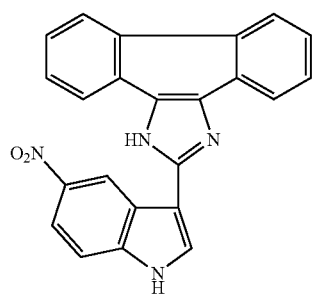
162
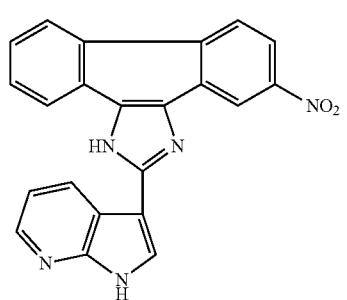
163
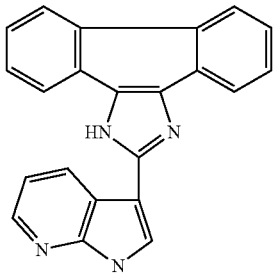
164
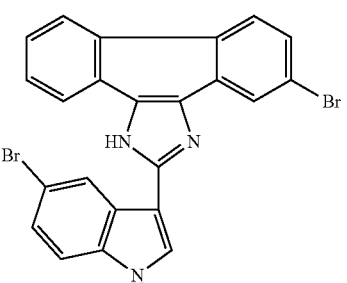
165
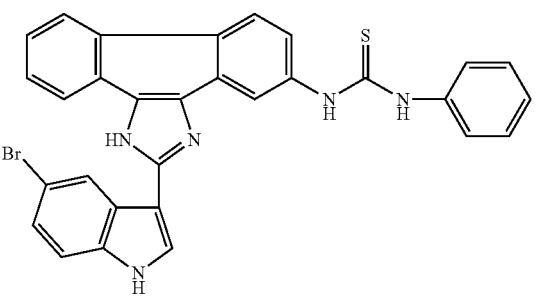
166
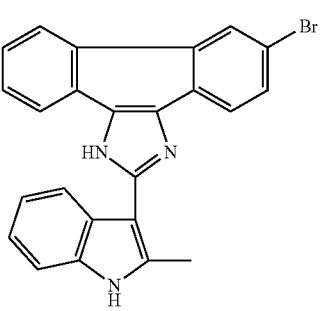
167
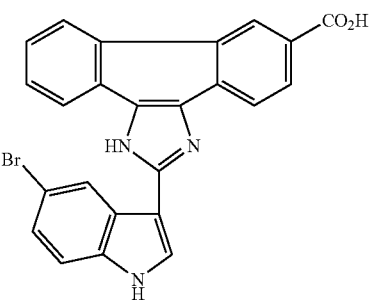

168 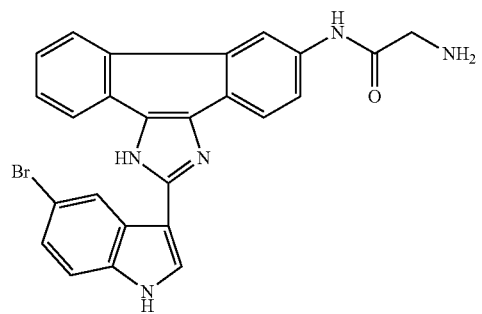
169 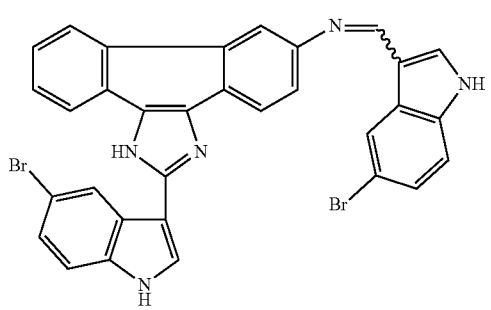
170 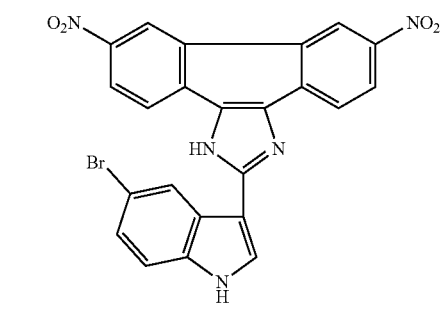
171 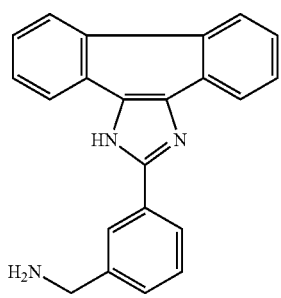
172 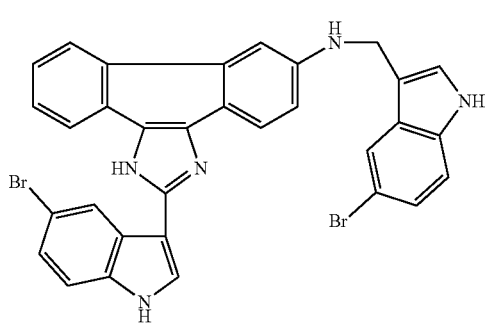
173 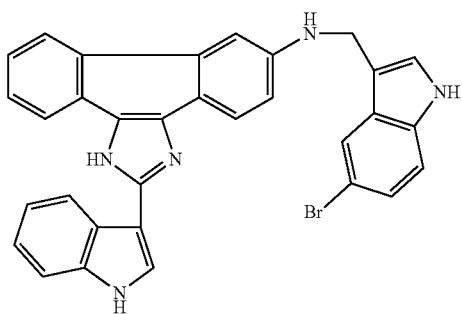
174 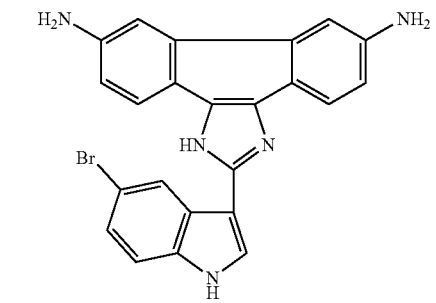
175 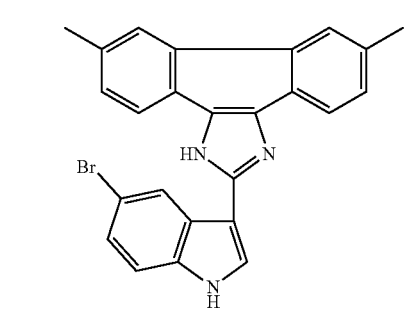
176 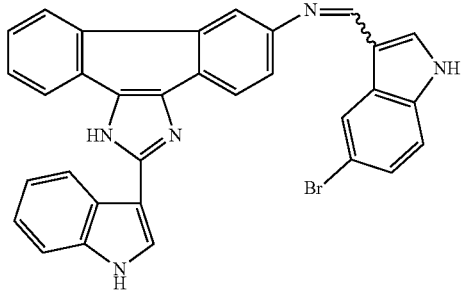
177 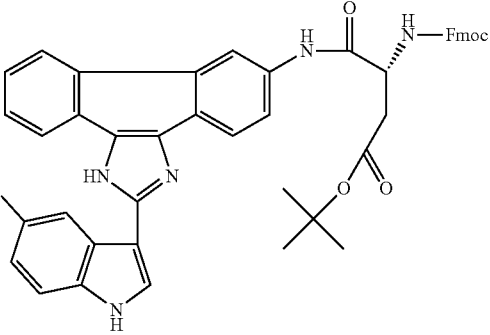

178
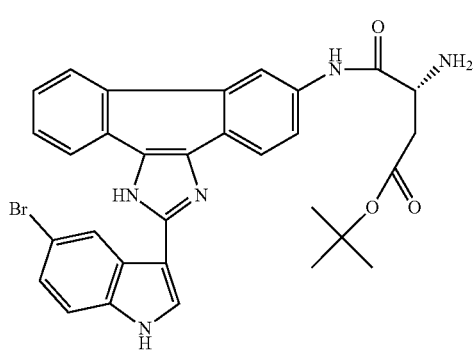
179
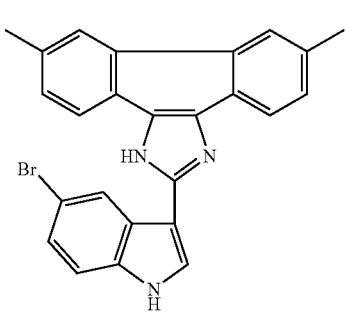
180
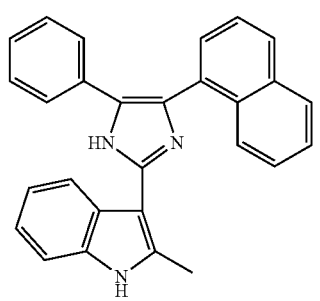
181
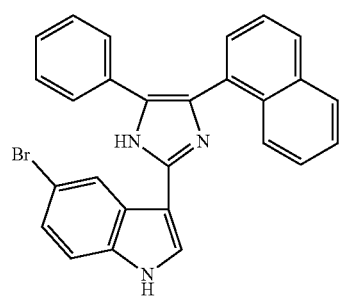
182
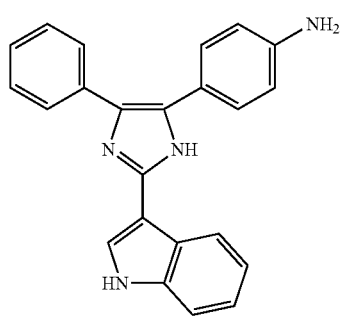
183
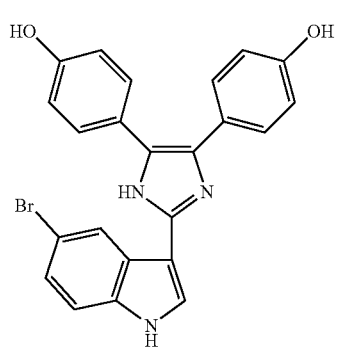
184
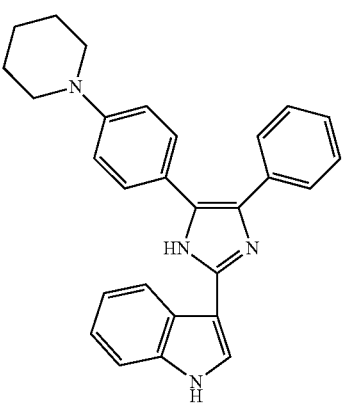
185
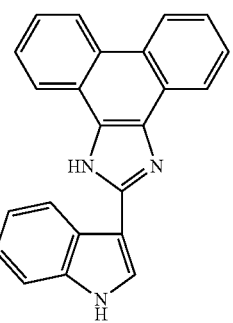
186
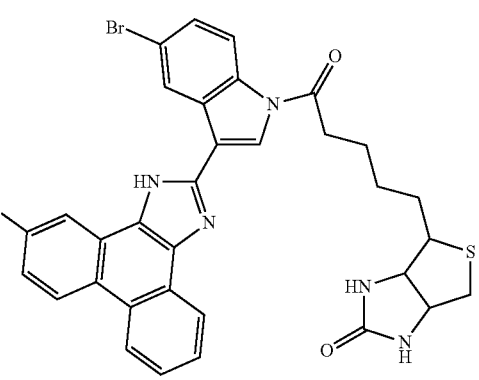

187
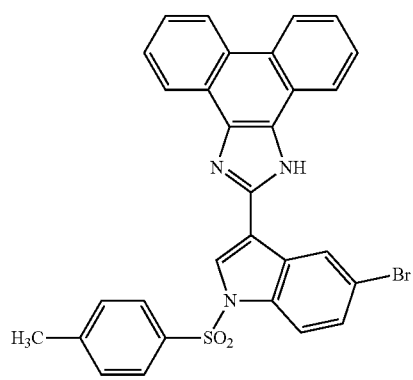
188
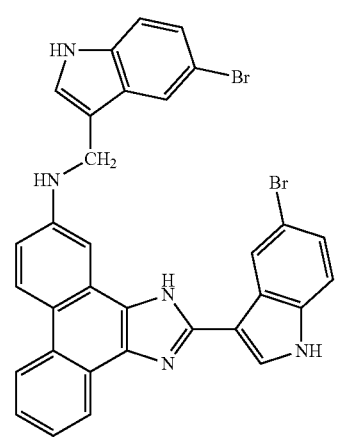
189
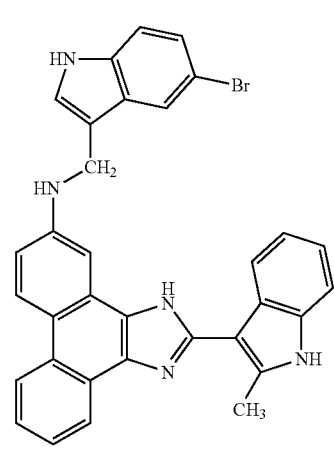
190
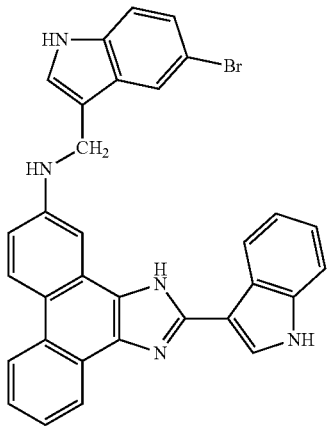
191
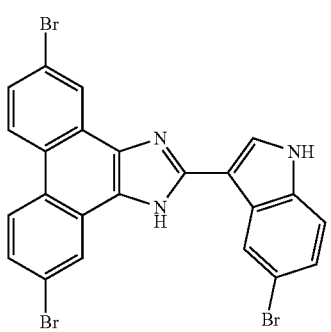
192
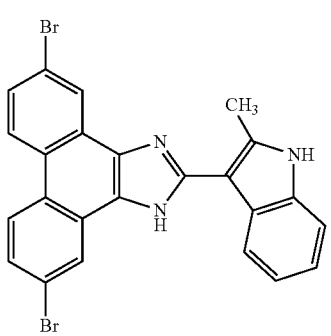
193
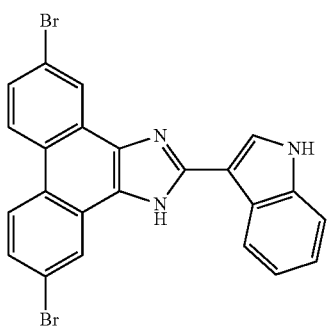

194 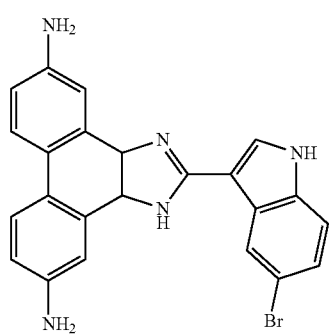
195 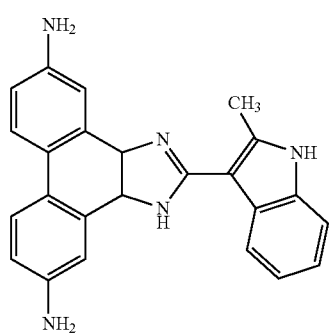
196 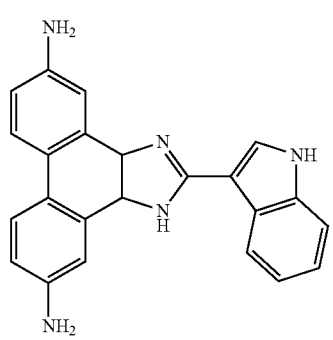
197 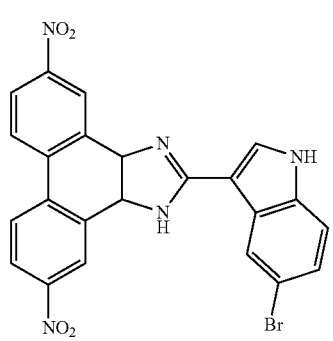
198 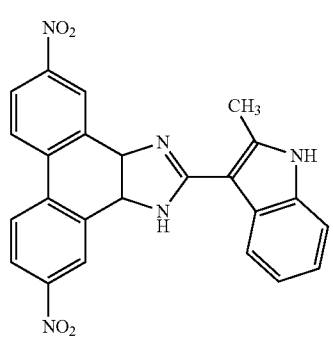
199 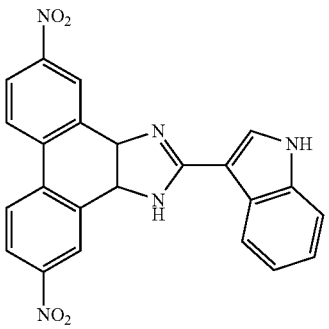
200 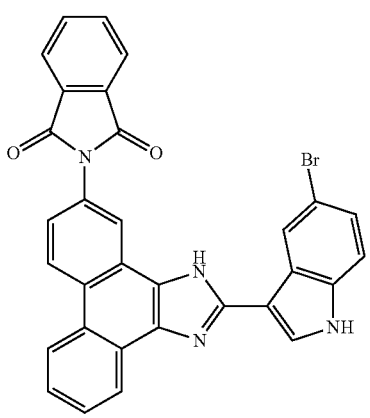
201 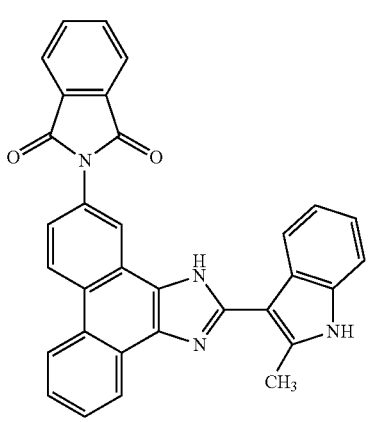
202 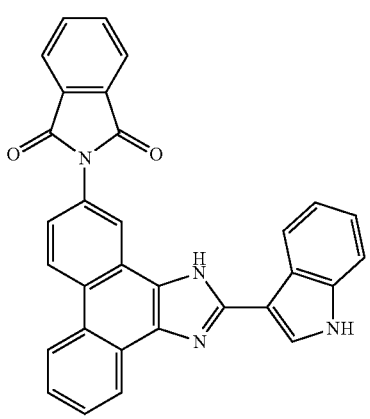

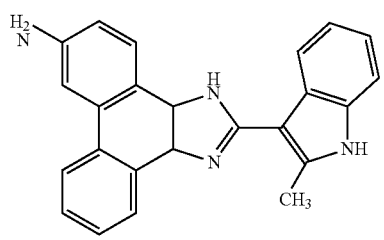
203
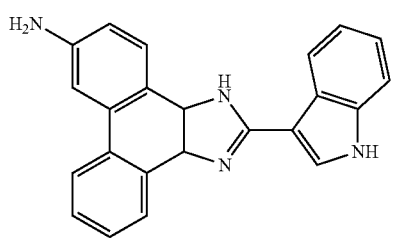
204
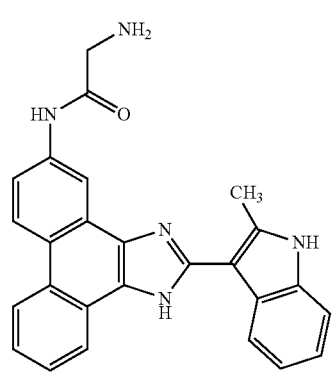
205
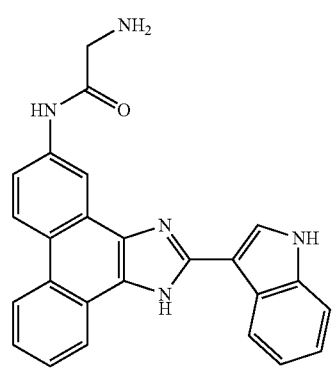
206
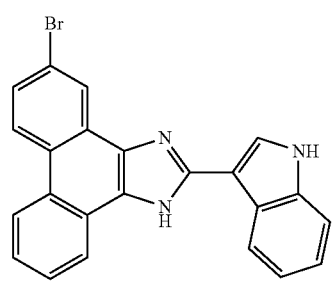
207
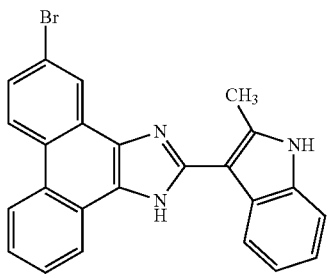
208
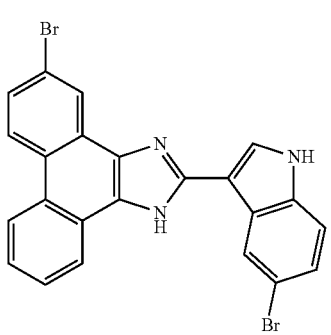
209
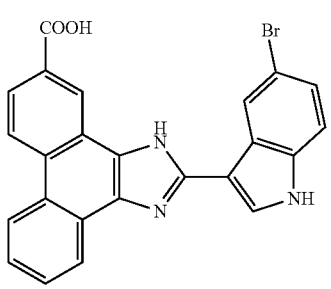
210
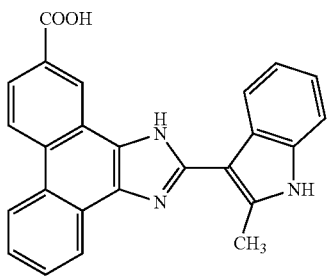
211
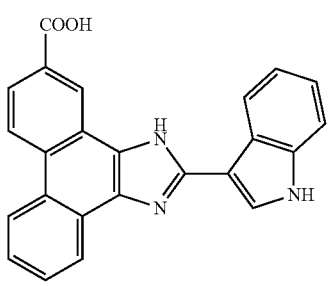
212

-continued
213
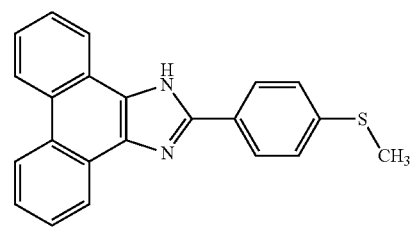
214
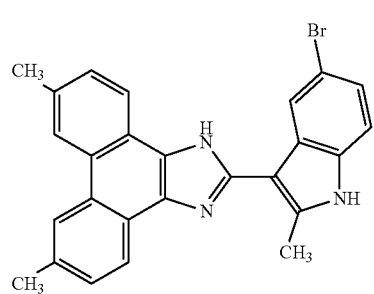
215
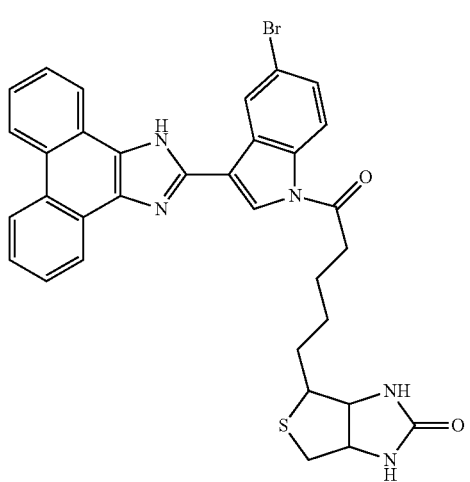
216
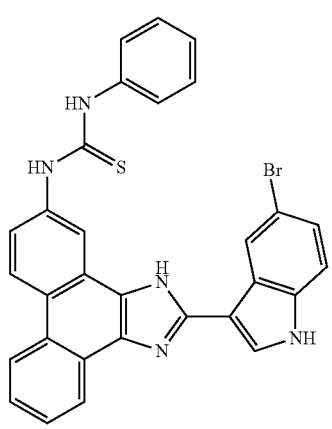
-continued
217
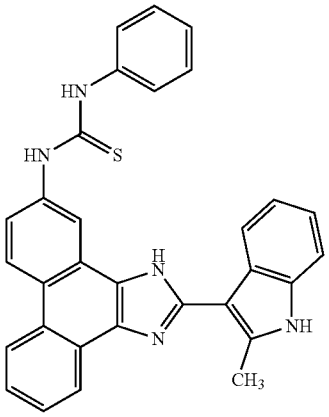
218
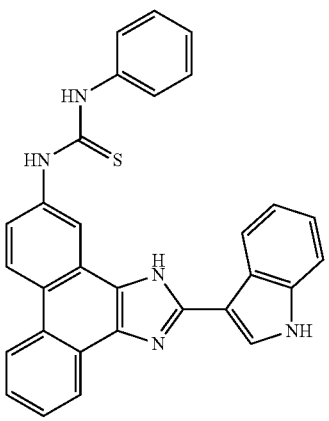
219
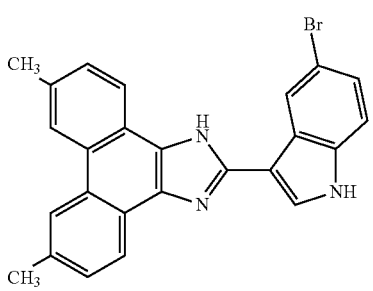
220
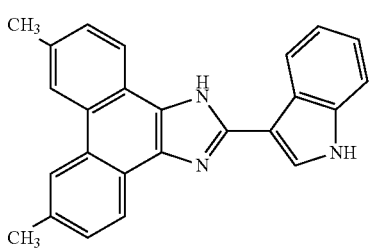
221
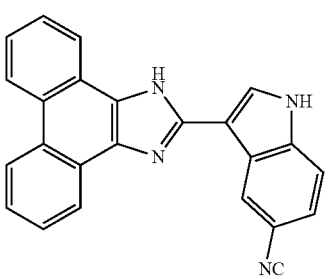

222 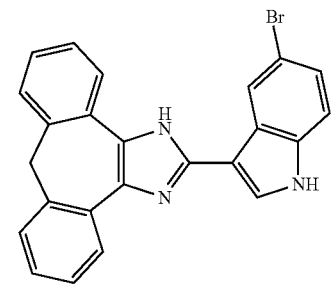
223 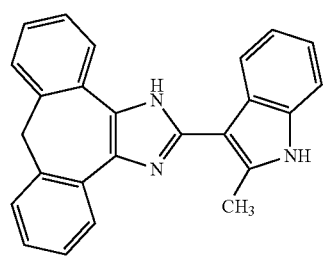
224 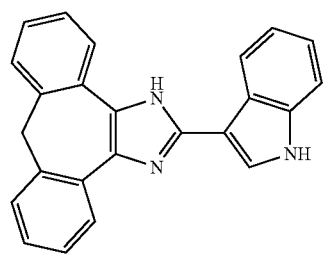
225 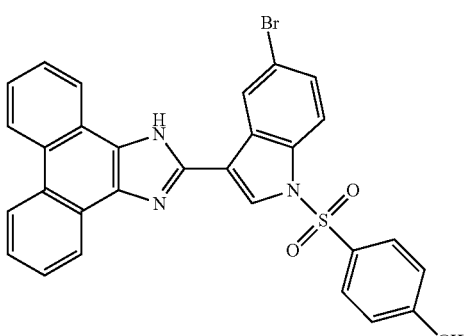
226 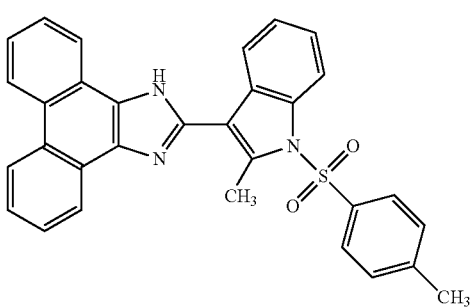
227 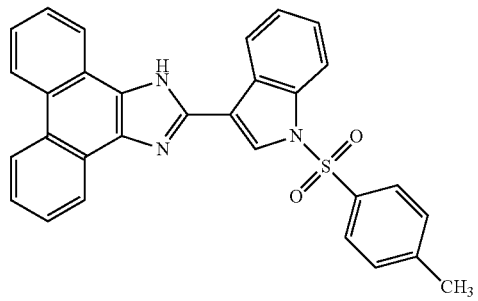
228 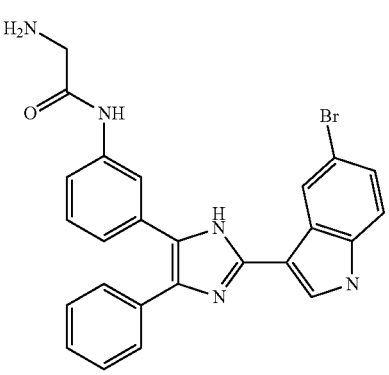
229 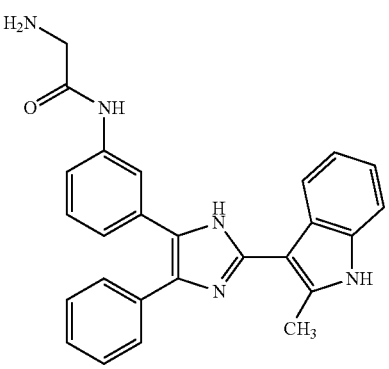
230 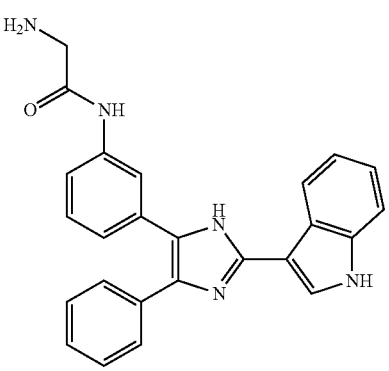

-continued

231

232

233

234

-continued

235

236

237

238

251 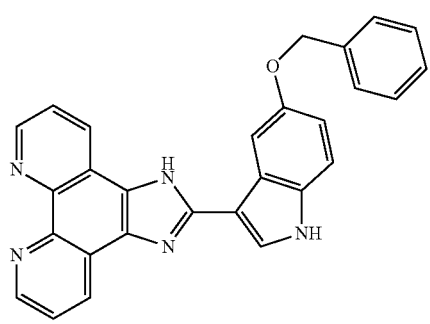
252 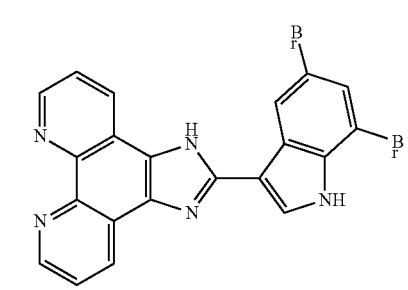
253 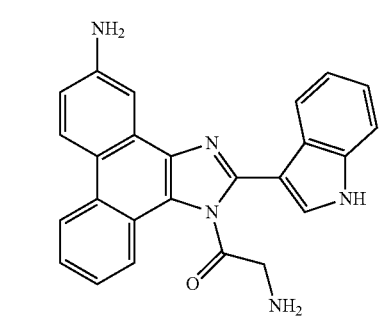
254 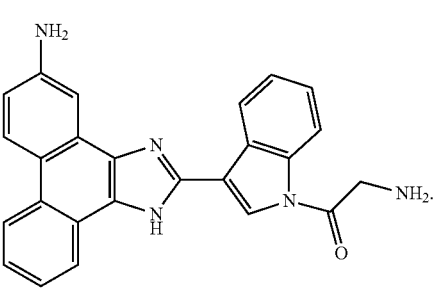
239 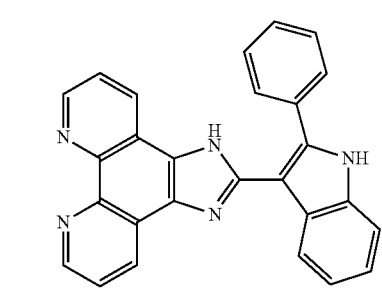
240 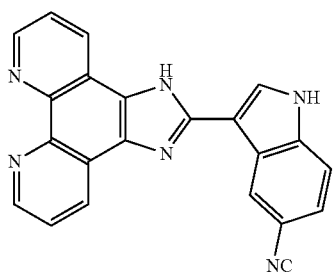
241 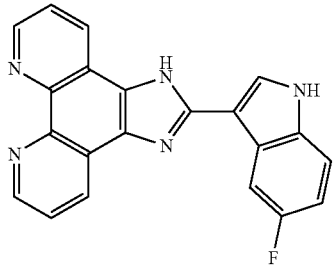
242 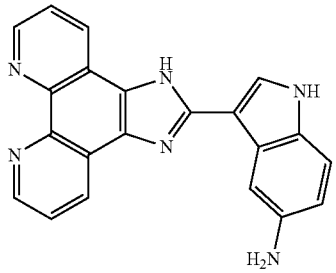
243 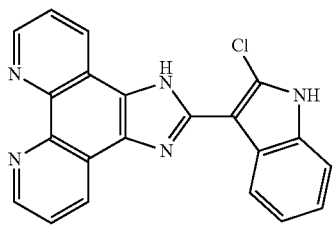
244 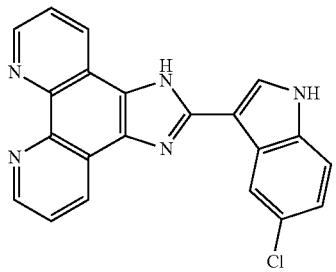
245 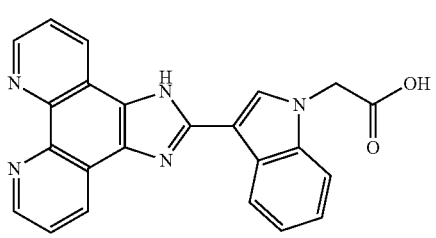

-continued

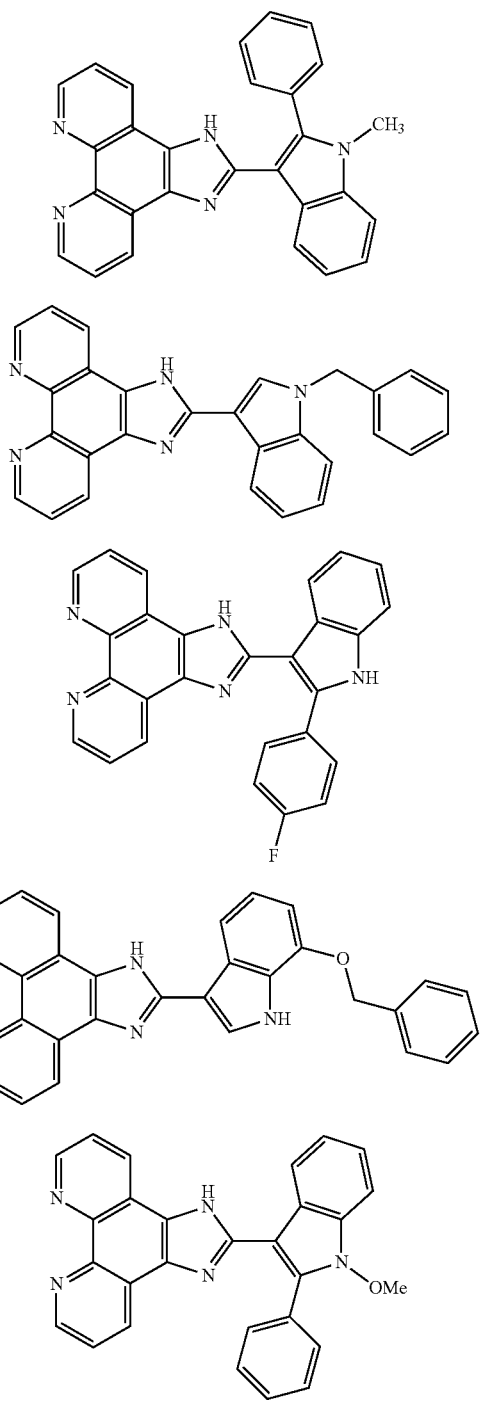

246

247

248

249

250

The present invention includes pharmaceutically acceptable salts of the compounds defined by Formula I. Compounds according to the present invention can possess a sufficiently acidic, a sufficiently basic, or both functional groups, and accordingly react with a number of organic and inorganic bases, and organic and inorganic acids, to form pharmaceutically acceptable salts.

The term "pharmaceutically acceptable salt" as used herein, refers to a salt of a compound of Formula I, which is substantially non-toxic to living organisms. Typical pharmaceutically acceptable salts include those salts prepared by reaction of the compound of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulphuric acid, phosphoric acid, and the like, and organic acids such as p-toluenesulphonic acid, methanesulphonic acid, oxalic acid, p-bromophenylsulphonic acid, carbonic acid, succinic acid, citric acid, benzoic acid, acetic acid, and the like. Examples of such pharmaceutically acceptable salts are the sulphate, pyrosulphate, bisulphate, sulphite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulphonate, phenylacetate, phenylpropionate, phenylbutyrate, citrate, lactate, gamma-hydroxybutyrate, glycolate, tartrate, methanesulphonate, propanesulphonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulphonic acid.

Salts of amine groups may also comprise quaternary ammonium salts in which the amino nitrogen carries a suitable organic group such as an alkyl, lower alkenyl, substituted lower alkenyl, lower alkynyl substituted lower alkynyl, or aralkyl moiety.

Base addition salts include those derived from inorganic bases, such as ammonium or alkali or alkaline earth metal hydroxides, carbonates, bicarbonates, and the like. Bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

One skilled in the art will understand that the particular counterion forming a part of a salt of this invention is usually not of a critical nature, so long as the salt as a whole is pharmacologically acceptable and as long as the counterion does not contribute undesired qualities to the salt as a whole. The present invention further encompasses the pharmaceutically acceptable solvates of a compound of Formula I. Many of the compounds of Formula I can combine with solvents such as water, methanol ethanol and acetonitrile to form pharmaceutically acceptable solvates such as the corresponding hydrate, methanolate, ethanolate and acetonitrilate.

The compounds of the present invention may have multiple asymmetric (chiral) centres. As a consequence of these chiral centres, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

It will be readily understood by one skilled in the art that if the stereochemistry of a compound of Formula I is critical to its activity, then the relative stereochemistry of the compound is established early during synthesis to avoid subsequent stereoisomer separation problems. Further manipulation of the molecule will then employ stereospecific procedures so as to maintain the desired chirality.

Non-toxic metabolically-labile esters or amides of a compound of Formula I are those that are hydrolysed in vivo to afford the compound of Formula I and a pharmaceutically acceptable alcohol or amine. Examples of metabolically-labile esters include esters formed with (1-6C) alkanols, in which the alkanol moiety may be optionally substituted by a (1-8C) alkoxy group, for example methanol, ethanol, propanol and methoxyethanol. Non-limiting examples of metabolically-labile amides include amides formed with amines such as methylamine.

II. Preparation of Compounds of Formula I

As is known in the art, triaryl imidazole compounds can be prepared by a number of standard techniques. Compounds of Formula I, therefore, can be prepared by several general synthetic methods, for example, as described by Grimmett, (Grimmett, M. R., *Comprehensive Heterocyclic Chemistry: The Structure, Reaction, Synthesis and Uses of Heterocyclic Compounds*, A. R. Katrizky and C. W. Rees, eds., Vol. 5, Pergamon Press. Oxford, 1984, pp. 457-498; Grimmett, M. R., *Imidazole and Benzimidazole Synthesis*, Academic Press, San Diego Calif., 1997).

In one embodiment of the present invention, compounds of Formula I are prepared via solution or solid phase synthesis, by reacting a dione of Formula II with the aldehyde (III) at elevated temperature in the presence of ammonium acetate in acetic acid (see, for example, Krieg et al., *Naturforsch.* 1967, 22b:132; Sarshar et al., *Tetrahedron Lett.* 1996, 37:835-838).

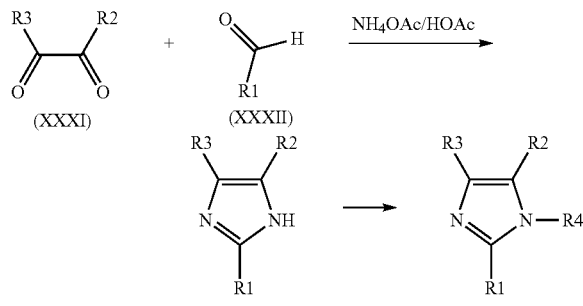

The compounds of Formula (XXXI) and (XXXII) are either commercially available or may be prepared using standard procedures known to a person skilled in the relevant art. Compounds of Formula (XXXI), therefore, can be prepared by several general synthetic methods, for example, as described by: Fischer et. al (*J. Am. Chem. Soc.* 1961, 83, 4208-4210); Guijarro et al. (*J. Am. Chem. Soc.* 1999, 121, 4155-4157); Chi et. al. (*Synth. Comm.* 1994, 24(15), 2119-2122) and Armesto et. al. (*Synthesis,* 1988, 799-801).

Compounds of formula XXXI can also be prepared:

i) by oxidizing a compound of formula (XXXIII). Compounds of formula (XXXIII), in turn can be prepared by reacting a compounds of formula (XXXIV) with sodium cyanide in the presence of a solvent as shown below, wherein R3=R2 and R2 is as defined above:

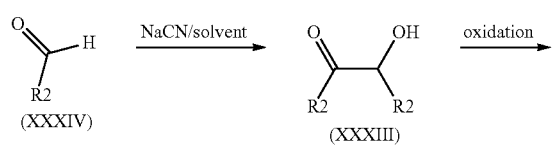

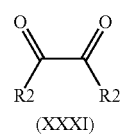

or, ii) by oxidizing a compound of formula (XXXV). Compounds of formula (XXXV), in turn can be prepared by treating a compound of formula (XXXIV) and a compound of formula (XXXVI) with sodium cyanide in the presence of a solvent as shown below, wherein R2 and R3 are as defined above:

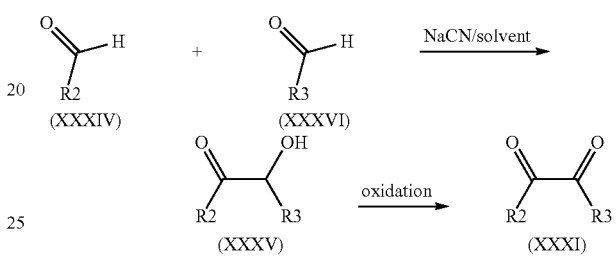

or, iii) by oxidizing a compound of formula (XXXVII). Compounds of formula (XXXVII) in turn can be prepared by oxidizing a compound of formula (XXXVIII) or (XXXIX) as shown below, wherein R2 and R3 are as defined above:

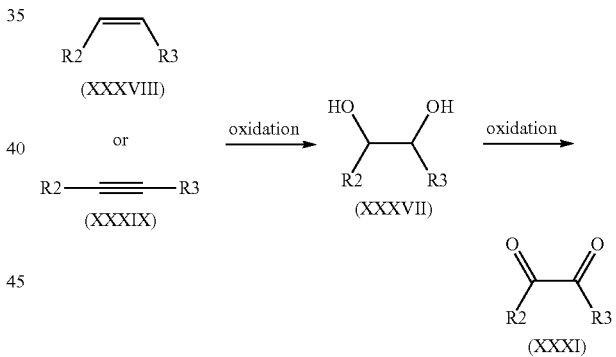

or, iv) by oxidizing a compound of formula (XXXIX) using PdCl₂ in DMSO, or, v) by deprotecting and oxidizing a compound of formula (XL). Compounds of formula (XL) in turn can be prepared by reacting a compound of formula (XLI) with a compound of formula (XLII) in the presence of a suitable base:

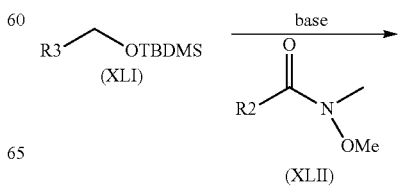

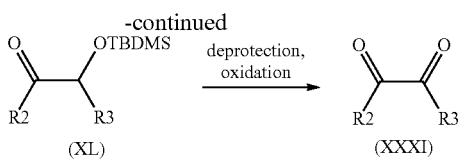

wherein R2 and R3 are independently aryl, substituted aryl, heteroaryl or substituted heteroaryl,
or,
vi) by reacting a compound of formula (XLIII) with a substituted or unsubstituted aryl or substituted or unsubstituted heteroaryl under Friedel-Crafts acylation conditions or by nucleophilic displacement of the chloride in compound of formula (XLIII). Compounds of formula (XLIII) in turn can be prepared by reacting a substituted or unsubstituted aryl or substituted heteroaryl or unsubstituted heteroaryl with oxalyl chloride under Friedel-Crafts acylation conditions:

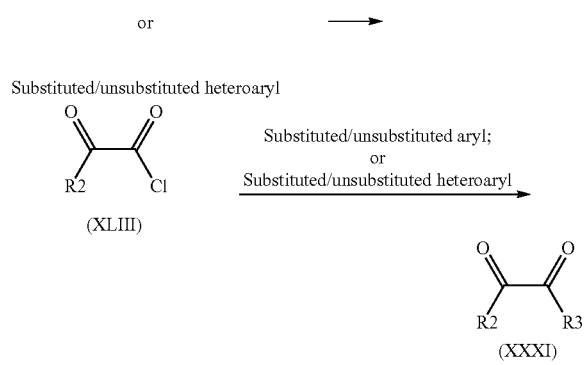

wherein R2 and R3 are independently aryl, substituted aryl, heteroaryl or substituted heteroaryl;
or
vii) by oxidising a compound of formula (XLIV). Compounds of formula (XLIV) in turn can be prepared by reacting a compound of formula (XLV) with thionyl chloride in benzene with catalytic dimethylformamide to form an intermediate (XLVI). This intermediate (XLVI) is then used directly without purification in a Freidel-Crafts reaction to produce the ketone (XLIV).

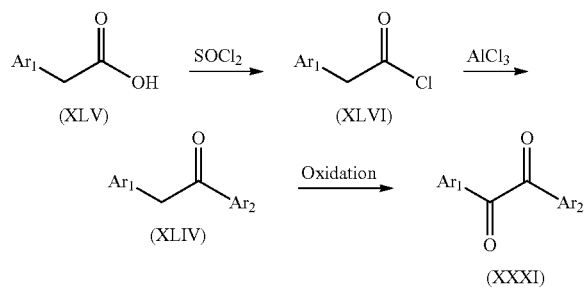

III. Anti-Cancer Activity of Compounds of Formula I

The ability of a candidate compound of Formula I to inhibit neoplastic cell growth and/or proliferation can be tested using standard techniques known in the art. In addition, compounds of Formula I that demonstrate inhibitory activity may be further tested in vitro and/or in vivo in combination with various known chemotherapeutics to evaluate their potential use in combination therapies. Exemplary methods of testing candidate compounds of Formula I are provided below and in the Examples included herein. One skilled in the art will understand that other methods of testing the compounds are known in the art and are also suitable for testing candidate compounds.

A. In Vitro Testing

Candidate compounds of Formula I can be assayed initially in vitro for their ability to inhibit cell growth (i.e. their cytotoxicity) using standard techniques. In general, cells of a specific test cell line (typically a cancer cell line) are grown to a suitable density (e.g. approximately $1 \times 10^4$) and the candidate compound is added. After an appropriate incubation time (typically between about 48 to 74 hours), cell survival is assessed, for example, by assaying for tetrazolium salt (or modified tetrazolium salt) cleavage, or by using the resazurin reduction test (see Fields & Lancaster (1993) *Am. Biotechnol. Lab.* 11:48-50; O'Brien et al., (2000) *Eur J. Biochem.* 267: 5421-5426 and U.S. Pat. No. 5,501,959), the sulforhodamine assay (Rubinstein et al., (1990) *J. Natl. Cancer Inst.* 82:113-118) or the neutral red dye test (Kitano et al. (1991) *Euro. J. Clin. Investg.* 21:53-58; West et. al. (1992) *J. Investigative Derm.* 99:95-100). Inhibition of cell growth is determined by comparison of cell survival in the treated culture with cell survival in one or more control cultures, for example, cultures not pre-treated with the candidate compound and/or those pre-treated with a control compound (typically a known therapeutic). Other suitable techniques for assessing cytotoxicity are known in the art.

Assays that measure metabolic activity (such as tetrazolium-based assays) can also be used to assess the effect of candidate compounds on cell activation and/or proliferation, due the fact that proliferating cells are metabolically more active than resting cells.

Candidate compounds can also be tested in vitro for their ability to inhibit anchorage-independent growth of tumour cells. Anchorage-independent growth is known in the art to be a good indicator of tumourigenicity. In general, anchorage-independent growth is assessed by plating cells from an appropriate cancer cell-line onto soft agar and determining the number of colonies formed after an appropriate incubation period. Growth of cells treated with the candidate compound can then be compared with that of cells treated with an appropriate control (as described above).

A variety of cancer cell-lines suitable for testing the candidate compounds are known in the art. In one embodiment of the present invention, in vitro testing of the candidate compounds is conducted in a human cancer cell-line. Examples of suitable human cancer cell-lines for in vitro testing of the compounds of the present invention include, but are not limited to, colon and colorectal carcinoma cell lines such as HT-29, CaCo, LoVo, COLO320 and HCT-116; non small cell lung cancer cell lines such as NCI-H460, small cell lung cancer cell lines such as H209; breast cancer cell lines such as MCF-7, T47D and MDA-MB-231; ovarian cancer cell lines such as SK-OV-3; prostate cancer cell lines such as PC-3 and DU-145; chronic myeloid leukaemia cell lines such as K562; bladder cancer cell lines such as T24; brain cancer cell lines such as U-87-MG; pancreatic cancer cell lines such as AsPC-1, SU.86.86 and BxPC-3; kidney cancer cell lines such as A498 and Caki-1; liver cancer cell lines such as HepG2, and skin cancer cell lines such as A2058 and C8161. Drug-resistant cancer cell lines can be used to determine the ability of the compounds of the present invention to inhibit growth and/or proliferation of drug- or multi-drug resistant neoplastic cells.

The selectivity of the candidate compounds of Formula I may also be tested, i.e. the ability of the compound to demonstrate some level of selective action toward neoplastic (or cancer) cells in comparison to normal proliferating cells. An exemplary method of assessing the differential sensitivity between normal and cancer cells for a compound has been described by Vassilev et al. (*Anti-Cancer Drug Design* (2001) 16:7). This method involves the comparison of $IC_{90}$ values, i.e. the molar concentration of a test compound required to cause 90% growth inhibition of exponentially growing cells. Thus, the $IC_{90}$ values for candidate compounds can be evaluated in various cancer cell lines (such as those outlined above) and normal cells (such as HUVEC and/or WI38 cells) and compared. $IC_{90}$ values can be measured using a variety of standard techniques including those described above for cytotoxicity testing.

While the mechanism of action of the compounds of Formula I is not relevant to the instant invention, assays to investigate potential mechanisms of action of the compounds may be conducted if desired in order to provide information useful in determining what aspects of tumour growth the compounds affect. This type of information may help to determine cancer types that will benefit from treatment with the compounds. Examples of such assays include, but are not limited to, cell-cycle analysis (for example, employing flow cytometry techniques), apoptosis assays (such as DNA fragmentation analysis), anti-angiogenesis assays (for example, various Matrigel assays, including cord formation and Matrigel plug assays) and immunohistochemical analysis.

Toxicity of the candidate compounds can also be initially assessed in vitro using standard techniques. For example, human primary fibroblasts can be treated in vitro with a compound of Formula I and then tested at different time points following treatment for their viability using a standard viability assay, such as the assays described above or the trypan-blue exclusion assay. Cells can also be assayed for their ability to synthesize DNA, for example, using a thymidine incorporation assay, and for changes in cell cycle dynamics, for example, using a standard cell sorting assay in conjunction with a fluorocytometer cell sorter (FACS).

B. In Vivo Testing

The ability of the candidate compounds to inhibit tumour growth, proliferation and/or metastasis in vivo can be determined in an appropriate animal model using standard techniques known in the art (see, for example, Enna, et al., *Current Protocols in Pharmacology*, J. Wiley & Sons, Inc., New York, N.Y.). Exemplary protocols are provided below and in the Examples. Non-limiting examples of suitable animal models are provided in Table 1.

In general, current animal models for screening anti-tumour compounds are xenograft models, in which a human tumour has been implanted into an animal. For example, the candidate compounds can be tested in vivo on solid tumours using mice that are subcutaneously grafted or injected with 30 to 60 mg of a tumour fragment, or an appropriate number of tumour cells (e.g. about $10^6$ to $10^7$) on day 0. The animals bearing tumours are mixed before being subjected to the various treatments and controls. In the case of treatment of advanced tumours, tumours are allowed to: develop to the desired size, animals having insufficiently developed tumours being eliminated. The selected animals are distributed at random to undergo the treatments and controls. Animals not bearing tumours may also be subjected to the same treatments as the tumour-bearing animals in order to be able to dissociate the toxic effect from the specific effect on the tumour. Chemotherapy generally begins from 3 to 22 days after grafting, depending on the type of tumour, and the animals are observed every day. Candidate compounds can be administered to the animals, for example, by bolus infusion. The different animal groups are weighed about 3 or 4 times a week until the maximum weight loss is attained, after which the groups are weighed at least once a week until the end of the trial.

The tumours are measured about 2 or 3 times a week until the tumour reaches a pre-determined size and/or weight, or until a pre-determined time period has passed, or until the animal dies (if this occurs before the tumour reaches the pre-determined size/weight). The animals are then sacrificed and the tissue histology, size and/or proliferation of the tumour assessed.

If desired, one or more standard immunohistochemical tests may also be conducted on tissues isolated from the test animals in order to, determine the effects of the compound on tumour growth, differentiation, apoptosis and/or angiogenesis. Examples of such tests include, but are not limited to, the use of specific antibodies (for example, antibodies against Ki-67 to assess proliferation, CD31 to assess angiogenesis, NK1.1 as an indication of the presence of NK cells, F4/80 as an indication of the presence of macrophages) and TUNEL assays to determine apoptosis.

Other models, such as orthopedic implantation of tumours into animals (i.e. the implantation of cancer cells of a certain type into the corresponding tissue in the animal, such as pancreatic cancer cells into the pancreas), may also be used to assess the effect of the candidate compounds on tumour growth and proliferation. In addition, the effect of the candidate compound on spontaneous tumours in normal mice can be assessed.

The effect of the candidate compounds on drug-resistant tumours can be assessed in vivo by utilising a drug- or multidrug-resistant cancer cell in the xenograft experiments.

For the study of the effect of the candidate compounds on haematologic tumours, such as lymphomas or leukaemias, the animals are grafted or injected with a particular number of cells, and the anti-tumour activity is determined by the increase in the survival time of the treated mice relative to the controls.

To study the effect of the candidate compounds on tumour metastasis, tumour cells are typically treated with the compound ex vivo and then injected into a suitable test animal. The spread of the tumour cells from the site of injection is then monitored over a suitable period of time.

The ability of the candidate compounds to act in combination with, or to sensitise a tumour to the effects of, another chemotherapeutic agent can also be tested in the above models. In this case, the test animals would be treated with both the chemotherapeutic agent and the candidate compound of Formula I. Control animals could include, animals treated with the chemotherapeutic alone, animals treated with the candidate compound alone and/or untreated animals.

In vivo toxic effects of the compounds of Formula I can be evaluated by standard techniques, for example, by measuring their effect on animal body weight during treatment and by performing haematological profiles and liver enzyme analysis after the animal has been sacrificed (survival assays).

TABLE I

Examples of in vivo models of human cancer

| Cancer Model | Cell Type |
| --- | --- |
| Tumour Growth Assay<br>Human solid tumour xenografts in mice (sub-cutaneous injection) | Prostate (PC-3, DU145)<br>Breast (MDA-MB-231, MVB-9)<br>Colon (HT-29)<br>Lung (NCI-H460, NCI-H209)<br>Pancreatic (ASPC-1, SU86.86)<br>Pancreatic: drug resistant (BxPC-3)<br>Skin (A2058, C8161)<br>Cervical (SIHA, HeLa-S3)<br>Cervical: drug resistant (HeLa S3-HU-resistance)<br>Liver (HepG2)<br>Brain (U87-MG)<br>Renal (Caki-1, A498)<br>Ovary (SK-OV-3)<br>Bladder (T24) |
| Tumour Growth Assay<br>Human solid tumour isografts in mice (fat pad injection) | Breast: drug resistant (MDA-CDDP-S4, MDA-MB435-To.1) |
| Survival Assay<br>Experimental model of lymphoma and leukaemia in mice | Human: Burkitts lymphoma (Non-Hodgkin's) (raji)<br>Murine: erythroleukemia (CB7 Friend retrovirus-induced) |
| Experimental model of lung. metastasis in mice | Human: melanoma (C8161)<br>Murine: fibrosarcoma (R3) |

IV. Toxicity Testing

It is important that the anti-cancer compounds of the present invention exhibit low toxicity in vivo. Toxicity tests for potential drugs are well-known in the art (see, for example, Hayes, A. W., ed., (1994), *Principles and Methods of Toxicology*, 3rd ed., Raven Press, NY; Maines, M., ed., *Current Protocols in Toxicology*, John Wiley & Sons, Inc., NY).

In vitro acute toxicity testing of a compound of Formula I can be performed using mammalian cell lines (see, for example, Ekwall, B., *Ann. N.Y. Acad. Sci.*, (1983) 407:64-77). Selection of an appropriate cell line is dependent on the potential application of the candidate compound and can be readily determined by one skilled in the art.

In vivo toxicity testing can be performed by standard methodology. For example, by injecting varying concentrations of the candidate compound into an appropriate animal model. The compound can be injected once, or administration can be repeated over several days. The toxic effects of the compound can be evaluated over an appropriate time period by monitoring the general health and body weight of the animals. After the completion of the period of assessment, the animals can be sacrificed and the appearance and weight of the relevant organs determined. An indication of the toxicity of a compound can also be obtained during the in vivo anti-cancer testing of the compound.

V. Therapeutic Uses of Compounds of Formula I

The compounds of Formula I can be used in the treatment and/or stabilisation of various types of cancers. In this context, the compounds may exert either a cytotoxic or cytostatic effect resulting in a reduction in the size of a tumour, the slowing or prevention of an increase in the size of a tumour, an increase in the disease-free survival time between the disappearance or removal of a tumour and its reappearance, prevention of an initial or subsequent occurrence of a tumour (e.g. metastasis), an increase in the time to progression, reduction of one or more adverse symptom associated with a tumour, or an increase in the overall survival time of a subject having cancer. The compounds can be used alone or they can be used as part of a multi-drug regimen in combination with one or more known therapeutics.

Examples of cancers which may be may be treated or stabilized in accordance with the present invention include, but are not limited to haematologic neoplasms, including leukaemias and lymphomas; carcinomas, including adenocarcinomas; melanomas and sarcomas. Carcinomas, adenocarcinomas and sarcomas are also frequently referred to as "solid tumours." Examples of commonly occurring solid tumours include, but are not limited to, cancer of the brain, breast, cervix, colon, head and neck, kidney, lung, ovary, pancreas, prostate, stomach and uterus, non-small cell lung cancer and colorectal cancer. Various forms of lymphoma also may result in the formation of a solid tumour and, therefore, are also often considered to be solid tumours. One embodiment of the present invention provides for the use of the compounds of Formula I in the treatment and/or stabilisation of a solid tumour.

The term "leukaemia" refers broadly to progressive, malignant diseases of the blood-forming organs. Leukaemia is typically characterized by a distorted proliferation and development of leukocytes and their precursors in the blood and bone marrow but can also refer to malignant diseases of other blood cells such as erythroleukaemia, which affects immature red blood cells. Leukaemia is generally clinically classified on the basis of (1) the duration and character of the disease—acute or chronic; (2) the type of cell involved—myeloid (myelogenous), lymphoid (lymphogenous) or monocytic, and (3) the increase or non-increase in the number of abnormal cells in the blood—leukaemic or aleukaemic (subleukaemic). Leukaemia includes, for example, acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, aleukocythemic leukaemia, basophylic leukaemia, blast cell leukaemia, bovine leukaemia, chronic myelocytic leukemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "sarcoma" generally refers to a tumour which originates in connective tissue, such as muscle, bone, cartilage or fat, and is made up of a substance like embryonic connective tissue and is generally composed of closely packed cells embedded in a fibrillar or homogeneous substance. Sarcomas include soft tissue sarcomas, chondrosarcoma, fibrosarcoma; lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumour sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented haemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumour arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colorectal carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, haematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, non-small cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "carcinoma" also encompasses adenocarcinomas. Adenocarcinomas are carcinomas that originate in cells that make organs which have glandular (secretory) properties or that originate in cells that line hollow viscera, such as the gastrointestinal tract or bronchial epithelia. Examples include, but are not limited to, adenocarcinomas of the breast, lung, colon, pancreas and prostate.

Additional cancers encompassed by the present invention include, for example, Hodgkin's Disease, Non-Hodgkin's lymphoma, multiple myeloma, neuroblastoma, rhabdomyosarcoma, primary thrombocytosis, primary macroglobulinemia, small-cell lung tumours, primary brain tumours, malignant pancreatic insulanoma, malignant carcinoid, urinary bladder cancer, premalignant skin lesions, gliomas, testicular cancer, thyroid cancer, esophageal cancer, genitourinary tract cancer, malignant hypercalcemia, endometrial cancer, adrenal cortical cancer, mesothelioma and medulloblastoma.

The cancer to be treated or stabilized may be indolent or it may be aggressive. The compounds of the invention can be used to treat refractory cancers, advanced cancers, recurrent cancers and metastatic cancers. One skilled in the art will appreciate that many of these categories may overlap, for example, aggressive cancers are typically also metastatic.

"Aggressive cancer," as used herein, refers to a rapidly growing cancer. One skilled in the art will appreciate that for some cancers, such as breast cancer or prostate cancer the term "aggressive cancer" will refer to an advanced cancer that has relapsed within approximately the earlier two-thirds of the spectrum of relapse times for a given cancer, whereas for other types of cancer, such as small cell lung carcinoma (SCLC), nearly all cases present rapidly growing cancers which are considered to be aggressive. The term can thus cover a subsection of a certain cancer type or it may encompass all of other cancer types. A "refractory" cancer or tumour refers to a cancer or tumour that has not responded to treatment. "Advanced cancer," refers to overt disease in a patient that is not amenable to cure by local modalities of treatment, such as surgery or radiotherapy. Advanced disease may refer to a locally advanced cancer or it may refer to metastatic cancer. The term "metastatic cancer" refers to cancer that has spread from one part of the body to another.

The present invention also contemplates the use of the compounds of Formula I as "sensitizing agents," which selectively inhibit the growth of cancer cells. In this case, the compound alone does not have a cytotoxic effect on the cancer cell, but provides a means of weakening the cancer cells, and thereby facilitates the benefit from conventional anti-cancer therapeutics.

Thus, the present invention contemplates the administration to a subject of a therapeutically effective amount of one or more compound of Formula I together with one or more anti-cancer therapeutics. The compound(s) can be administered before, during or after treatment with the anti-cancer therapeutic. An "anti-cancer therapeutic" is a compound, composition or treatment that prevents or delays the growth and/or metastasis of cancer cells. Such anti-cancer therapeutics include, but are not limited to, chemotherapeutic drug treatment, radiation, gene therapy, hormonal manipulation, immunotherapy and antisense oligonucleotide therapy. A wide variety of chemotherapeutic drugs are known in the art and can be used in combination therapies with a compound of the present invention. Examples of useful chemotherapeutic drugs include broad spectrum chemotherapeutics, i.e. those that are useful in the treatment of a range of cancers, such as doxorubicin, capecitabine, mitoxantrone, irinotecan (CPT-11), cisplatin and gemcitabine. Other examples of useful chemotherapeutic agents include, but are not limited to, hydroxyurea, busulphan, carboplatin, chlorambucil, melphalan, cyclophosphamide, Ifosphamide, danorubicin, epirubicin, vincristine, vinblastine, Navelbine® (vinorelbine), etoposide, teniposide, paclitaxel, docetaxel, cytosine, arabinoside, bleomycin, neocarcinostatin, suramin, taxol, mitomycin C and the like. The compounds of the invention are also suitable for use with standard combination therapies employing two or more chemotherapeutic agents. It is to be understood that anti-cancer therapeutics for use in the present invention also include novel compounds or treatments developed in the future.

VI. Pharmaceutical Compositions

The compounds of the present invention are typically formulated prior to administration. The present invention thus provides pharmaceutical compositions comprising one or more compounds of Formula I and a pharmaceutically acceptable carrier, diluent, or excipient. The pharmaceutical compositions are prepared by known procedures using well-known and readily available ingredients. Pharmaceutical compositions comprising one or more compounds of Formula I in combination with one or more known cancer chemotherapeutics are also contemplated by the present invention.

Compounds of the general Formula I or pharmaceutical compositions comprising the compounds may be administered orally, topically, parenterally, by inhalation or spray, or rectally in dosage unit formulations containing conventional non-toxic pharmaceutically acceptable carriers, adjuvants and vehicles. In the usual course of therapy, the active compound is incorporated into an acceptable vehicle to form a composition for topical administration to the affected area, such as hydropohobic or hydrophilic creams or lotions, or into a form suitable for oral, rectal or parenteral administration, such as syrups, elixirs, tablets, troches, lozenges, hard or soft capsules, pills, suppositiories, oily or aqueous suspensions, dispersible powders or granules, emulsions, injectables, or solutions. The term parenteral as used herein includes subcutaneous injections, intradermal, intra-articular, intravenous, intramuscular, intravascular, intrasternal, intrathecal injection or infusion techniques.

Compositions intended for oral use may be prepared in either solid or fluid unit dosage forms. Fluid unit dosage form can be prepared according to procedures known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Solid formulations such as tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anaesthetics, preservatives and buffering agents can also be included in the injectable solution or suspension.

The compound(s) of the general Formula I may be administered, together or separately, in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A, Lippincott, Williams & Wilkins, Philidelphia, Pa. (2000).

VII. Administration of Compounds of Formula I

Compounds of Formula I may be administered to a subject by a variety of routes depending on the cancer to be treated, for example, the compounds may be administered orally, topically, parenterally, by inhalation or spray, or rectally in dosage unit formulations. In one embodiment, the compounds are administered systemically to a subject, for example, by bolus injection or continuous infusion into a subject's bloodstream or by oral administration. When used in conjunction with one or more known chemotherapeutic agents, the compounds can be administered prior to, or after, administration of the chemotherapeutic agents, or they can be administered concomitantly. The one or more chemotherapeutic may also be administered systemically, for example, by bolus injection, continuous infusion, or oral administration.

The compounds of Formula I may be used as part of a neo-adjuvant therapy (to primary therapy), or as part of an adjuvant therapy regimen, where the intention is to cure the cancer in a subject. The present invention contemplates the use of the compounds of Formula I at various stages in tumour development and progression, including in the treatment of advanced and/or aggressive neoplasias (i.e. overt disease in a subject that is not amenable to cure by local modalities of treatment, such as surgery or radiotherapy), metastatic disease, locally advanced disease and/or refractory tumours (i.e. a cancer or tumour that has not responded to treatment).

"Primary therapy" refers to a first line of treatment upon the initial diagnosis of cancer in a subject. Exemplary primary therapies may involve surgery, a wide range of chemotherapies and radiotherapy. "Adjuvant therapy" refers to a therapy that follows a primary therapy and that is administered to subjects at risk of relapsing. Adjuvant systemic therapy is usually begun soon after primary therapy to delay recurrence, prolong survival or cure a subject.

It is contemplated that the compounds of the invention can be used alone or in combination with one or more other chemotherapeutic agents as part of a primary therapy or an adjuvant therapy. Combinations of the compounds of Formula I and standard chemotherapeutics may act to improve the efficacy of the chemotherapeutic and, therefore, can be used to improve standard-cancer therapies. This application can be important in the treatment of drug-resistant cancers which are not responsive to standard treatment. Drug-resistant cancers can arise, for example, from heterogeneity of tumour cell populations, alterations in response to chemotherapy and increased malignant potential. Such changes are often more pronounced at advanced stages of disease.

The dosage to be administered is not subject to defined limits, but it will usually be an effective amount. It will usually be the equivalent, on a molar basis of the pharmacologically active free form produced from a dosage formulation upon the metabolic release of the active free drug to achieve its desired pharmacological and physiological effects. The compositions may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. Examples of ranges for the compound(s) in each dosage unit are from about 0.05 to about 100 mg, or more usually, from about 1.0 to about 50 mg.

Daily dosages of the compounds of the present invention will typically fall within the range of about 0.01 to about 100 mg/kg of body weight, in single or divided dose. However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above, dosage range is given by way of example only and is not intended to limit the scope of the invention in any way. In some instances dosage levels below the lower limit of the aforesaid range may be more than adequate, while in other cases still larger doses may be employed without causing harmful side effects, for example, by first dividing the larger dose into several smaller doses for administration throughout the day.

VII. Kits

The present invention additionally provides for therapeutic kits containing one or more compounds of Formula I for use in the treatment of cancer. The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, for use or sale for human or animal administration.

When the components of the kit are provided in one or more liquid solutions, the liquid solution can be an aqueous solution, for example a sterile aqueous solution. For in vivo use, the compounds may be formulated into a pharmaceutically acceptable syringeable composition. In this case the container means may itself be an inhalant, syringe, pipette, eye dropper, or other such like apparatus, from which the formulation may be applied to an infected area of the subject, such as the lungs, injected into an subject, or even applied to and mixed with the other components of the kit.

Pharmaceutical kits or packs comprising one or more compound of the present invention in combination with one or more standard chemotherapeutic for combination therapy applications are also contemplated by the present invention. To gain a better understanding of the invention described herein, the following examples are set forth. It should be understood that these examples are for illustrative purposes only. Therefore, they should not limit the scope of this invention in any way.

EXAMPLES

Preparation of Compounds

All reactions have been carried out according to the scheme shown below:

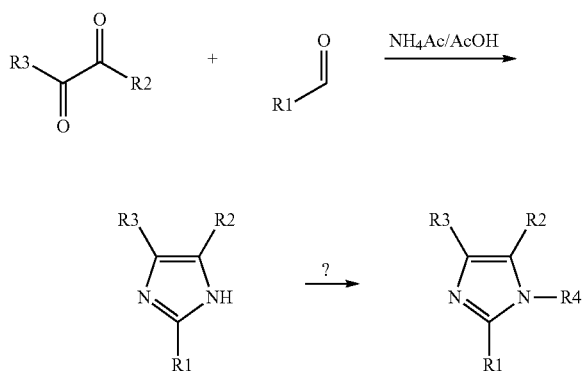

In a typical experimental procedure 1 mmol (1 equiv.) of the carboxyaldehyde was combined with 1.05-1.10 mmole (1.05-1.1 equiv.) of the dione- and 20 mmole (20 equiv.) of ammonium acetate and 5 ml of acetic acid. The mixture was magnetically stirred and heated to reflux for 3-5 hr. The reaction process was monitored by TLC, until complete consumption of the indole was achieved. The reaction mixture was cooled to room temperature and added drop-wise into well-stirred ice-water. The suspension solid was then filtered and the crude solid was dissolved in ethyl acetate, dried over sodium sulfate and filtered, the organic solvent was removed by vacuum. The products was then either recrystalized with alcohol or separated by column chromatography using petroleum ether-Ethyl acetate as an eluant.

Melting points were recorded using a MEL-TEMP capillary melting point apparatus, the melting point are uncorrected. $^1$H-NMR was performed in a 500 MHz Brucker instrument at room temperature using a suitable deuterated solvent.

Example 1

Preparation of Compound 2

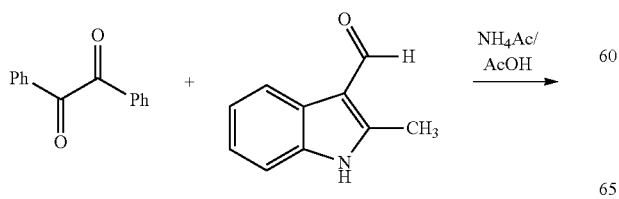

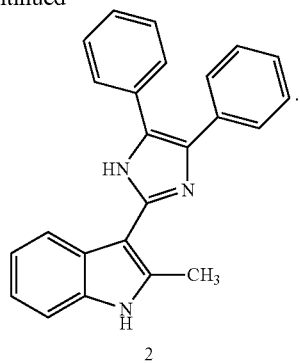

2

1 mmol (1 equiv.) of the indole carboxyaldehyde was combined with 1.05-1.10 mmole (1.05-1.1 equiv.) of the benzil and 20 mmole (20 equiv.) of ammonium acetate and 5 ml of acetic acid. The mixture was magnetically stirred and heated to reflux for 3-5 hr. The reaction process was monitored by TLC, until complete consumption of the indole was achieved. The reaction mixture was cooled to room temperature and added drop-wise into well-stirred ice-water. The suspension solid was then filtered and the crude solid was dissolved in ethyl acetate, dried over sodium sulfate and filtered, the organic solvent was removed by vacuum. The products was then either recrystalized with alcohol or separated by column chromatography using petroleum ether-Ethyl acetate as an eluant.

It is noteworthy that, the TLC of the products shows a characteristic blue florescent color under the UV (wave length λ=254 nm), a property used as an additional characterization feature.

$^1$H-NMR: δ (DMSO-$d_6$), 12.10 (s, 1H), 11.30 (s, 1H), 7.98 (d, 1H), 7.62 (d, 2H), 7.56 (d, 2H), 7.45 (t, 2H), 7.28-7.40 (m, 4H), 7.24 (t, 1H), 7.03-7.14 (m, 2H), 2.70 (s, 3H). HRMS m/z for $C_{24}H_{19}N_3$ calc. Is 349.157898. Found 349.157897. M.p.=decomposed at 260-264.

The following exemplary compounds were also prepared from the appropriate starting materials following the general synthetic procedure as discussed above.

Example 2

Compound 5

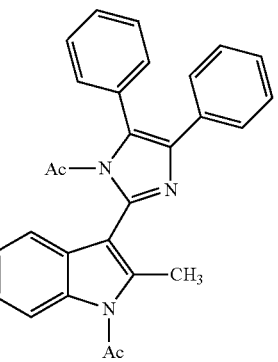

¹H-NMR (CDCl₃): δ=8.02 (d, 2H), 7.53 (d, 1H), 7.43-7.52 (m, 6H), 7.41 (d, 1H), 7.21-7.34 (m, 6H), 2.81 (s, 3H), 2.75 (s, 3H). EIMS [M⁺·] m/z for C₂₈H₂₃N₃O₂ is 433. M.p.=224-227.

Example 3

Compound 10

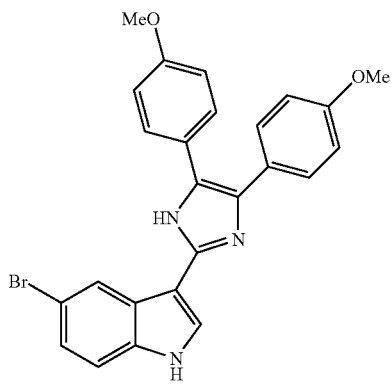

¹H-NMR (CDCl₃): δ=10.68 (bs, 1H), 7.73 (bs, 1H), 7.22 (d, 4H), 6.99 (bs, 1H), 6.92 (bd, 2H), 6.85 (bd, 2H), 6.611 (d, 4H), 3.70 (s, 6H). EIMS [M⁺·] m/z for C₂₅H₂₀BrO₂ is 474. M.p.=135.

Example 4

Compound 11

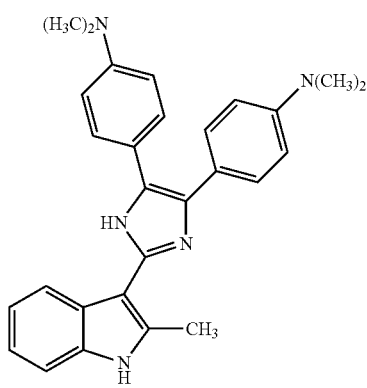

¹H-NMR (CDCl₃): δ=7.70 (d, 1H), 7.41 (d, 4H), 7.32 (d, 1H), 7.09 (q, 2H), 6.77 (d, 4H), 2.95 (s, 12H), 2.67 (s, 3H). EIMS [M⁺·] m/z for C₂₉H₂₉N₅ is 435, M.p.=decomposed at 236-238.

Example 5

Compound 13

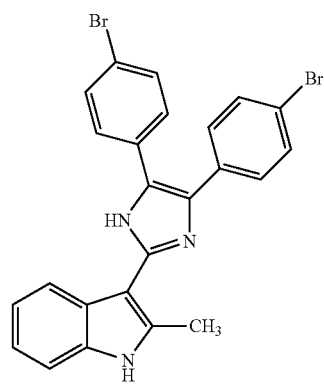

¹H-NMR (CDCl₃): δ=7.47 (d, 4H), 7.44 (d, 4H), 7.30-7.34 (m, 1H), 7.14-7.19 (m, 3H), 2.68 (bs, 3H), EIMS [M⁺·] m/z for C₂₄H₁₇N₃Br₂ is 507. M.p.=240-245.

Example 6

Compound 19

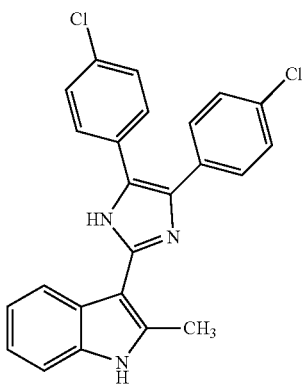

¹H-NMR (DMSO-d₆): δ=12.13 (s, 1H), 11.33 (s, 1H), 7.94 (d, 2H), 7.57 (d, 2H), 7.52 (bd, 2H), 7.39 (bd, 2H), 7.35 (d,

1H), 7.05-7.12 (m, 3H), 2.50 (s, 3H). EIMS [M+·] m/z for C$_{24}$H$_{17}$N$_3$Cl$_2$ is 418. M.p.=165-167.
Example 7
Compound 22
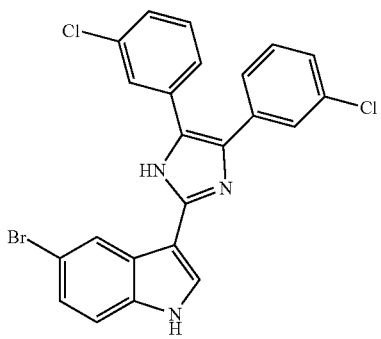
$^1$H-NMR (DMSO-d$_6$): δ=13.176 (s) 1H, 12.130 (s) 1H, 8.996 (d) 1H, 8.889 (d) 1H, 8.852 (d) 1H, 8.671 (d) 1H 8.412 (d) 1H, 8.378 (d) 1H, 7.775-7.750 (m) 2H, 7.640-7.600 (m) 2H.
Example 8
Compound 26
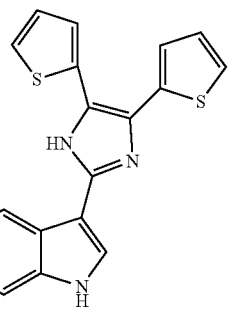
$^1$H-NMR (DMSO-d$_6$): δ=12.60 (s, 1H), 11.70 (s, 1H), 8.60 (d, 1H), 8.17 (s, 1H), 7.68 (bs, 1H), 7.46 (d, 2H), 7.33 (d, 2H), 7.25 (bs, 2H), 7.09 (bs, 1H). EIMS [M+·] m/z for C$_{19}$H$_{12}$N$_3$BrS$_2$ is 426.
Example 9
Compound 28
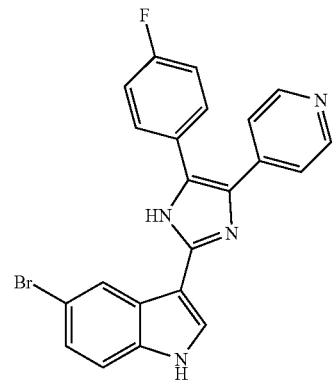
$^1$H-NMR (DMSO-d$_6$): δ=12.60 (s, 1H), 11.65 (s, 1H), 8.44-8.64 (m, 3H), 8.01-8.14 (m, 1H), 7.22-7.66 (m, 8H). EIMS [M+·] m/z for C$_{22}$H$_{14}$N$_4$BrF is 433. M.p.=decomposed at 343.
Example 10
Compound 29
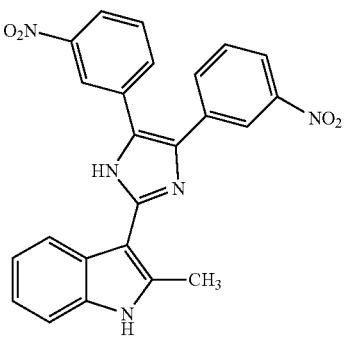
$^1$H-NMR (DMSO-d$_6$): δ=8.83 (q, 2H), 8.73 (m, 1H), 8.68 (d, 1H), 8.46 (d, 1H), 8.24 (s, 1H), 7.74 (t, 2H), 7.62 (t, 2H), 7.51-7.56 (m, 1H), 7.23-7.27 (m, 2H), 2.71 (s, 3H). EIMS [M+·] m/z for C$_{23}$H$_{15}$N$_3$ is 303. M.p.=135-137.
¹H-NMR (CDCl$_3$): δ=8.12 (bs, 1H), 7.48 (d, 2H), 7.46 (d, 2H), 7.23-7.34 (m, 8H). M.p.=230-232.
Example 11
Compound 31
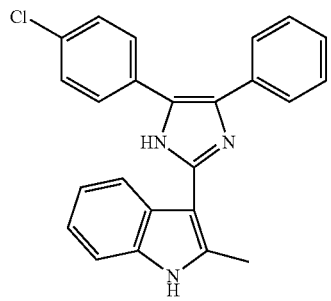
31
¹H-NMR (CDCl$_3$): δ=8.90 (s, 1H), 7.62 (bs, 1H), 7.48 (bd, 4H), 7.34 (m, 4H), 7.21 (m, 1H), 7.13 (m, 2H), 2.43 (bs, 3H). EIMS [M+·] m/z for C$_{23}$H$_{15}$N$_3$ClBr is 448. M.p.=decomposed at 218-220.
Example 13
Compound 34
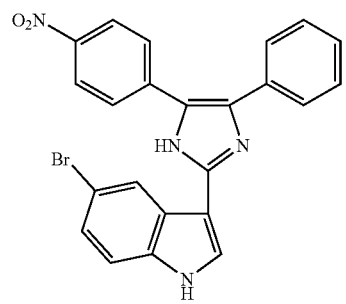
34
¹H-NMR (DMSO-d$_6$): δ=12.63 (s, 1H), 11.67 (s, 1H), 8.62 (d, 1H), 8.21 (d, 2H), 8.08 (d, 1H), 7.86 (d, 2H), 7.39-7.64 (m, 6H), 7.32 (dd, 1H). EIMS [M+·] m/z for C$_{23}$H$_{15}$N$_4$BrFO$_2$ is 459. M.p.=decomposed at 250-253.
Example 12
Compound 32
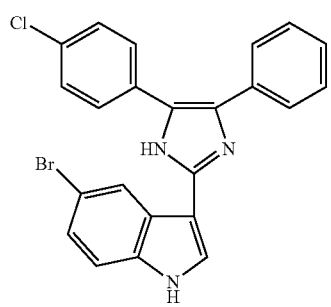
32
Example 14
Compound 35
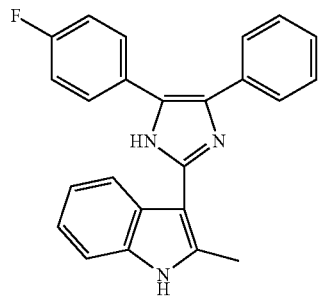
35
¹H-NMR (CDCl$_3$): δ=7.78 (bs, 1H), 7.59 (d, 2H), 7.54 (d, 2H), 7.35-7.39 (m, 2H), 7.28-7.34 (m, 2H), 7.13-7.18 (m, 2H), 7.01-7.05 (m, 2H), 2.72 (bs, 3H). EIMS [M+·] m/z for C$_{24}$H$_{18}$N$_3$F is 367. M.p.=decomposed at 247-250.

Example 15

Compound 36

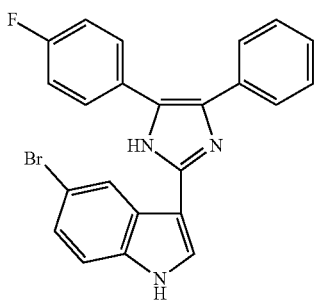

$^1$H-NMR (CDCl$_3$): δ=10.42 (bs, 1H), 7.86 (s, 1H), 7.16-7.33 (m, 6H), 7.04 (dd, 2H), 6.95 (dd, 2H), 6.88 (t, 3H). EIMS [M] m/z for C$_{23}$H$_{15}$N$_3$BrF is 432. M.p.=decomposed at 83-86.

Example 16

Compound 37

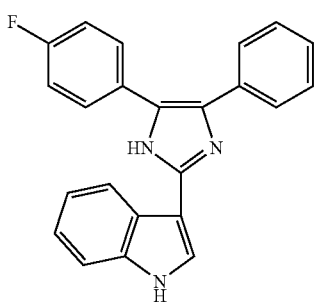

$^1$H-NMR (CDCl$_3$): δ=9.92 (bs, 1H), 8.17 (bs, 1H), 7.87 (t, 1H), 7.55 (bs, 1H), 7.21-7.33 (m, 6H), 7.15-7.2 (m, 1H), 7.04-7.07 (m, 2H), 6.90 (t, 2H)). EIMS [M+·] m/z for C$_{23}$H$_{16}$N$_3$F is 353. M.p.=51.

Example 17

Compound 38

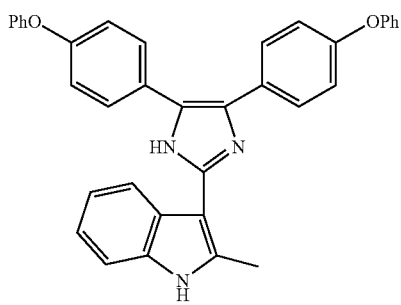

$^1$H-NMR (Acetone-d$_6$): δ=11.12 (bs, 1H), 10.46 (bs, 1H), 8.12 (d, 1H), 7.80 (bd, 2H), 7.62 (bd, 2H), 7.38-7.48 (m, 5H), 6.98-7.22 (m, 12H), 2.84 (bs, 3H). EIMS [M+·] m/z for C$_{36}$H$_{27}$N$_3$O$_2$ is 533. M.p.=decomposed at 128-130.

Example 18

Compound 40

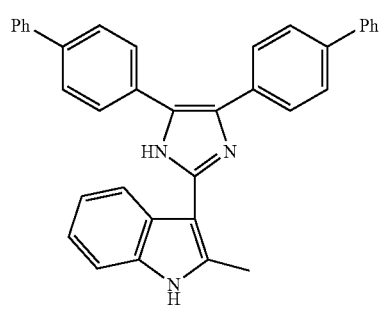

$^1$H-NMR (CDCl$_3$): δ=8.12 (dd, 2H), 7.60 (m, 6H), 7.24-7.53 (m, 10H), 6.87 (bd, 2H), 6.61 (bd, 2H), 2.08 (s, 3H). M.p.=decomposed at 142.

Example 19

Compound 41

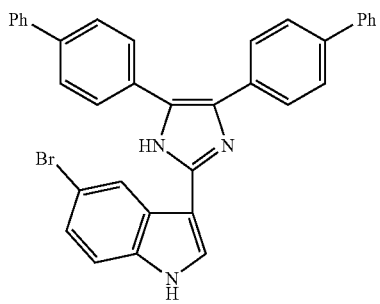

$^1$H-NMR (CDCl$_3$): δ=8.08 (d, 4H), 8.07 (bs, 1H), 7.75 (d, 4H), 7.28-7.50 (m, 10H), 7.12 (bd, 2H), 6.97 (bs, 1H) M.p.=155-158.

Example 20

Compound 42

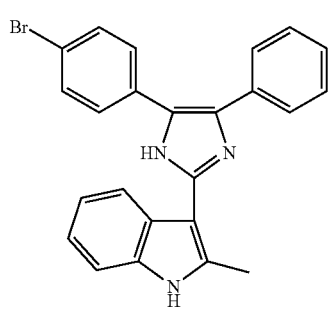

$^1$H-NMR (CDCl$_3$): δ=9.39 (bs, 1H), 7.39-7.50 (m, 4H), 7.28-7.38 (m, 6H), 7.06 (bs, 1H), 6.94 (bs, 2H), 2.08 (bs, 3H). EIMS [M$^{+\cdot}$] m/z for C$_{24}$H$_{18}$N$_3$Br is 428. M.p.=decomposed at 155-157.

Example 21

Compound 43

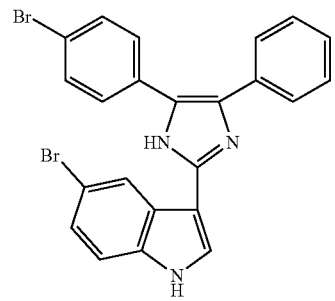

$^1$H-NMR (CDCl$_3$): δ=9.75 (bs, 1H), 7.83 (bs, 1H), 7.36 (m, 3H), 7.25-7.29 (m, 5H), 7.12 (m, 3H), 7.10 (bd, 1H). EIMS [M$^{+\cdot}$] m/z for C$_{23}$H$_{15}$N$_3$Br$_2$ is 493. M.p.=decomposed at 230.

Example 22

Compound 44

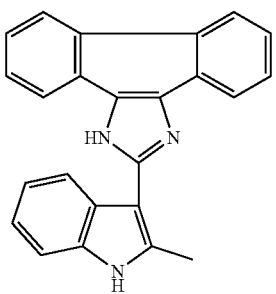

$^1$H-NMR (CDCl$_3$): δ=8.78 (dd, 2H), 8.19 (dd, 1H), 7.96 (bs, 1H), 7.80 (dd, 1H), 7.80 (dd, 1H), 7.55-7.77 (m, 6H), 7.16-7.42 (m, 2H), 2.87 (bs, 3H). EIMS [M+·] m/z for C₂₄H₁₇N₃ is 347. M.p.=decomposed at 167.

Example 23

Compound 45

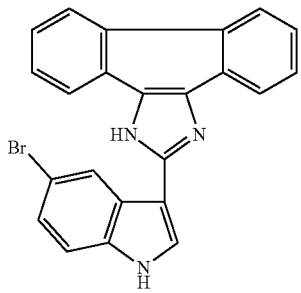

¹H-NMR (DMSO-d₆): δ=13.30 (bs, 1H), 11.62 (d, 1H), 8.87 (bd, 2H, 8.64 (bs, 1H), 8.44 (bs, 1H), 8.29 (t, 1H), 7.76 (t, 2H), 1.62 (t, 2H), 7.52 (d, 1H), 7.35-7.41 (m, 2H). EIMS [M+·] m/z for C₂₃H₁₄N₁₄Br is 412.

Example 24

Compound 46

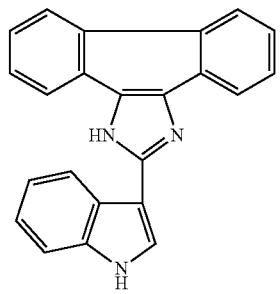

¹H-NMR (DMSO-d₆): δ=13.09 (s, 1H), 11.61 (d, 1H), 8.83 (q, 2H), 8.73 (m, 1H), 8.68 (d, 1H), 8.46 (d, 1H), 8.24 (s, 1H), 7.74 (t, 2H), 7.62 (t, 2H), 7.51-7.56 (m, 1H), 7.23-7.27 (m, 2H). EIMS [M+·] m/z for C₂₃H₁₅N₃ is 333. M.p.=135-137.

Example 25

Compound 74

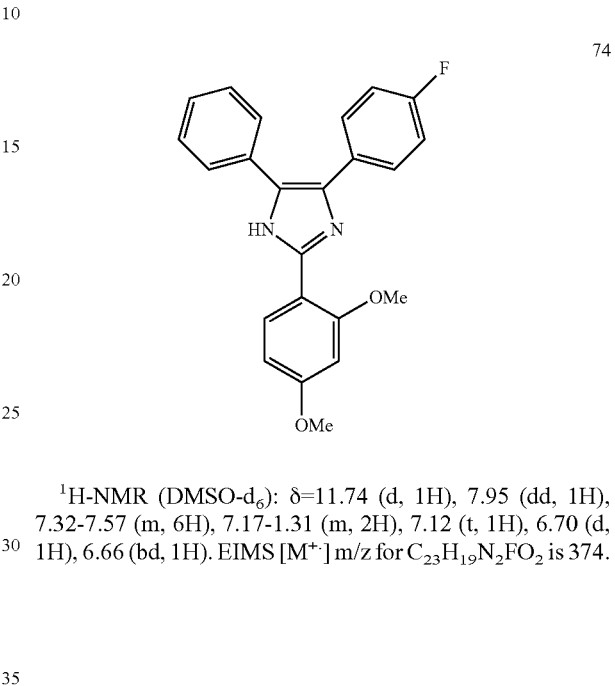

¹H-NMR (DMSO-d₆): δ=11.74 (d, 1H), 7.95 (dd, 1H), 7.32-7.57 (m, 6H), 7.17-1.31 (m, 2H), 7.12 (t, 1H), 6.70 (d, 1H), 6.66 (bd, 1H). EIMS [M+·] m/z for C₂₃H₁₉N₂FO₂ is 374.

Example 26

Compound 83

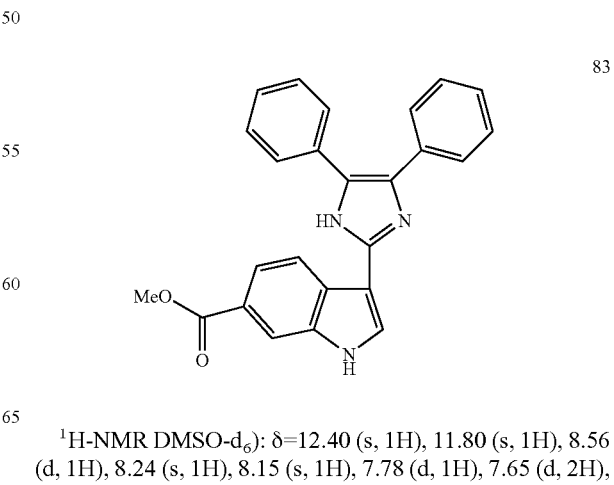

¹H-NMR DMSO-d₆): δ=12.40 (s, 1H), 11.80 (s, 1H), 8.56 (d, 1H), 8.24 (s, 1H), 8.15 (s, 1H), 7.78 (d, 1H), 7.65 (d, 2H), 7.54 (d, 2H), 747 (t, 2H), 7.32-7.42 (m, 3H), 7.24 (t, 1H), 3.90 (s, 3H). EIMS [M+] m/z for $C_{25}H_{19}N_3O_2$ is 393. M.p.=293-295.

Example 27

Compound 84

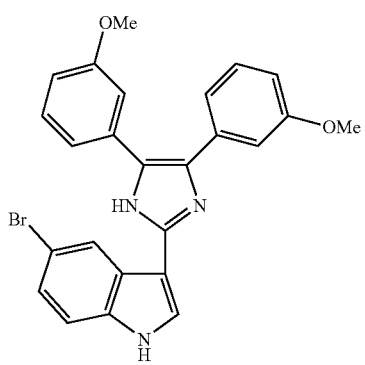

$^1$H-NMR (DMSO-$d_6$): δ=8.64 (d, 1H), 8.17 (d, 1H), 7.47 (d, 1H), 7.39 (t, 1H), 7.33 (dd, 1H), 7.20-7.31 (m, 2H), 7.12 (bd, 2H), 6.97 (bd, 1H), 6.84 (d, 1H), 3.77 (s, 3H), 3.72 (s, 3H), EIMS [M+] m/z for $C_{25}H_{20}N_3BrO_2$ is 474. M.p.=decomposed at 250-253.

Example 28

Compound 88

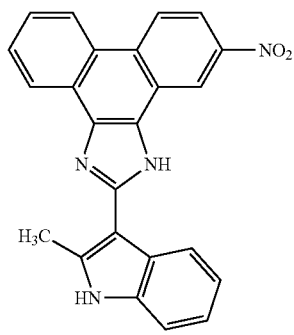 [SMILES: Cc1[nH]c2ccccc2c1-c1nc2c3ccccc3c3ccc([N+](=O)[O-])cc3c2[nH]1]

Mp 335-336° C. $^1$H-NMR DMSO-$d_6$), two isomers: 1) δ=13.160 (s) 1H, 11.602 (s) 1H, 9.720 (s) 1H, 9.143 (dd) 1H, 8.975 (dd) 1H, 8.680 (d) 1H, 8.345 (t) 1H, 8.160 (d) 1H, 7.870 (t) 1H, 7.720 (t) 1H, 7.420 (d) 1H, 7.200 (d) 2H, 2.862 (s) 3H.

2): δ=13.090 (s) 1H, 11.602 (s) 1H, 9.370 (s) 1H, 9.143 (dd) 1H, 8.975 (dd) 1H, 8.680 (d) 1H, 8.345 (t) 1H, 8.099 (d) 1H, 7.870 (t) 1H, 7.720 (t) 1H, 7.420 (d) 1H, 7.200 (d) 2H, 2.847 (s) 3H. EI-MS ($C_{24}H_{16}N_4O_2$)=392.

Example 29

Compound 90

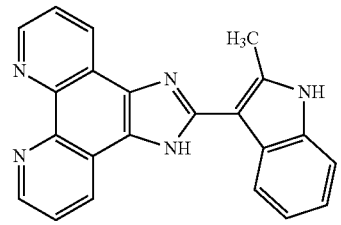 [SMILES: Cc1[nH]c2ccccc2c1-c1nc2c3cccnc3c3ncccc3c2[nH]1]

$^1$H-NMR (DMSO-$d_6$): δ=13.083 (s) 1H, 11.595 (s) 1H, 9.040-9.010 (m) 4H, 8.950 (d) 1H, 8.120 (m) 1H, 7.821 (t) 1H, 7.432 (m) 1H, 7.176 (m) 2H, 2.830 (s) 3H.

Example 30

Compound 92

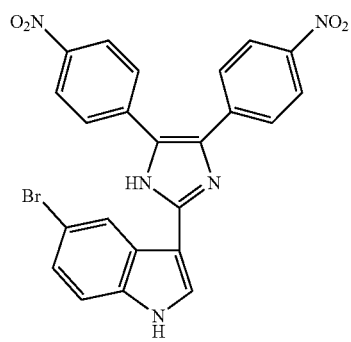 [SMILES: O=[N+]([O-])c1ccc(-c2nc(-c3c[nH]c4ccc(Br)cc34)[nH]c2-c2ccc([N+](=O)[O-])cc2)cc1]

$^1$H-NMR (DMSO-$d_6$): δ=12.729 (s) 1H, 11.724 (s) 1H, 8.578 (d) 1H, 8.325 (d) 2H, 8.260 (d) 2H, 8.127 (d) 1H, 7.871 (m) 2H, 7.810-7.785 (m) 2H, 7.454 (d) 1H, 7.330 (d) 1H.

Example 31

Compound 94

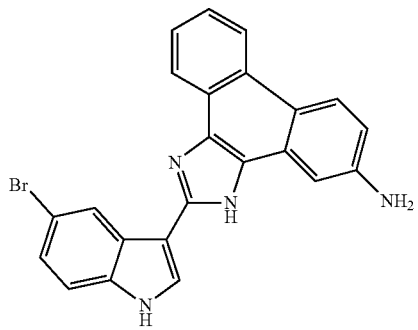 [SMILES: Nc1ccc2c3ccccc3c3nc(-c4c[nH]c5ccc(Br)cc45)[nH]c3c2c1]

Mp 300-303° C. $^1$H-NMR (DMSO-$d_6$): δ=12.55 (s) 1H, 8.83 (m) 3H, 8.68 (m) 1H, 8.50 (m) 1H, 8.15 (m) 1H, 7.75 (m) 2H, 7.65 (m) 1H, 7.47 (m) 1H, 7.40 (m) 1H. ESI-MS ($C_{23}H_{15}BrN_4$)=427.
Example 32
Compound 96
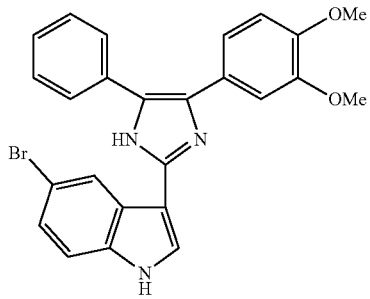 [SMILES: COc1ccc(-c2nc(-c3c[nH]c4ccc(Br)cc34)[nH]c2-c2ccccc2)cc1OC]
Mp 265-266° C. $^1$H-NMR (DMSO-$d_6$): δ=12.1 (s) 1H, 11.6 (s) 1H, 8.7 (d) 1H, 8.0 (d) 1H, 7.3 (m) 10H, 3.8 (d) 3H, 3.6 (d) 3H. ESI-MS ($C_{25}H_{20}BrN_3O_2$)=474.
Example 33
Compound 97
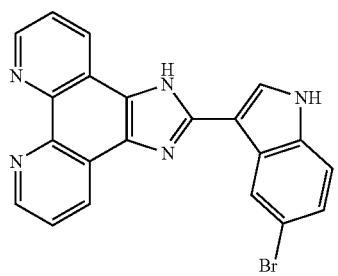
$^1$H-NMR (DMSO-$d_6$): δ=13.460 (s) 1H, 11.890 (s) 1H, 9.080-8.985 (m) 4H, 8.860-8.825 (m) 1H, 8.285 (d) 1H, 7.890-7.840 (m) 2H, 7.560-7.540 (m) 1H, 7.420-7.390 (m) 1H. ESI-MS ($C_{21}H_{12}BrN_5$)=414.
Example 34
Compound 101
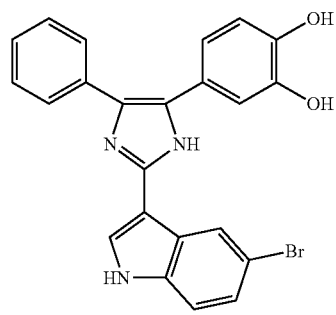 [SMILES: Oc1ccc(-c2[nH]c(-c3c[nH]c4ccc(Br)cc34)nc2-c2ccccc2)cc1O]
EI-MS: 484.00 ($C_{25}H_{18}BrN_5O$ requires 483.07) H$^1$ NMR (DMSO-$d_6$) d=13.167 (s) 1H, 11.845 (s) 1H, 8.839-8.781 (m) 4H, 8.292-8.405 (m) 2H, 7.364-7.697 (m) 5H, 3.543 (s) 1H, 3.410 (s) 2H, 1.463 (s) 2H.
Example 35
Compound 140

Mp 210-215° C. ¹H-NMR (DMSO-d₆): δ=12.18 (s) 1H, 11.54 (s) 1H, 9.08 (d) 1H, 8.62 (s) 1H, 8.65 (s) 1H, 7.20 (m) 10H.
Example 36
Compound 141
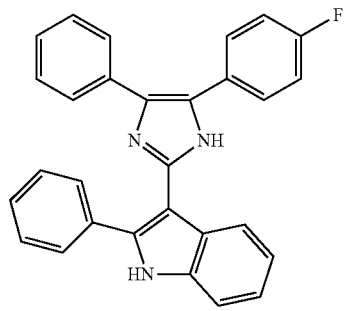 [SMILES: Fc1ccc(-c2[nH]c(-c3c(-c4ccccc4)[nH]c4ccccc34)nc2-c2ccccc2)cc1]
¹H-NMR (DMSO-d₆): δ=12.30 (s) 1H, 11.70 (s) 1H, 7.79 (m) 3H, 7.58 (m) 2H, 7.43 (m) 7H, 7.32 (m) 2H, 7.23 (m) 2H, 7.14 (m) 2H.
Example 37
Compound 146
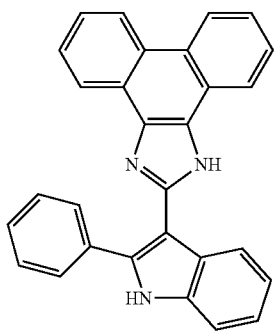 [SMILES: c1ccc(-c2[nH]c3ccccc3c2-c2nc3c4ccccc4c4ccccc4c3[nH]2)cc1]
Mp 240-242° C. ¹H-NMR DMSO-d₆): δ=12.20 (s) 1H, 11.90 (s) 1H, 8.85 (m) 2H, 8.60 (d) 1H, 8.40 (d) 1H, 7.70 (m) 8H, 7.30 (m) 5H.
Example 38
Compound 152
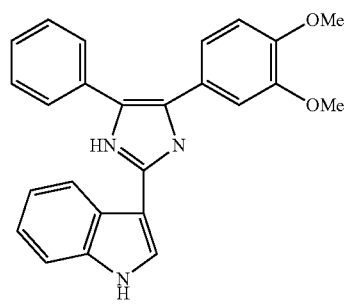 [SMILES: COc1ccc(-c2[nH]c(-c3c[nH]c4ccccc34)nc2-c2ccccc2)cc1OC]
Mp 258-259° C. ¹H-NM (DMSO-d₆), two isomers: 1) δ=12.160 (s) 1H, 11.350 (s) 1H, 8.480 (t) 1H, 7.995 (d) 1H, 6.995 (d) 1H, 7.440-7.420 (m) 2H, 7.360-7.300 (m) 2H, 7.220-7.020 (m) 5H, 3.805 (s) 3H, 3.695 (s) 3H.
2) δ=12.190 (s) 1H, 11.350 (s) 1H, 8.480 (t) 1H, 7.995 (d) 1H, 6.995 (d) 1H, 7.440-7.420 (m) 2H, 7.360-7.300 (m) 2H, 7.220-7.020 (m) 5H, 3.762 (s) 3H, 3.617 (s) 3H.
Example 39
Compound 156
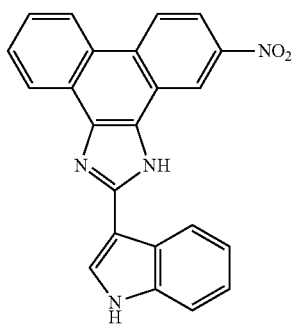 [SMILES: O=[N+]([O-])c1ccc2c3ccccc3c3nc(-c4c[nH]c5ccccc45)[nH]c3c2c1]
Mp 365-366° C. ¹H-NMR (DMSO-d₆), two isomers: a) δ=13.410 (s) 1H, 11.670 (s) 1H, 9.40 (d) 1H, 9.11 (d) 1H, 8.96 (d) 1H, 8.70 (d) 1H, 8.35-8.18 (m) 2H, 7.96 (s) 1H, 7.70 (t) 1H, 7.56 (t) 1H, 7.28 (m) 2H.

b) δ=13.290 (s) 1H, 11.67 (s) 1H, 9.305 (d) 1H, 9.095 (d) 1H, 8.960 (d) 1H, (d) 1H, 8.70 (d) 1H, 8.495 (d) 1H, 7.87 (d) 1H, 7.70 (t) 1H, 7.56 (t) 1H, 7.28 (m) 2H. EI-MS ($C_{23}H_{14}N_4O_2$)=378.

Example 40

Compound 157

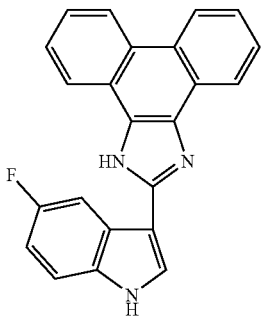 [SMILES: Fc1ccc2[nH]cc(-c3nc4c5ccccc5c5ccccc5c4[nH]3)c2c1]

$^1$H-NMR (DMSO-$d_6$): δ=13.102 (s) 1H, 11.702 (s) 1H, 8.900-8.840 (m) 3H, 8.690 (d) 1H, 8.445-8.400 (m) 3H, 8.301 (d) 1H, 7.747 (t) 1H, 7.644-7.624 (m) 1H, 7.622-7.605 (m) 1H, 7.585-7.529 (m) 1H, 7.128-7.086 (m) 1H, EI-MS ($C_{23}H_{14}N_3F$)=351.

Example 41

Compound 160

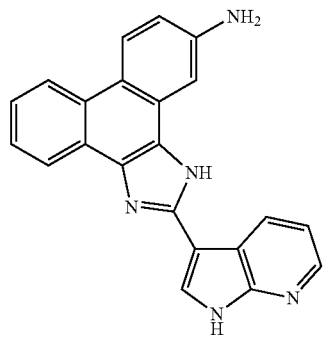 [SMILES: Nc1ccc2c3ccccc3c3nc(-c4c[nH]c5ncccc45)[nH]c3c2c1]

Mp 320=330° C. $^1$H-NMR (DMSO-$d_6$): δ=13.30 (exc.) 1H, 12.92 (d) 1H, 8.64 (d) 1H, 8.56 (d) 1H, 8.43 (m) 2H, 7.62 (m) 4H, 7.34 (t) 1H, 7.03 (d) 1H, 5.95 (exc.) 2H.

Example 42

Compound 162

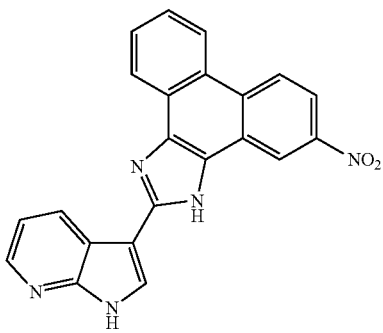 [SMILES: O=[N+]([O-])c1ccc2c3ccccc3c3nc(-c4c[nH]c5ncccc45)[nH]c3c2c1]

Mp>400° C. $^1$H NMR (DMSO-$d_6$): δ=13. (s) 1H, 12.25 (s) 1H, 9.41 (d) 1H, 9.13 (t) 1H, 8.98 (m) 2H, 8.37 (m) 3H, 7.96 (s) 1H, 7.89 (t) 1H, 7.73 (t) 1H, 7.36 (m) 1H. EI-MS ($C_{22}H_{13}N_5O_2$)=379.

Example 43

Compound 169

Mp 236-237° C. EI-MS: 633.87 ($C_{32}H_{19}Br_2N_5$) require 633.33. $^1$H-NM (DMSO-$d_6$), two isomers: 1) δ=13.190 (s) 1H, 11820 (s) 1H, 8.955 (s) 1H, 8.910-8.883 (m) 3H, 8.640 (d) 1H, 8.590 (d) 1H, 8.280 (d) 2H, 8.157 (d) 1H, 7.730 (t) 1H, 8.620 (t) 1H, 7.525 (s) 1H, 7.509 (s) 1H, 7.410 (d) 1H, 7.375 (d) 1H.

2) δ=13.190 (s) 1H, 12.060 (s) 1H, 8.955 (s) 1H, 8.910-8.883 (m) 3H, 8.640 (d) 1H, 8.590 (d) 1H, 8.280 (d) 2H, 8.157 (d) 1H, 7.730 (t) 1H, 8.620 (t) 1H, 7.525 (s) 1H, 7.509 (s) 1H, 7.410 (d) 1H, 7.375 (d) 1H.
Example 44
Compound 175
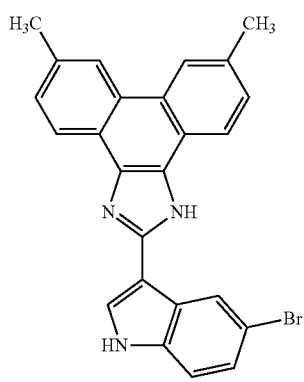 [SMILES: Cc1ccc2c(c1)c1cc(C)ccc1c1[nH]c(-c3c[nH]c4ccc(Br)cc34)nc21]
EI-MS: 440.11 ($C_{25}H_{18}BrN_3$ requires 440.07. $^1$H-NMR (DMSO-d$_6$): δ=13.141 (s) 1H, 11.779 (s) 1H, 8.842 (d) 1H, 8.673 (s) 1H, 8.636 (s) 1H, 8.508 (d) 1H, 8.295 (d) 1H, 8.242 (d) 1H, 7.553 (d) 2H, 7.508 (d) 1H, 7.365 (d) 1H, 2.612 (s) 6H.
1H, 7.65 (m) 2H, 7.54 (t) 1H, 7.47 (m) 3H, 7.28 (m) 3H, 7.08 (m) 4H, 2.70 (s) 3H, EI-MS ($C_{28}H_{21}N_3$)=399.
Example 46
Compound 181
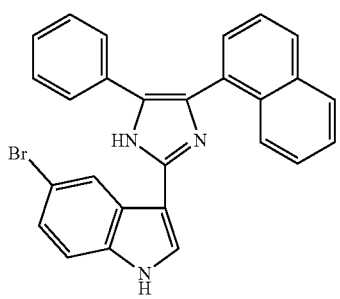
Mp 308-310° C. $^1$H-NMR (DMSO-d$_6$), two isomers: 1) δ=12.547 (s) 1H, 11.570 (s) 1H, 8.739 (d) 1H, 8.200-8.790 (m) 3H, 7.695 (m) 2H, 7.570-7.060 (m) 10H.
2) δ=12.575 (s) 1H, 11.620 (s) 1H, 8.478 (d) 1H, 8.200-8.790 (m) 3H, 7.695 (m) 2H, 7.570-7.060 (m) 10H, ESI-MS ($C_{27}H_{18}BrN_3$)=464.
Example 45
Compound 180
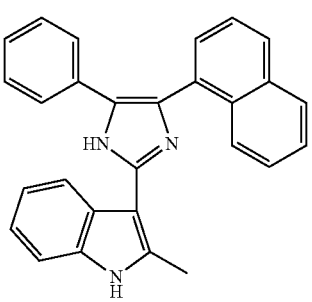 [SMILES: Cc1[nH]c2ccccc2c1-c1nc(-c2cccc3ccccc23)c(-c2ccccc2)[nH]1]
Mp 239-240° C. $^1$H-NMR (DMSO-d$_6$): δ=12.12 (s) 1H, 11.30 (s) 1H, 8.07 (d) 1H, 8.03 (d) 1H, 7.93 (d) 1H, 7.72 (d)
Example 47
Compound 182
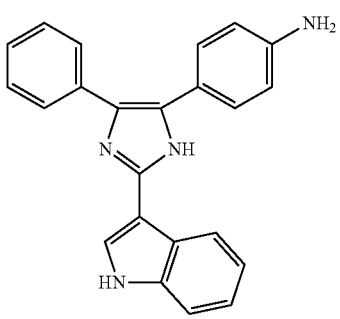 [SMILES: Nc1ccc(-c2[nH]c(-c3c[nH]c4ccccc34)nc2-c2ccccc2)cc1]

Mp 264-265° C. $^1$H-NMR (DMSO-$d_6$): δ=12.0 (s) 1H, 11.3 (s) 1H, 8.46 (d) 1H, 7.96 (d) 1H, 7.67 (d) 2H, 7.51 (d) 1H, 7.43 (d) 1H, 7.39 (t) 1H, 7.28 (t) 2H, 7.15 (m) 1H, 6.62 (d) 2H, EI-MS ($C_{23}H_{18}N_4$)=350.

Example 48

Compound 183

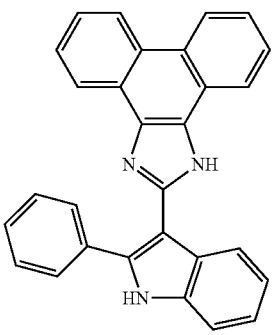 [SMILES: c1ccc(-c2[nH]c3ccccc3c2-c2nc3c4ccccc4c4ccccc4c3[nH]2)cc1]

Mp 240-242° C. $^1$H-NMR (DMSO-$d_6$): δ=12.20 (s) 1H, 11.90 (s) 1H, 8.85 (m) 2H, 8.60 (d) 1H, 8.40 (d) 1H, 7.70 (m) 8H, 7.30 (m) 5H.

Example 49

In Vitro Inhibition of Proliferation of Cancer Cells #1

Selected compounds of Formula I were tested for anti-cancer activity in vitro using a human colon carcinoma cells (HT-29) and human non-small cell lung cancer cells (H460). The cells were maintained in α-MEM medium (Wisent, St-Bruno, Qc) supplemented with 10% FBS, and grown at 37° C. in an atmosphere of 5% $CO_2$. Cells were transferred onto 150 mm tissue culture plates and grown until sub-confluency (70-80%) prior to their use.

The anti-cancer activity in vitro was evaluated by a cell proliferation assay based on the ability of live cells to reduce the tetrazolium salt XTT to orange coloured compounds of formazan (XTT cell proliferation kit II, Roche Applied Science, Montreal, QC).

Approximately $4 \times 10^3$ colon cancer cells (HT-29) or $2 \times 10^3$ non-small cell lung cancer cells (NCI-H460) in 100 μl of complete culture medium were plated onto 96 well microtiter plates and incubated overnight at 37° C. The medium was then removed by inverting the plate and patting on a sterile absorbent cloth. Fifty μl of medium containing the test compound at either 25 or 100 μM were added to the wells containing cells and incubated at 37° C. in an atmosphere of 5% $CO_2$ for 48 h. Following incubation, 25 μl of an XTT reaction mixture (XTT at a final concentration of 0.3 mg/ml) were added to each well and the plates were incubated for a further 4 h. The absorbance of each sample was then determined at a wavelength of 490 nm/650 nm as reference. Each compound was tested in duplicate and the results are reported as averages. Table II shows the effect that different compounds of Formula I have on the growth of human colon carcinoma HT-29. Table III shows the effect that different compounds of Formula I have on the growth of human non-small cell lung cancer cells (H460).

TABLE II

Inhibition of Proliferation of Human Colon Carcinoma (HT-29) Cells

| | 100 μM | | 25 μM | |
|---|---|---|---|---|
| Compound | % Survival | SD (%) | % Survival | SD (%) |
| 5 | 110.7 | 1.9 | 110.9 | 2.8 |
| 6 | 3.2 | 0.2 | 11.7 | 1.6 |
| 9 | 15.1 | 2.8 | 68.3 | 16 |
| 10 | 7.6 | 0.5 | 25.8 | 2.6 |
| 11 | 94.3 | 3.6 | 107.8 | 1 |
| 13 | 82.4 | 0.8 | 105.9 | 5.4 |
| 14 | 3.8 | 0.5 | 55.2 | 15.7 |
| 19 | 37.1 | 7.2 | 105.5 | 2.9 |
| 20 | 28.1 | 5 | 100 | 2.7 |
| 23 | 45.7 | 5.8 | 98.2 | 0 |
| 25 | 39.8 | 4.7 | 63.9 | 1.6 |
| 27 | 35 | 0.6 | 62.3 | 2.4 |
| 29 | 20.9 | 1 | 37.1 | 6.2 |
| 31 | 24.9 | 1.8 | 98.6 | 3.3 |
| 32 | 7.7 | 0.6 | 22.7 | 0 |
| 33 | 10 | 0.3 | 56.1 | 5.9 |
| 34 | 10.8 | 0 | 22.8 | 2 |
| 35 | 2.5 | 0.3 | 44.1 | 4.4 |
| 36 | 4.7 | 0.8 | 31.6 | 2.2 |
| 38 | 35.7 | 1.5 | 67 | 7.9 |
| 39 | 53 | 0.3 | 96.2 | 4 |
| 40 | 36.7 | 1.8 | 79.1 | 1.4 |
| 42 | 1.8 | 0 | 59.9 | 0.1 |
| 43 | 5.7 | 0.3 | 28 | 6.8 |
| 44 | 6.5 | 0.4 | 63.6 | 2.9 |
| 45 | 35 | 0.6 | 88.9 | 3.3 |
| 46 | 4.5 | 0 | 16.1 | 1 |
| 73 | 62.2 | 3.2 | 65 | 2 |
| 83 | 109.5 | 4.7 | 100.3 | 1.1 |
| CPT-11 | 51.1 | 3.2 | 82.3 | 10 |
| Vehicle | 100 | 7 | 100 | 7 |

TABLE III

Inhibition of Proliferation of Human Lung Carcinoma (NCI-460) Cells

| | 100 μM | | 25 μM | |
|---|---|---|---|---|
| Compound | % Survival | SD (%) | % Survival | SD (%) |
| 5 | 106 | 2.6 | 102 | 0.7 |
| 6 | 1.9 | 0.5 | 10.4 | 0.8 |
| 9 | 8.4 | 1.6 | 98.2 | 1 |
| 10 | 2.7 | 0.1 | 26.9 | 1.6 |
| 11 | 101.6 | 8.3 | 98.8 | 3.3 |
| 13 | 96.2 | 1.1 | 101.9 | 4 |
| 14 | 1.8 | 0.1 | 83.5 | 20.4 |
| 19 | 27.3 | 6.1 | 89.2 | 0.2 |
| 20 | 82.1 | 20.6 | 98.6 | 2.1 |
| 23 | 92.1 | 0 | 96.3 | 0.9 |
| 25 | 89 | 3.4 | 99.5 | 0.8 |
| 27 | 43.1 | 1.4 | 93.5 | 0.2 |
| 29 | 20.2 | 1.4 | 73.8 | 2.2 |
| 31 | 37.6 | 5.6 | 94 | 2.3 |
| 32 | 2.9 | 0.5 | 15 | 0.2 |
| 33 | 9.4 | 2 | 73.4 | 2.2 |
| 34 | 7.6 | 0.9 | 17.4 | 0.2 |
| 35 | 1.2 | 0.1 | 83.8 | 8 |
| 36 | 2.4 | 0.3 | 24.5 | 2.1 |
| 38 | 12.2 | 1.6 | 98.8 | 2 |
| 39 | 17 | 0.7 | 98.1 | 0.3 |
| 40 | 7.7 | 0.5 | 97.6 | 3 |
| 42 | 1.2 | 0.1 | 66.1 | 16.9 |
| 43 | 3 | 0.1 | 18.8 | 1.5 |
| 44 | 3.4 | 1 | 77.3 | 5.3 |
| 45 | 32.7 | 5.5 | 96 | 1.1 |
| 46 | 1.9 | 0.1 | 11.5 | 1.4 |
| 73 | 53.5 | 1.3 | 89.2 | 0.6 |
| 83 | 109.2 | 1.5 | 100.9 | 2.6 |

TABLE III-continued
Inhibition of Proliferation of
Human Lung Carcinoma (NCI-460) Cells
| Compound | 100 μM | | 25 μM | |
|---|---|---|---|---|
| | % Survival | SD (%) | % Survival | SD (%) |
| CPT-11 | 6.1 | 0.5 | 32.2 | 4.5 |
| Vehicle | 100 | 3.4 | 100 | 3.4 |
Example 50
In Vitro Inhibition of Proliferation of Cancer Cells
2
The compounds listed below were tested for anti-cancer activity against several carcinoma cell lines as described below and in Examples 51-53.
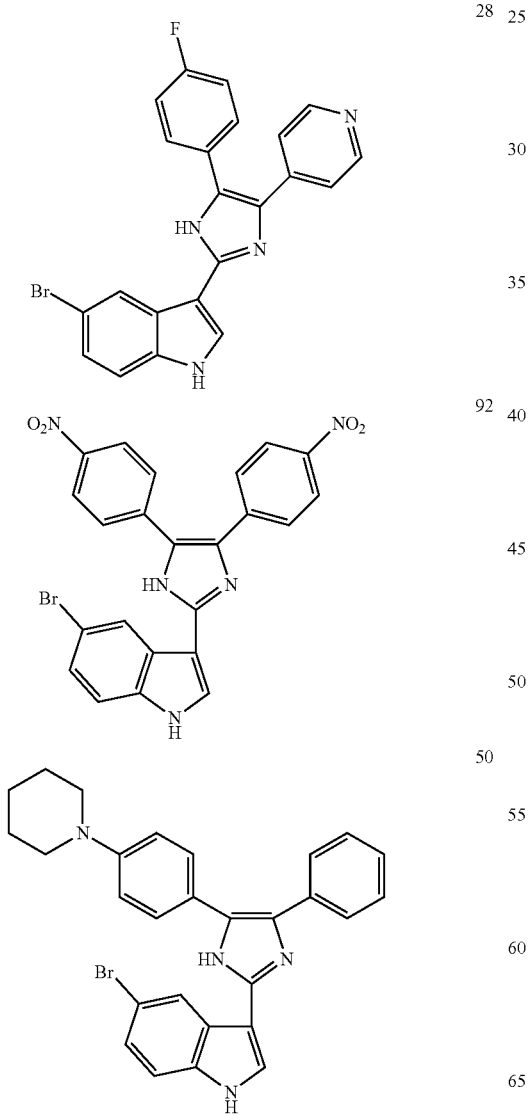
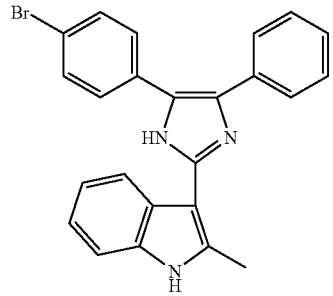
42
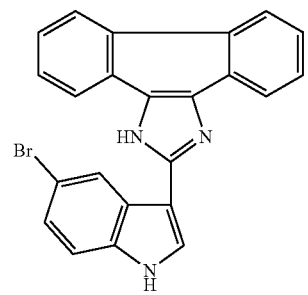
45
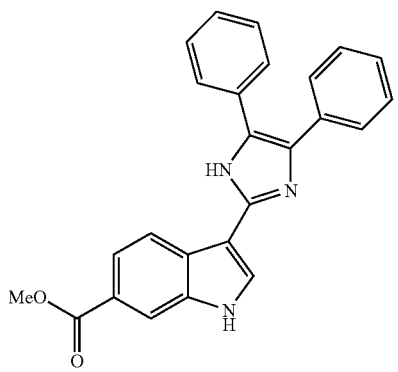
83
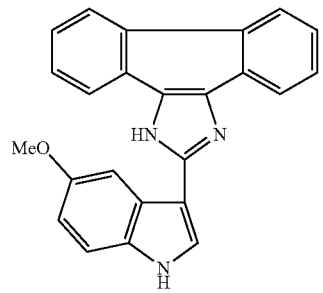
99
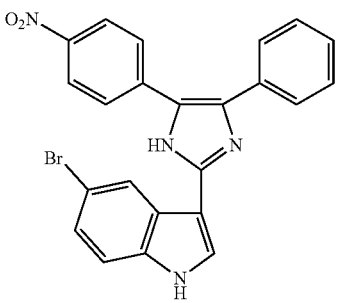
34

123
-continued
97
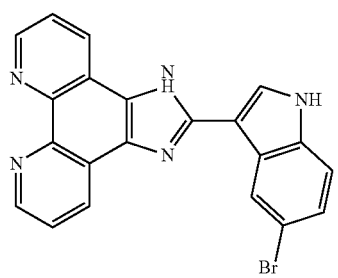
94
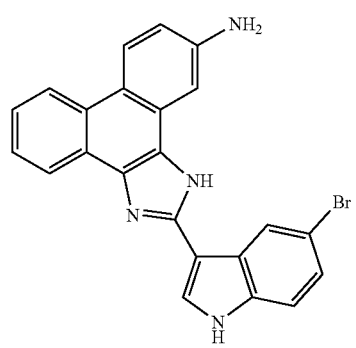
100
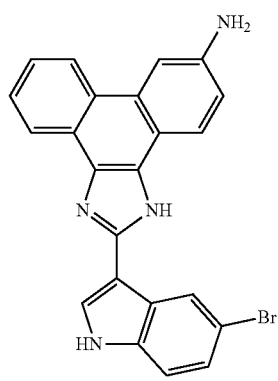
101
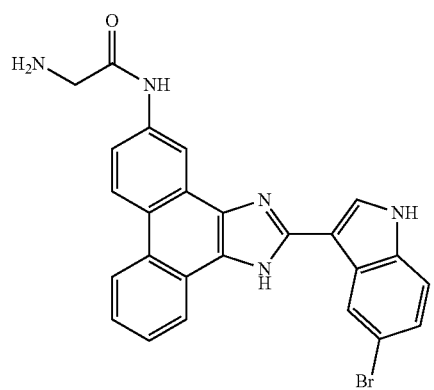
124
-continued
102
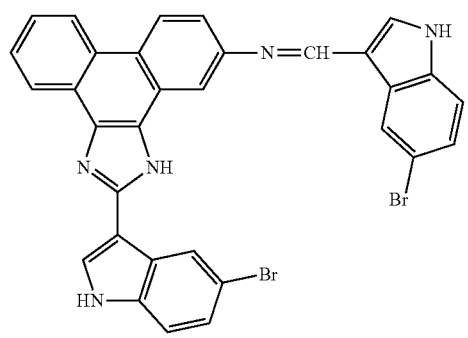
103
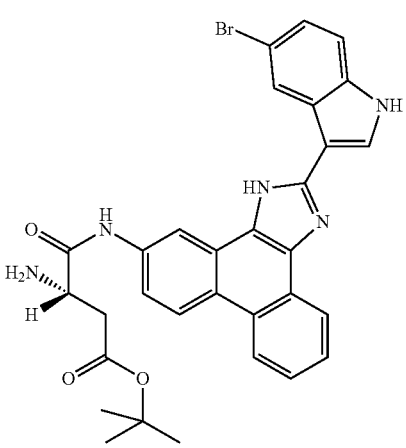
104
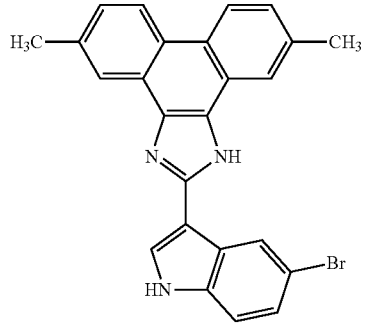
105
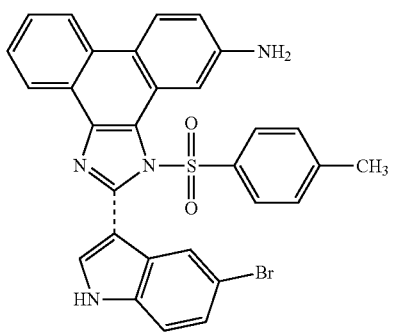

-continued

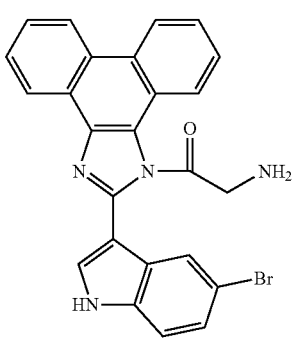

106

Cells were maintained in α-MEM medium (Wisent, St-Bruno, QC) supplemented with 10% FBS, and grown at 37° C. in an atmosphere of 5% $CO_2$. They were transferred onto 150 mm tissue culture plates and grown until sub-confluency (70-80%) prior to their use.

The anti-cancer activity in vitro was evaluated by a cell proliferation assay based in the ability of live cells to reduce the tetrazolium salt XTT to orange coloured compounds of formazan (XTT cell proliferation kit II, Roche Applied Science, Montreal, QC). The following cancer cell lines were tested: HT-29 colon carcinoma, A498 renal carcinoma, Caki-1 renal carcinoma, C8161 melanoma, MA-MB-231 breast adenocarcinoma, A2058 metastatic melanoma, SK-OV-3 ovarian adenocarcinoma, Hep G2 liver carcinoma, AsPC-1 pancreatic adenocarcinoma, PC3 metastatic prostate adenocarcinoma WI 38 is a human lung fibroblast cell line.

Approximately $2-3 \times 10^3$ cells in 100 μl of complete culture medium were plated onto 96-well microtiter plates and incubated overnight at 37° C., the medium was removed by inverting plate and patting on sterile absorbent cloth. Fifty μl of medium containing the different compounds at different concentrations were added and wells were incubated at 37° C. with 5% $CO_2$ for 48 h. Following incubation, 25 μl of an XTT reaction mixture (XTT at a final concentration of 0.3 mg/ml) were added and wells were incubated for 4 h. The absorbance of each sample was determined at a wavelength of 490 nm/650 nm as reference. The percentage of survival was determined by the ratio between absorbance values of cells incubated with the different compounds and their respective controls (cells incubated with vehicle only). The results are shown in FIGS. 1-4.

Figure 2:
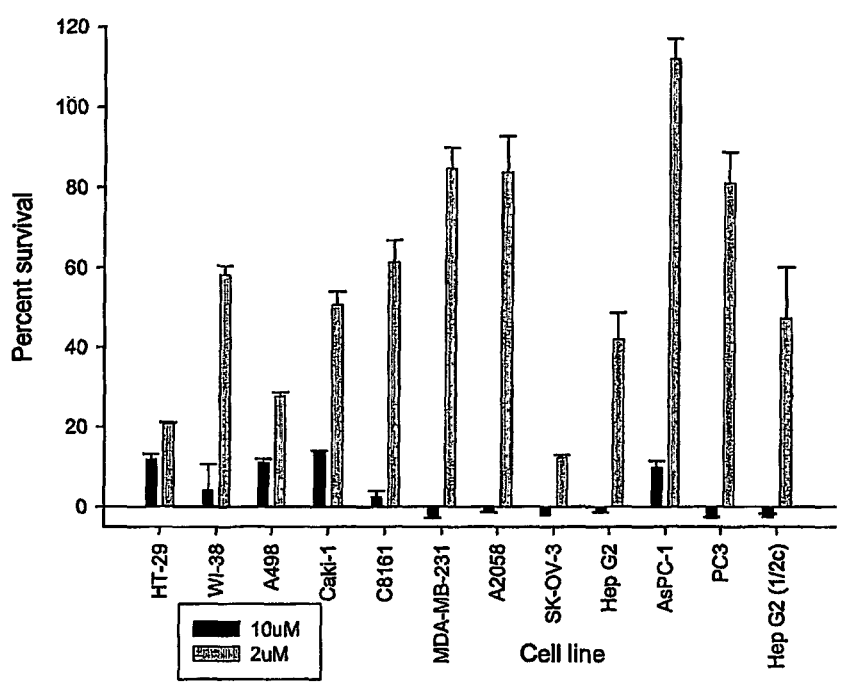
FIG. 2 depicts the effects of a compound 28 on the proliferation of various cancer cell lines in vitro.
Figure 3:
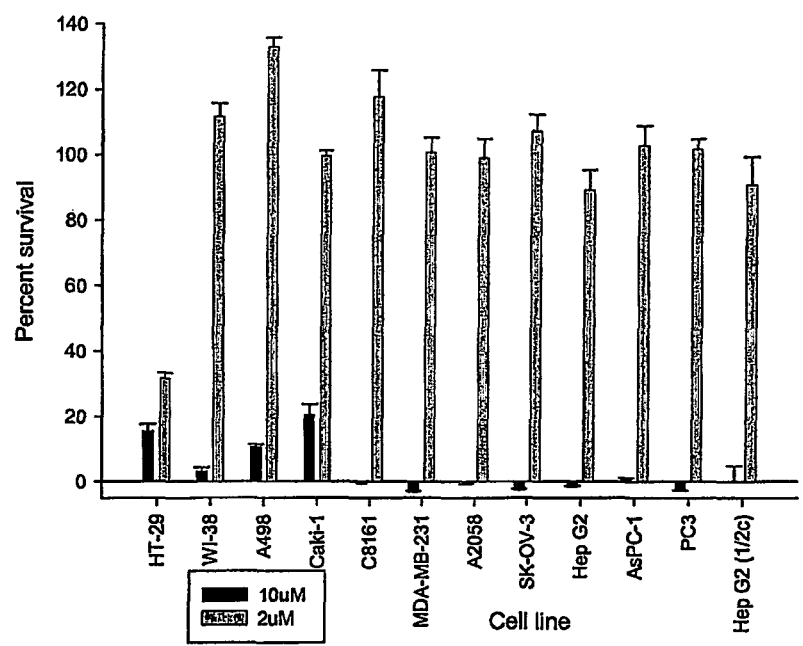
FIG. 3 depicts the effects of a compound 50 on the proliferation of various cancer cell lines in vitro.
Figure 4:
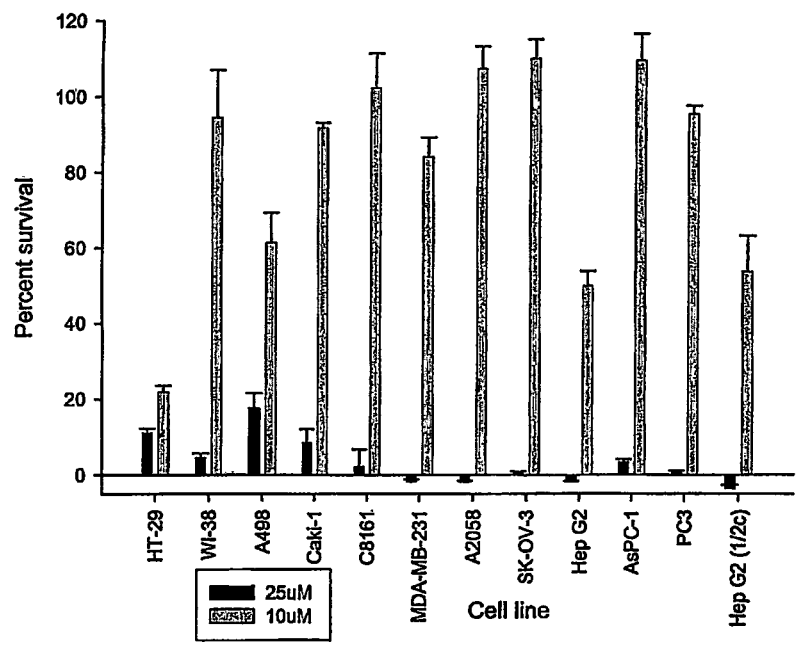
FIG. 4 depicts the effects of a compound 42 on the proliferation of various cancer cell lines in vitro.

FIG. 1 depicts the results with compound 92; FIG. 2 depicts the results with compound 28; FIG. 3 depicts the results with compound 50; and FIG. 4 depicts the results with compound 42.

Example 51

Concentration Dependence of Inhibition of Cancer Cell Proliferation by Compound 45 In Vitro The effect of various concentrations of compound 45 on various cancer cell lines was tested following the general protocol outlined in Example 50, with the following exceptions. Cell survival was assessed 48 h, 72 h and 6 days post-treatment by incubating cells with XTT for 2 h. The cancer cell lines utilised in this example were the same as those listed in Example 50, together with the cervical carcinoma cell line KB. The results are shown in FIGS. 5 and 6, which depict cell survival after treatment with various concentrations of compound 45. A. 48 h after treatment, B. 72 h after treatment and C. 6 days after treatment.

Example 52

Figure 7:
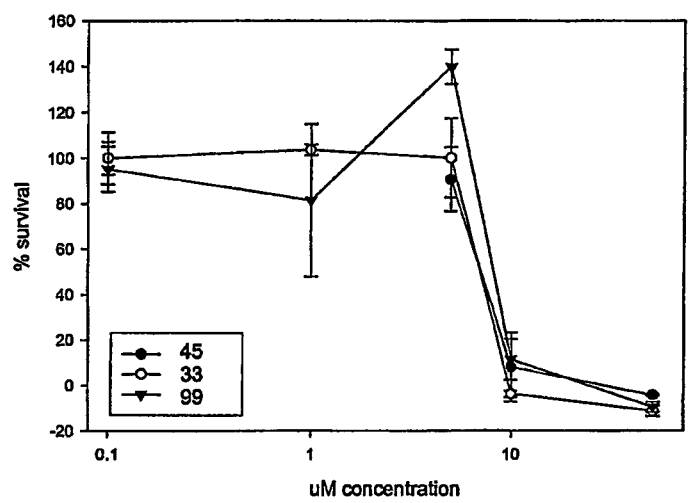
FIG. 7 depicts the effects of compounds 83 and 99 on the proliferation of LS 513 colon carcinoma cells in vitro.

Concentration Dependence of Inhibition of Cancer Cell Proliferation by Compounds 45, 33 and 99 In Vitro The effect of various concentrations of compounds 45, 33 and 99' on the colon carcinoma cancer cell line LS513 was tested following the general protocol outlined in Example 50, with cell survival being assessed 6 days post-treatment. The results are shown in FIG. 7.

Example 53

In Vitro Inhibition of Proliferation of Colon Carcinoma Cells #1

Figure 8:
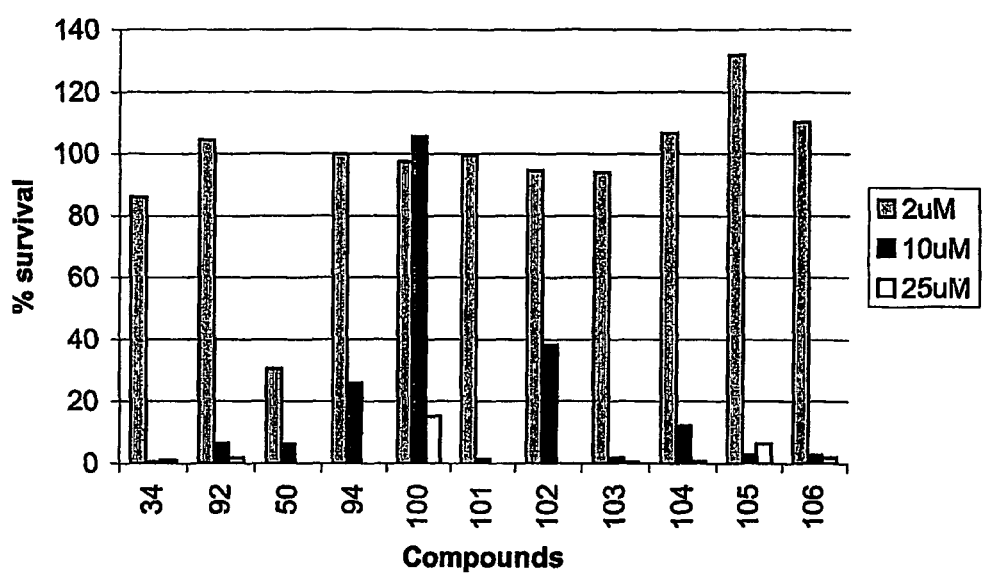
FIG. 8 depicts the effects of compounds of Formula I on the proliferation of HT-29 colon adenocarcinoma cells in vitro.

The effect of various compounds of Formula I on the proliferation of HT-29 colon carconoma cells was tested following the general protocol outlined in Example 50 with the exception that cell survival was assessed after 5 to 7 days of treatment. The results using concentrations of 2, 10 and 25 μM of each compound are shown in FIG. 8. Results were compiled from different experiments with 5 to 7 days of treatment. The co-efficient of variation for most samples were-within 5%.

Example 54

In Vitro Inhibition of Proliferation of Cancer Cells #3

The twenty-three compounds of Formula I shown below were evaluated for their antiproliferative effects in a panel of 60 human cancer cell lines as part of the in vitro anticancer screening services provided by the DTP (Developmental Therapeutics Program) of the US National Cancer Institute (NCI) U.S. National Cancer Institute (NCI) of the National Institutes of Health (NIH) in Rockwell, Md. The cancer cell lines used in this screen are provided in FIG. 9.

19

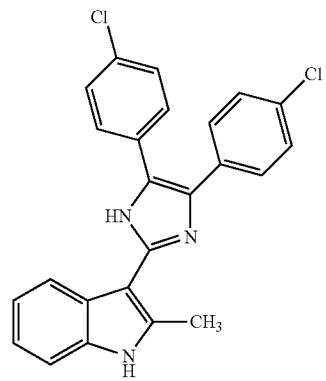

127 -continued
42
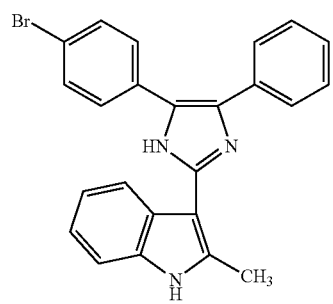
44
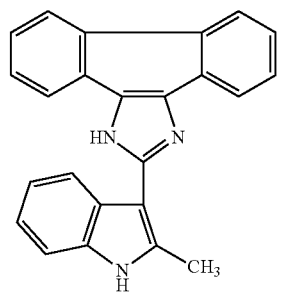
86
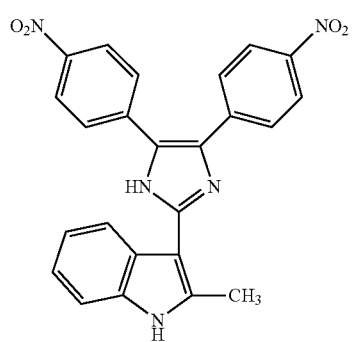
87
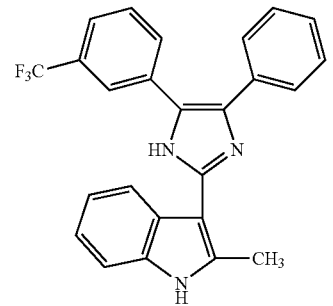
88
128 -continued
89
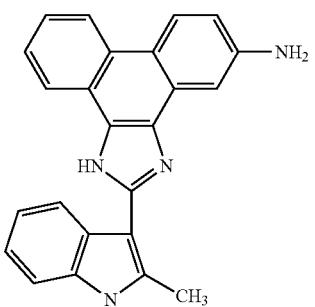
90
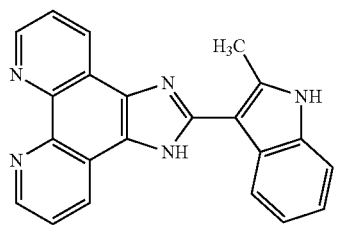
91
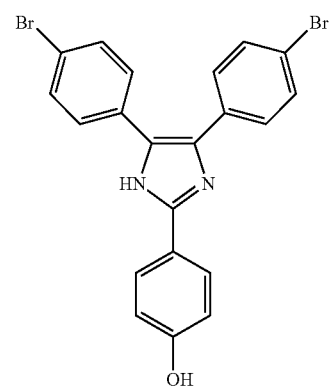
22
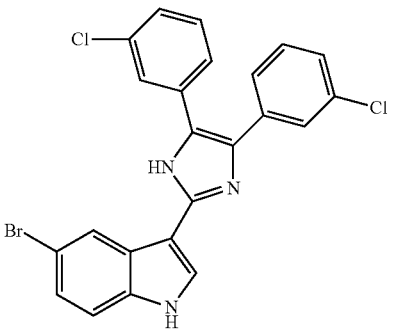
26
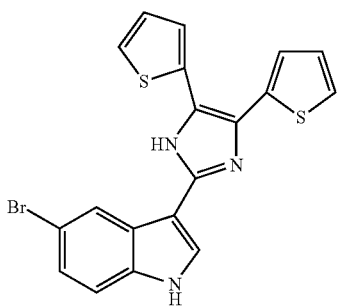

-continued
28
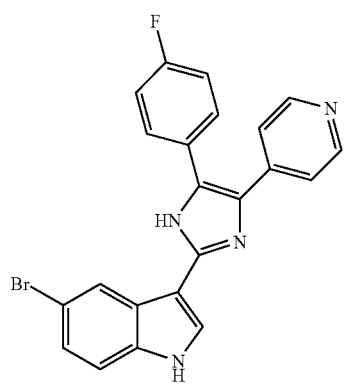
43
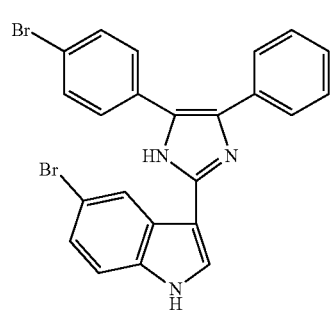
45
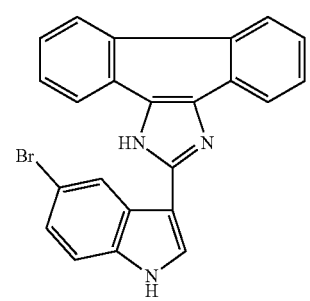
50
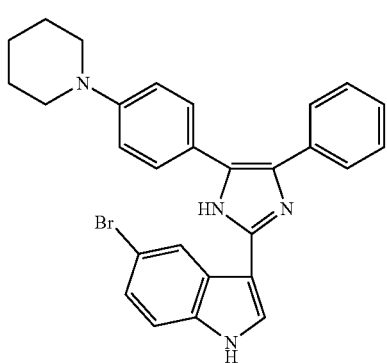
-continued
51
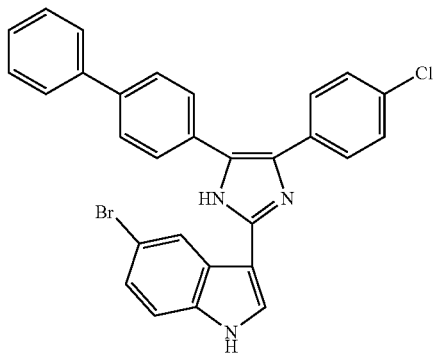
92
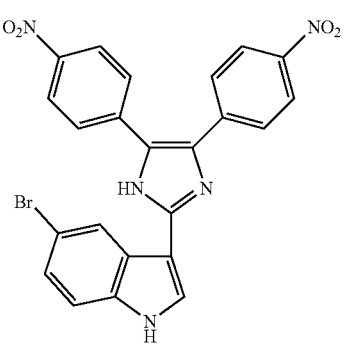
93
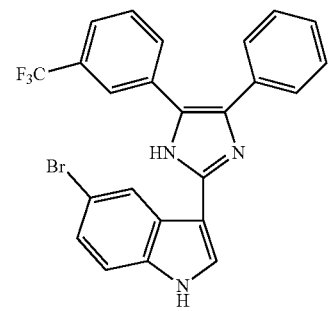
94
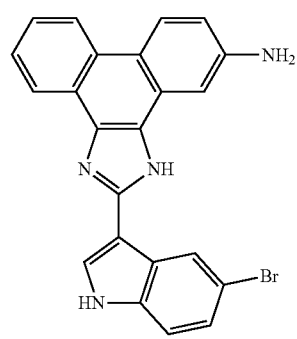

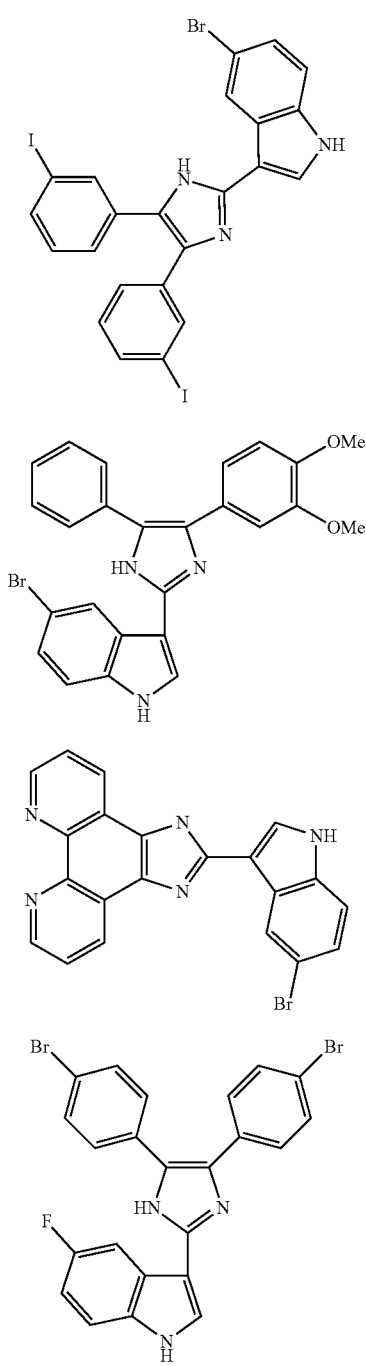

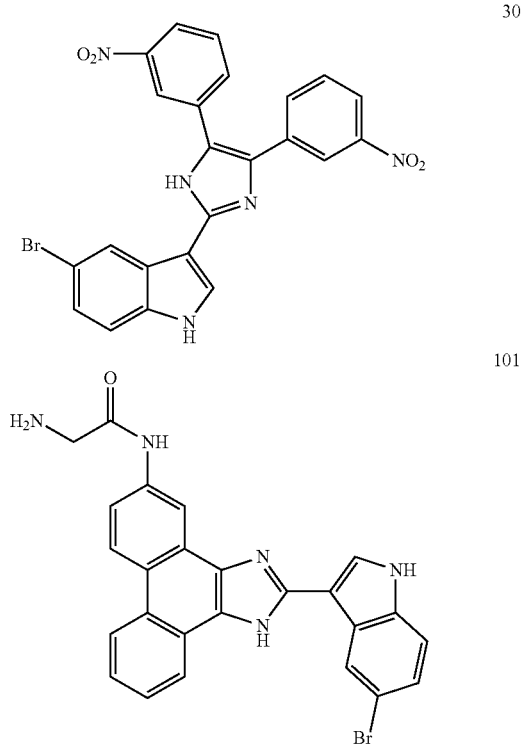

assay (similar to the XTT assay described above) and the concentration of the test compound required for growth inhibition is determined. The inhibitory effect of the test compounds are expressed as a $GI_{50}$ value, which represents the molar concentration of the test compound that results in 50% growth inhibition.

All compounds exhibited antiproliferative activity against all human tumour cell lines including NSCLC, leukemia, colon cancer, prostate cancer, melanoma, ovarian cancer, renal cancer, CNS cancer, and breast cancer, with $GI_{50}$ (growth inhibition by 50%) values ranging from 0.61 µM to 12.3 µM, with an average of 2 µM. The compound 45 had a $GI_{50}$ value of 2.0 µM, while the most effective compound was 90 FIG. 10A). The compounds affected the growth of all cell lines comparatively equally. The average $GI_{50}$ values for compound 45 ranged from 1.3 µM (renal) to 3.4 µM (leukemia) (FIG. 10B). These results suggest that compound 45 affects a ubiquitous target. The TGI (total growth inhibition) for this compound towards leukemia cell lines was significantly different from that of other cell types. These cell lines were not 100% growth inhibited, even at 100 µM, the highest concentration used (FIG. 10C).

Example 55

In Vitro Inhibition of Proliferation of Lung Cancer Cells

The following compounds were tested for their ability to inhibit the proliferation of H460 non-small cell lung carcinoma cells in vitro. The protocol described in Example 50 was utilised with the exception that cell survival was assessed after 6 days of treatment. Each compound was tested at concentrations of 0.2, 2, 10 and 25 µM. The results are shown in FIG. 11.

The NCI conducts a standard 48/72 hour 60 cell line assay and an in vitro time course assay as described in Alley et al. (*Cancer Res* (1988) 48:589). In the standard 60 cell line assay, a minimum of 5 concentrations of the test compound are tested at 10-fold dilutions against 60 cell lines and cell growth is assayed at 48 and 72 hours using a sulphorhodamine B assay. For the time course analysis, tumour cells are treated with the test compound at various time points, then washed and grown in medium free of the test compound until the end of the experiment at 144 hrs. This assay employs 20% FBS to better approximate the minimum cxt (concentrations and times) test compound exposure conditions that are required to achieve activity in vivo. Cell growth is quantified by an MIT

103

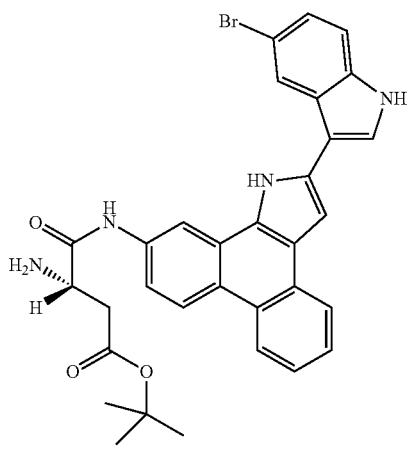

107

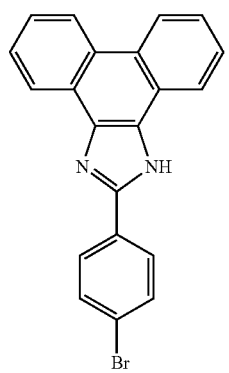

108

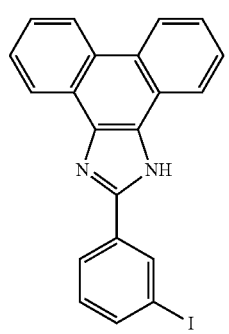

109

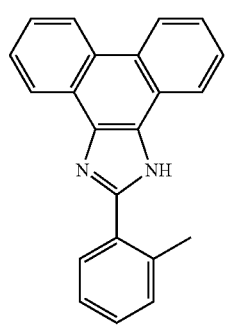

110

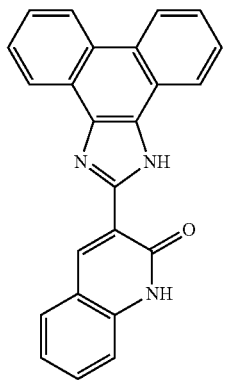

113

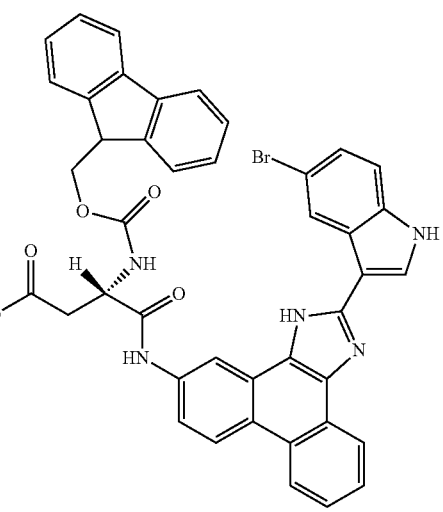

Example 56

In Vitro Inhibition of Proliferation of Colon Carcinoma Cells #2

The above compounds (as shown in Example 55), together with those shown below, were tested for their ability to inhibit the proliferation of HT-29 colon carcinoma cells in vitro. The protocol described in Example 50 was utilised with the exception that cell survival was assessed after either 2 or 6 days of treatment. Each compound was tested at concentrations of 0.2, 2, 10 and 25 µM (compounds 110, 30, 101, 113, 103, 107, 108 and 109) or at concentrations of 2.5, 10 and 25 µM (compounds 112, 114, 78, 111 and 45). The results are shown in FIGS. 12 and 13. The results shown in FIG. 12 reflect cell survival 6 days after treatment with the listed compounds. FIG. 13A shows cell survival 2 days after treatment with the listed compounds and FIG. 13B shows cell survival 6 days after treatment.

135
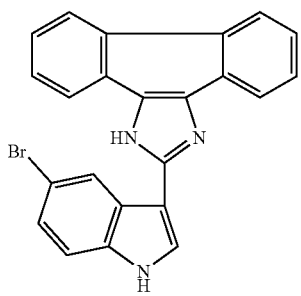
45
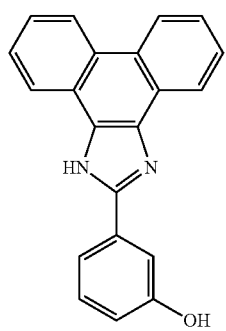
78
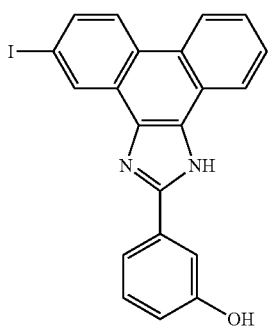
111
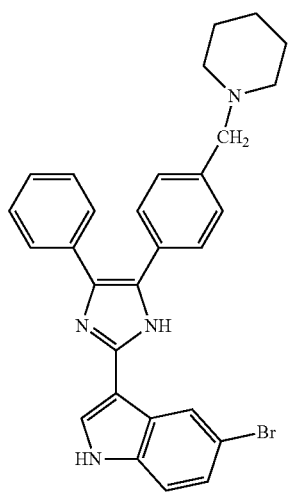
112
136
-continued
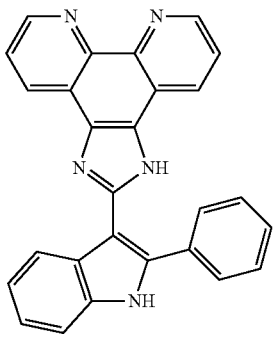
114
Example 57
Inhibition of Colon Carcinoma Growth In Vivo #1
This Example and the following Example 58 describe in vivo efficacy studies of various compounds of Formula I performed using a mouse xenograft model using the human colon adenocarcinoma cell line HT-29. The following compounds were tested.
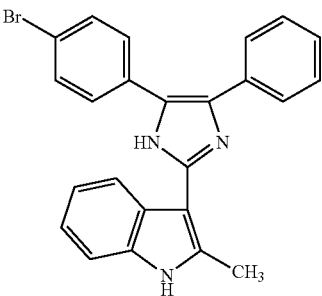
42
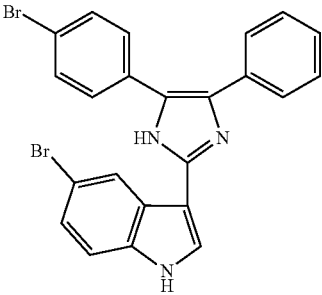
43
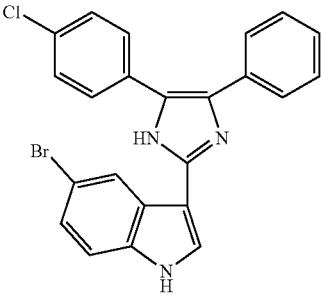
32

| 33 | 13 |
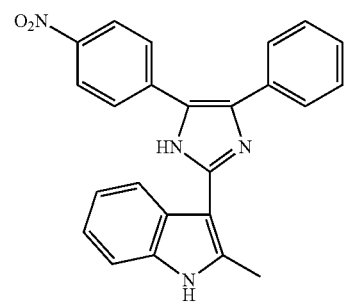 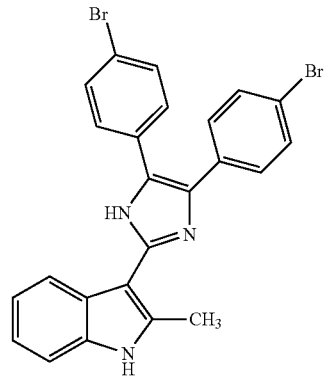
| 35 | 45 |
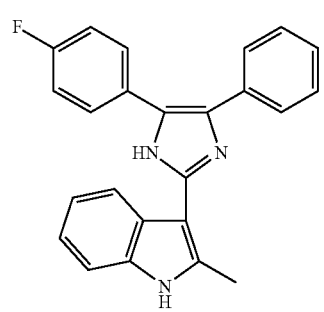 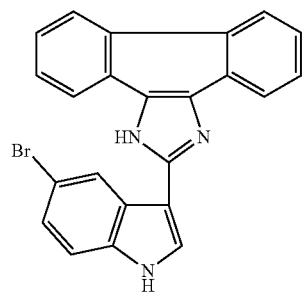
| | 46 |
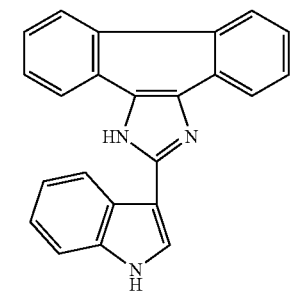
| 10 | |
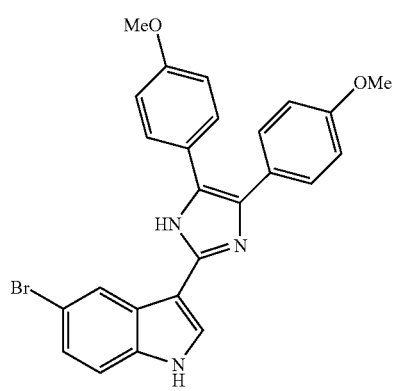
| | 36 |
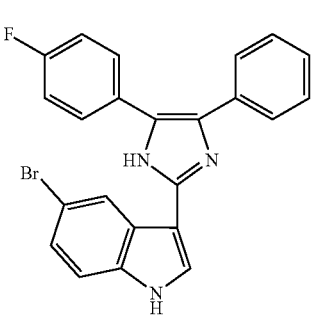
| | 73 |
| 44 | |
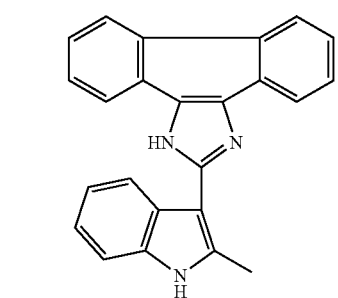 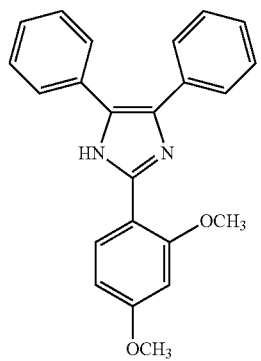

-continued

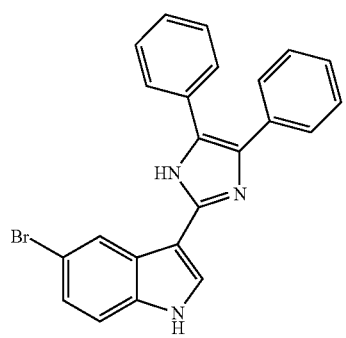
6

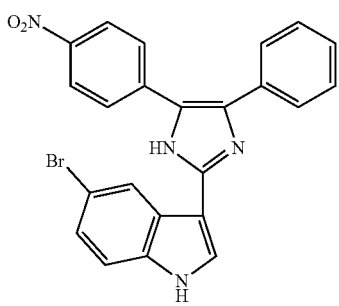
34

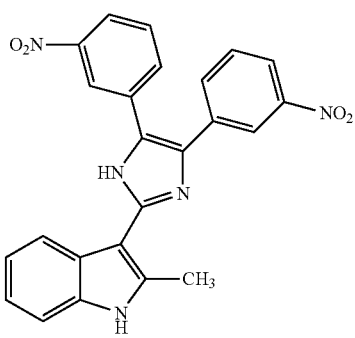
29

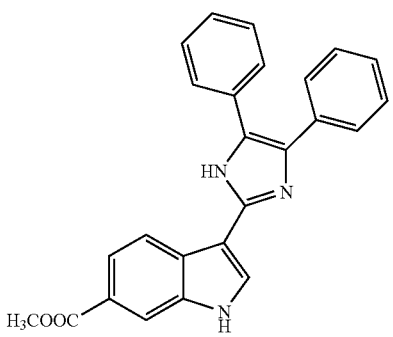
83

-continued

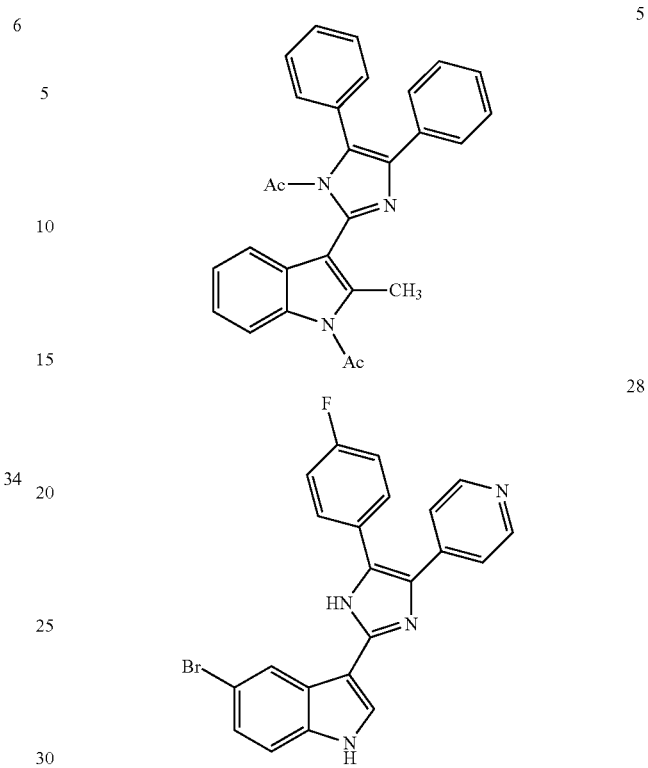

Figure 14:
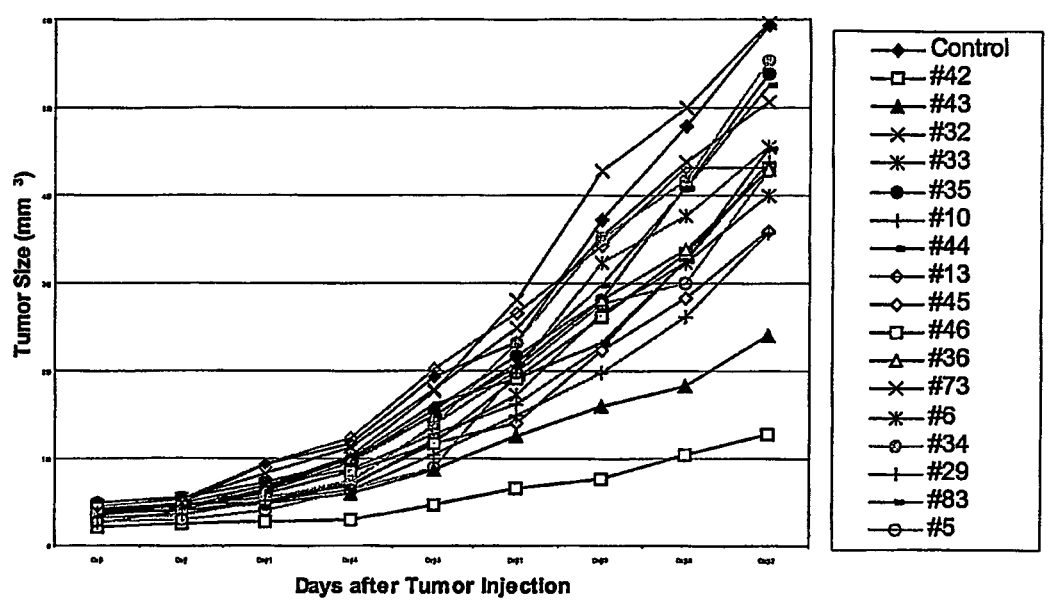
FIG. 14 depicts the effects of compounds of Formula I on the growth of HT-29 colon adenocarcinoma cells in vivo in CD-1 nude mice.
Figure 15:
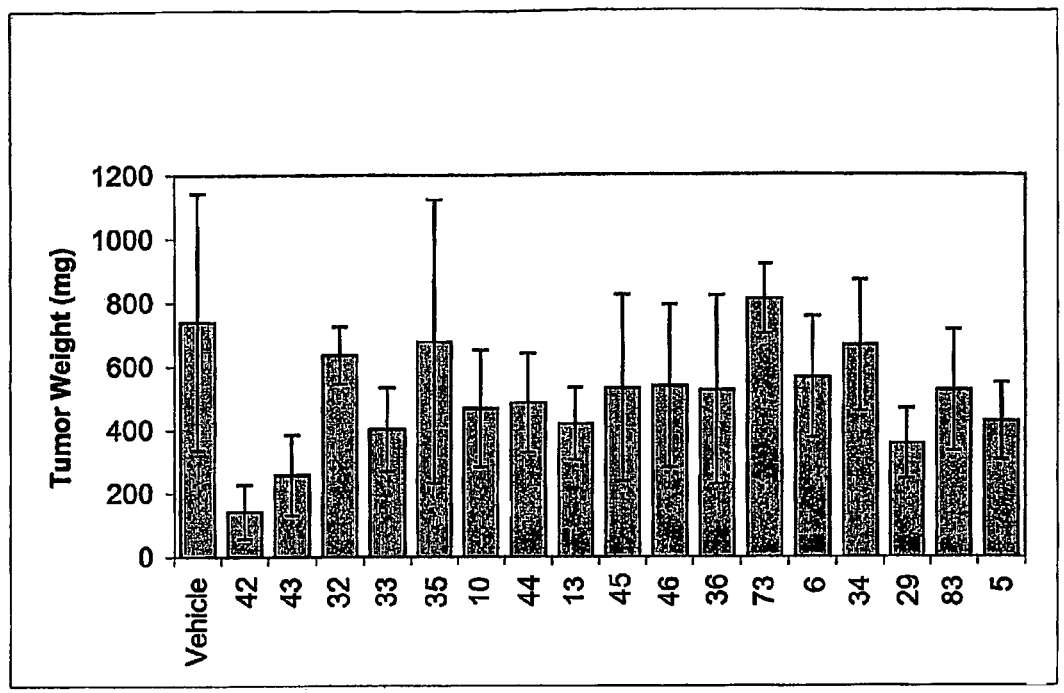
FIG. 15 depicts the effects of compounds of Formula I on the average weight of tumours in CD-1 nude mice (average weight per group of mice).
Figure 16:
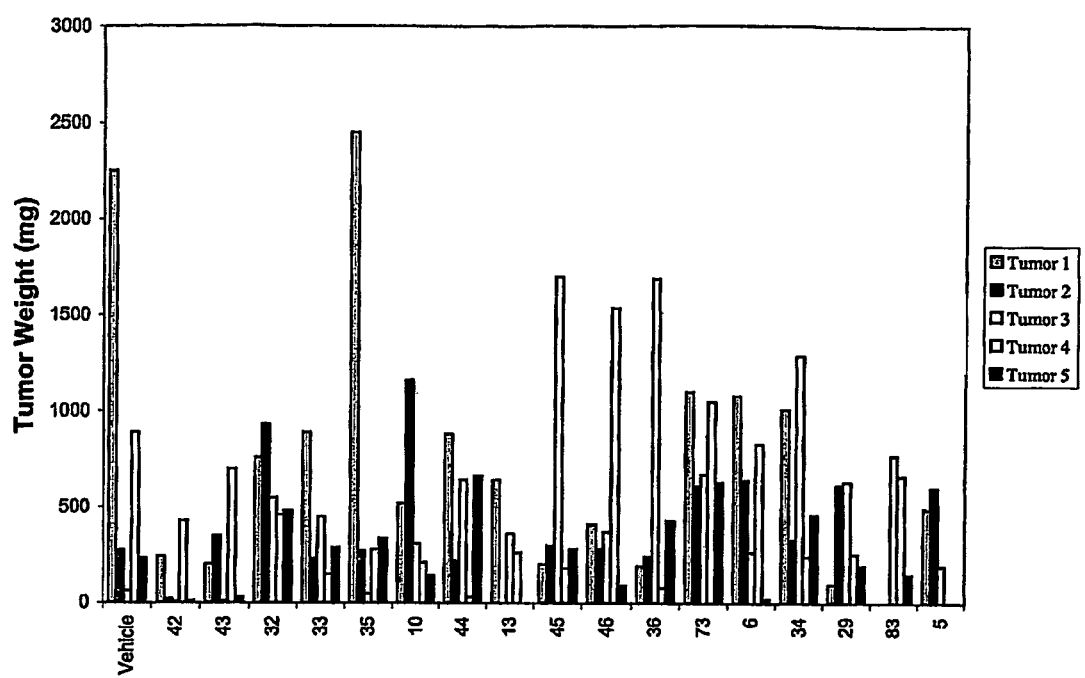
FIG. 16 depicts the effects of compounds of Formula I on the weight of tumours in CD-1 nude mice (individual tumour weights).

Groups of five to 10 CD-1 female nude mice (6-7 weeks) were injected in the lower mid back with human colon adenocarcinoma cells HT-29 ($3\times10^6$ cells in 0.11 ml PBS) subcutaneously, and the treatment initiated 5 days post-inoculation (size of tumours=20-40 mm³). The treatment schedule consisted of 2×200 µl intraperitoneal injections per day of 5 mg/ml (100 mg/Kg/d) for five days and 2 days break, for 4 weeks. Tumour sizes were measured during the course of the treatment using calipers, mice were then sacrificed by cervical dislocation and tumours surgically removed and weighed. FIG. 14 shows the average tumour size (mm³) in the different groups of mice. FIGS. 15 and 16 show the average tumour weight per group of mice and per individual mouse, respectively.

Example 58

Inhibition of Colon Carcinoma Growth In Vivo #2

Figure 17:
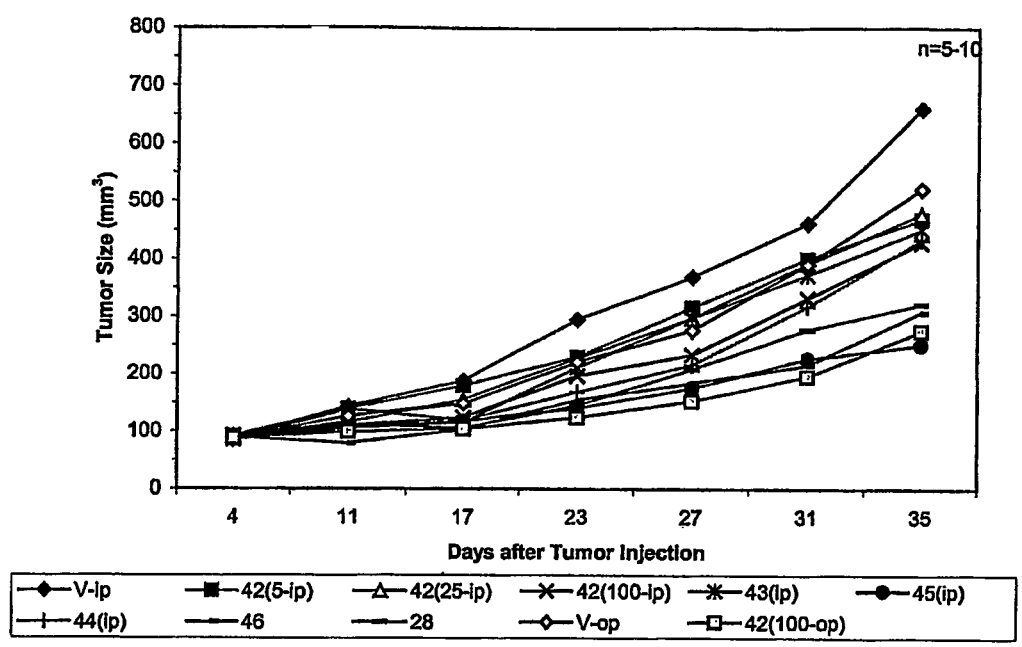
FIG. 17 depicts the effects of compounds of Formula I on the growth of HT-29 colon adenocarcinoma cells in vivo in CD-1 nude mice.

The protocol described in Example 55 was followed. The results are shown in FIG. 17, which depicts the average tumour size (mm³) in the different groups of mice. Abbreviations used in FIG. 17 are as follows: V-ip=Vehicle (i.p); 42 (5-ip)=5 mg/Kg (i.p.); 42 (25-1p)=25 mg/Kg; 42 (100-ip); 100 mg/Kg (i.p.); 43 (ip)-100 mg/Kg (i.p.); 45 (ip)=100 mg/Kg (i.p); 44 (ip)=100 mg/Kg (i.p.); 46=100 mg/Kg (i.p); 28=100 mg/kg (i.p); V-op=vehicle, oral; 42 (100-op)=100 mg (Kg (oral).

Example 59

In Vivo Inhibition of Cancer Cell Growth by Compound 45

The ability of compound 45 to inhibit the growth of cancer cells in vivo was further investigated in a mouse xenograft model of hepatocellular (liver), cancer. Groups of five to 10 CD-1 female nude mice were injected subcutaneously in the mid right flank with HepG2 human hepatocarcinoma cells ($1\times10^7$ cells). The treatment was initiated 7 days post-inoculation and consisted of 2×200 µl intraperitoneal injections per day (100 mg/kg/d). Tumour sizes were measured during the course of the treatment using calipers, and were surgically removed and weighed after 10 weeks. The results obtained are shown in FIGS. 18A & B.

Notably, none of the compounds tested in the preceding Examples 57-59 showed toxic effects in vivo.

Example 60

Effect of Compound 45 on the Activity of Various Human Kinase Enzymes #1

Compound 45 was tested for its ability to function as a kinase inhibitor using the kinase profiler service from Upstate Biotechnologies. The general protocol employed is as follows: recombinant kinases were incubated with specific substrates, 10 mM MgAcetate, and [$\gamma$-$^{33}$P-ATP]. The reaction was initiated by the addition of MgATP mix. After incubation at room temperature for 40 minutes, the reaction was stopped by the addition of 5 µl of a 3% phosphoric acid solution. 10 µl of the reaction was then spotted on to a P30 filtermat and washed 3 times for 5 min. in 75 mM phosphoric acid and once in methanol prior to drying and scintillation counting. Each reaction was performed in duplicate with 100 µM ATP−/+10 µM compound 45. Results are presented in Table IV and are expressed as the mean of % control (no compound). PI 3-kinase-$\gamma$ (PI3K-$\gamma$) activity was determined with the PIProfiler™ assay, which measures the binding of the GRP1 pleckstrin homology (PH) domain to PIP3, the product of PI3K acting on its physiological substrate PIP2.

Seventy-nine recombinant kinases were tested. Of these 87% retained greater then 60% activity in the presence of 10 µM ML-220. Four kinases retained between 40 and 60% activity (Alk-60%; Aurora-A, 54%; PKD2, 52%; SAPK3, 54%; TrkA, 56%), whereas 5 kinases had less than 40% activity (CaMKII, 32%; PI3K$\alpha$, 30%; PI3K$\beta$, 11%; PI3K$\delta$, 9%; and PI3K$\gamma$, 22%). These results indicate that compound 45 can function as a kinase inhibitor, and it has a high degree of selectivity for particular kinases.

TABLE IV

Kinase Inhibiting Activity of Compound 45

| Kinase | Family | % activity |
| --- | --- | --- |
| Abl | TK | 107 |
| ALK | TK | 60 |
| AMPK | CAMK | 100 |
| ASK1 | STE | 99 |
| Aurora-A | other | 54 |
| Axl | TK | 100 |
| BRK | TK | 112 |
| CaMKII | CAMK | 32 |
| CaMKIV | CAMK | 98 |
| CDK1/cyclinB | CMGC | 156 |
| CDK2/cyclinA | CMGC | 95 |
| CDK2/cyclinE | CMGC | 117 |
| CDK3/cyclinE | CMGC | 107 |
| CDK6/cyclinD3 | CMGC | 87 |
| CDK7/cyclinH/MAT1 | CMGC | 95 |
| CHK1 | CAMK | 111 |
| CK2 | other | 91 |
| EGFR | TK | 105 |
| EphA2 | TK | 95 |
| EphB4 | TK | 95 |
| ErbB4 | TK | 73 |
| Fes | TK | 99 |
| FGFR3 | TK | 82 |
| Fms | TK | 135 |
| Fyn | TK | 103 |
| GSK3$\alpha$ | CMGC | 96 |
| IGF-1R | TK | 80 |
| IKK$\beta$ | other | 111 |
| IKK$\alpha$ | other | 150 |
| JNK1$\alpha$1 | CMGC | 85 |
| JNK3 | CMGC | 121 |
| Lyn | TK | 81 |
| MAPK1 | CMGC | 85 |
| MAPK2 | CMGC | 99 |
| MAPKAP-K2 | CAMK | 119 |
| MEK1 | STE | 88 |
| Met | TK | 129 |
| MINK | STE | 91 |
| MKK4 | STE | 96 |
| MKK6 | STE | 86 |
| MSK1 | AGC | 76 |
| MST2 | STE | 77 |
| NEK2 | other | 90 |
| p70S6K | AGC | 64 |
| PAK2 | STE | 89 |
| PAR-1B$\alpha$ | CAMK | 88 |
| PDGFR$\alpha$ | TK | 117 |
| PDK1 | AGC | 106 |
| PI3K□ | LIPID | 22 |
| PI3K-$\beta$ | LIPID | 11 |
| PI3K-$\alpha$ | LIPID | 30 |
| PI3K-$\delta$ | LIPID | 9 |
| Pim-1 | CAMK | 70 |
| PKA | AGC | 83 |
| PKB$\alpha$ | AGC | 95 |
| PKC$\mu$ | AGC | 90 |
| PKC$\alpha$ | AGC | 92 |
| PKC$\delta$ | AGC | 87 |
| PKC$\zeta$ | AGC | 96 |
| PKD2 | CAMK | 52 |
| Plk3 | other | 132 |
| PRK2 | AGC | 83 |
| RAF | TKL | 100 |
| Ret | TK | 82 |
| ROCK-II | AGC | 86 |
| Ros | TK | 107 |
| Rse | K | 176 |
| Rsk1 | AGC | 183 |
| SAPK2a | CMGC | 62 |
| SAPK2b | CMGC | 80 |
| SAPK3 | CMGC | 54 |
| SAPK4 | CMGC | 77 |
| SGK | AGC | 89 |
| SRC | TK | 102 |
| TAK1 | TKL | 104 |
| Tie2 | TK | 109 |
| TrkA | TK | 56 |
| Yes | TK | 91 |

Example 61

Figure 19:
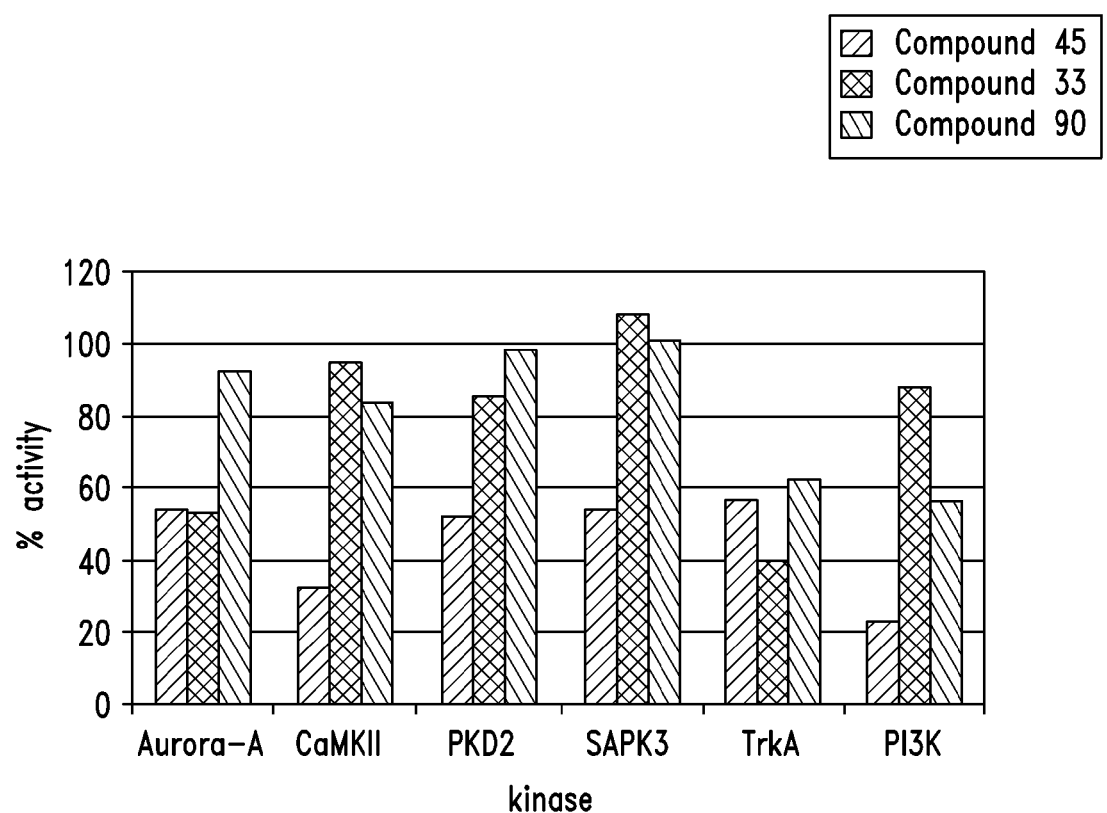
FIG. 19 depicts the effects of compounds 45, 33 and 90 on the activity of various human kinases.

Effect of Other Compounds of Formula I on the Activity of Various Human Kinase Enzymes To assess whether other compounds of Formula I also affected the same kinases, the inhibitory activity of 10 µM of compound 30 or compound 90 was tested on five kinases: Aurora-A, CaMKII, PKD2, SAPK3, TrkA and PI3K. The results are, shown in FIG. 19 The results indicated that these two compounds have a different pattern of kinase inhibition than compound 45.

Example 62

Determination of the Subcellular Localization of Compound 45 in Various Cancer Cells Compound 45 is intrinsically fluorescent, which allowed the subcellular localization of this compound to be examined by fluorescent microscopy. Fluorescent microscopy was performed at the Microscopy Imaging Centre, Faculty of Medicine, University of Toronto. Cells were treated with 100 µM of compound 45 (FIG. 20A, B, D, E) or 1 µM doxorubicin (FIG. 20C) for 1 hour, washed once in PBS, fixed in 3.7% formaldehyde/PBS for 10 minutes, washed three times in PBS and mounted with Immuno-fluoro. Images were obtained with a Zeiss laser scanning fluorescent microscope with an excitation filter range of 360-370 nm (compound 45) or 530-560 nm (doxorubicin). For FIGS. 20B and C, differential interference contrast images were overlaid with fluorescent images.

Figure 20:
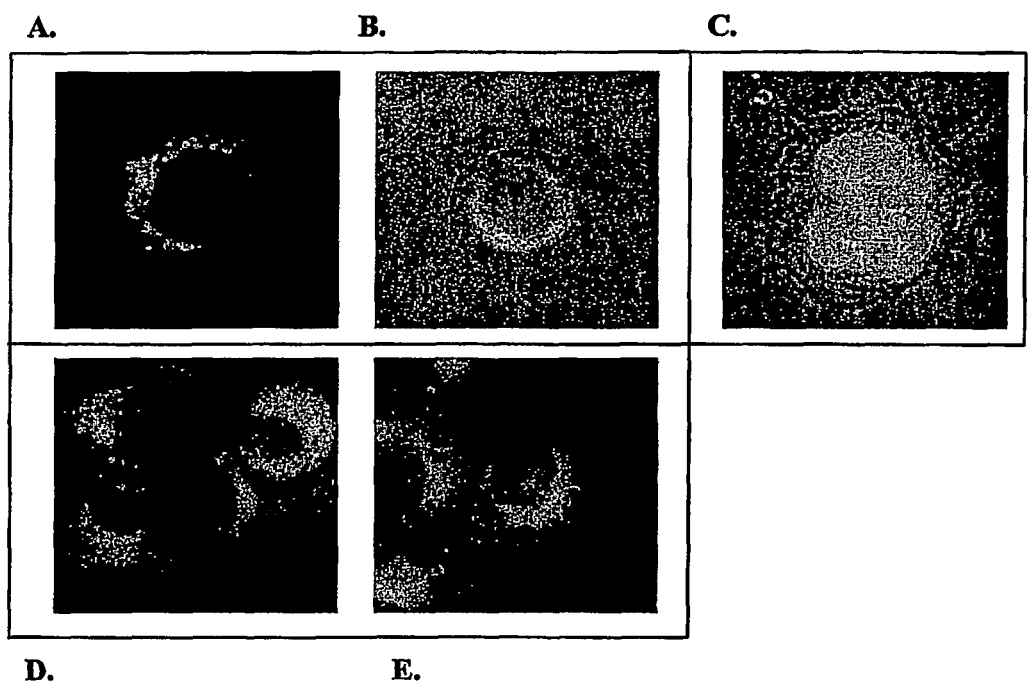
FIG. 20 depicts the subcellular location of compound 45 in HT-29 colon adenocarcinoma cells (A, B); of doxorubicin in HT-29 colon adenocarcinoma cells (C); of compound 45 in A498 renal cancer cells (D), and of compound 45 in C8161 melanoma cells (E).

Compound 45 localizes to punctuate spots in the perinuclear area of HT-29 colon adenocarcinoma cells (FIG. 20A), and is excluded from the nucleus and plasma membrane regions (FIG. 20B). In contrast, the anti-cancer agent, doxorubicin, which is also intrinsically fluorescent, is localized in the nucleus (FIG. 20C). A similar localization for compound 45 was observed in A498 renal carcinoma cells (FIG. 20D) and C8161 melanoma cells (FIG. 20E).

Example 63

Determination of Morphological Changes in Cells Treated with Compound 45

Figure 21:
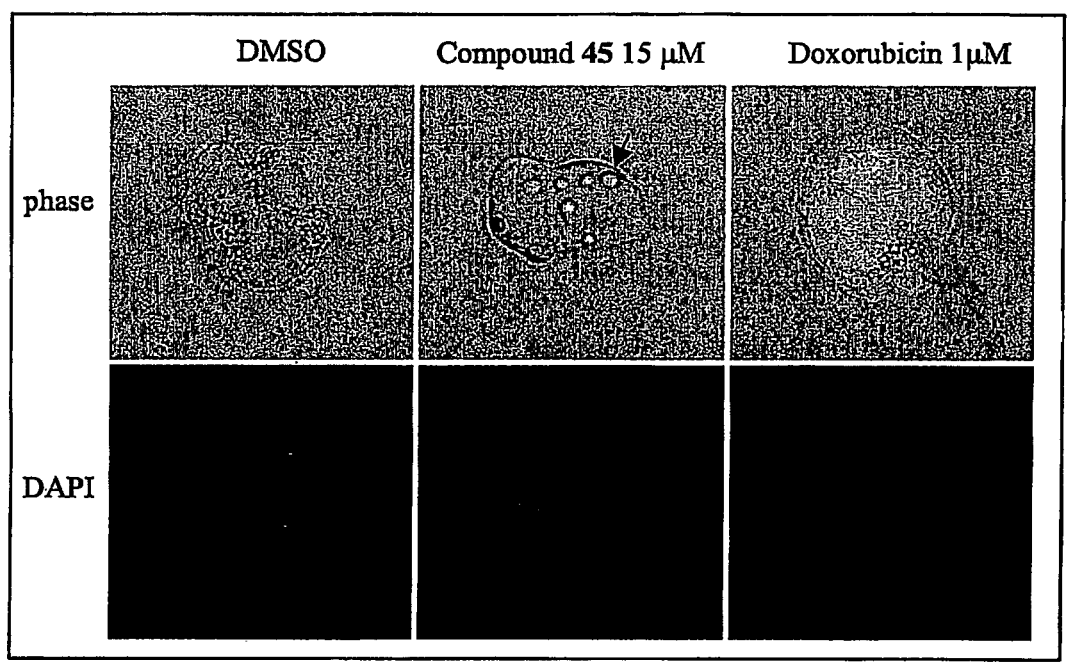
FIG. 21 depicts the formation of vacuoles in HT-29 colon adenocarcinoma cells treated with compound 45 or doxorubicin.

Treatment with compound 45 for 24 hours leads to the formation of large vacuoles within the cytoplasm of HT29 colon adenocarcinoma cells FIG. 21), A498 renal carcinoma cells and MDA-MB-231 breast adenocarcinoma cells. These vacuoles are not formed in DMSO- or doxorubicin-treated cells. Moreover, the nuclear membrane is no longer evident in the phase-contrast images of cells treated with compound 45, even though the nucleus is still intact, as shown by DAPI staining. FIG. 21 shows differential interference contrast (DIC) images (top row) and fluorescent images (lower row) of the same cells stained with DAPI, a cell permeable marker for the nucleus.

Example 64

Cell Cycle Analysis

The effect of treatment with compound 45 on cell cycle progression in HT-29 colon adenocarcinoma cells was examined by flow cytometry (FIG. 22). Values were determined by gate analysis of flow cytometric plots and are presented in FIG. 22 as a percentage of the total cell population, after eliminating doubles. Apoptotic events inferred by the surface area preceding G1 phase. Cells were starved for 3 days, and treated with 15 µM or 25 µM compound 45 for 24 or 48 hours in the presence of 10% serum, followed by flow cytometric analysis. Treatment with compound 45 led to an increase of cells in the G1 phase and a decrease in the S and G2/M phases.

The results presented above in this Example and in Examples 58, 60 and 61 indicate that compound 45 suppressed the growth of HT-29 colon cancer cells with a $GI_{50}$ of 2.6 µM, and induced a partial arrest in the G0/G1 phase of the cell cycle. Fluorescent microscopy revealed the presence of compound 45 within the cytoplasm, but not the nucleus or plasma membrane regions of the cell. In addition, compound 45 was found to inhibit kinase activity in a screen of protein kinases, indicating that the cellular target may be a cytoplasmic protein kinase. These results indicate that compound 45 and related derivatives have potential as therapeutic agents for the treatment of human cancer.

Example 65

Selectivity of Compounds of Formula I

Compounds of Formula I that demonstrate the ability to decrease the growth or proliferation of at least one cancer cell line may undergo further testing to evaluate their selectivity towards cancer cells. An exemplary method to measure the selectivity of the compounds of the present invention is provided below.

$IC_{90}$ values of selected compounds on a panel of normal actively proliferating cells (HUVEC and WI38) and cancer cells representing colon (HT-29), lung (NCI-H460), breast (MDA-MB-231) and prostate cancer (PC-3) are measured. Compounds with 2-fold or higher overall selectivity to the panel of cancer cell lines at $IC_{90}$ are identified as potential therapeutics.

$IC_{90}$ values are determined using the XTT assay as an indicator of growth arrest and/or cytotoxicity. This assay is conducted as outlined in Example 50. Percentage inhibition is calculated for each cell line and $IC_{90}$ values for each compound and cell type determined. The average $IC_{90}$ values for the normal cells are calculated and divided by the average $IC_{90}$ values for the cancer cell lines. Compounds with a selectivity ratio of >2 are identified and chosen for further optimization and/or testing.

Example 66

Additional In Vivo Anti-Tumour Efficacy Evaluations

Further pharmacological evaluation of selected compounds is conducted in animal models of human tumour growth. Data from these studies provide evidence of the therapeutic efficacy of selected compounds against various types of cancer and help to identify compounds with better pharmacological properties and potency.

Examples of mouse models that can be utilized to investigate the efficacy of selected compounds include, but are not limited to, xenografts of various human tumour types, inoculated subcutaneously into nude mice or mice with severe combined immunodeficiency disorder (SCID) as described above; orthotopic implantation of various human tumours in nude or SCID mice for investigation of effects on the tumour in the target organ (for example, a pancreatic cancer cell graft implanted directly into the pancreas of the animal), and investigation of spontaneous tumours in normal mice.

In order to provide evidence of the efficacy of a selected compound as a single agent, it may be evaluated, for example, in specific models (xenograft or orthotopic) for representative human cancers such as pancreas, skin (melanoma), kidney, colon, breast, lung, liver, ovary, prostate, bladder and brain. Similar studies can be conducted to evaluate the performance of test compounds in combination with other standard therapeutic modalities used in the treatment of human cancers.

For typical xenograft studies, 5-6 week old, female, CD-1 athymic nude mice, (Charles River, Montreal, QC) are acclimatized in a pathogen-free facility for at least 1 week. Animal protocols followed are in compliance with the Guide for the Care and Use of Laboratory Animals in Canada Approximately $10^6$-$10^7$ human tumour cells in 100 ml PBS are subcutaneously injected into the right flank of each mouse. Once tumours reach an approximate volume of 100 mm$^3$ (several days post tumour cell injection), mice are randomized by tumour size into control and treatment groups. Test compounds are administered at various doses 5 days a week for several weeks. Control animals receive vehicle alone (negative control) and/or a standard chemotherapeutic (positive control) for the same period. The tumour dimensions (length, width, and height) are measured using calipers twice a week over the treatment period. Tumour volume is calculated by the formula L×W×H/2, where L indicates length, W indicates width and H indicates height. The mice are sacrificed when the tumour burden reaches approximately 10% of total body weight and excised tumours are weighed. A standard bar graph is used to demonstrate the differences in tumour weights with each bar representing mean tumour weight.

Example 67

Additional Assays to Investigate Potential Mechanism of Action

The potential mechanism of action of selected compounds can be investigated using assays such as cell-cycle analysis, apoptosis assays, anti-angiogenesis assays and immunohistochemical analysis. A representative example of each type of assay is provided below.

i) Cell-Cycle Analysis

Alterations in cell cycle are determined using flow cytometric analyses. Tumour cells sensitive to a test compound are synchronized by plating in medium containing 0.5% FBS for 24 h followed by culturing in FBS-free medium for 48 h. The cells are then released into complete medium containing 0.1% DMSO (vehicle control) or the test compound at an appropriate concentration (e.g. 3×IC$_{90}$ value), harvested 16 to 24 h following treatment, washed twice with cold PBS and fixed in 70% ethanol at 4° C. for at least 4 h. The fixed cells are centrifuged at 1500 rpm for 4 minute at 4° C., washed twice with cold PBS containing 2% FBS, treated with 3 mg/ml ribonuclease (Sigma Chemical Co. Oakville, ON) and 50 µg/ml propidium iodide (PI) (Sigma Chemical Co.) for 30 minutes at 37° C. The fluorescence of the stained cells is measured using a FACScan flow cytometer and the CellQuest program (Becton Dickinson, San Jose, Calif.). Data are evaluated using Modfit software (Verity software House, Topsham, Me.) and the effects of the selected compounds on cell cycle are evaluated.

ii) Apoptosis Assay.

DNA fragmentation analysis is used to evaluate the apoptotic effects of test compounds. Briefly, cells are plated in six-well culture plates 24 hr prior to treatment. After incubation with the test compound, medium containing detached cells is transferred to 15 ml conical tubes while cells still attached to the plate are trypsinized and then added to the same tubes. After centrifugation, collected cells are washed with PBS and resuspended in 0.5 ml lysis buffer containing 50 mM Tris-HCl, pH 8.0, 1.0 M NaCl, 10 mM EDTA and 0.5% SDS. Cell lysates are transferred to microfuge tubes and proteinase K is added to a final concentration of 0.2 ml/ml and incubated overnight at 37° C. DNA is extracted by phenol:chloroform:isoamyl alcohol (24:24:1), dried and dissolved in 40 µM of 10 µM Tris-HCl (pH 8.0) and 0.1 mM EDTA. DNase-free RNase A is added to each sample for 30 min at 37° C. and 12 µl of each sample are loaded onto a 2% agarose gel containing 0.5 µg/ml ethidium bromide and electrophoresed. DNA is visualized under UV illumination and the induction of apoptosis by the test compound is evaluated based on the generation of a nucleosomal-size DNA ladder.

iii) Anti-Angiogenesis Assay

Proliferation of new capillaries, i.e. angiogenesis or neovascularization, is critical for the transition of a small localized tumour to expand into a large malignant growth. The Matrigel Plug Assay (see, Passaniti et al., *Lab. Invest.* (1992) 67:519) is a simple method for assessing angiogenesis and the possible anti-angiogenic effect of selected compounds in mice. Briefly, liquid Matrigel (Becton Dickinson & Co., NJ) is injected subcutaneously near the abdominal midline or the dorsal flank of the animal using a 25-gauge needle. Growth factor-reduced Matrigel supplemented with 8.3 nM basic fibroblast growth factor (bFGF, Collaborative Biomedical Products, MA) stays in liquid form at 4° C. bFGF is a proven and potent inducer of angiogenesis. When injected into a mouse (0.5 ml/mouse), Matrigel immediately forms a readily recoverable solid gel, which is removed at various times (not exceeding 10 days) to assess neo-vessel growth around and into the gel. Test compounds are administered according to appropriate doses and schedules. Typically at a 5-day point, mice are sacrificed, overlying skin is removed and the gels are cut out retaining the peritoneal lining for support. For quantitation of angiogenesis, two methods are employed: 1. haemoglobin content in the gel is measured using the Drabkin method (Drabkin and Austin, *J. Biol. Chem.* (1932) 98:719) and Drabkin reagent kit 525 (Sigma, Mo.); 2, the number of blood vessels invading the Matrigel is determined by microscopic analysis after the gels are fixed, embedded in paraffin, sectioned and stained.

iv) Immunohistochemistry

The anti-cancer effects of test compounds can be evaluated in mouse xenograft models (as described above) by quantitating the effects of these compounds on tumour growth, differentiation, apoptosis and angiogenesis using immunohistochemical methods.

Tumour cell proliferation, angiogenesis and tumour immune infiltrates are delineated immunohistochemically using specific antibodies (Ki-67 for proliferation, CD31 for angiogenesis and NK1.1 for NK cells and F4/80 for macrophage). Apoptosis is delineated utilising the TUNEL assay (In Situ Cell Death Detection kit; Boehringer Mannheim, Laval, QC). Signal generation is accomplished by peroxidase catalyzed generation of enzyme product which is visualized microscopically. Tissue histology is determined after H&E staining of separate sections.

Briefly, tumour xenografts from treated mice are isolated, fixed and paraffin embedded individually in blocks and several 5 µm sections are cut for immunostaining and TUNEL assays. One additional section is obtained for H&E staining. For all immunohistochemical labeling, prior antigen retrieval is employed to improve detection. Typically, a 3-step amplification method is used to generate signals in immunohistochemistry that consists essentially of applying a biotinylated secondary antibody that recognizes the primary antibody, followed by avidin-peroxidase incubation. The final step is enzyme reaction in stable DAB solution. Immunohistochemical sections are counterstained with hematoxylin for tissue histology. To eliminate non-specific immunostaining with mouse monoclonal antibodies applied to mouse tissues, a specific blocking step is included in the procedure. Staining patterns are documented photographically, examined by at least two independent observers and quantitated by counting a pre-determined number of cells.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A compound of formula (VI):

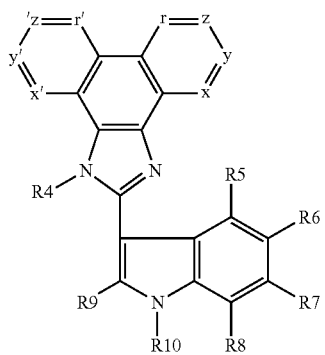

or a salt thereof, wherein:
R4, R5, R7 and R8 are independently hydrogen, halogen, hydroxyl, thiol, lower alkyl, substituted lower alkyl, lower alkenyl, substituted lower alkenyl, lower alkynyl, substituted lower alkynyl, alkylalkenyl, alkylalkynyl, alkoxy, alkylthio, acyl, aryloxy, amino, amido, carboxyl, aryl, substituted aryl, heterocycle, heteroaryl, substituted heterocycle, substituted heteroaryl, heteroalkyl, cycloalkyl, substituted cycloalkyl, alkylcycloalkyl, alkylcycloheteroalkyl, nitro, cyano, —CONHHN$_2$ or —S(O)$_{0-2}$R wherein R is alkyl, substituted alkyl, aryl, substituted aryl, heterocycle, heteroaryl, substituted heterocycle, or substituted heteroaryl;
R6 is hydrogen, halogen, CN, NO$_2$, HN$_2$, or —OR, wherein R is C1-C10 alkyl or arylalky;
R9 is hydrogen, C1-C10 alkyl, aryl, or halogen;
x is CR11;
y is CR12 or N;
z is CR13 or N;
r is CR14 or N;
x' is CR15;
y' is CR16 or N;
z' is CR17 or N;
r' is CR18 or N;
R10 is H, lower alkyl, substituted lower alkyl, lower alkenyl, substituted lower alkenyl, lower alkynyl, substituted lower alkynyl, methoxy, aryl, substituted aryl, heteroaryl, substituted heteroaryl, acyl or —SO$_2$PhCH$_3$;
R11, R12, R14, R15, R16, and R18 are independently hydrogen, halogen, hydroxyl, thiol, lower alkyl, substituted lower alkyl, lower alkenyl, substituted lower alkenyl, lower alkynyl, substituted lower alkynyl, alkylalkenyl, alkylalkynyl, alkoxy, alkylthio, acyl, aryloxy, amino, amido, carboxyl, aryl, substituted aryl, heterocycle, heteroaryl, substituted heterocycle, substituted heteroaryl, heteroalkyl, cycloalkyl, substituted cycloalkyl, alkylcycloalkyl, alkylcycloheteroalkyl, nitro, cyano, —N=CRR', wherein R and R' are independently selected from H, alkyl, substituted alkyl, aryl, substituted aryl, heterocycle, substituted heterocycle, heteroaryl, substituted heteroaryl; or —NHC(S)NH-phenyl (substituted or unsubstituted); and,
R13 and R17 are independently hydrogen, halogen, hydroxyl, thiol, lower alkyl, substituted lower alkyl, lower alkenyl, substituted lower alkenyl, lower alkynyl, substituted lower alkynyl, alkylalkenyl, alkylalkynyl, alkoxy, alkylthio, acyl, aryloxy, amino, amido, carboxyl, aryl, substituted aryl, heterocycle, heteroaryl, substituted heterocycle, substituted heteroaryl, heteroalkyl, cycloalkyl, substituted cycloalkyl, alkylcycloalkyl, alkylcycloheteroalkyl, nitro, cyano, —N=CRR', wherein R and R' are independently selected from H, alkyl, substituted alkyl, aryl, substituted aryl, heterocycle, substituted heterocycle, heteroaryl, substituted heteroaryl; or —NHC(S)NH-phenyl (substituted or unsubstituted).

2. The compound accordingly to claim 1, wherein:
R4, R5, R7 and R8 are independently hydrogen, halogen, hydroxyl, thiol, lower alkyl, substituted lower alkyl, alkoxy, alkylthio, acyl, aryloxy, amino, amido, carboxyl, aryl, substituted aryl, nitro, cyano, —CONHHN$_2$ or —S(O)$_{0-2}$R wherein R is alkyl, substituted alkyl, aryl, substituted aryl, heterocycle, heteroaryl, substituted heterocycle, or substituted heteroaryl.

3. The compound according to claim 1, wherein:
x is CR11;
y is CR12;
z is CR13;
r is CR14;
x' is CR15;
y' is CR16;
z' is CR17; and
r' is CR18.

4. The compound according to claim 1, wherein:
x is CR11;
y is CR12;
z is CR13;
r is CR14 or N;
x' is CR15;
y' is CR16;
z' is CR17; and
r' is CR18 or N.

5. The compound according to claim 1, wherein:
x is CR11;
y is CR12;
z is CR13;
r is N;
x' is CR15;
y' is CR16;
z' is CR17; and
r' is N.

6. The compound according to claim 1, wherein:
x is CR11;
y is CR12;
z is CR13;
r is N;
x' is CR15;
y' is CR16;
z' is CR17;
r' is N; and
wherein R11, R12, R13, R15, R16, and R17 are hydrogen.

7. The compound according to claim 1, wherein:
x is CR11;
y is CR12;
z is CR13;
r is N;
x' is CR15;
y' is CR16;
z' is CR17;
r' is N; and
R4, R5, R7 and R8 are independently hydrogen, halogen, hydroxyl, thiol, lower alkyl, substituted lower alkyl, alkoxy, alkylthio, acyl, aryloxy, amino, amido, carboxyl, aryl, substituted aryl, nitro, cyano, —CONHHN$_2$ or —S(O)$_{0-2}$R wherein R is alkyl, substituted alkyl, aryl, substituted aryl, heterocycle, heteroaryl, substituted heterocycle, or substituted heteroaryl; and
wherein R11, R12, R13, R15, R16, and R17 are hydrogen.

8. The compound according to claim 1, wherein:
x is CR11;
y is CR12;
z is CR13;
r is N;
x' is CR15;
y' is CR16;
z' is CR17;
r' is N; and
R4 is hydrogen;
R5, R7 and R8 are independently hydrogen, halogen, hydroxyl, thiol, lower alkyl, substituted lower alkyl, alkoxy, alkylthio, acyl, aryloxy, amino, amido, carboxyl, aryl, substituted aryl, nitro, cyano, —CONHHN$_2$ or —S(O)$_{0-2}$R wherein R is alkyl, substituted alkyl, aryl, substituted aryl, heterocycle, heteroaryl, substituted heterocycle, or substituted heteroaryl; and
wherein R11, R12, R13, R15, R16, and R17 are hydrogen.

9. The compound according to claim 1, wherein:
x is CR11;
y is CR12;
z is CR13;
r is N;
x' is CR15;
y' is CR16;
z' is CR17;
r' is N; and
R4 is hydrogen;
R5, R7 and R8 are independently hydrogen, halogen, hydroxyl, thiol, lower alkyl, substituted lower alkyl, alkoxy, alkylthio, acyl, aryloxy, amino, amido, carboxyl, aryl, substituted aryl, nitro, cyano, —CONHHN$_2$ or —S(O)$_{0-2}$R wherein R is alkyl, substituted alkyl, aryl, substituted aryl, heterocycle, heteroaryl, substituted heterocycle, or substituted heteroaryl;
R10 is lower alkyl, substituted lower alkyl, methoxy, acyl or —SO$_2$PhCH$_3$; and R11, R12, R13, R15, R16, and R17 are hydrogen.

10. The compound according to claim 1, wherein:
x is CR11;
y is CR12;
z is CR13;
r is N;
x' is CR15;
y' is CR16;
z' is CR17;
r' is N; and
R4 is hydrogen;
R5, R7 and R8 are independently hydrogen, halogen, hydroxyl, thiol, lower alkyl, substituted lower alkyl, alkoxy, alkylthio, acyl, aryloxy, amino, amido, carboxyl, aryl, substituted aryl, nitro, cyano, —CONHHN$_2$ or —S(O)$_{0-2}$R wherein R is alkyl, substituted alkyl, aryl, substituted aryl, heterocycle, heteroaryl, substituted heterocycle, or substituted heteroaryl;

R10 is hydrogen; and

R11, R12, R13, R15, R16, and R17 are hydrogen.

11. The compound according to claim 1, selected from:

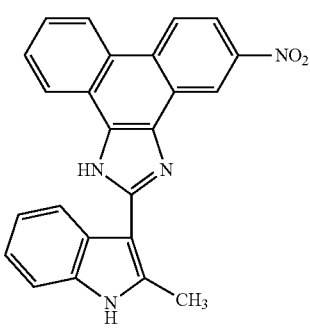

88

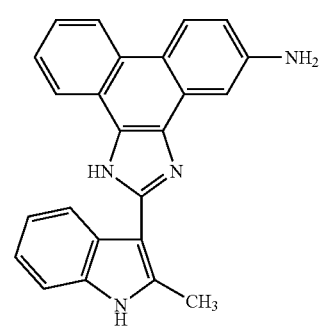

89

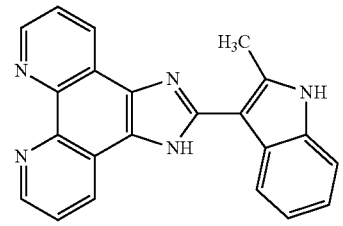

90

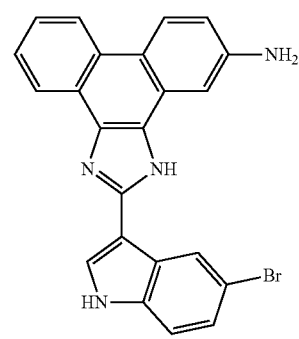

94

97
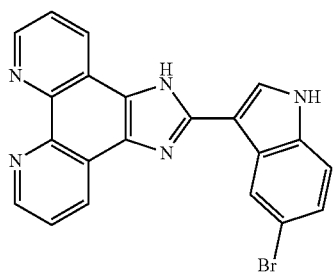
99
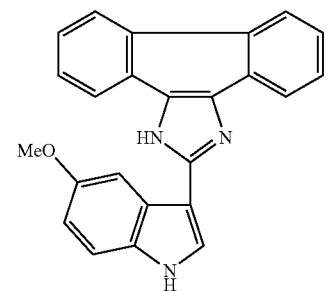
100
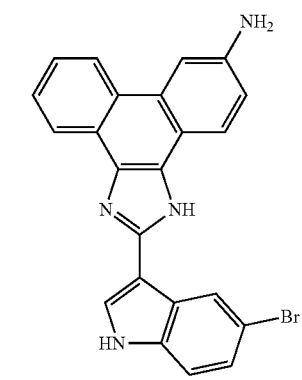
101
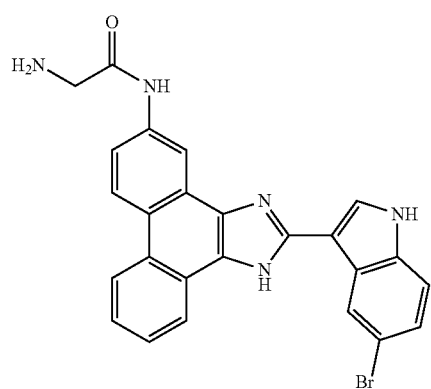
102
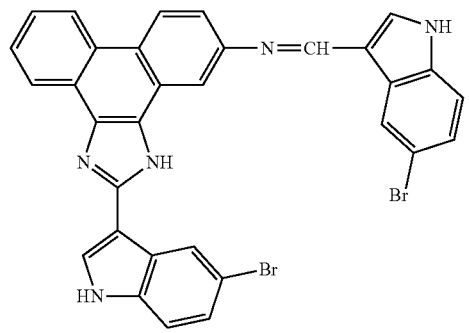
103
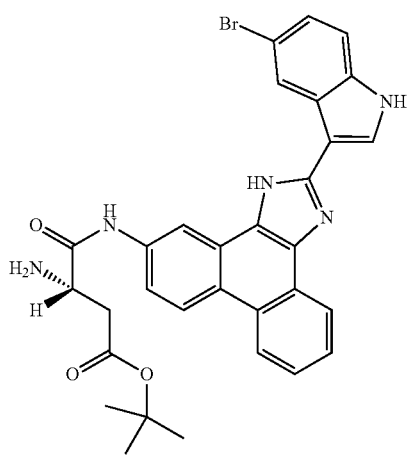
104
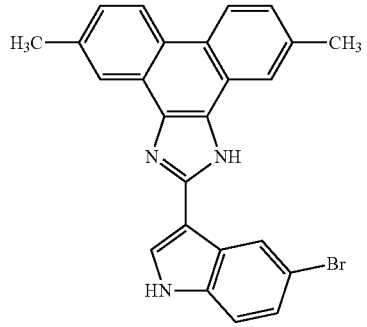
105
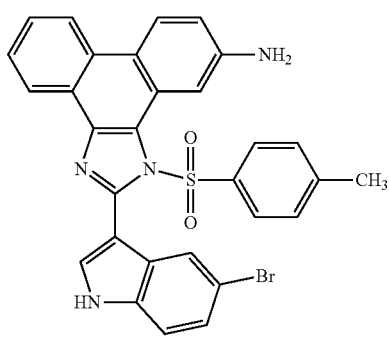

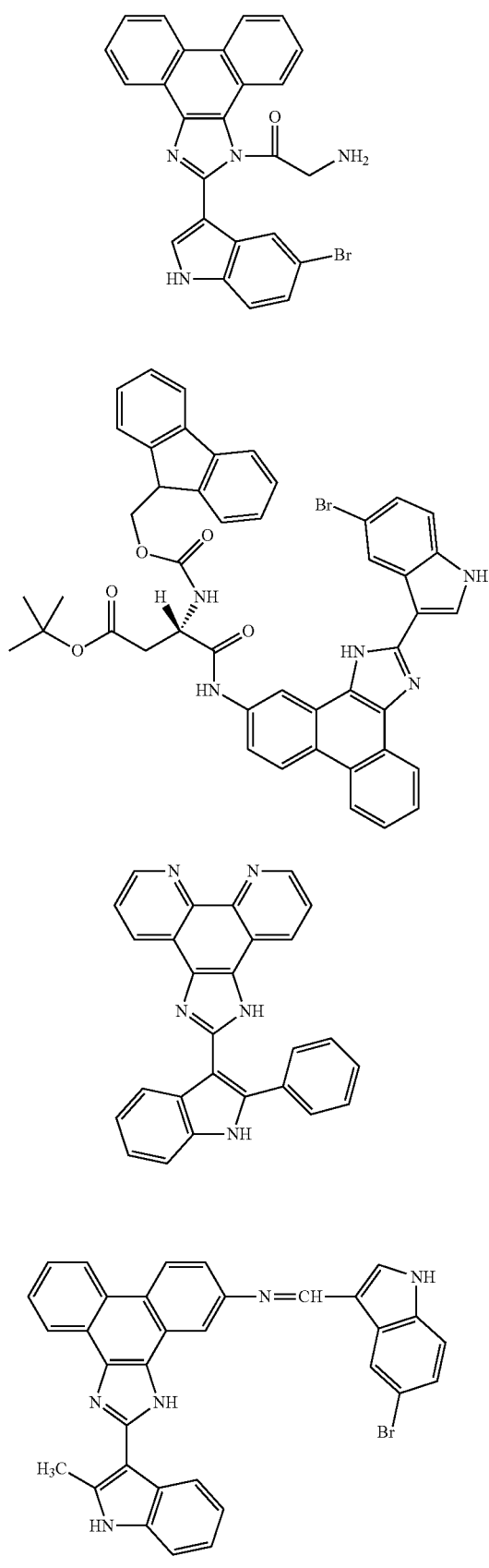
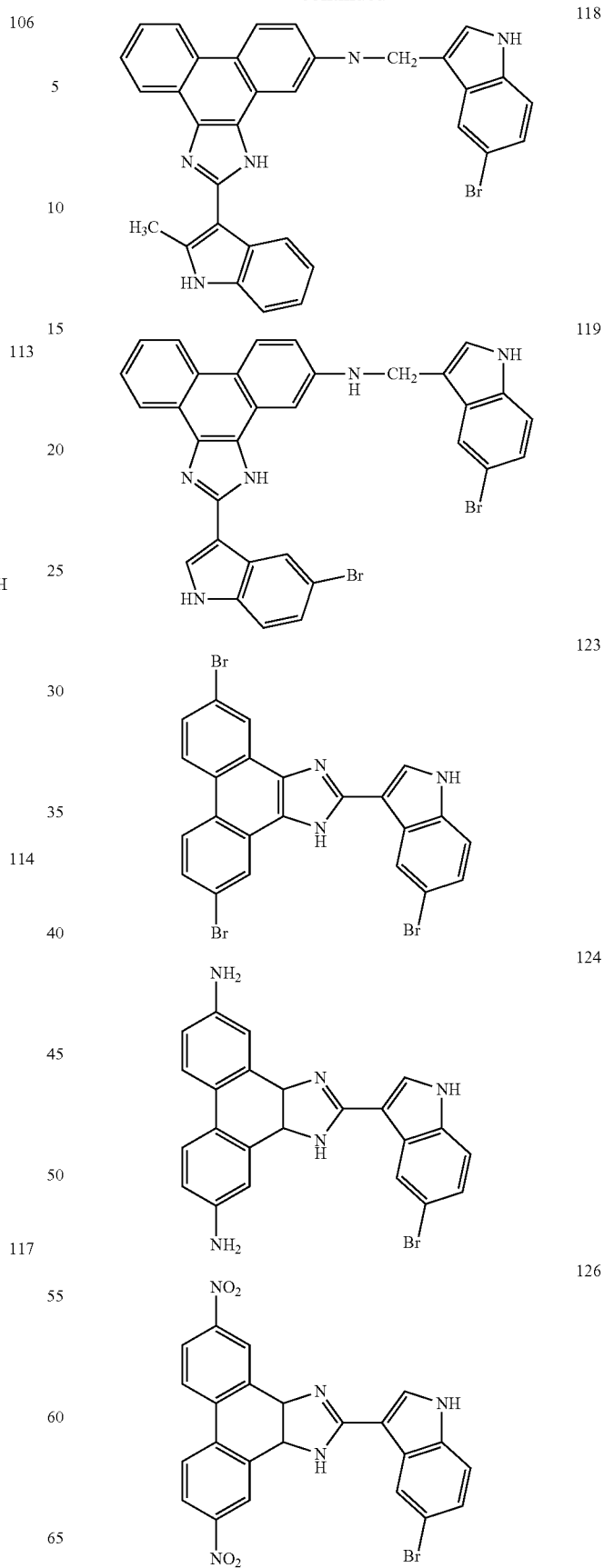

127
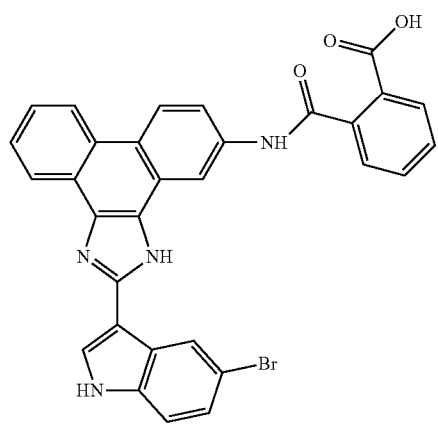
129
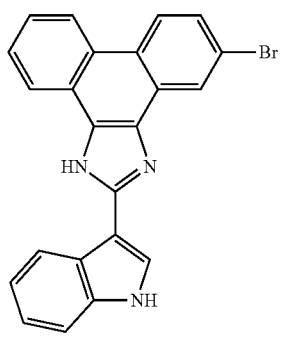
130
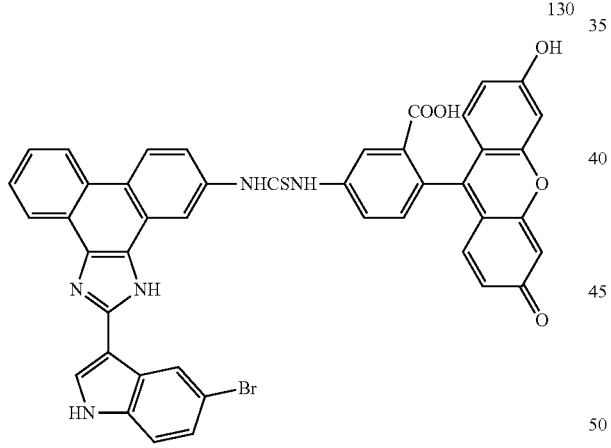
131
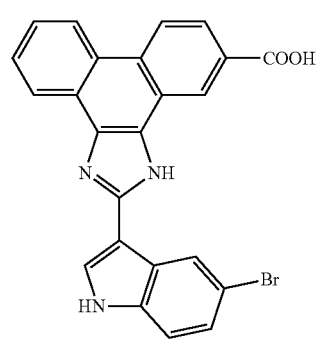
132
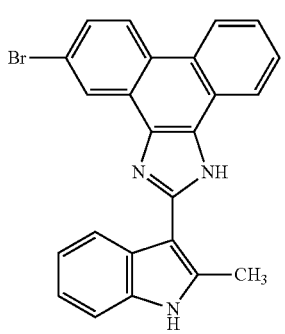
133
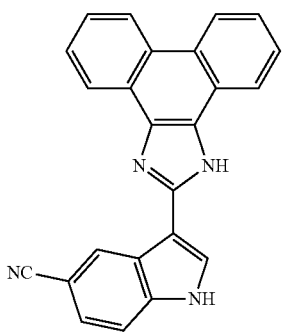
134
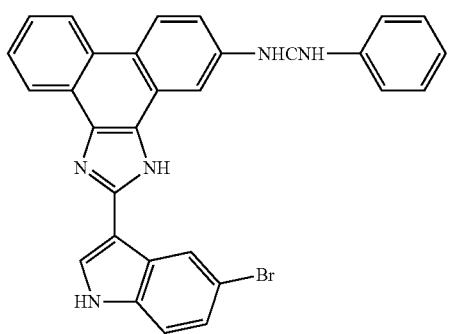

157                                                 158
-continued                                          -continued
135
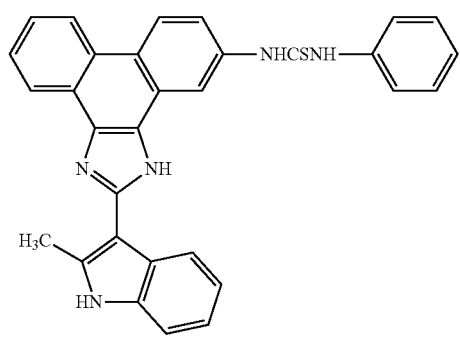
143
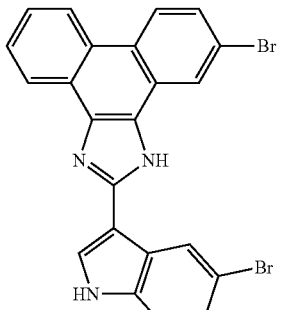
136
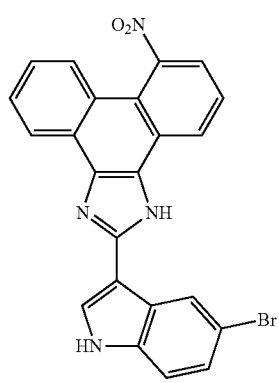
145
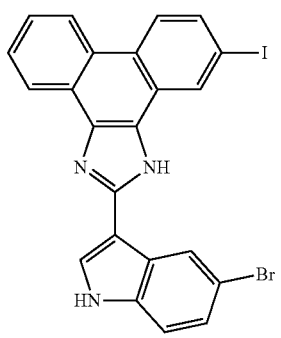
139
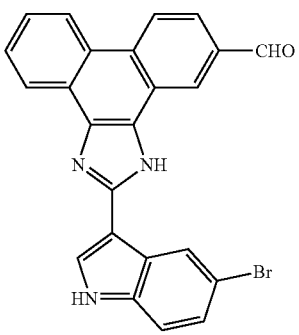
146
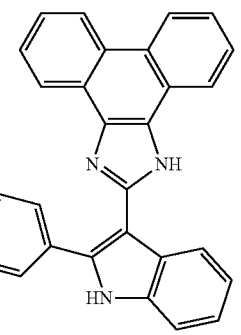
147
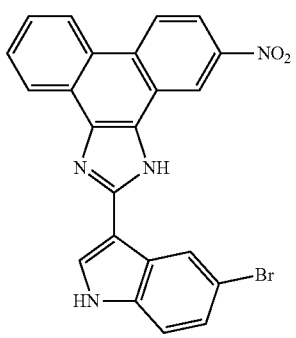
142
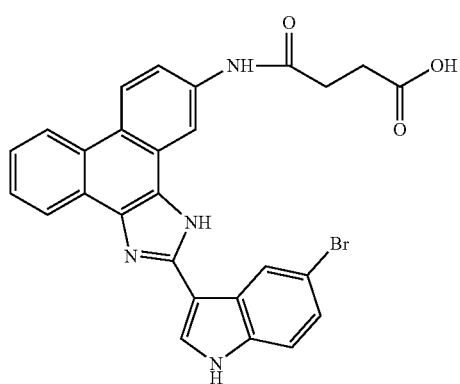
155
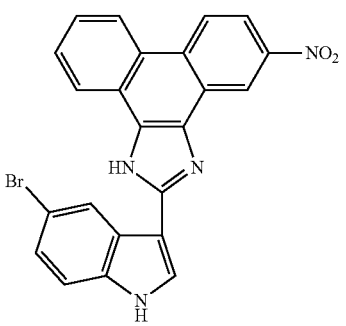

156
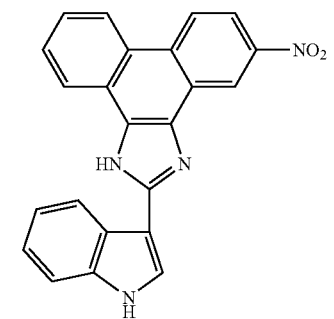
157
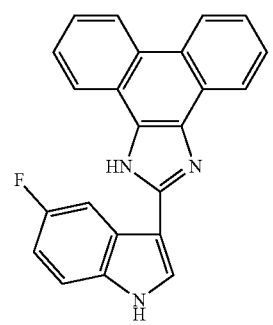
158
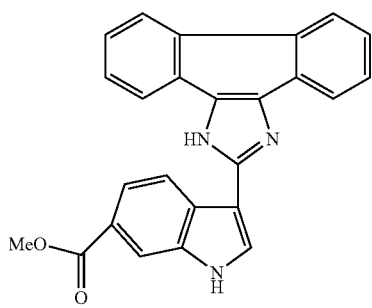
161
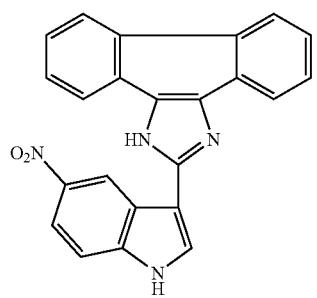
164
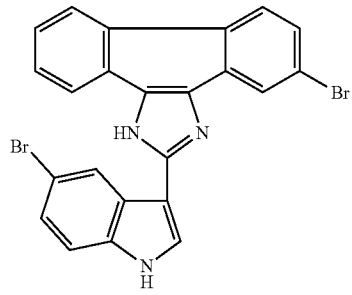
165
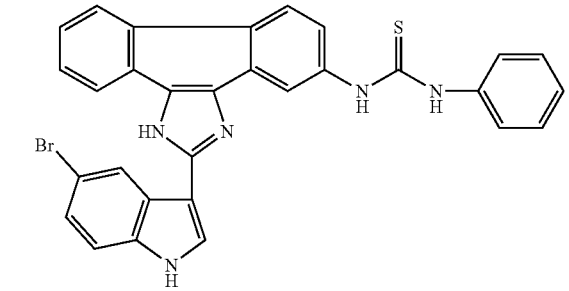
167
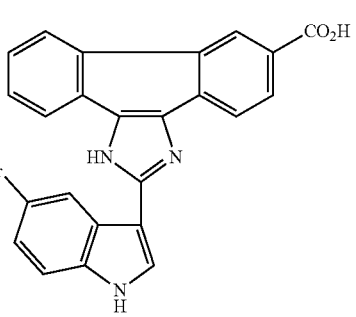
168
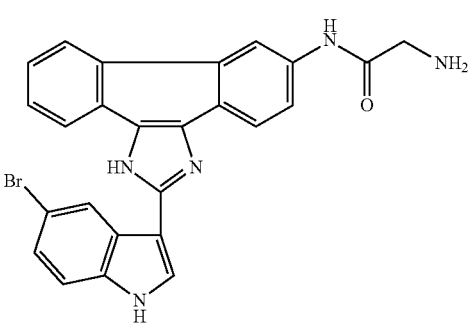
169
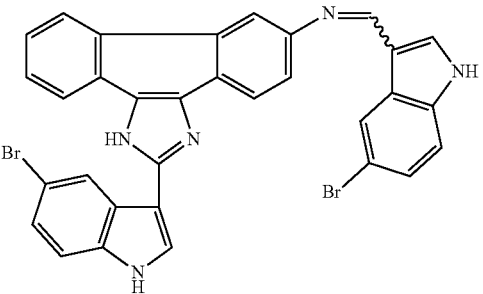
170
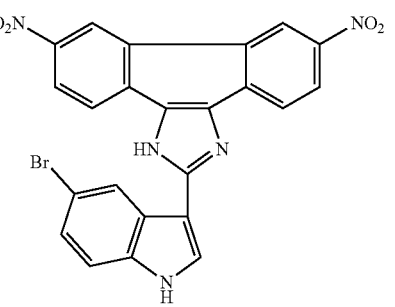

172 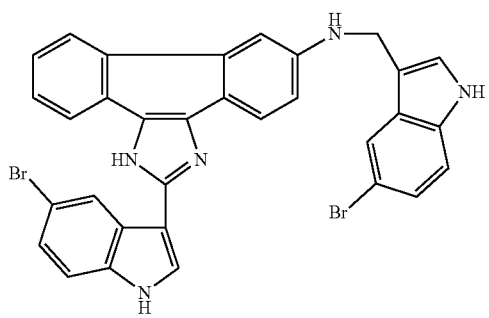
177 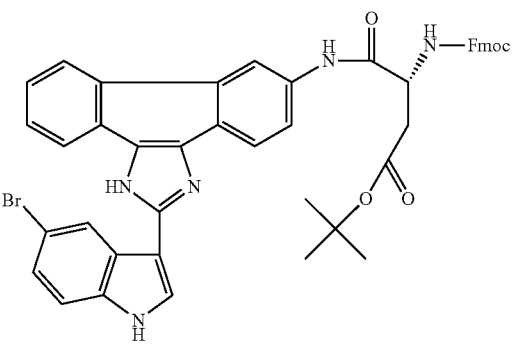
173 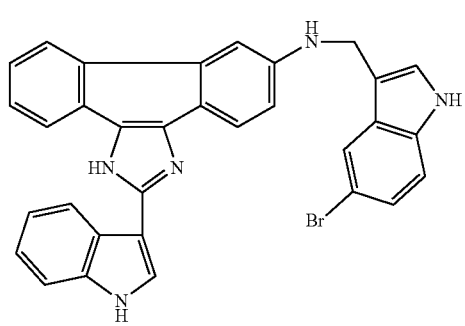
178 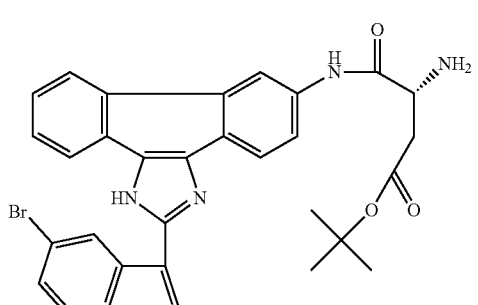
174 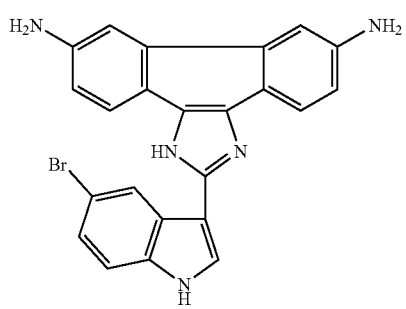
175 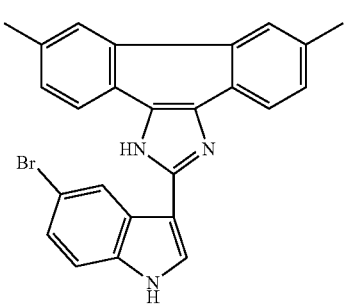
179 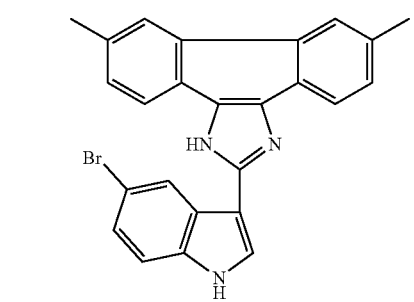
176 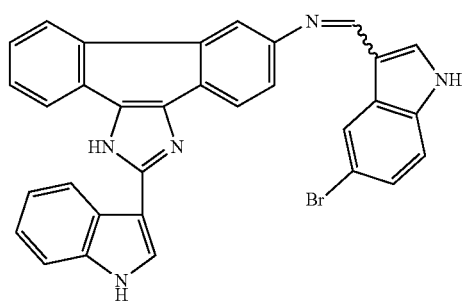
185 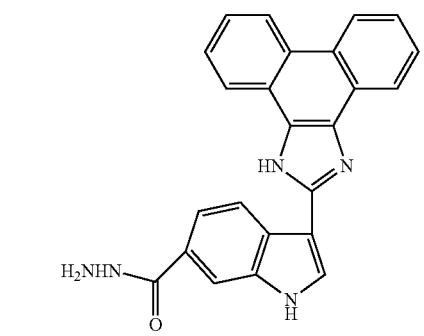

186
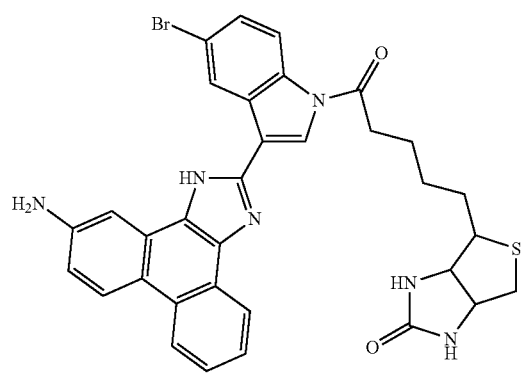
187
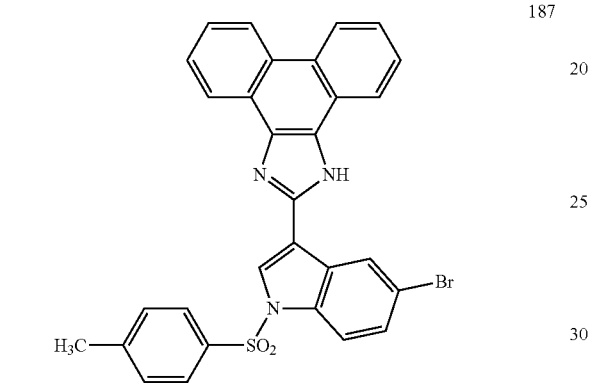
188
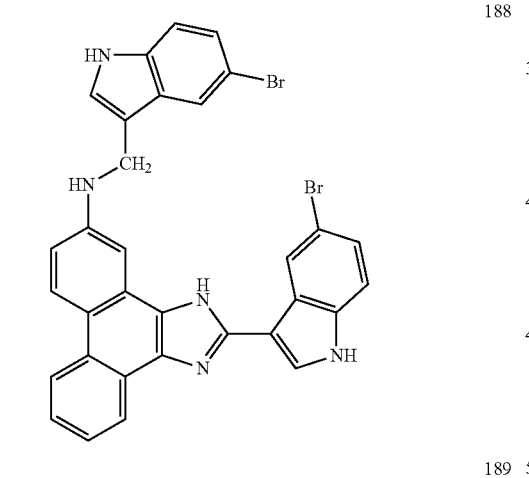
189
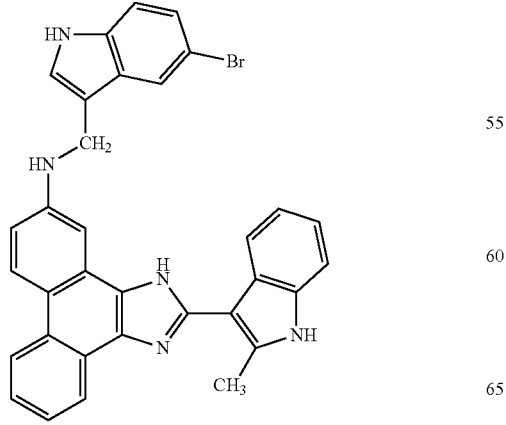
190
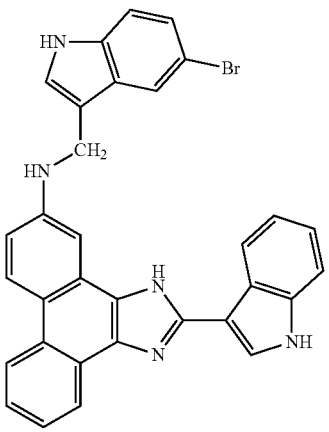
191
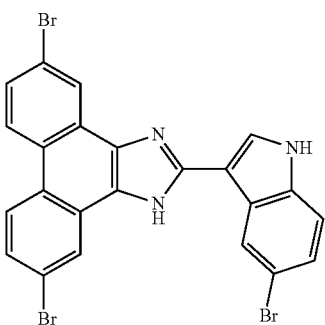
192
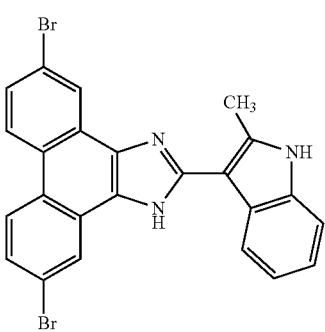
193
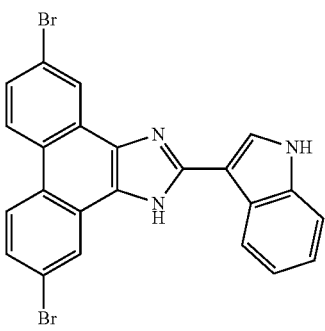

-continued
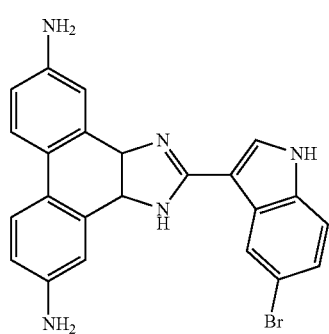
194
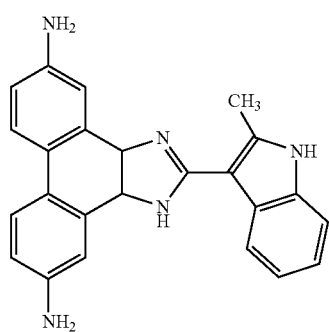
195
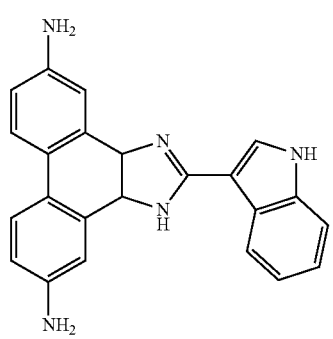
196
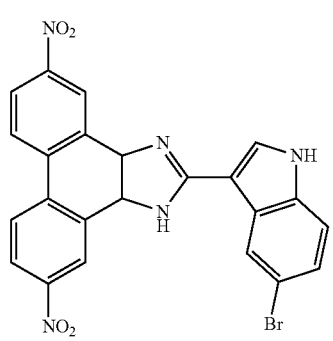
197
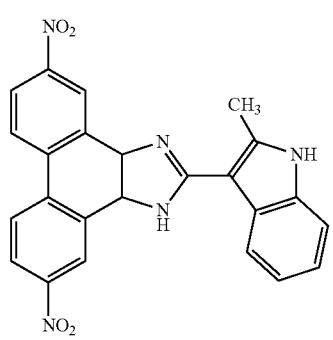
198
-continued
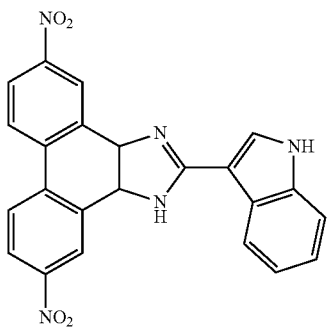
199
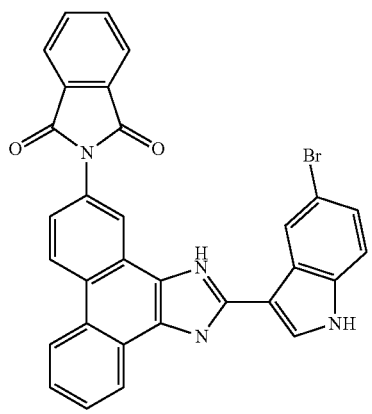
200
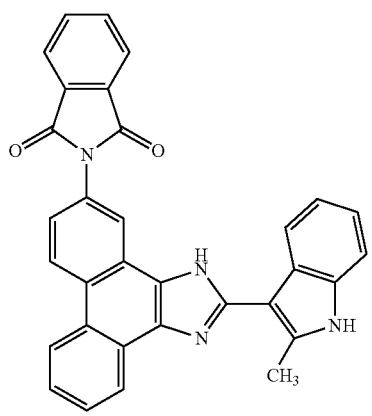
201
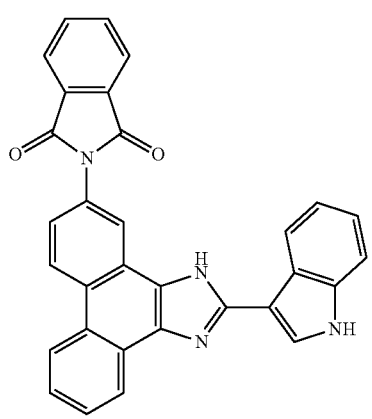
202

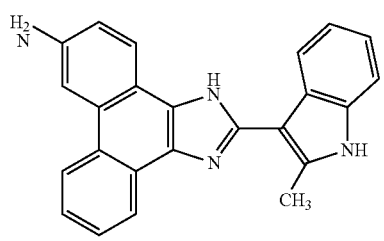
203
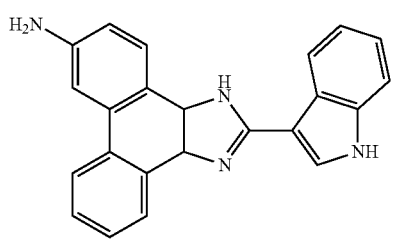
204
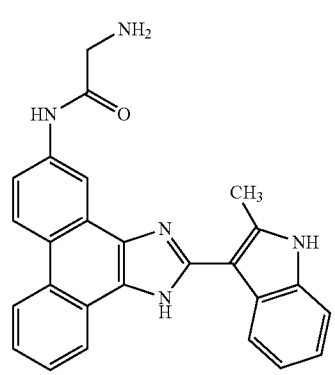
205
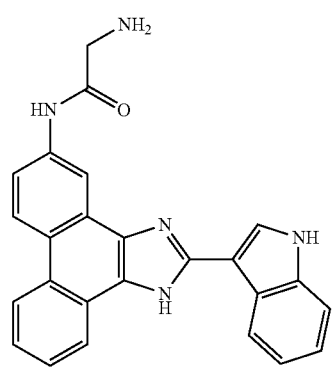
206
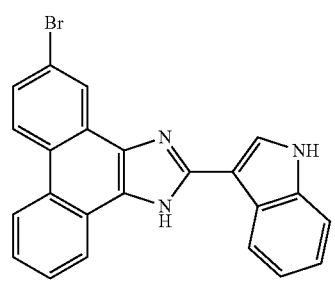
207
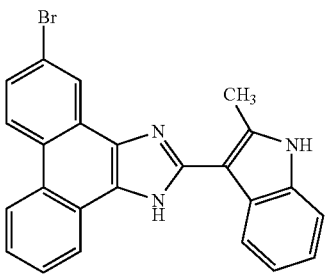
208
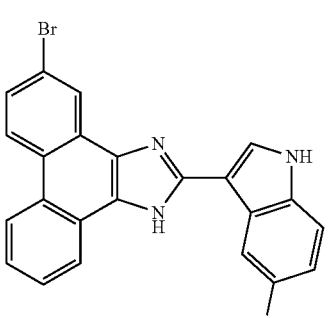
209
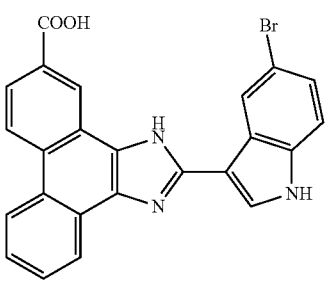
210
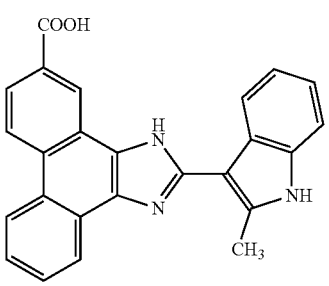
211
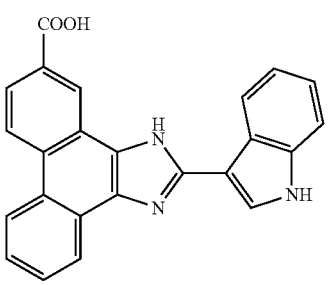
212

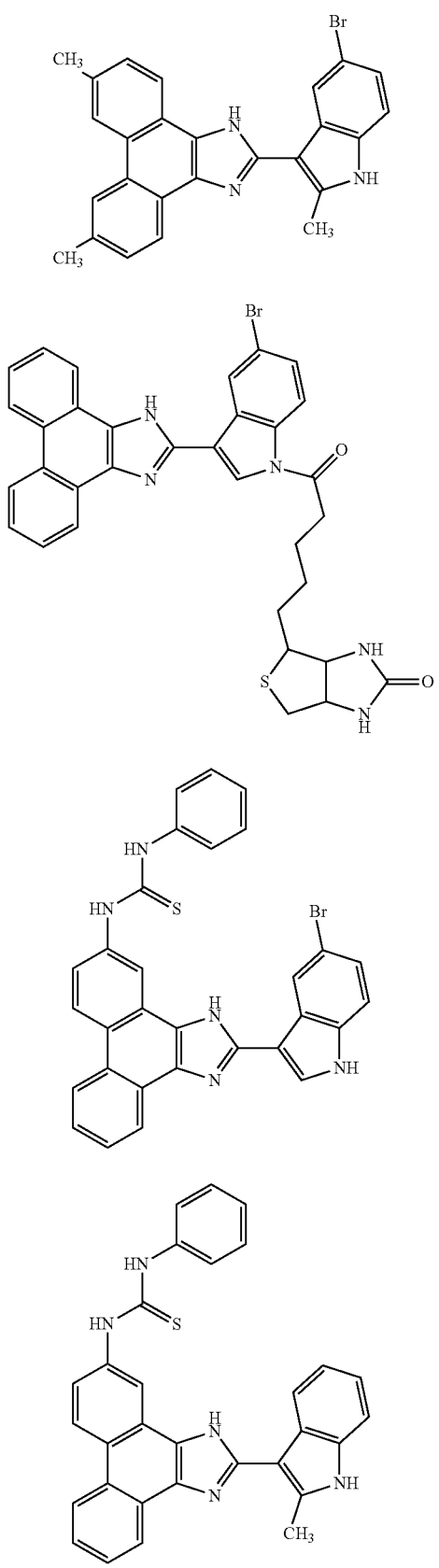
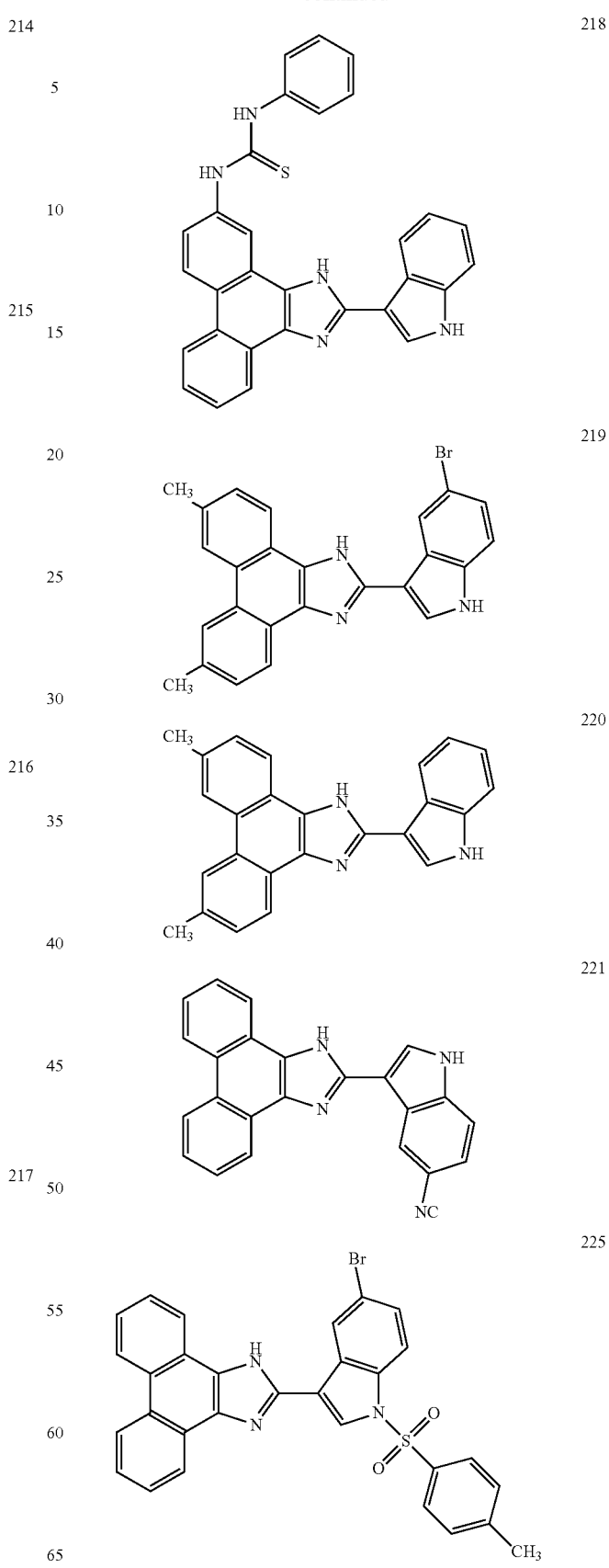

| 226 | 233 |
|---|---|
| 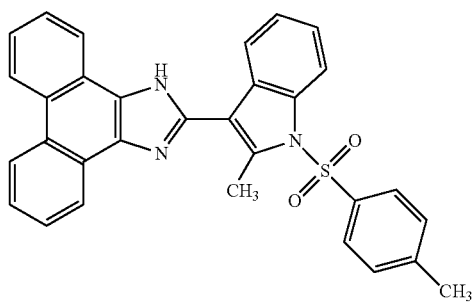 | 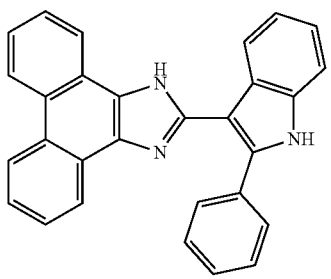 |
| 227 | 234 |
| 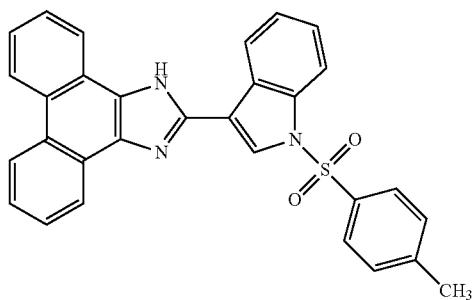 | 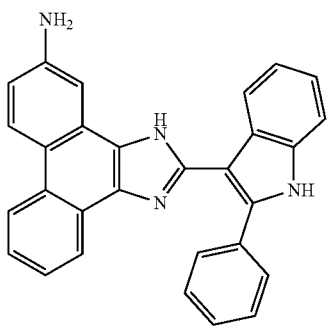 |
| 231 | 235 |
| 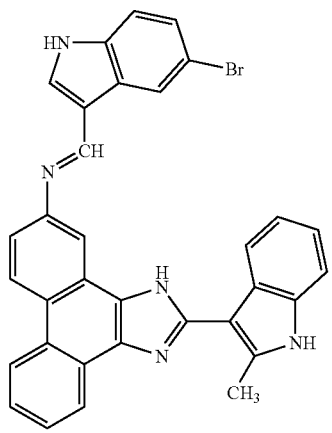 | 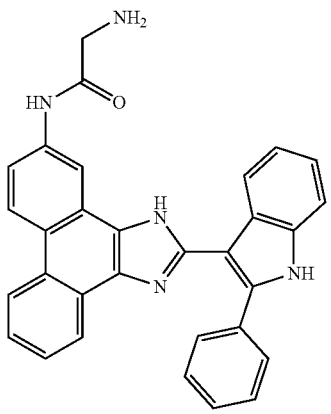 |
| 232 | 236 |
| 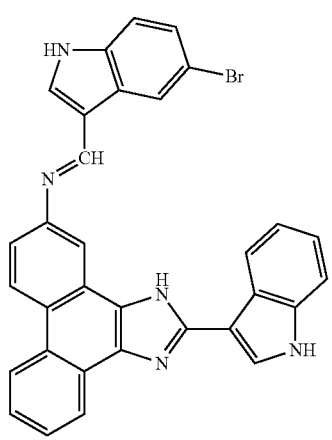 | 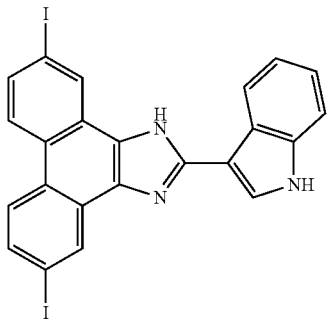 |

173
-continued
237
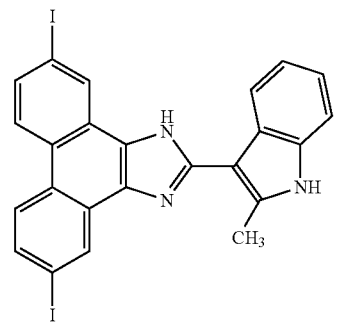
238
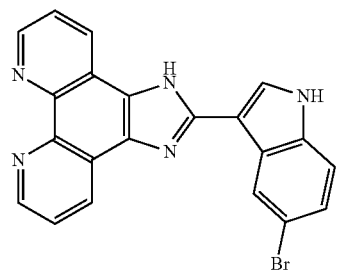
239
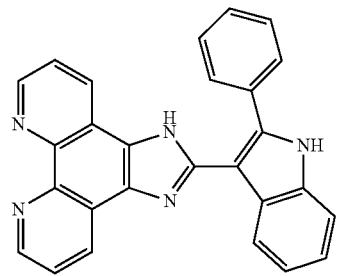
240
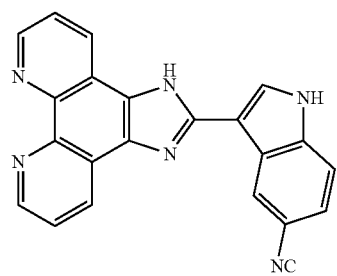
241
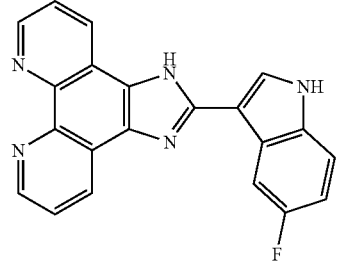
174
-continued
242
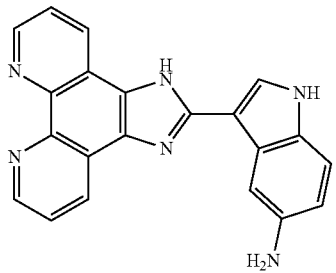
243
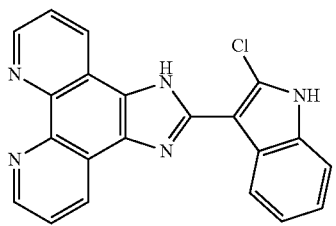
244
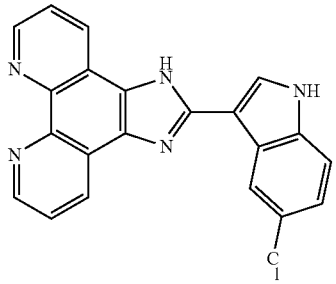
245
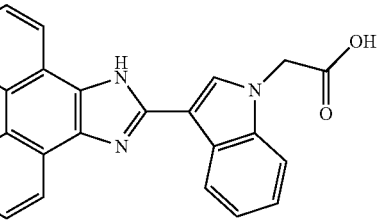
246
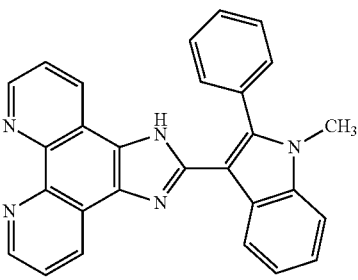
247
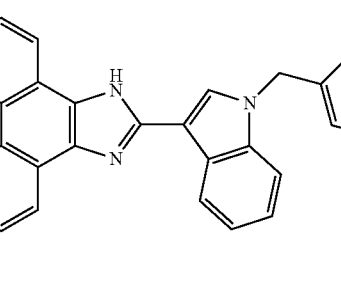

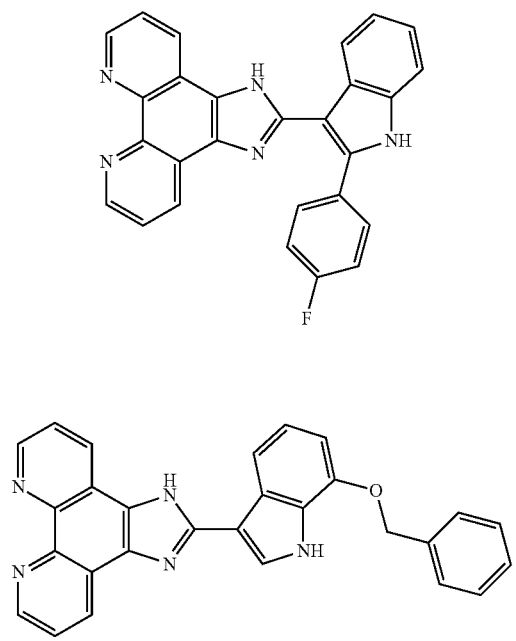
248
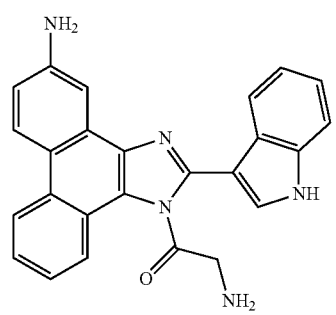
253
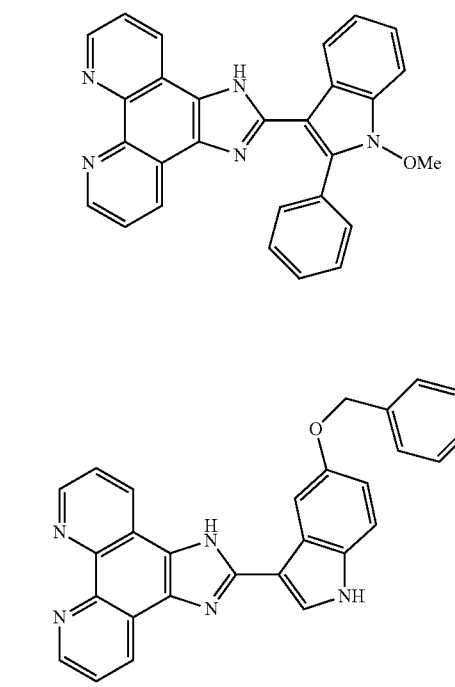
249
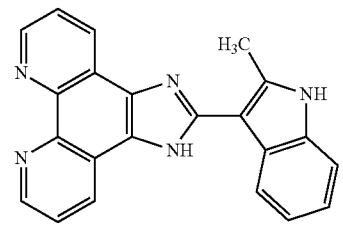
254
12. The compound according to claim 1, selected from:
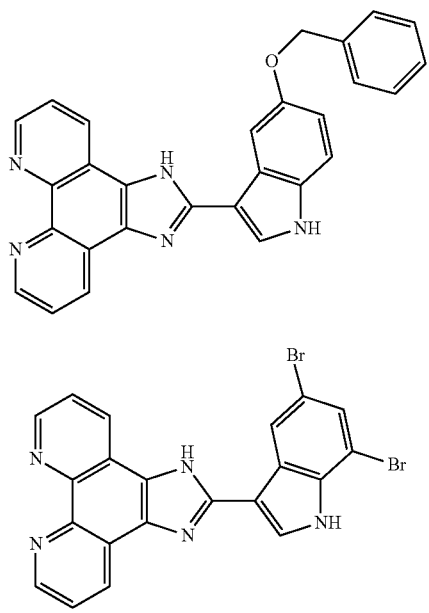
250
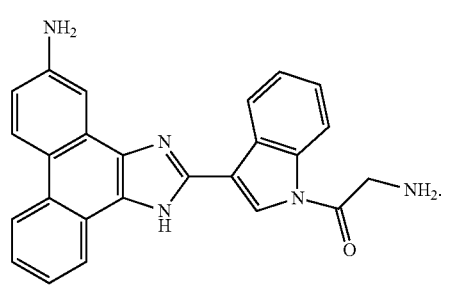
90
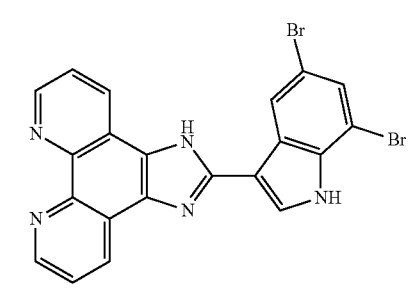
251
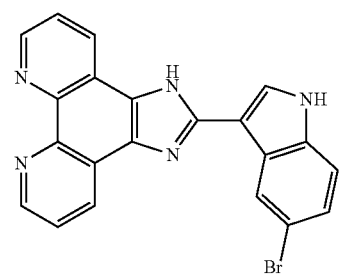
97
252
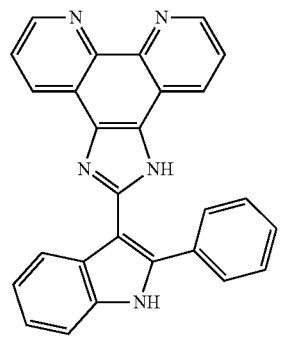
114

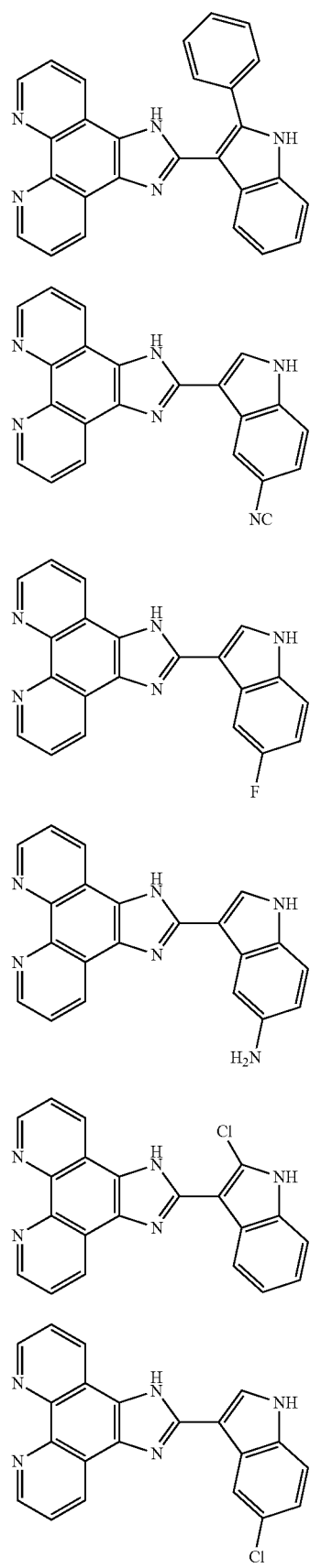
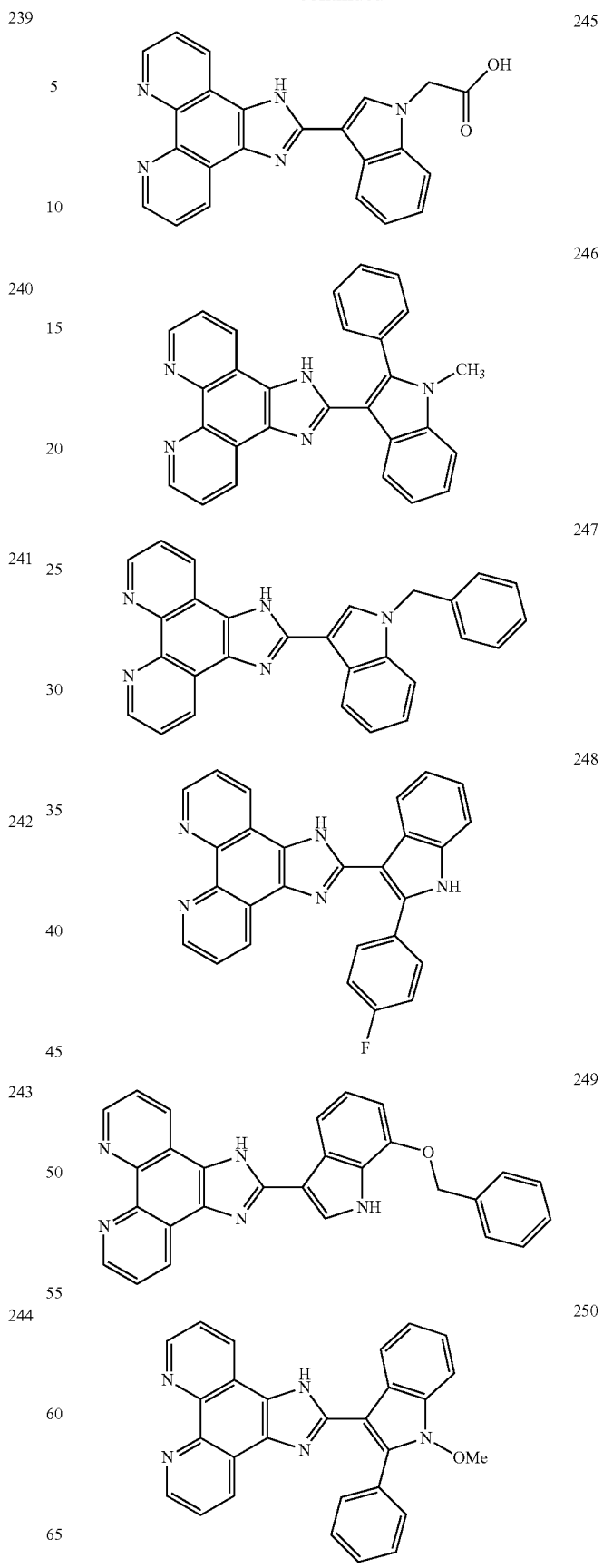

-continued
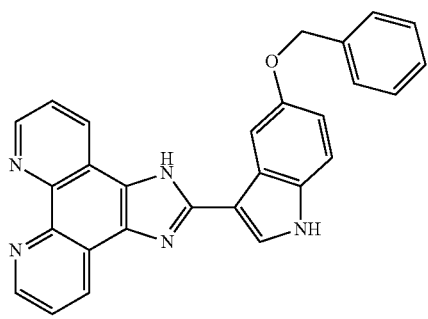
251
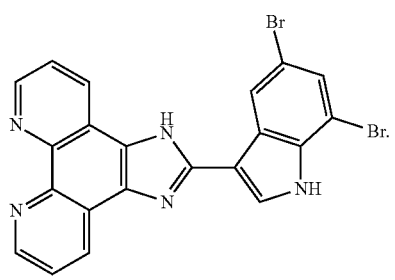
252
13. The compound according to claim 1, wherein said compound is:
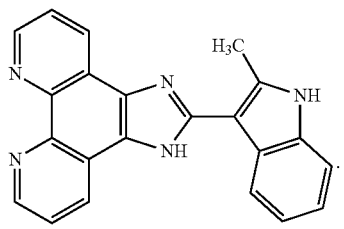
90
14. A pharmaceutical composition comprising the compound of claim 1 and a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 8,969,372 B2 | Page 1 of 1 |
| APPLICATION NO. | : 10/579149 | |
| DATED | : March 3, 2015 | |
| INVENTOR(S) | : Huesca et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1029 days.

Signed and Sealed this
Twenty-second Day of September, 2015

Michelle K. Lee
*Director of the United States Patent and Trademark Office*